(12) United States Patent
Hertz et al.

(10) Patent No.: US 10,723,737 B2
(45) Date of Patent: Jul. 28, 2020

(54) COMPOSITIONS AND METHODS FOR TREATING NEURODEGENERATIVE DISEASES AND CARDIOMYOPATHY

(71) Applicants: The Regents of the University of California, Oakland, CA (US); Mitokinin LLC, New York, NY (US)

(72) Inventors: Nicholas T. Hertz, San Francisco, CA (US); Kevan M. Shokat, San Francisco, CA (US); Robert DeVita, Westfield, NJ (US)

(73) Assignees: THE REGENTS OF THE UNIVERSITY OF CALIFORNIA, Oakland, CA (US); MITOKININ LLC, New York, NY (US)

( * ) Notice: Subject to any disclaimer, the term of this patent is extended or adjusted under 35 U.S.C. 154(b) by 0 days.

(21) Appl. No.: 15/438,496

(22) Filed: Feb. 21, 2017

(65) Prior Publication Data

US 2018/0072731 A1 Mar. 15, 2018

Related U.S. Application Data

(63) Continuation of application No. 14/823,934, filed on Aug. 11, 2015, which is a continuation of application No. PCT/US2014/015863, filed on Feb. 11, 2014.

(60) Provisional application No. 61/763,444, filed on Feb. 11, 2013, provisional application No. 61/845,529, filed on Jul. 12, 2013.

(51) Int. Cl.
C07D 473/34 (2006.01)

(52) U.S. Cl.
CPC .................................. *C07D 473/34* (2013.01)

(58) Field of Classification Search
CPC .................................................... C07D 473/34
See application file for complete search history.

(56) References Cited

U.S. PATENT DOCUMENTS

| | | |
|---|---|---|
| 3,863,633 A | 2/1975 | Ryde et al. |
| 3,867,519 A | 2/1975 | Michaels |
| 3,868,445 A | 2/1975 | Ryde et al. |
| 3,960,150 A | 6/1976 | Hussain et al. |
| 3,963,025 A | 6/1976 | Whitaker et al. |
| 4,115,538 A | 9/1978 | Satoh et al. |
| 4,186,184 A | 1/1980 | Zaffaroni |
| 4,303,637 A | 12/1981 | Shell et al. |
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 5,436,128 A | 7/1995 | Harpold et al. |
| 5,443,505 A | 8/1995 | Wong et al. |
| 5,869,079 A | 2/1999 | Wong et al. |
| 2007/0270362 A1 | 11/2007 | Harlan et al. |
| 2009/0247557 A1 | 10/2009 | Dhalla et al. |
| 2009/0253718 A1* | 10/2009 | Davies ................. C07D 471/04 514/263.22 |
| 2011/0092583 A1 | 4/2011 | Murty et al. |
| 2011/0288106 A1 | 11/2011 | Mueller et al. |
| 2016/0108044 A1 | 4/2016 | Hertz et al. |

FOREIGN PATENT DOCUMENTS

| | | |
|---|---|---|
| CN | 101066268 | * 11/2007 |
| CN | 101066268 A | 11/2007 |
| CN | 101066272 A | 11/2007 |
| CN | 102727499 A | 10/2012 |
| EP | 2 511 283 A1 | 10/2012 |
| WO | WO-94/27583 A2 | 12/1994 |
| WO | WO-94/27583 A3 | 12/1994 |
| WO | WO-01/044260 A2 | 6/2001 |
| WO | WO-01/044260 A3 | 6/2001 |
| WO | WO-01/044260 A8 | 6/2001 |
| WO | WO-01/044260 A9 | 6/2001 |
| WO | WO-02/18404 A2 | 3/2002 |
| WO | WO-02/18404 A3 | 3/2002 |
| WO | WO-02/18404 A9 | 3/2002 |
| WO | WO-2006/011130 A1 | 2/2006 |
| WO | WO-2006/084281 A1 | 8/2006 |
| WO | WO-2007/125315 A2 | 11/2007 |
| WO | WO-2007/125315 A3 | 11/2007 |
| WO | WO-2009/086457 A2 | 7/2009 |
| WO | WO-2009/086457 A3 | 7/2009 |
| WO | WO-2010/046710 A1 | 4/2010 |
| WO | WO-2011/006061 A1 | 1/2011 |
| WO | WO-2011/069294 A1 | 6/2011 |
| WO | WO-2011/109469 A1 | 9/2011 |
| WO | WO-2012/080727 A2 | 6/2012 |
| WO | WO-2012/080727 A3 | 6/2012 |
| WO | WO-2012/080727 A4 | 6/2012 |
| WO | WO-2014/124458 A1 | 8/2014 |

OTHER PUBLICATIONS

Choi, "Zeatin Prevents Amyloid-Induced Neurotoxicity and Scopolamine-Induced Cognitive Deficits", J Med Food 12 (2), 2009, 271-277.*
Arena, G. et al. (Jul. 2013, e-published Mar. 22, 2013). "PINK1 protects against cell death induced by mitochondrial depolarization, by phosphorylating Bcl-xL and impairing its pro-apoptotic cleavage," *Cell Death Differ* 20(7):920-930.
Beilina, A. et al. (Apr. 19, 2005, e-published Apr. 11, 2005). "Mutations in PTEN-induced putative kinase 1 associated with recessive parkinsonism have differential effects on protein stability," *PNAS USA* 102(16):5703-5708.
Berge, S.M. et al. (1977). "Pharmaceutical Salts," *Journal of Pharmaceutical Sciences* 66(1):1-19.
Billia, F. et al. (Jun. 7, 2011, e-published May 23, 2011). "PTEN-inducible kinase 1 (PINK1)/Park6 is indispensable for normal heart function," *PNAS USA* 108(23):9572-9577.
Blethrow, J.D. et al. (Feb. 5, 2008, e-published Jan. 30, 2008). "Covalent capture of kinase-specific phosphopeptides reveals Cdk1-cyclin B substrates," *PNAS USA* 105(5):1442-1447.

(Continued)

*Primary Examiner* — Sahar Javanmard
(74) *Attorney, Agent, or Firm* — Mintz, Levin, Cohn, Ferris, Glovsky and Popeo, P.C.; Doris Lee

(57) ABSTRACT

Disclosed herein inter alia are compositions and methods useful in the treatment neurodegenerative diseases and cardiomyopathy, and for modulating the activity of PINK1.

7 Claims, 35 Drawing Sheets

Specification includes a Sequence Listing.

(56) References Cited

OTHER PUBLICATIONS

Chang, W. et al. (Dec. 17, 2010, e-published Feb. 10, 2011). "Discovery of PSI-353661, a Novel Purine Nucleotide Prodrug for the Treatment of HCV Infection," *ACS Med Chem Lett* 2(2):130-135.
Chen, Y. et al. (Apr. 26, 2013). "PINK1-phosphorylated mitofusin 2 is a Parkin receptor for culling damaged mitochondria," *Science* 340(6131):471-475.
Clark, I.E. et al. (Jun. 29, 2006, e-published May 3, 2006). "Drosophila pink1 is required for mitochondrial function and interacts genetically with parkin," *Nature* 44197097):1162-1166.
Deng, H. et al. (Dec. 2, 2005, e-published Oct. 6, 2005). "Small interfering RNA targeting the PINK1 induces apoptosis in dopaminergic cells SH-SY5Y," *Biochem Biophys Res Commun* 337(4):1133-1138.
Deng, H. et al. (Sep. 23, 2008, e-published Sep. 17, 2008). "The Parkinson's disease genes pink1 and parkin promote mitochondrial fission and/or inhibit fusion in Drosophila," *PNAS USA* 105(38):14503-14508.
Felley-Bosco, E. et al. (Aug. 1994). "Constitutive expression of inducible nitric oxide synthase in human bronchial epithelial cells induces c-fos and stimulates the cGMP pathway," Am J Respir Cell Mol Biol 11(2):159-164.
Furman, P.A. et al. (Aug. 2011, e-published May 12, 2011). "Activity and the metabolic activation pathway of the potent and selective hepatitis C virus pronucleotide inhibitor PSI-353661," *Antiviral Res* 91(2):120-132.
Ganetzky, B. et al. (Apr. 1982). "Indirect Suppression Involving Behavioral Mutants with Altered Nerve Excitability in Drosophila Melanogaster," *Genetics* 100(4):597-614.
Gautier, C.A. et al. (Aug. 12, 2008, e-published Aug. 7, 2008). "Loss of PINK1 causes mitochondrial functional defects and increased sensitivity to oxidative stress," *PNAS USA* 105(32)11364-11369.
Geisler, S. et al. (Oct. 2010, e-published Oct. 3, 2010). "The PINK1/Parkin-mediated mitophagy is compromised by PD-associated mutations," *Autophagy*6(7):871-878.
Göransson, O. et al. (Nov. 9, 2007, e-published Sep. 12, 2007). "Mechanism of action of A-769662, a valuable tool for activation of AMP-activated protein kinase," *J Biol Chem* 282(45):32549-32560.
Groarke, D.A. et al. (1999). "Visualization of Agonist-induced Association and Trafficking of Green Fluorescent Protein-tagged Forms of Both β-Arrestin-1 and the Thyrotropin-releasing Hormone Receptor-1," *The Journal of Biological Chemistry* 274(33):23263-23269.
Haque, M.E. et al. (Feb. 5, 2008, e-published Jan. 24, 2008). "Cytoplasmic Pink1 activity protects neurons from dopaminergic neurotoxin MPTP," *PNAS USA* 105(5):1716-1721.
Hecker, S.J. et al. (Apr. 24, 2008, e-published Feb. 1, 2008). "Prodrugs of phosphates and phosphonates," J Med Chem 51(8):2328-2345.
Henchcliffe, C. et al. (Nov. 2008). "Mitochondrial biology and oxidative stress in Parkinson disease pathogenesis," *Nat Clin Pract Neurol* 4(11):600-609.
Hertz, N. T. et al. (Mar. 2010). "Chemical genetic approach for kinase-substrate mapping by covalent capture of thiophosphopeptides and analysis by mass spectrometry," *Curr Protoc Chem Biol* 2(1):15-36.
Hertz, N. T. et al. (Aug. 15, 2013). "A neo-substrate that amplifies catalytic activity of parkinson's-disease-related kinase PINK1," *Cell* 154(4):737-747.
Hims, M.M. et al. (Feb. 2007, e-published Jan. 6, 2007). "Therapeutic potential and mechanism of kinetin as a treatment for the human splicing disease familial dysautonomia," *J Mol Med (Berl)* 85(2):149-161.
International Search Report dated May 30, 2014, for PCT Application No. PCT/US2014/015863, filed on Feb. 11, 2014, 4 pages.
Ishii, Y. et al. (Dec. 7, 2003). "Cytokinin-induced differentiation of human myeloid leukemia HL-60 cells is associated with the formation of nucleotides, but not with incorporation into DNA or RNA," *Biochim Biophys Acta* 1643(1-3):11-24.
Kaneti, J. et al. (Jan. 1983). "Conformational analysis of cytokinins and analogs," *Chem Biol Interact* 43(1):73-85.
Kim, K.H. et al. (Dec. 28, 2012, e-published Nov. 9, 2012). "Rescue of PINK1 protein null-specific mitochondrial complex IV deficits by ginsenoside Re activation of nitric oxide signaling," *J Biol Chem* 287(53):44109-44120.
Koh, H. et al. (Jul. 2012, e-published May 18, 2012). "PINK1 as a molecular checkpoint in the maintenance of mitochondrial function and integrity," *Mol Cells* 34(1):7-13.
Kondapalli, C. et al. (May 2012). "PINK1 is activated by mitochondrial membrane potential depolarization and stimulates Parkin E3 ligase activity by phosphorylating Serine 65," *Open Biol* 2(5):120080.
Kopecny, D. et al. (Jul. 25, 2008, e-published May 24, 2008). "Mechanism-based inhibitors of cytokinin oxidase/dehydrogenase attack FAD cofactor," J Mol Biol 380(5):886-899.
Kroeger, K.M. et al. (Apr. 20, 2001, e-published Jan. 18, 2001). "Constitutive and agonist-dependent homo-oligomerization of the thyrotropin-releasing hormone receptor. Detection in living cells using bioluminescence resonance energy transfer," *J Biol Chem* 276(6):12736-12743.
Kruse, S.E. et al. (Apr. 2008). "Mice with mitochondrial complex I deficiency develop a fatal encephalomyopathy," *Cell Metab* 7(4):312-320.
Lam, A.M. et al. (Aug. 2010). "PSI-7851, a pronucleotide of β-D-2'-deoxy-2'-fluoro-2'-C-methyluridine monophosphate, is a potent and pan-genotype inhibitor of hepatitis C virus replication," *Antimicrobial Agents and Chemotherapy* 54(8):3187-3196.
Lam, A.M. et al. (Dec. 2011, e-published Sep. 28, 2011). "Hepatitis C virus nucleotide inhibitors PSI-352938 and PSI-353661 exhibit a novel mechanism of resistance requiring multiple mutations within replicon RNA," *J Virol* 85(23):12334-12342.
Liu, Y. et al. (Aug. 1998). "A molecular gate which controls unnatural ATP analogue recognition by the tyrosine kinase v-Src," *Bioorg Med Chem* 6(8):1219-1226.
Lourido, S. et al. (May 20, 2010). "Calcium-dependent protein kinase 1 is an essential regulator of exocytosis in Toxoplasma," *Nature* 465(7296):359-362.
Martin, I. et al. (2011). "Recent advances in the genetics of Parkinson's disease," *Annu Rev Genomics Hum Genet* 12:301-325.
Meissner, C. et al. (Jun. 2011, e-published Apr. 13, 2011). "The mitochondrial intramembrane protease PARL cleaves human Pink1 to regulate Pink1 trafficking," *J Neurochem* 117(5):856-867.
Merrick, K.A. et al. (Jun. 10, 2011). "Switching Cdk2 on or off with small molecules to reveal requirements in human cell proliferation," *Mol Cell* 42(5):624-636.
Mills, R.D. et al. (Apr. 2008, e-published Jan. 23, 2008). "Biochemical aspects of the neuroprotective mechanism of PTEN-induced kinase-1 (PINK1)," *J Neurochem* 105(1):18-33.
Misteli, T. et al. (Oct. 1997). "Applications of the green fluorescent protein in cell biology and biotechnology," *Nat Biotechnol* 15(10):961-964.
Murakami, E. et al. (Aug. 2011, e-published Jul. 22, 2011). "Adenosine deaminase-like protein 1 (ADAL1): characterization and substrate specificity in the hydrolysis of N(6)- or O(6)-substituted purine or 2-aminopurine nucleoside monophosphates," *J Med Chem* 54(16):59025914.
Narendra, D. et al. (Dec. 1, 2008, e-published Nov. 24, 2008). "Parkin is recruited selectively to impaired mitochondria and promotes their autophagy," *J Cell Biol* 183(5):795-803.
Narendra, D. P. et al. (Jan. 26 2010). "PINK1 is selectively stabilized on impaired mitochondria to activate Parkin," *PLoS Biol* 8(1):e1000298.
Offermanns, S. et al. (Jun. 23, 1995). "G alpha 15 and G alpha 16 couple a wide variety of receptors to phospholipase C," J Biol Chem 270(25):15175-15180.
Petit, A. et al. (Oct. 7, 2005, e-published Aug. 2, 2005). "Wild-type PINK1 prevents basal and induced neuronal apoptosis, a protective effect abrogated by Parkinson disease-related mutations," *J Biol Chem* 280(40):34025-34032.

(56) References Cited

OTHER PUBLICATIONS

Priyadarshini, M. et al. (Jun. 2013, e-published Feb. 27, 2013). "A zebrafish model of PINK1 deficiency reveals key pathway dysfunction including HIF signaling," *Neurobiol Dis* 54:127-138.
Pridgeon, J.W. et al. (Jul. 2007, e-published Jun. 19, 2007). "PINK1 protects against oxidative stress by phosphorylating mitochondrial chaperone TRAP1," *PLoS Biol* 5(7):e172.
Rao, S. et al. (2012). "In Vitro Propagation of *Withania somnifera* and Estimation of Withanolides for Neurological Disorders," *Journal of Pharmacognosy* 3(2):85-87.
Rautio, J. et al. (Mar. 2008). "Prodrugs: design and clinical applications," *Nat Rev Drug Discov* 7(3):255-270.
Reddy, P.G. et al. (Dec. 15, 2010, e-published Oct. 15, 2010). "2'-deoxy-2'-α-fluoro-2'β-C-methyl 3',5'-cyclic phosphate nucleotide prodrug analogs as inhibitors of HCV NS5B polymerase: discovery of PSI-352938," *Bioorg Med Chem Lett* 20(24):7376-7380.
Sadowsky, J.D. et al. (Apr. 12, 2011, e-published Mar. 23, 2011). "Turning a protein kinase on or off from a single allosteric site via disulfide trapping," *PNAS USA* 108(15):6056-6061.
Samaranch, L. et al. (Apr. 2010, e-published Mar. 30, 2010). "PINK1-linked parkinsonism is associated with Lewy body pathology," *Brain* 133(Pt 4):1128-1142.
Shaw. G. et al. (1971). "The Structure and Physiological Activity of Some W-Substituted Adenines," *Phytochemistry* 10(10):2329-2336.
Shetty, R.S. et al. (Nov. 1, 2011, e-published Aug. 5, 2011). "Specific correction of a splice defect in brain by nutritional supplementation," *Hum Mol Genet* 20(21):4093-4101.
Shin, J-H. et al. (Mar. 4, 2011). "Paris (ZNF746) repression of PGC-α contributes to neurodegeneration in Parkinson's disease," Cell 144(5):689-702.
Siddall, H.K. et al. (Dec. 2008, e-published Sep. 30, 2008). "Mitochondrial PINK1—a novel cardioprotective kinase?" *Cardiovasc Drugs Ther* 22(6):507-508.
Siddall, H.K. et al. (Apr. 29, 2013). "Loss of PINK1 increases the heart's vulnerability to ischemia-reperfusion injury," *PLoS One* 8(4):e62400.
Sofia, M.J. et al. (Oct. 14, 2010). "Discovery of a β-d-2'-deoxy-2'-60-fluoro-2'- β-C-methyluridine nucleotide prodrug (PSI-7977) for the treatment of hepatitis C virus," *J Med Chem* 53(19):7202-7218.
Sofia, M.J. et al. (Mar. 22, 2012, e-published Jan. 23, 2012). "Nucleoside, nucleotide, and non-nucleoside inhibitors of hepatitis C virus NS5B RNA-dependent RNA-polymerase," *J Med Chem* 55(6):2481-2531.
Sue M. et al., "Specific interaction of cytokinins and their analogs with rotenone-sensitive internal NADH dehydrogenase in potato tuber mitochondria", Bioscience Biotechnology Biochemistry, 61(11):1806-1809.
Vernachio, J.H. et al. (May 2011, e-published Feb. 28, 2011). "INX-08189, a phosphoramidate prodrug of 6-O-methyl-2'-C-methyl guanosine, is a potent inhibitor of hepatitis C virus replication with excellent pharmacokinetic and pharmacodynamic properties," *Antimicrob Agents Chemother* 55(5):1843-1851.
Wang, J. et al. (2006). "A Simple and Fast Experimental Model of Myocardial Infarction in the Mouse," *Tex Heart Inst J* 33(3):290-293.
Wang, X. et al. (Nov. 11, 2011). "PINK1 and Parkin target Miro for phosphorylation and degradation to arrest mitochondrial motility," *Cell* 147(4):893-906.
Written Opinion dated May 30, 2014, for PCT Application No. PCT/US2014/015863, filed on Feb. 11, 2014, 5 pages.
Zhou, Z. et al. (Nov. 2011, e-published Aug. 29, 2011). "Clinical Carbapenem-Resistant Acinetobacter baylyi Strain Coharboring $bla_{sim\text{-}1}$ and $bla_{oxA\text{-}23}$ from China," *Antimicrobial Agents and Chemotherapy* 55(11):5347-5349.
CAS RN 1410085-94-7, entered STN Dec. 3, 2012, 1 page.
CAS RN 1394724-43-6, entered STN Sep. 18, 2012, 1 page.
CAS RN 1340091-74-8, entered STN Nov. 3, 2011, 1 page.
CAS RN 1306077-81-5, entered STN Jun. 5, 2011, 1 page.
CAS RN 1281418-20-9, entered STN Apr. 17, 2011, 1 page.
CAS RN 1348978-79-9, entered STN Dec. 5, 2011, 1 page.
CAS RN 1125434-33-4, entered STN Mar. 23, 2009, 1 page.
CAS RN 75737-38-1, entered STN Nov. 16, 1984, 1 page.
CAS RN 327771-64-5, entered STN Nov. 16, 1984, 1 page.
CAS RN 15396-42-6, entered STN Nov. 16, 1984, 1 page.
CAS RN 1637-39-4, entered STN Nov. 16, 1984, 1 page.
CAS RN 1214-39-7, entered STN Nov. 16, 1984, 1 page.
CAS RN 73-24-5, entered STN Nov. 16, 1984, 1 page.
International Search Report, International Preliminary Report on Patentability and Written Opinion for PCT/US2015/015513 dated Apr. 29, 2015, 11 pages.
Supplementary Search Report dated Jun. 27, 2017 and Written Opinion for EP 15748579.8 available as of Jul. 7, 2016, 7 pages.
GPRI09a: Accession No. NP 808219.1; hydroxycarboxylic acid receptor 2 [Homo sapiens]; date downloaded Sep. 13, 2017, 5 pages.
Human PINK 1: Accession No. AY 358957.1; Homo sapiens clone DNA71277 PINK1 (UNQ740) mRNA, complete cds; date downloaded Sep. 13, 2017, 2 pages.
NP 115785.1; serine/threonine-protein kinase PINK1, mitochondrial precursor [Homo sapiens]; date downloaded Sep. 13, 2017, 6 pages.
Leibovitz (L15; PanBiotech; ref: P04-27055, batch: 4290114), 1 page.
Heo, H.J. et al. (Feb. 28, 2002). "Inhibitory effect of zeatin, isolated from Fiatoua villosa, on acetylcholinesterase activity from PC12 cells," *Mol Cells* 13(1):113-117.
Okamoto, M. et al. (Jan. 1, 2011, e-published). "Identification of novel ASK1 inhibitors using virtual screening," *Bioorg Med Chem* 19(1):486-489.
CAS Registry No. 16370-48-2, Nov. 16, 1984, 1 page.
CAS Registry No. 18453-04-8, Nov. 16, 1984, 1 page.
CAS Registry No. 1152983-86-2, Jun. 7, 2009, 1 page.
CAS Registry No. 1239372-50-9, Aug. 27, 2010, 1 page.
Rückle, T. et al. (Dec. 1, 2004, e-published Nov. 26, 2004). "Design, synthesis, and biological activity of novel, potent, and selective (benzoylaminomethyl)thiophene sulfonamide inhibitors of c-Jun-N-terminal kinase," *J Med Chem* 47(27):6921-6934.

\* cited by examiner

FIG. 2A    FIG. 2B
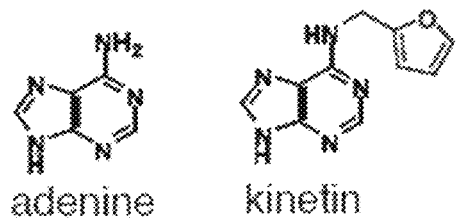
FIG. 2C                    FIG. 2D
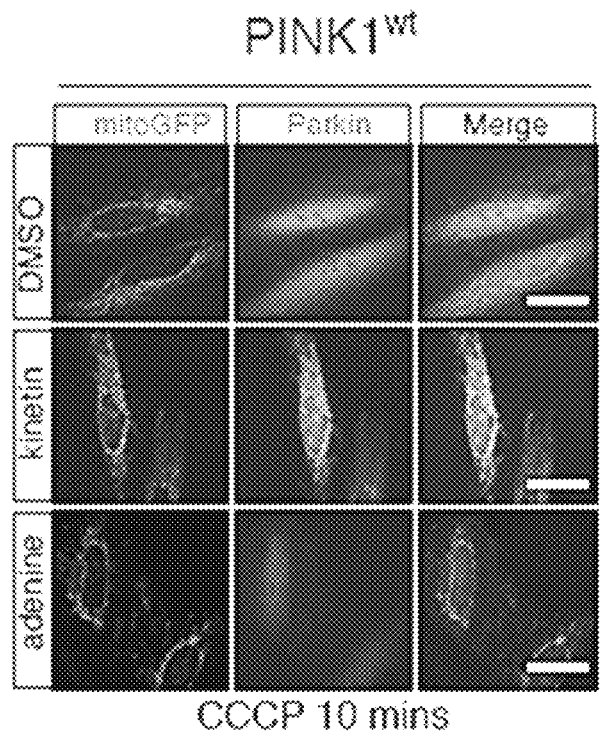 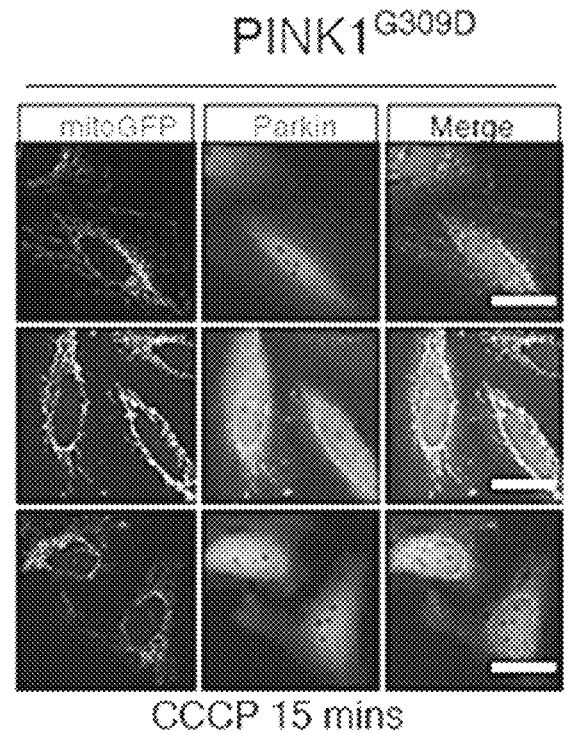
FIG. 2E
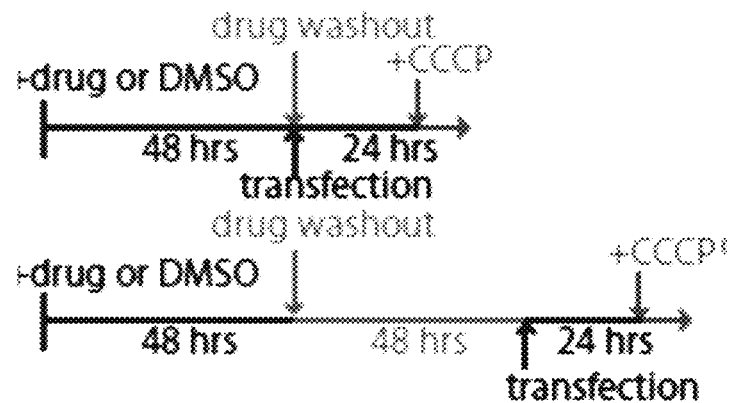

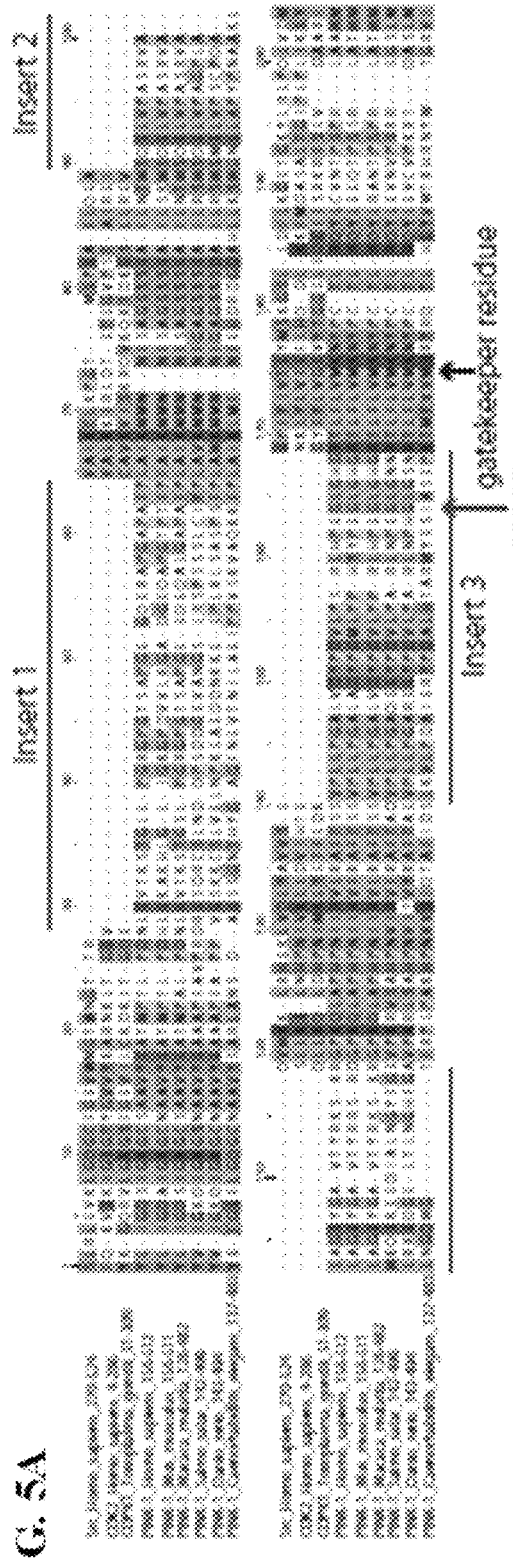
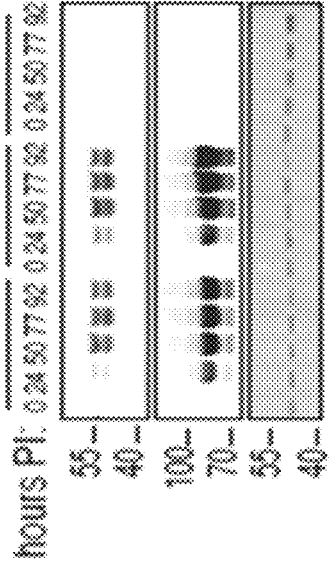
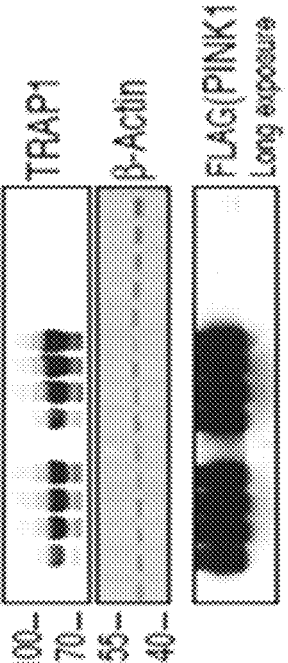
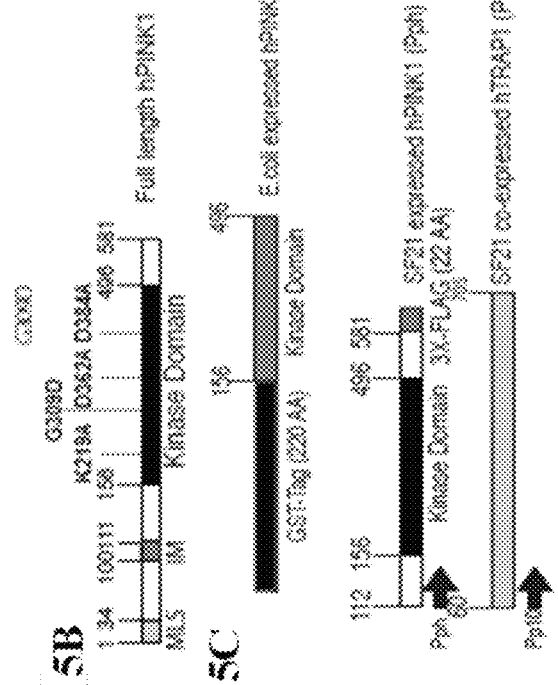
FIG. 5A
FIG. 5B
FIG. 5C
FIG. 5D
FIG. 5E co-localization = (mCherry Parkin on mitochondria) / (total mCherry Parkin)

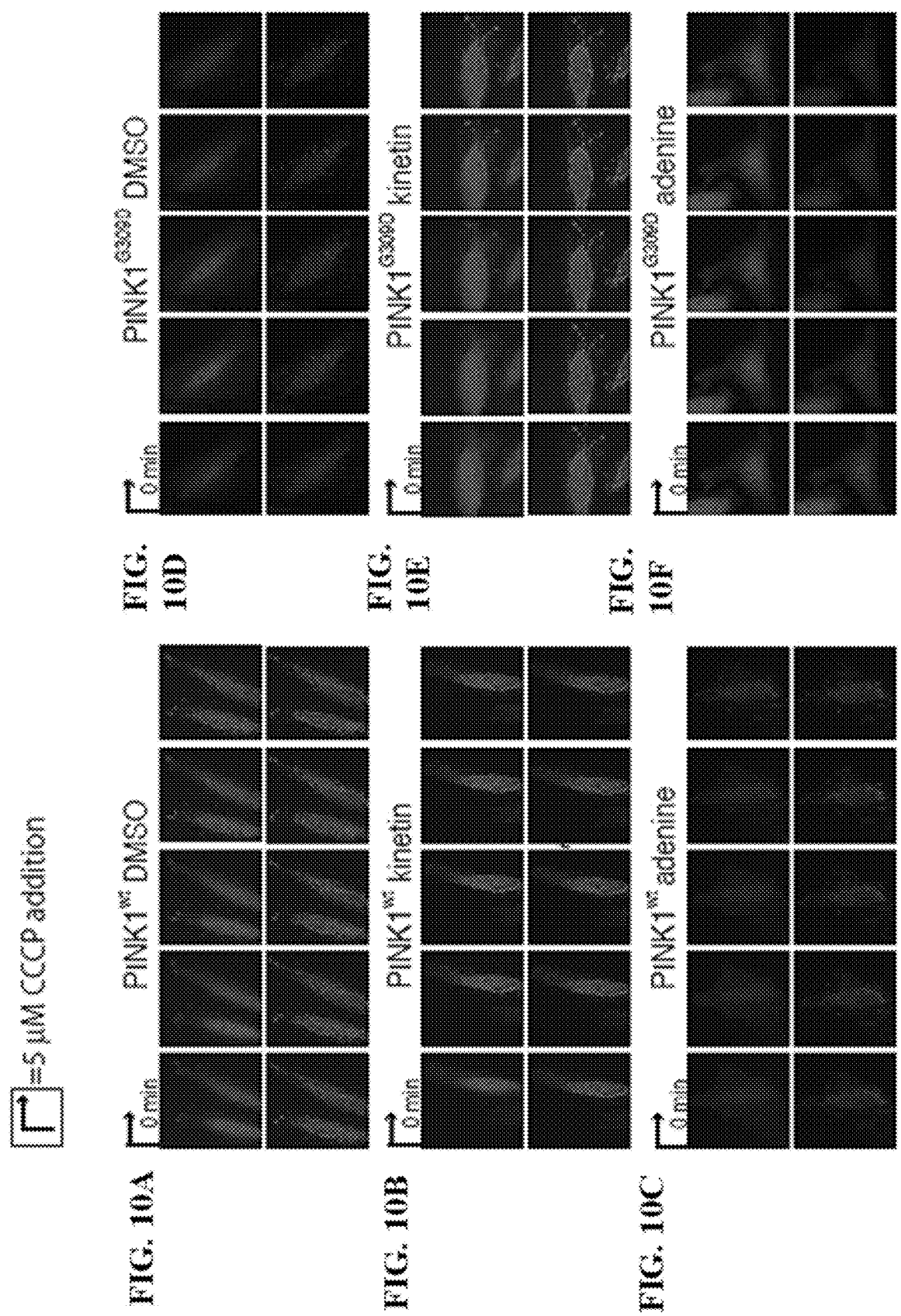

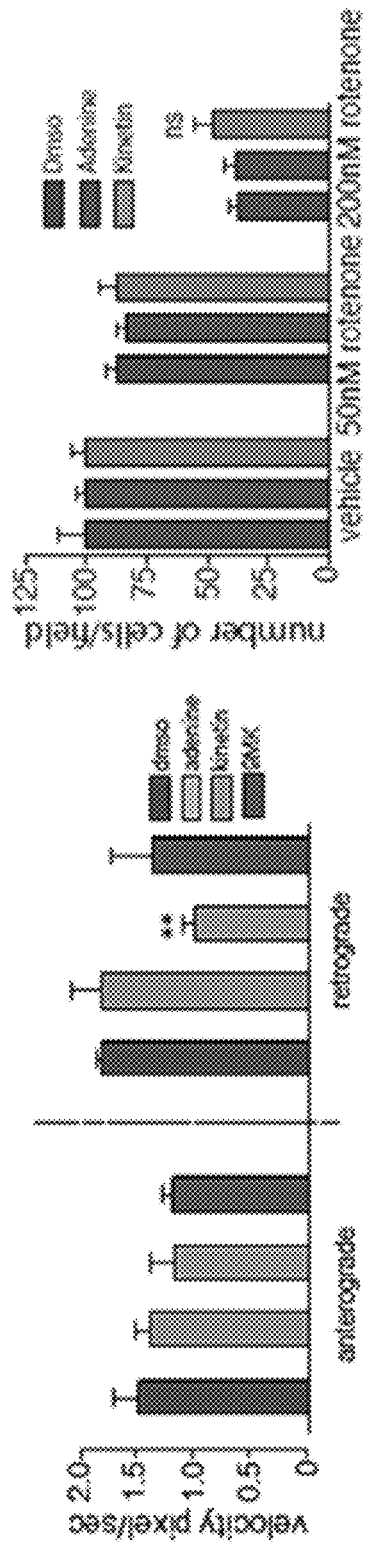
FIG. 11A
FIG. 11B
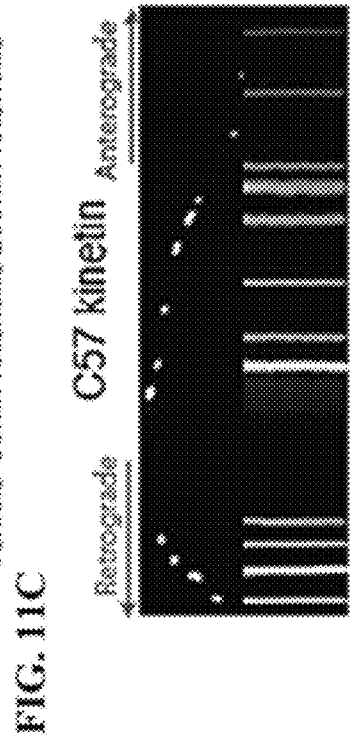
FIG. 11F
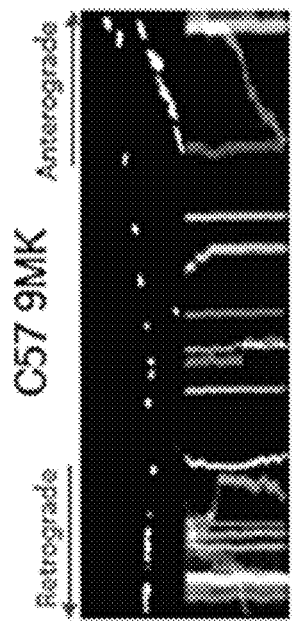
FIG. 11C
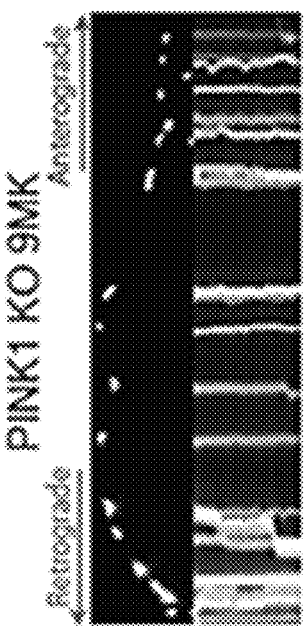
FIG. 11E
FIG. 11D

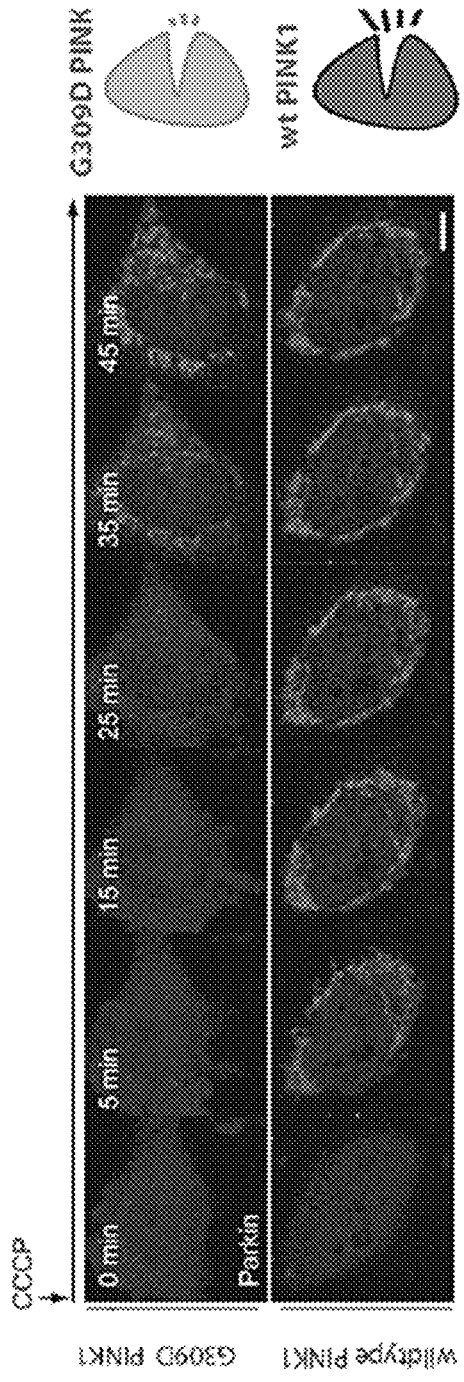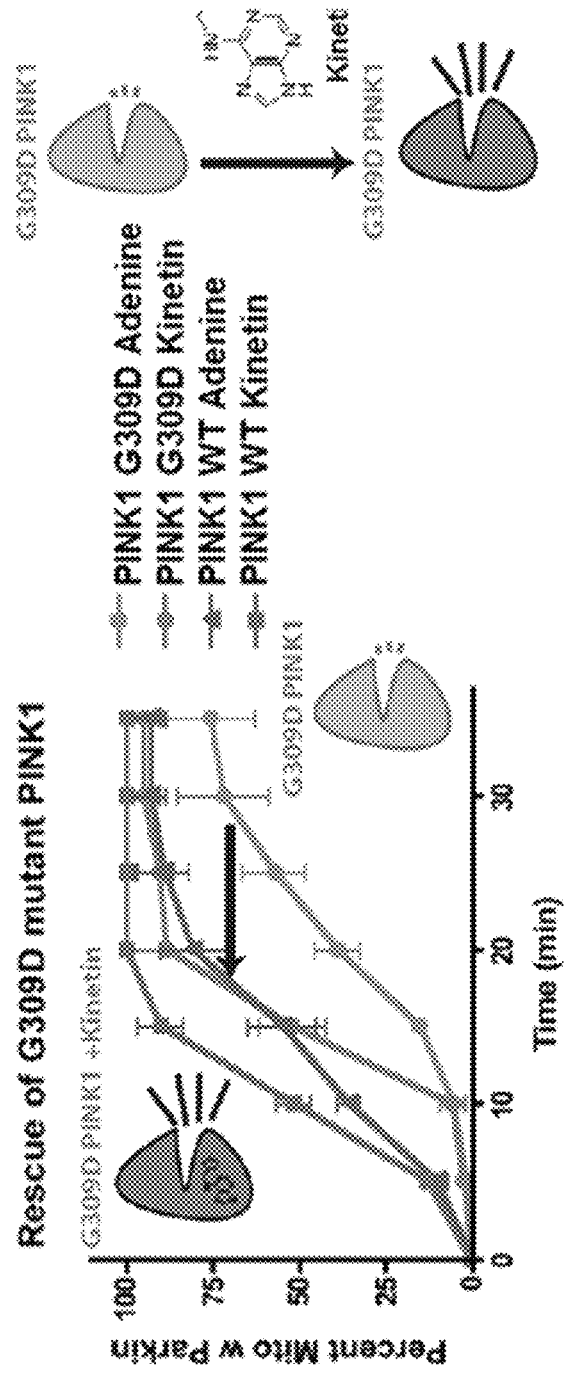
FIG. 16A
FIG. 16B

FIG. 17
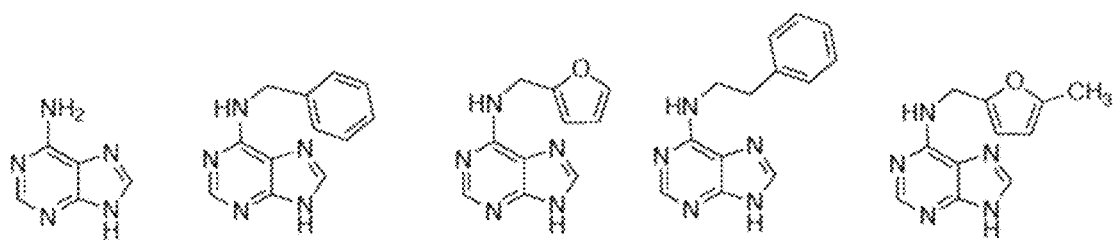
| Adenine | Benzyl | Furfuryl | Phenyl Ethyl | 5 Methyl Furfuryl |
|---------|--------|----------|--------------|-------------------|
| 466 uM  | 246 uM | 589 uM   | 98 uM        | 322 uM            |
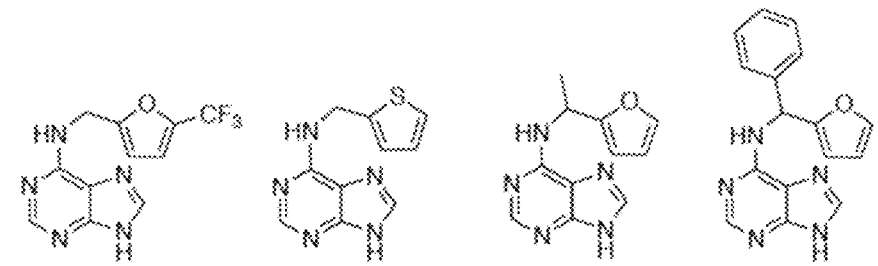
| TFM Furfuryl | Thiophene | 2 Methyl Furfuryl | 2 Phenyl Furfuryl |
|--------------|-----------|-------------------|-------------------|
| 263 uM       | 224 uM    | 2.5 uM            | 82 uM             |

FIG. 27
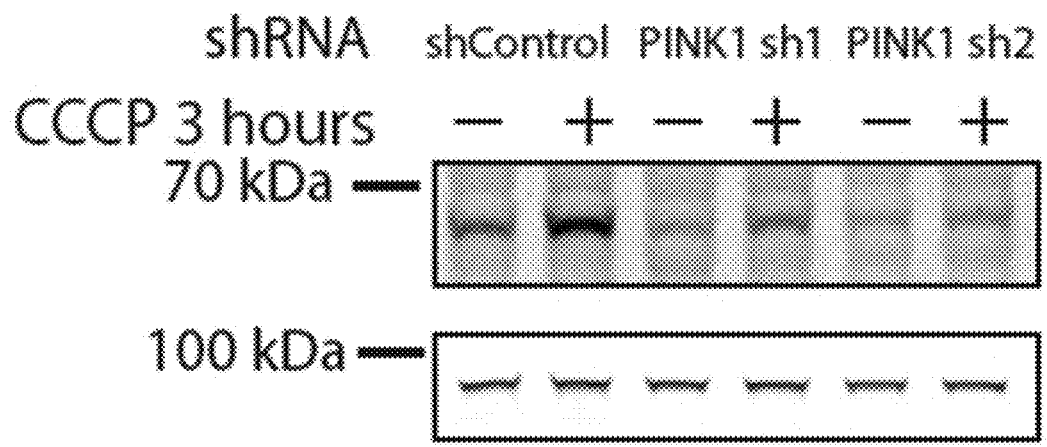
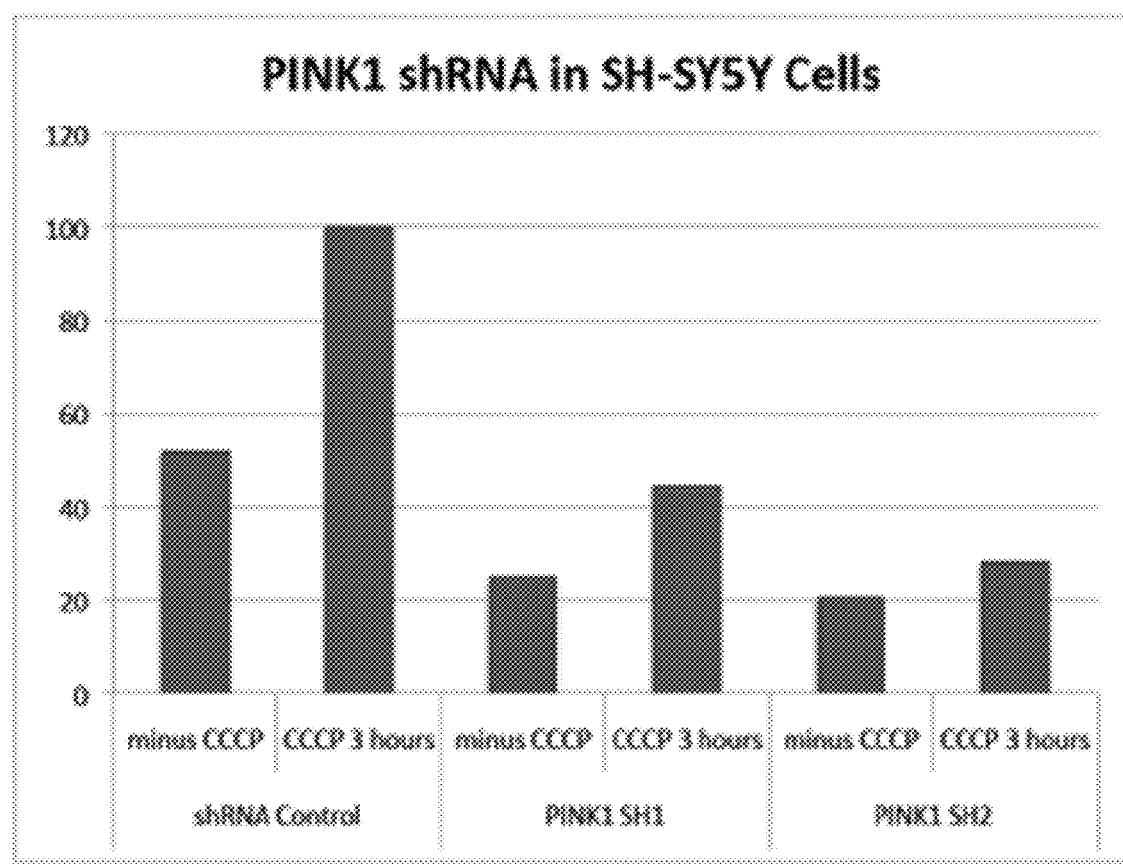

COMPOSITIONS AND METHODS FOR TREATING NEURODEGENERATIVE DISEASES AND CARDIOMYOPATHY

CROSS-REFERENCES TO RELATED APPLICATIONS

This application is a continuation of U.S. patent application Ser. No. 14/823,934, filed on Aug. 11, 2015, which is a continuation of international application PCT/US2014/015863, filed Feb. 11, 2014, which claims the benefit of U.S. Patent Application No. 61/763,444, filed Feb. 11, 2013 and to U.S. Patent Application No. 61/845,529, filed Jul. 12, 2103, all of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant no. R01 EB1987, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 48536-533C01_ST25.txt, created Apr. 25, 2017, 13,399 bytes, machine format IBM-PC, MS-Windows operating system, is hereby incorporated by reference.

BACKGROUND OF THE INVENTION

Studies have correlated mitochondrial function with the disease of cardiomyopathy and for neuron health and survival. Specifically, aberrant mitochondrial quality control has been demonstrated to be an important factor in the development of neurodegenerative diseases and cardiomyopathy.[1,2] The mitochondrial kinase PTEN Induced Kinase 1 (PINK1) plays an important role in the mitochondrial quality control processes by responding to damage at the level of individual mitochondria. The PINK1 pathway has also been linked to the induction of mitochondrial biogenesis, and, critically, the reduction of mitochondrially induced apoptosis.[3,4,11]

Parkinson's Disease (PD) is one of the most common neurodegenerative disorders, however no disease modifying therapies are currently approved to treat PD. Both environmental and genetic factors lead to progressive apoptosis of dopaminergic neurons, lowered dopamine levels and ultimately PD. PINK1 kinase activity appears to mediate its neuroprotective activity. The regulation of mitochondrial movement, distribution and clearance is a key part of neuronal oxidative stress response. Disruptions to these regulatory pathways have been shown to contribute to chronic neurodegenerative disease[1,2].

Cardiomyopathy refers to a disease of cardiac muscle tissue, and it is estimated that cardiomyopathy accounts for 5-10% of the 5-6 million patients already diagnosed with heart failure in the United States. Based on etiology and pathophysiology, the World Health Organization created a classification of cardiomyopathy types which includes dilated cardiomyopathy, hypertrophic cardiomyopathy, restrictive cardiomyopathy, arrhythmogenic right ventricular cardiomyopathy, and unclassified cardiomyopathy.[5] PINK1 kinase activity appears to mediate its cardioprotective activity. The regulation of mitochondrial movement, distribution and clearance is a key part of cardiac cell oxidative stress response. Disruptions to these regulatory pathways have been shown to contribute to cardiomyopathy.[1,2] Thus, there is a need in the art for effective PINK1 agonists and compounds for treating neurodegenerative diseases such as Parkinson's disease and cardiomyopathy. Disclosed herein are solutions to these and other problems in the art.

BRIEF SUMMARY OF THE INVENTION

Provided herein are compositions having the formula:

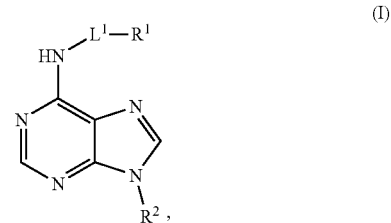

(I)

In the compound of formula (I), $L^1$ is a bond, substituted or unsubstituted alkylene, or substituted or unsubstituted heteroalkylene. $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted cycloalkyl, substituted or unsubstituted heterocycloalkyl, substituted or unsubstituted aryl, or substituted or unsubstituted heteroaryl. In embodiments, if $R^2$ is hydrogen, then -$L^1$-$R^1$ is not hydrogen,

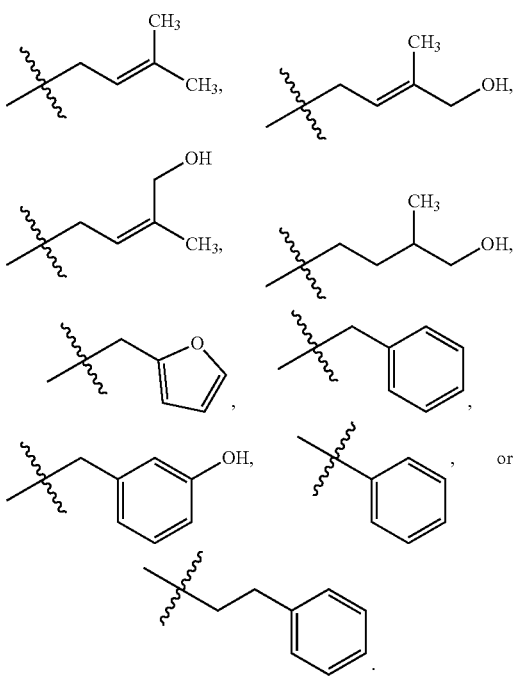

Provided herein are pharmaceutical compositions which include a pharmaceutically acceptable excipient and a compound of formula (I), including pharmaceutically acceptable salts and embodiments thereof.

Provided herein are methods of treating a neurodegenerative disease in a subject in need thereof. The method includes administering to the subject, a therapeutically effective amount of a compound having the formula:

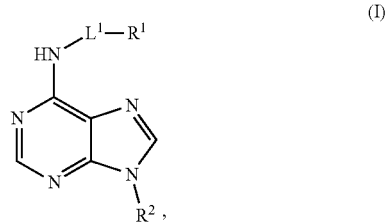

(I)

In the compound of formula (I), $L^1$ is a bond, substituted or unsubstituted alkylene, or substituted or unsubstituted heteroalkylene. $R^1$ is hydrogen, oxo, halogen, —$CX_3$, —CN, —$SO_2Cl$, —$SO_nR_{10}$, —$SO_vNR^7R^8$, —$NHNH_2$, —$ONR^7R^8$, —$NHC(O)NHNH_2$, —$NHC(O)NR^7R^8$, —$N(O)_m$, —$NR^7R^8$, —$C(O)R^9$, —$C(O)OR^9$, —$C(O)NR^7R^8$, —$OR^{10}$, —$NR^7SO_2R^{10}$, —$N(R^7)C(O)R^9$, —$NR^7C(O)$—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)NHNH_2, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently —Cl, —Br, —I, or —F.

Also provided herein are methods of treating a cardiomyopathy in a patient in need thereof. The method includes administering to the subject, a therapeutically effective amount of a compound having formula (I), including pharmaceutically acceptable salts and embodiments thereof.

Further provided herein are methods of increasing the level of activity of PINK1 in a cell by contacting the cell with a neo-substrate of PINK1.

BRIEF DESCRIPTION OF THE DRAWINGS

(FIG. 1A) Chemical structure of kinase substrate adenosine triphosphate with gamma thiophosphate (ATPγS) and neo-substrate kinetin triphosphate gamma thiophosphate (KTPγS); (FIG. 1B) Incubation of the kinase domain of PINK1$^{G309D}$ and PINK1$^{wt}$ with KTP and a substrate protein (TRAP1); (FIG. 1C) C-terminally tagged$_{148-581}$PINK1FLAG$_3$ expressed soluble protein; (FIG. 1D) PINK1$^{G309D}$ displayed reduced activity with ATP; however, incubation with N$^6$ furfuryl ATP (kinetin triphosphate or KTP) led to increased levels of autophosphorylation; (FIG. 1E) Identification of the T257 autophosphorylation site[21] using KTP as the phospho-donor for PINK1; (FIG. 1F) PINK1$^{G309D}$ displayed reduced activity with ATP; however, incubation with N$^6$ furfuryl ATP (kinetin triphosphate or KTP) led to increased levels of autophosphorylation—PINK1$^{kddd}$ had no activity and PINK1 could autophosphorylate at a 1.84 fold higher $V_{max}$ with the neosubstrate KTP versus ATP.

FIGS. 2A-2I. PINK1 neo-substrate kinetin accelerates PINK1 dependent Parkin recruitment in cells: (FIG. 2A) adenine; (FIG. 2B) kinetin; (FIG. 2C) Parkin localization following mitochondrial depolarization with CCCP where Transfection of PINK1$^{G309D}$ slowed the 50% recruitment ($R_{50}$) time of mCherryParkin to depolarized mitochondri. (FIG. 2D) Parkin localization following mitochondrial depolarization with CCCP where transfection of PINK1$^{G309D}$ slowed the 50% recruitment ($R_{50}$) time of mCherryParkin to depolarized mitochondria; (FIG. 2E) Schematic depicting treatment HeLa cell drug treatment. HeLa cells were incubated for 48 hours with drug or DMSO, transfected and analyzed for PINK1 dependent Parkin recruitment to CCCP depolarized mitochondria; (FIG. 2F) Percentage of GFP labeled mitochondria with mCherryParkin associated where transfection of PINK1$^{G309D}$ slowed the 50% recruitment ($R_{50}$) time of mCherryParkin to depolarized mitochondria; (FIG. 2G) Cells treated with fresh medium for 96 hours before performing a new recruitment assay (Similar recruitment rates were observed following the washout); (FIG. 2H) Addition of neo-substrate kinetin to PINK1$^{G309D}$ mutant expressing cells significantly increased the phosphorylation levels of Parkin—the addition of an adenosine kinase inhibitor (AKI) blocking the conversion of kinetin to KTP prevented this effect; (FIG. 2I) G309DPINK1 expressing cells treated with DMSO or Adenine, achieved delta co-localization of 0.075 but upon addition of kinetin indicating rescue to the wt level.

(FIG. 3A) through (FIG. 3F) Cells were pre-treated for 48 hours with 50 μM Kinetin, adenine or equivalent DMSO and mitochondrial motility was imaged live and kymographs were generated; (FIG. 3A) and (FIG. 3D) and (FIG. 3F) Kinetin analog 9-methyl-Kinetin (9MK) did not affect mitochondrial motility; (FIG. 3A) and (FIG. 3E) and (FIG. 3F) Kinetin potently and specifically inhibited mitochondrial movement in rat hippocampal neurons; (FIG. 3G) Kinetin has an effect on velocity of mitochondria that remain in motion; (FIG. 3H) and (FIG. 3I) Decrease in motility in C57 derived neurons, but no change in motility when PINK1–/– derived neurons were treated with kinetin or 9MK.

(FIG. 4A) Kinetin and adenine have no effect on cell density, indicating both are non-toxic to DA neurons; (FIG. 4B) Rat derived hippocampal neurons cultured with 50 mM drug for 48 hours were treated with 200 nM rotenone) Total cells in each field were counted manually in randomized fields); (FIG. 4C) No kinetin effect with infection of a lentivirus expressing PINK1-silencing shRNA; (FIG. 4D) Pre-incubation with kinetin protects SH-SY5Y cells from $H_2O_2$ induced apoptosis; (FIG. 4E) Significant decrease in the total amount of apoptotic cells following kinetin treatment but no significant change with adenine, no kinetin effect with infection of a lentivirus expressing PINK1-silencing shRNA; (FIG. 4F) schematic depicting PINK1 effects.

FIGS. 5A-5E. (FIG. 5A). Comparison of the sequence of PINK1 to kinases for which structural data is available revealed large insertions in several regions of the n-lobe of the PINK1 kinase domain surrounding the ATP binding site; (FIG. 5B) A schematic depicting PINK1 including the mitochondrial localization sequence (1-34), predicted intermembrane (100-111) and kinase domain (156-496) with the location of G309D, and the three mutations used to generate kinase dead PINK1; (FIG. 5C) GST tagged PINK1 kinase domain (156-496) expressed in bacteria; (FIG. 5D) Schematic depicting the expression construct for PINK1 kinase domain (112-581) co-expression with TRAP1 in insect cells. PINK1 is driven by the Pph promotor and TRAP1 is driven by the Pp10 promotor; (FIG. 5E) SF21 infected insect cells were lysed and analyzed by immunoblotting for FLAG PINK1, TRAP1 and β-actin. TRAP1 expression leads to much higher amounts of PINK1 expression. Sequence legend (FIG. 5A): SEQ ID NOS: 1-9 (in order top to bottom).

(FIG. 6A) Baculovirus produced PINK1KDDD has very low kinase activity with γ32P ATP, whereas PINK1wt shows robust autophosphorylation activity; (FIG. 6B) PINK1$^{G309D}$ displayed reduced activity with ATP; however, incubation with $N^6$ furfuryl ATP (kinetin triphosphate or KTP) led to increased levels of autophosphorylation; (FIG. 6C) PINK1$^{G309D}$ displayed reduced activity with ATP; however, incubation with $N^6$ furfuryl ATP (kinetin triphosphate or KTP) led to increased levels of autophosphorylation; KTP with a $\gamma^{32}P$ labeled phosphate showed increased transphosphorylation of TRAP1.

(FIG. 7A) increase in the phosphorylation levels of Parkin following CCCP treatment in a PINK1-dependent manner. The addition of an adenosine kinase inhibitor (AKI) blocking the conversion of kinetin to KTP prevented this effect; (FIG. 7B) A cell mask was determined for each cell by manually drawing the cell boundary and a mitochondrial mask was determined; (FIG. 7C) mitochondrial mask was determined, depicted in the lower panel; (FIG. 7D) Merge full color processed image after CCCP mediated depolarization and PINK1 dependent Parkin recruitment; (FIG. 7E) Schematic depicting Parkin recruitment via PINK1 to depolarized mitochondria; (FIG. 7F) PINK1$^{wt}$ expressing cells achieved a mean change in co-localization of 0.112 with DMSO or adenine and 0.13 with kinetin treatment.

(FIG. 8A) HeLa cells were divided into quartiles and scored when punctate Parkin staining appeared co-localized with mitochondria (the percentage of co-localized cells is plotted in relationship to time. (3 separate wells with n>150 cells per condition per experiment n=3 experiments)); (FIG. 8B) HeLa cells were divided into quartiles and scored when punctate Parkin staining appeared co-localized with mitochondria (the percentage of co-localized cells is plotted in relationship to time. (3 separate wells with n>150 cells per condition per experiment n=3 experiments)); (FIG. 8C) Algorithm quantitated Parkin recruitment to depolarized mitochondria for DMSO, adenine, kinetin and benzyl adenine; (FIG. 8D) Algorithm quantitated Parkin recruitment to depolarized mitochondria for DMSO, adenine, kinetin and benzyl adenine.

(FIG. 9A)-(FIG. 9F) Parkin recruitment with PINK1$^{G309D}$ and PINK1$^{wt}$ with adenine and kinetin.

FIGS. 10A-10F. Sequential images of HeLa cells expressing mCherryParkin, mitoGFP and PINK1$^{wt}$ (FIGS. 10A-10C) or PINK1$^{G309D}$ (FIGS. 10D-10F) following CCCP induced depolarization.

FIGS. 11A-11F. (FIG. 11A) Velocity of mitochondrion in Rat derived hippocampal neuronal axons where Kinetin but not adenine or 9MK slows mitochondrial velocity in the retrograde direction; (FIG. 11B)-(FIG. 11E), Mitochondrial movement in representative PINK1$^{wt}$ expressing (C57) or PINK1 KO derived hippocampal axons transfected with mitoGFP—the first frame of each live-imaging series is shown above a kymograph generated from the movie and the x-axis of each represents mitochondrial position, and the y-axis is time (moving from top to bottom).

(FIG. 14A) Kinetin analog 9-methyl-Kinetin (9MK); (FIG. 14B)-(FIG. 14C) Kinetin activates PINK1 to halt mitochondrial motility (DMSO).

(FIG. 15A) cross section of the brain, the substantia nigra contains Da neurons that deliver dopamine to the rest of the brain where PINK1 inhibits apoptosis in these neurons; (FIG. 15B) schematic depicting PINK1 interacting directly with Parkin to stimulate mitophagy; (FIG. 15C)-(FIG. 15D) wt-PINK1 recruits Parkin to damaged mitochondria and leads to selective elimination PD Disease related G309D mutant PINK1 recruits Parkin at a lower rate.

FIGS. 16A-16B. Drug Accelerated Mitochondrial Localization of Parkin in CCCP HeLa cells: (FIG. 16A) E3 Ubiquitin Ligase Parkin is recruited rapidly to depolarized mitochondria by wt-PINK1, but much less rapidly by G309D PINK1; (FIG. 16B) Addition of kinetin to HeLa cells accelerates the recruitment of Parkin to CCCP depolarized mitochondria.

FIG. 17. Exemplary kinetin analogs tested for toxicity tested in a growth inhibition assay in human dopaminergic neurons: The cells were grown with several concentrations of the different analogs for 5 days until the DMSO only had reached confluency and the cellular viability was measure by staining with resazurin which will enter polarized mitochondria as an indicator of cellular viability.

FIG. 27. PINK1 knockdown in SH-SY5Y cells to determine if Kinetin only affects apoptosis when PINK1 is present; Knockdown of PINK1 in SH-SY5Y cells, around 60-70% knockdown of PINK1.

DETAILED DESCRIPTION OF THE INVENTION

Figure 1A:
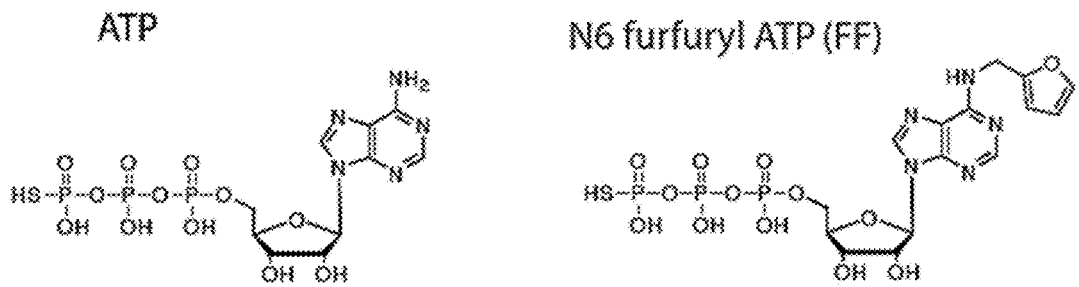
FIGS. 1A-1F. Neo-substrate Kinetin Triphosphate (KTP) amplifies PINK1 kinase activity in-vitro.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds (e.g. alkene, alkyne). Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. Heteroalkyl is not cyclized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Cycloalkyl and heterocycloalkyl are non-aromatic. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, monophosphate (or derivatives thereof), diphosphate (or derivatives thereof), triphosphate (or derivatives thereof), in a number ranging from zero to (2 m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro($C_1$-$C_4$)alkoxy, and fluoro($C_1$-$C_4$)alkyl, monophosphate (or derivatives thereof), diphosphate (or derivatives thereof), triphosphate (or derivatives thereof), in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In embodiments, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (B) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (ii) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from:

(a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), or triphosphate (or derivatives thereof), and (b) alkyl, heteroalkyl, cycloalkyl, heterocycloalkyl, aryl, heteroaryl, monophosphate (or derivatives thereof), diphosphate (or derivatives thereof), or triphosphate (or derivatives thereof), substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, —NHSO$_2$CH$_3$, —N$_3$, unsubstituted alkyl, unsubstituted heteroalkyl, unsubstituted cycloalkyl, unsubstituted heterocycloalkyl, unsubstituted aryl, unsubstituted heteroaryl, monophosphate (or derivatives thereof), diphosphate (or derivatives thereof), and triphosphate (or derivatives thereof).

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, In embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In embodiments herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

In embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. In embodiments, the prodrug form may include a phosphate derivative or a sugar (e.g. ribose) derivative. For example prodrugs moieties used in HCV nucleoside and nucleotide prodrugs may be added to the compounds described herein or the compounds used in methods described herein. In embodiments, prodrug moieties described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, all of which are incorporated herein by reference in their entirety for all purposes, may be added to compounds described herein or used in methods described herein.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, electrocardiogram, echocardiography, radio-imaging, nuclear scan, and/or stress testing, neuropsychiatric exams, and/or a psychiatric evaluation. For example, certain methods herein treat a neurodegenerative disease or a cardiomyopathy. In embodiments, certain methods herein treat Parkinson's disease by decreasing the production of Lewy bodies, decreasing the accumulation of alpha-synuclein, decreasing cell death, decreasing loss of dopamine-generating cells, decreasing loss of cells in the substantia nigra, decreasing loss of dopamine production, decreasing a symptom of Parkinson's disease, decreasing loss of motor function, decreasing shaking or slowing an increase in shaking (tremor), decreasing rigidity or an increase in rigidity, decreasing slowness (bradykinesia) of movement or a slowing of movement, decreasing sensory symptoms, decreasing insomnia, decreasing sleepiness, increasing mental wellbeing, increasing mental function, slowing the decrease of mental function, decreasing dementia, delaying the onset of dementia, improving cognitive skills, decreasing the loss of cognitive skills, improving memory, decreasing the degradation of memory, or extending survival. In embodiments, certain methods herein treat cardiomyopathy by increasing cardiac performance, improving exercise tolerance, preventing heart failure, increasing blood oxygen content, or improving respiratory function. The term "treating" and conjugations thereof, include prevention of an injury, pathology, condition, or disease (e.g. preventing the development of one or more symptoms of a neurodegenerative disease such as Parkinson's disease, or of a cardiomyopathy).

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. a protein associated disease, a symptom associated with a cardiomyopathy, neurodegenerative disease, or symptom associated with Parkinson's disease) means that the disease (e.g. cardiomyopathy, neurodegenerative disease or Parkinson's disease) is caused by (in whole or in part), or a symptom of the disease is caused by (in whole or in part) the substance or substance activity or function. For example, a symptom of a disease or condition associated with a reduction in the level of PINK1 activity may be a symptom that results (entirely or partially) from a reduction in the level of PINK1 activity (e.g. loss of function mutation or gene deletion or modulation of PINK1 signal transduction pathway). As used herein, what is described as being associated with a disease, if a causative agent, could be a target for treatment of the disease. For example, a disease associated with PINK1, may be treated with an agent (e.g. compound as described herein) effective for increasing the level of activity of PINK1.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme (e.g. PINK1). In embodiments contacting includes allowing a compound described herein to interact with a protein or enzyme that is involved in a signaling pathway.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. In embodiments, inhibition refers to a reduction in the activity of a signal transduction pathway or signaling pathway. Thus, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein (e.g. PINK1) relative to the activity or function of the protein in the absence of the activator (e.g. compound described herein). In embodiments, activation refers to an increase in the activity of a signal transduction pathway or signaling pathway (e.g. PINK1 pathway). Thus, activation may include, at least in part, partially or totally increasing stimulation, increasing or enabling activation, or activating, sensitizing, or up-regulating signal transduction or enzymatic activity or the amount of a protein decreased in a disease (e.g. reduction of the level of PINK1 activity or protein associated with a cardiomyopathy or a neurodegenerative disease such as Parkinson's disease). Activation may include, at least in part, partially or totally increasing stimulation, increasing or enabling activation, or activating, sensitizing, or up-regulating signal transduction or enzymatic activity or the amount of a protein (e.g. PINK1) that may modulate the level of another protein or increase cell survival (e.g. increase in PINK1 activity may increase cell survival in cells that may or may not have a reduction in PINK1 activity relative to a non-disease control).

The term "modulator" refers to a composition that increases or decreases the level of a target molecule or the function of a target molecule. In embodiments, the modulator is a modulator of PINK1. In embodiments, the modulator is a modulator of PINK1 and is a compound that reduces the severity of one or more symptoms of a disease associated with PINK1 (e.g. reduction of the level of PINK1 activity or protein associated with a cardiomyopathy, neurodegenerative disease such as Parkinson's disease). In embodiments, a modulator is a compound that reduces the severity of one or more symptoms of a cardiomyopathy or neurodegenerative disease that is not caused or characterized by PINK1 (e.g. loss of PINK1 function) but may benefit from modulation of PINK1 activity (e.g. increase in level of PINK1 or PINK1 activity).

"Patient" or "subject in need thereof" refers to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a patient is human.

"Disease" or "condition" refer to a state of being or health status of a patient or subject capable of being treated with a compound, pharmaceutical composition, or method provided herein. In embodiments, the disease is a disease related to (e.g. characterized by) a reduction in the level of PINK1. In embodiments, the disease is a disease characterized by loss of dopamine-producing cells (e.g. Parkinson's disease). In embodiments, the disease is a disease characterized by neurodegeneration. In embodiments, the disease is a disease characterized by neural cell death. In embodiments, the disease is a disease characterized by a reduction in the level of PINK1 activity. In embodiments, the disease is Parkinson's disease. In embodiments, the disease is a neurodegenerative disease. In embodiments, the disease is a cardiomyopathy.

As used herein, the term "cardiomyopathy" refers to a disease condition that adversely affects cardiac cell tissue leading to a measurable deterioration in myocardial function (e.g. systolic function, diastolic function). Dilated cardiomyopathy is characterized by ventricular chamber enlargement with systolic dysfunction and no hypertrophy.[6] Hypertrophic cardiomyopathy, is a genetic disease transmitted as an autosomal dominant trait.[6] Hypertrophic cardiomyopathy is morphologically characterized by a hypertrophied and non-dialated left ventricle.[6] Restrictive cardiomyopathy is characterized by nondialated nonhypertrophied morphology with diminished ventricular volume leading to poor ventricular filling.[6] Arrhythmogenic right ventricular cardiomyopathy is an inheritable heart disease characterized by myocardial electric instability.[6] Unclassified cardiomyopathy is a category for cardiomyopathies that do not match the features of any one of the other types. Unclassified cardiomyopathies may have features of multiple types or, for example, have the features of fibroelastosis, noncompacted myocardium, or systolic dysfunction with minimal dilatation.[5]

As used herein, the term "neurodegenerative disease" refers to a disease or condition in which the function of a subject's nervous system becomes impaired. Examples of neurodegenerative diseases that may be treated with a compound or method described herein include Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes *dorsalis*, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), or Mitochondrial Parkinson's disease. In embodiments, dysautonomia is not a neurodegenerative disease.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. cardiomyopathy therapies including, for example, Angiotensin Converting Enzyme Inhibitors (e.g. Enalipril, Lisinopril), Angiotensin Receptor Blockers (e.g. Losartan, Valsartan), Beta Blockers (e.g. Lopressor, Toprol-XL), Digoxin, or Diuretics (e.g. Lasix; or Parkinson's disease therapies including, for example, levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs.

The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. PINK1), and/or reducing, eliminating, or slowing the progression of disease symptoms (e.g. symptoms of cardiomyopathy or a neurodegeneration such as symptoms of Parkinson's disease). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cardiomyopathy or neurodegeneration such as Parkinson's disease and severity of such symptoms), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating a disease associated neurodegeneration (e.g. Parkinson's disease such as levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs), or with adjunctive agents that may not be effective alone, but may contribute to the efficacy of the active agent.

The compounds described herein can be used in combination with one another, with other active agents known to be useful in treating a cardiomyopathy such as Angiotensin Converting Enzyme Inhibitors (e.g. Enalipril, Lisinopril), Angiotensin Receptor Blockers (e.g. Losartan, Valsartan), Beta Blockers (e.g. Lopressor, Toprol-XL), Digoxin, or Diuretics (e.g. Lasixdisease associated neurodegeneration (e.g. Parkinson's disease such as levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, or non-steroidal anti-inflammatory drugs), or with adjunctive agents that may not be effective alone, but may contribute to the efficacy of the active agent.

In embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In embodiments, co-administration can be accomplished by co-formulation, i.e., preparing a single pharmaceutical composition including both active agents. In other embodiments, the active agents can be formulated separately. In embodiments, the active and/or adjunctive agents may be linked or conjugated to one another. In embodiments, the compounds described herein may be combined with treatments for neurodegeneration such as surgery. In embodiments, the compounds described herein may be combined with treatments for cardiomyopathy such as surgery.

"PINK1" is used according to its common, ordinary meaning and refers to proteins of the same or similar names and functional fragments and homologs thereof. The term includes and recombinant or naturally occurring form of PINK1 (e.g. "PTEN induced putative kinase 1"; Entrez Gene 65018, OMIM 608309, UniProtKB Q9BXM7, and/or RefSeq (protein) NP_115785.1). The term includes PINK1 and variants thereof that maintain PINK1 activity (e.g. within at least 30%, 40%, 50%, 60%, 70%, 80%, 90%, 95%, or 100% activity compared to PINK1)

The term "neo-substrate" refers to a composition that is structurally similar to a composition that is a substrate for a protein or enzyme during the normal functioning of the protein or enzyme, but that is structurally distinct from the normal substrate of the protein or enzyme. In embodiments, the neo-substrate is a better substrate for the protein or enzyme than the normal substrate (e.g. the reaction kinetics are better (e.g. faster), binding is stronger, turnover rate is higher, reaction is more productive, equilibrium favors product formation). In embodiments, the neo-substrate is a derivative of adenine, adenosine, AMP, ADP, or ATP. In embodiments, the neo-substrate is a substrate for PINK1. In embodiments, the neo-substrate is an N6 substituted adenine, adenosine, AMP, ADP, or ATP.

The term "derivative" as applied to a phosphate containing, monophosphate, diphosphate, or triphosphate group or moiety refers to a chemical modification of such group wherein the modification may include the addition, removal, or substitution of one or more atoms of the phosphate containing, monophosphate, diphosphate, or triphosphate group or moiety. In embodiments, such a derivative is a prodrug of the phosphate containing, monophosphate, diphosphate, or triphosphate group or moiety, which is converted to the phosphate containing, monophosphate, diphosphate, or triphosphate group or moiety from the derivative following administration to a subject, patient, cell, biological sample, or following contact with a subject, patient, cell, biological sample, or protein (e.g. enzyme). In an embodiment, a triphosphate derivative is a gamma-thio triphosphate. In an embodiment, a derivative is a phosphoramidate. In embodiments, the derivative of a phosphate containing, monophosphate, diphosphate, or triphosphate group or moiety is as described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, all of which are incorporated herein by reference in their entirety for all purposes.

The term "mitochondrial dysfunction" is used in accordance with its ordinary meaning and refers to aberrant activity of function of the mitochondria, including for example aberrant respiratory chain activity, reactive oxygen species levels, calcium homeostasis, programmed cell death mediated by the mitochondria, mitochondrial fusion, mitochondrial fission, lipid concentrations in the mitochondrial membrane, and/or mitochondrial permeability transition.

The term "oxidative stress" is used in accordance with its ordinary meaning and refers to aberrant levels of reactive oxygen species.

The term "in embodiments," as used herein, refers to the recited elements as an embodiment of all applicable aspects of the invention as well as permutations thereof in combination with other appropriate embodiments disclosed herein. Thus, the recited elements described "in embodiments" of the invention are not absolute requirements of any or all particular aspects of the invention, but rather specific examples of aspects of the invention described herein.

I. COMPOUNDS

Provided herein is a compound having the formula:

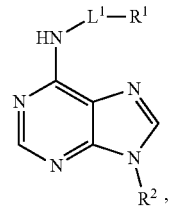
(I)

In the compound of formula (I), $L^1$ is a bond, substituted or unsubstituted alkylene, or substituted or unsubstituted heteroalkylene. $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted cycloalkyl, substituted or unsubstituted heterocycloalkyl, substituted or unsubstituted aryl, or substituted or unsubstituted heteroaryl. In embodiments, if $R^2$ is hydrogen, then -$L^1$-$R^1$ is not hydrogen,

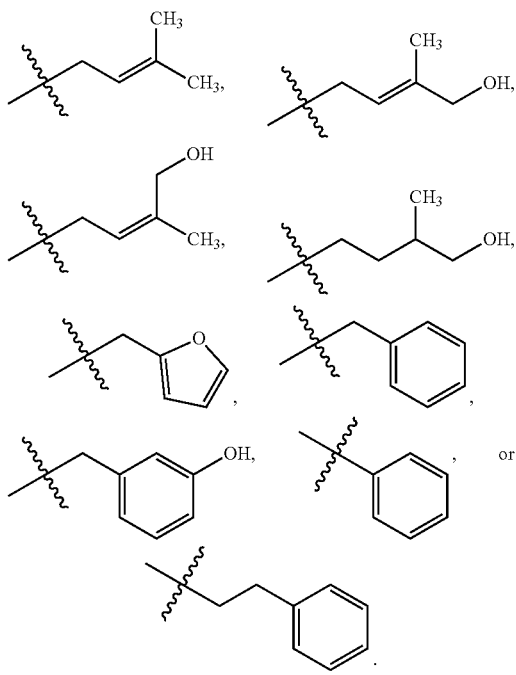

In embodiments, -$L^1$-$R^1$ is not hydrogen,

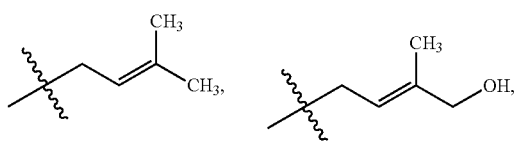

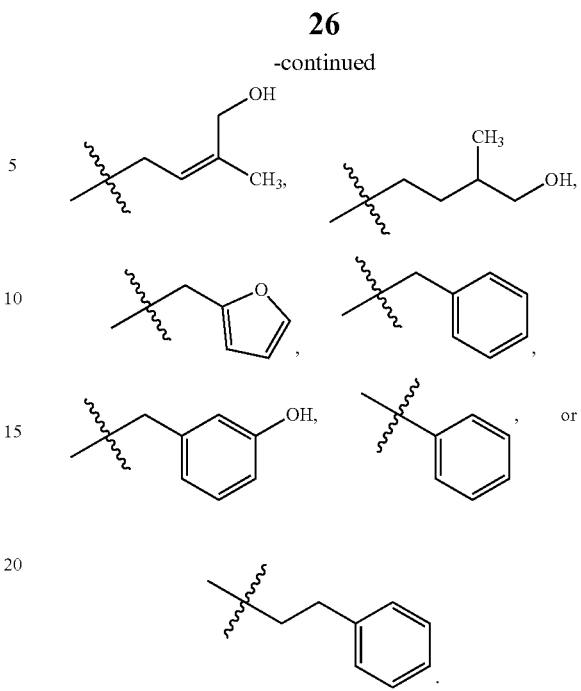

In embodiments, the compound is not kinetin. In embodiments, the compound is not kinetin riboside. In embodiments, the compound is not kinetin riboside 5' monophosphate. In embodiments, the compound is not kinetin riboside 5' diphosphate. In embodiments of the method, the compound is not kinetin riboside 5' triphosphate. In embodiments, the compound is not a derivative (e.g. prodrug) of kinetin, kinetin riboside, kinetin riboside 5' monophosphate, kinetin riboside 5' diphosphate, or kinetin riboside 5' triphosphate. In embodiments, the compound is not N6-(delta 2-Isopentenyl)-adenine. In embodiments, the compound is not N6-(delta 2-Isopentenyl)-adenosine, N6-(delta 2-Isopentenyl)-adenosine 5' monophosphate, N6-(delta 2-Isopentenyl)-adenosine 5' diphosphate, N6-(delta 2-Isopentenyl)-adenosine 5' triphosphate, or a derivative (e.g. prodrug) thereof. In embodiments, the compound is not a cytokinin. In embodiments, the compound is not a cytokinin riboside, cytokinin riboside 5' monophosphate, cytokinin riboside 5' diphosphate, cytokinin riboside 5' triphosphate, or a derivative (e.g. prodrug) thereof.

In embodiments, -$L^1$-$R^1$ is not hydrogen. In embodiments, -$L^1$-$R^1$ is not

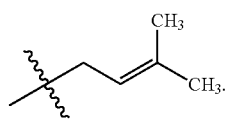

In embodiments, -$L^1$-$R^1$ is not

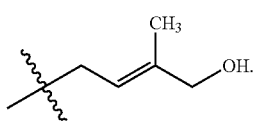 [SMILES: *C/C=C(\C)CO]

In embodiments, -L¹-R¹ is not

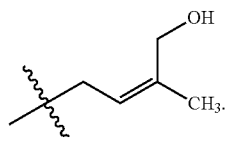 [SMILES: *C/C=C(/C)CO]

In embodiments, -L¹-R¹ is not

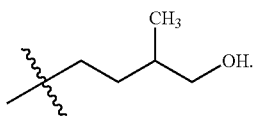 [SMILES: *CCC(C)CO]

In embodiments, -L¹-R¹ is not

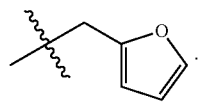 [SMILES: *Cc1ccco1]

In embodiments, -L¹-R¹ is not

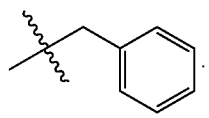

In embodiments, -L¹-R¹ is not

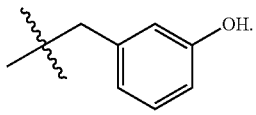 [SMILES: *Cc1cccc(O)c1]

In embodiments, -L¹-R¹ is not

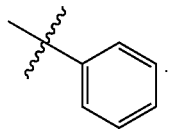 [SMILES: *c1ccccc1]

In embodiments, -L¹-R¹ is not

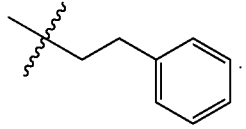

In embodiments, -L¹-R¹ is not

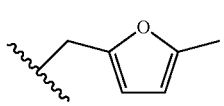

In embodiments, -L¹-R¹ is not

In embodiments, -L¹-R¹ is not

In embodiments, -L¹-R¹ is not

In embodiments, -L¹-R¹ is not

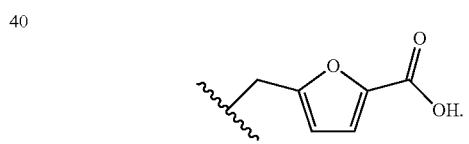

In embodiments, -L¹-R¹ is not

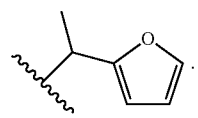

In embodiments, -L¹-R¹ is not

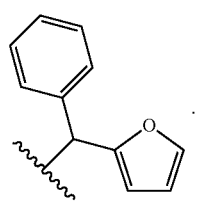 [SMILES: *C(c1ccccc1)c1ccco1]

In embodiments, -L¹-R¹ is not

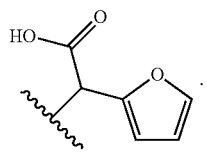

In embodiments, -L¹-R¹ is not

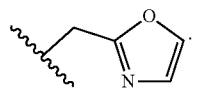 [SMILES: *Cc1ncco1]

In embodiments, -L¹-R¹ is not

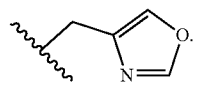

In embodiments, -L¹-R¹ is not

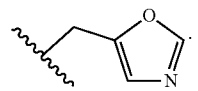 [SMILES: *Cc1cnco1]

In embodiments, -L¹-R¹ is not

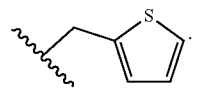 [SMILES: *Cc1cccs1]

In embodiments, -L¹-R¹ is not

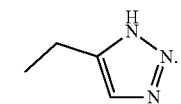

In embodiments, -L¹-R¹ is not

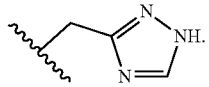

In embodiments, -L¹-R¹ is not

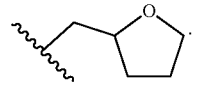

In embodiments, -L¹-R¹ is not

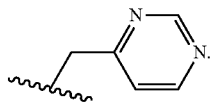 [SMILES: *Cc1ccncn1]

In embodiments, -L¹-R¹ is not

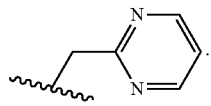 [SMILES: *Cc1ncccn1]

In embodiments, -L¹-R¹ is not

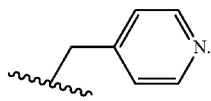

In embodiments, -L¹-R¹ is not

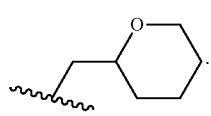 [SMILES: *CC1CCCCO1]

In embodiments, -L¹-R¹ is not

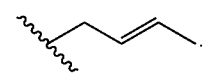 [SMILES: *C/C=C/C]

In embodiments, -L¹-R¹ is not

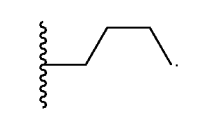

In embodiments, $L^1$ is a bond or substituted or unsubstituted alkylene. $L^1$ is substituted or unsubstituted heteroalkylene.

In embodiments, $L^1$ is substituted or unsubstituted alkylene. $L^1$ may be substituted or unsubstituted $C_1$-$C_5$ alkylene. $L^1$ may be substituted or unsubstituted $C_1$-$C_4$ alkylene. $L^1$ may be substituted or unsubstituted methylene. $L^1$ may be substituted or unsubstituted heteroalkylene (e.g. 2 to 6 membered heteroalkylene). $L^1$ may be a bond. $L^1$ may be unsubstituted ethylene. $L^1$ may be substituted $C_1$-$C_4$ alkylene. $L^1$ may be $R^{29}$-substituted $C_1$-$C_4$ alkylene. $L^1$ may be $R^{29}$-substituted ethylene. $L^1$ may be $R^{29}$-substituted methylene. In embodiments, $R^{29}$ is unsubstituted $C_1$-$C_4$ alkyl. $R^{29}$ may be unsubstituted methyl, ethyl, or isopropyl. $R^{29}$ may be unsubstituted methyl. $R^{29}$ may be unsubstituted $C_6$-$C_{10}$ aryl. $R^{29}$ may be unsubstituted phenyl. $R^{29}$ may be $R^{30}$-substituted phenyl. $R^{29}$ may be —COOH. $R^{29}$ may be —OH. $R^{29}$ may be —SH. $R^{29}$ may be —NH$_2$. $R^{29}$ may be halogen. $R^{29}$ may be —CF$_3$. $R^{29}$ may be —F.

In embodiments of the method, $L^1$ is substituted or unsubstituted alkylene. In embodiments of the method, $L^1$ is substituted or unsubstituted $C_1$-$C_8$ alkylene. In embodiments of the method, $L^1$ is substituted or unsubstituted $C_1$-$C_4$ alkylene. In embodiments of the method, $L^1$ is substituted or unsubstituted methylene. In embodiments of the method, $L^1$ is substituted or unsubstituted heteroalkylene. In embodiments of the method, $L^1$ is a bond. In embodiments of the method, $L^1$ is unsubstituted ethylene. In embodiments of the method, $L^1$ is substituted $C_1$-$C_4$ alkylene. In embodiments of the method, $L^1$ is $R^{29}$-substituted $C_1$-$C_4$ alkylene. In embodiments of the method, $L^1$ is $R^{29}$-substituted ethylene. In embodiments of the method, $L^1$ is $R^{29}$-substituted methylene. In embodiments of the method, $R^{29}$ is unsubstituted $C_1$-$C_4$ alkyl. In embodiments of the method, $R^{29}$ is unsubstituted methyl, ethyl, or isopropyl. In embodiments of the method, $R^{29}$ is unsubstituted methyl. In embodiments of the method, $R^{29}$ is unsubstituted $C_6$-$C_{10}$ aryl. In embodiments of the method, $R^{29}$ is unsubstituted phenyl. In embodiments of the method, $R^{29}$ is —COOH. In embodiments of the method, $R^{29}$ is —OH. In embodiments of the method, $R^{29}$ is —SH. In embodiments of the method, $R^{29}$ is —NH$_2$. In embodiments of the method, $R^{29}$ is halogen. In embodiments of the method, $R^{29}$ is —CF$_3$. In embodiments of the method, $R^{29}$ is —F.

In embodiments and methods provided herein, $L^1$ is independently a bond, $R^{29}$-substituted or unsubstituted alkylene or $R^{29}$-substituted or unsubstituted heteroalkylene.

$R^{29}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{30}$-substituted or unsubstituted monophosphate (or derivatives thereof), $R^{30}$-substituted or unsubstituted diphosphate (or derivatives thereof), $R^{30}$-substituted or unsubstituted triphosphate (or derivatives thereof), $R^{30}$-substituted or unsubstituted alkyl, $R^{30}$-substituted or unsubstituted heteroalkyl, $R^{30}$-substituted or unsubstituted cycloalkyl, $R^{30}$ substituted or unsubstituted heterocycloalkyl, $R^{30}$-substituted or unsubstituted aryl, or $R^{30}$-substituted or unsubstituted heteroaryl.

$R^{30}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{31}$-substituted or unsubstituted monophosphate (or derivatives thereof), $R^{31}$-substituted or unsubstituted diphosphate (or derivatives thereof), $R^{31}$-substituted or unsubstituted triphosphate (or derivatives thereof), $R^3$-substituted or unsubstituted alkyl, $R^3$-substituted or unsubstituted heteroalkyl, $R^3$-substituted or unsubstituted cycloalkyl, $R^{31}$-substituted or unsubstituted heterocycloalkyl, $R^{31}$-substituted or unsubstituted aryl, or $R^{31}$-substituted or unsubstituted heteroaryl.

$R^{31}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted monophosphate, unsubstituted diphosphate, unsubstituted triphosphate, unsubstituted alkyl, unsubstituted heteroalkyl, unsubstituted cycloalkyl, unsubstituted heterocycloalkyl, unsubstituted aryl, or unsubstituted heteroaryl.

$R^1$ may be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ may be hydrogen. $R^1$ may be hydrogen, substituted or unsubstituted alkenyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^1$ may be hydrogen, substituted or unsubstituted alkenyl, substituted or unsubstituted cycloalkyl, substituted or unsubstituted heterocycloalkyl, substituted or unsubstituted aryl, or substituted or unsubstituted heteroaryl. $R^1$ may be substituted or unsubstituted cycloalkyl, substituted or unsubstituted heterocycloalkyl, substituted or unsubstituted aryl, or substituted or unsubstituted heteroaryl. $R^1$ may be substituted or unsubstituted aryl or substituted or unsubstituted heteroaryl.

$R^1$ may be substituted or unsubstituted alkyl. $R^1$ may be unsubstituted alkyl. $R^1$ may be $R^{20}$-substituted or unsubstituted alkyl. $R^1$ may be substituted or unsubstituted alkyl. $R^1$ may be substituted or unsubstituted $C_1$-$C_{20}$ alkyl. $R^1$ may be $R^{20}$-substituted or unsubstituted $C_1$-$C_{20}$ alkyl. $R^1$ may be substituted or unsubstituted $C_1$-$C_{10}$ alkyl. $R^1$ may be $R^{20}$-substituted or unsubstituted $C_1$-$C_{10}$ alkyl. $R^1$ may be substituted or unsubstituted $C_1$-$C_5$ alkyl. $R^1$ may be $R^{20}$-substituted or unsubstituted $C_1$-$C_5$ alkyl.

$R^1$ may be saturated substituted or unsubstituted alkyl. $R^1$ may be saturated $R^{20}$-substituted or unsubstituted alkyl. $R^1$ may be saturated substituted or unsubstituted $C_1$-$C_{20}$ alkyl. $R^1$ may be saturated $R^{20}$-substituted or unsubstituted $C_1$-$C_{20}$ alkyl. $R^1$ may be saturated substituted or unsubstituted $C_1$-$C_{10}$ alkyl. $R^1$ may be saturated $R^{20}$-substituted or unsubstituted $C_1$-$C_5$ alkyl. $R^1$ may be saturated substituted or unsubstituted $C_1$-$C_{10}$ alkyl. $R^1$ may be saturated $R^{20}$-substituted or unsubstituted $C_1$-$C_5$ alkyl. $R^1$ may be saturated substituted or unsubstituted $C_1$-$C_5$ alkyl.

$R^1$ may be unsaturated substituted or unsubstituted alkyl. $R^1$ may be unsaturated $R^{20}$-substituted or unsubstituted alkyl. $R^1$ may be unsaturated substituted or unsubstituted $C_1$-$C_{20}$ alkyl. $R^1$ may be unsaturated $R^{20}$-substituted or unsubstituted $C_1$-$C_{20}$ alkyl. $R^1$ may be unsaturated substituted or unsubstituted $C_1$-$C_{10}$ alkyl. $R^1$ may be unsaturated $R^{20}$-substituted or unsubstituted $C_1$-$C_5$ alkyl. $R^1$ may be unsaturated substituted or unsubstituted $C_1$-$C_{10}$ alkyl. $R^1$ may be unsaturated $R^{20}$-substituted or unsubstituted $C_1$-$C_5$ alkyl. $R^1$ may be unsaturated substituted or unsubstituted $C_1$-$C_5$ alkyl.

$R^1$ may be substituted or unsubstituted iso-pentenyl, substituted or unsubstituted hexenyl, substituted or unsubstituted propenyl, substituted or unsubstituted ethenyl, substituted or unsubstituted pentenyl, substituted or unsubstituted butenyl, substituted or unsubstituted 2-methylbut-1-enyl, substituted or unsubstituted 3-methylbut-1-enyl, substituted or unsubstituted 2-methylbut-2-enyl, substituted or unsubstituted 1-pentenyl, cis-2-pentenyl, or substituted or unsubstituted trans-2-pentenyl. $R^1$ may be substituted or unsubstituted iso-pentenyl. $R^1$ may be substituted or unsubstituted hexenyl. $R^1$ may be substituted or unsubstituted propenyl. $R^1$ may be substituted or unsubstituted ethenyl. $R^1$ may be substituted or unsubstituted pentenyl. $R^1$ may be substituted or unsubstituted butenyl. $R^1$ may be substituted or unsubstituted 2-methylbut-1-enyl. $R^1$ may be substituted or unsubstituted 3-methylbut-1-enyl. $R^1$ may be substituted or unsubstituted 2-methylbut-2-enyl. $R^1$ may be substituted or unsubstituted 1-pentenyl, cis-2-pentenyl. $R^1$ may be substituted or unsubstituted trans-2-pentenyl.

$R^1$ may be substituted or unsubstituted heteroalkyl. $R^1$ may be unsubstituted heteroalkyl. $R^1$ may be substituted or unsubstituted 2 to 20 membered heteroalkyl. $R^1$ may be $R^{20}$-substituted or unsubstituted 2 to 20 membered heteroalkyl. $R^1$ may be substituted or unsubstituted 2 to 10 membered heteroalkyl. $R^1$ may be $R^{20}$-substituted or unsubstituted 2 to 10 membered heteroalkyl. $R^1$ may be substituted or unsubstituted 2 to 6 membered heteroalkyl. $R^1$ may be $R^{20}$-substituted or unsubstituted 2 to 6 membered heteroalkyl.

$R^1$ may be substituted or unsubstituted cycloalkyl. $R^1$ may be unsubstituted cycloalkyl. $R^1$ may be $R^{20}$-substituted or unsubstituted 3 to 20 membered cycloalkyl. $R^1$ may be substituted or unsubstituted 3 to 20 membered cycloalkyl. $R^1$ may be substituted or unsubstituted 3 to 10 membered cycloalkyl. $R^1$ may be $R^{20}$-substituted or unsubstituted 3 to 10 membered cycloalkyl. $R^1$ may be substituted or unsubstituted 3 to 6 membered cycloalkyl. $R^1$ may be $R^{20}$-substituted or unsubstituted 3 to 6 membered cycloalkyl.

$R^1$ may be substituted or unsubstituted heterocycloalkyl. $R^1$ may be unsubstituted heterocycloalkyl. $R^1$ may be substituted or unsubstituted 3 to 20 membered heterocycloalkyl. $R^1$ may be $R^{20}$-substituted or unsubstituted 3 to 20 membered heterocycloalkyl. $R^1$ may be substituted or unsubstituted 3 to 10 membered heterocycloalkyl. $R^1$ may be $R^{20}$-substituted or unsubstituted 3 to 10 membered heterocycloalkyl. $R^1$ may be substituted or unsubstituted 3 to 6 membered heterocycloalkyl. $R^1$ may be $R^{20}$-substituted or unsubstituted 3 to 6 membered heterocycloalkyl.

$R^1$ may be substituted or unsubstituted aryl. $R^1$ may be unsubstituted aryl. $R^1$ may be substituted or unsubstituted 6 to 10 membered aryl. $R^1$ may be $R^{20}$-substituted or unsubstituted 6 to 10 membered aryl. $R^1$ may be substituted or unsubstituted 6 to 8 membered aryl. $R^1$ may be $R^{20}$-substituted or unsubstituted 6 to 8 membered aryl. $R^1$ may be substituted or unsubstituted 5 or 6 membered aryl. $R^1$ may be $R^{20}$-substituted or unsubstituted 5 or 6 membered aryl.

$R^1$ may be substituted or unsubstituted heteroaryl. $R^1$ may be unsubstituted heteroaryl. $R^1$ may be substituted or unsubstituted 6 to 10 membered heteroaryl. $R^1$ may be $R^{20}$-substituted or unsubstituted 6 to 10 membered heteroaryl. $R^1$ may be substituted or unsubstituted 6 to 8 membered heteroaryl. $R^1$ may be $R^{20}$-substituted or unsubstituted 6 to 8 membered heteroaryl. $R^1$ may be substituted or unsubstituted 5 or 6 membered heteroaryl. $R^1$ may be $R^{20}$-substituted or unsubstituted 5 or 6 membered heteroaryl.

In embodiments, $R^1$ is substituted or unsubstituted cycloalkyl, substituted or unsubstituted heterocycloalkyl, substituted or unsubstituted aryl, or substituted or unsubstituted heteroaryl. In embodiments, $R^1$ is substituted or unsubstituted aryl, or substituted or unsubstituted heteroaryl. In embodiments, $R^1$ is substituted or unsubstituted $C_6$-$C_{10}$ aryl (e.g. a substituted or unsubstituted 6 to 10 membered aryl). In embodiments, $R^1$ is substituted or unsubstituted $C_6$-$C_{10}$ heteroaryl (e.g. a substituted or unsubstituted 6 to 10 membered heteroaryl).

In embodiments, $R^1$ is substituted or unsubstituted furanyl, pyrrolyl, thienyl, imidazolyl, pyrazolyl, oxazolyl, isoxazolyl, or thiazolyl. $R^1$ may be unsubstituted furanyl. $R^1$ may be unsubstituted pyrrolyl. $R^1$ may be unsubstituted thienyl. $R^1$ may be unsubstituted imidazolyl. $R^1$ may be unsubstituted pyrazolyl. $R^1$ may be unsubstituted oxazolyl. $R^1$ may be unsubstituted isoxazolyl. $R^1$ may be unsubstituted thiazolyl.

$R^1$ may be $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. $R^{20}$ is as described herein, including embodiments thereof.

In embodiments, $R^1$ is substituted or unsubstituted furanyl, substituted or unsubstituted tetrahydrofuranyl, substituted or unsubstituted thiofuranyl, substituted or unsubstituted pyrrolyl, substituted or unsubstituted thienyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted triazolyl, substituted or unsubstituted tetrahydropyranyl, substituted or unsubstituted pyrimidinyl, substituted or unsubstituted pyrazinyl, or substituted or unsubstituted pyridinyl. $R^1$ may be substituted or unsubstituted furanyl. $R^1$ may be substituted or unsubstituted tetrahydrofuranyl. $R^1$ may be substituted or unsubstituted thiofuranyl. $R^1$ may be substituted or unsubstituted pyrrolyl. $R^1$ may be substituted or unsubstituted thienyl. $R^1$ may be substituted or unsubstituted imidazolyl. $R^1$ may be substituted or unsubstituted pyrazolyl. $R^1$ may be substituted or unsubstituted oxazolyl. $R^1$ may be substituted or unsubstituted isoxazolyl. $R^1$ may be substituted or unsubstituted thiazolyl. $R^1$ may be substituted or unsubstituted triazolyl. $R^1$ may be substituted or unsubstituted tetrahydropyranyl. $R^1$ may be substituted or unsubstituted pyrimidinyl. $R^1$ may be substituted or unsubstituted pyrazinyl. $R^1$ may be substituted or unsubstituted pyridinyl. $R^1$ may independently be $R^{20}$-substituted, where $R^{20}$ is as described herein, including embodiments thereof.

$R^1$ may be $R^{20}$-substituted furanyl. $R^1$ may be $R^{20}$-substituted pyrrolyl. $R^1$ may be $R^{20}$-substituted thienyl. $R^1$ may be $R^{20}$-substituted imidazolyl. $R^1$ may be $R^{20}$-substituted pyrazolyl. $R^1$ may be $R^{20}$-substituted oxazolyl. $R^1$ may be $R^{20}$-substituted isoxazolyl. $R^1$ may be $R^{20}$-substituted thiazolyl. $R^1$ may be $R^{20}$-substituted pentenyl. $R^1$ may be $R^{20}$-substituted iso-pentenyl. $R^1$ may be $R^{20}$-substituted hexenyl, propenyl, ethenyl, pentenyl, butenyl, 2-methylbut-1-enyl, 3-methylbut-1-enyl, 2-methylbut-2-enyl, 1-pentenyl, cis-2-pentenyl, or trans-2-pentenyl.

$R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{21}$-substituted or unsubstituted monophosphate (or derivatives thereof), $R^{21}$-substituted or unsubstituted diphosphate (or derivatives thereof), $R^{21}$-substituted or unsubstituted triphosphate (or derivatives thereof), $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl.

$R^{20}$ may independently be oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted monophosphate (or derivatives thereof), substituted or unsubstituted diphosphate (or derivatives thereof), substituted or unsubstituted triphosphate (or derivatives thereof), substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{20}$ may independently be oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, or —$OCHF_2$. $R^{20}$ may independently be oxo, halogen, —$CF_3$, —CN, —OH, —$NH_2$, —COOH, —$CONH_2$, —$NO_2$, —SH, —$OCF_3$, or —$OCHF_2$.

$R^{20}$ may independently be $R^{21}$-substituted or unsubstituted monophosphate (or derivatives thereof), $R^{21}$-substituted or unsubstituted diphosphate (or derivatives thereof), $R^{21}$-substituted or unsubstituted triphosphate (or derivatives thereof), $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. $R^{20}$ may independently be $R^{21}$-substituted or unsubstituted monophosphate (or derivatives thereof). $R^{20}$ may independently be $R^{21}$-substituted or unsubstituted diphosphate (or derivatives thereof). $R^{20}$ may independently be $R^{21}$-substituted or unsubstituted triphosphate (or derivatives thereof). $R^{20}$ may independently be $R^{21}$-substituted or unsubstituted alkyl. $R^{20}$ may independently be $R^{21}$-substituted or unsubstituted heteroalkyl. $R^{20}$ may independently be $R^{21}$-substituted or unsubstituted cycloalkyl. $R^{20}$ may independently be $R^{21}$-substituted or unsubstituted heterocycloalkyl. $R^{20}$ may independently be $R^{21}$-substituted or unsubstituted aryl. $R^{20}$ may independently be $R^{21}$-substituted or unsubstituted heteroaryl.

$R^{21}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{22}$-substituted or unsubstituted monophosphate (or derivatives thereof), $R^{22}$-substituted or unsubstituted diphosphate (or derivatives thereof), $R^{22}$-substituted or unsubstituted triphosphate (or derivatives thereof), $R^{22}$-substituted or unsubstituted alkyl, $R^{22}$-substituted or unsubstituted heteroalkyl, $R^{22}$-substituted or unsubstituted cycloalkyl, $R^{22}$-substituted or unsubstituted heterocycloalkyl, $R^{22}$-substituted or unsubstituted aryl, or $R^{22}$-substituted or unsubstituted heteroaryl.

$R^{22}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted monophosphate, unsubstituted diphosphate, unsubstituted triphosphate, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^{20}$ is substituted or unsubstituted alkyl. $R^{20}$ may be unsubstituted alkyl. $R^{20}$ may be unsubstituted $C_1$-$C_8$ alkyl. $R^{20}$ may be unsubstituted $C_1$-$C_4$ alkyl. $R^{20}$ may be unsubstituted methyl. $R^{20}$ may be unsubstituted ethyl. $R^{20}$ may be halogen (e.g. —F, —Cl, —I or —Br). $R^{20}$ may be —$CF_3$. $R^{20}$ may be —$CCl_3$. $R^{20}$ may be —OH. $R^1$ may be substituted with one $R^{20}$ substituent. $R^1$ may be substituted with two, optionally different, $R^{20}$ substituent. $R^1$ may be substituted with three, optionally different, $R^{20}$ substituent. $R^1$ may be substituted with four, optionally different, $R^{20}$ substituent. $R^1$ may be substituted with five, optionally different, $R^{20}$ substituent. $R^1$ may be substituted aryl or substituted heteroaryl. $L^1$ may be a bond.

The compound of formula (I) may have the formula:

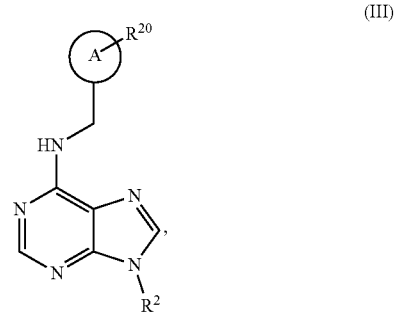

(III)

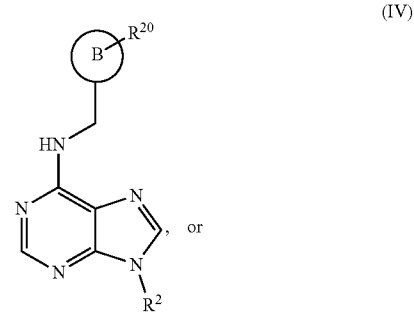

(IV)

or

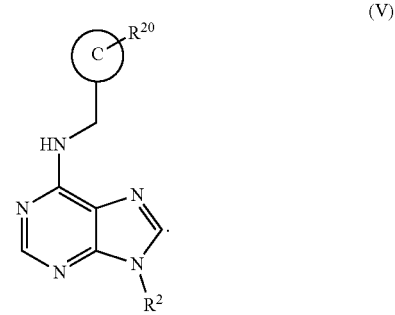

(V)

Ring A is substituted or unsubstituted furanyl, substituted or unsubstituted thiofuranyl, substituted or unsubstituted oxazolyl, substituted or unsubstituted isoxazolyl, or substituted or unsubstituted triazolyl. Ring B is substituted or unsubstituted pyrimidinyl, substituted or unsubstituted pyrazinyl, or substituted or unsubstituted pyridinyl. Ring C is substituted or unsubstituted tetrahydrofuranyl, or substituted or unsubstituted tetrahydropyranyl. $R^{20}$ is as described herein, including embodiments thereof. In embodiments, $R^{20}$ is independently halogen, —$CF_3$, —CN, —OH, —$NH_2$, —COOH, substituted or unsubstituted monophosphate, substituted or unsubstituted diphosphate, substituted or unsubstituted triphosphate, substituted or unsubstituted alkyl, or substituted or unsubstituted heteroalkyl. In embodiments, $R^2$ of formula (III), (IV), and (V) are as described herein, including embodiments thereof. $R^2$ may be hydrogen, substituted or unsubstituted heterocycloalkyl, or substituted or unsubstituted heteroaryl. $R^2$ may be a ribose moiety as described herein, including embodiments thereof.

The compound described herein (e.g. compound of formula (I), (III), (IV), and (V)), may have the formula:

(VI) 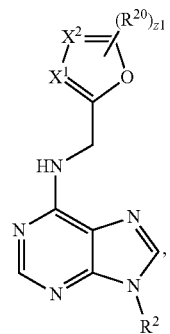

(VII) 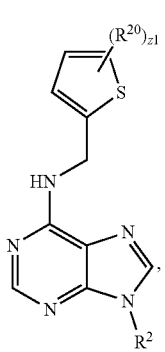

(VIII) 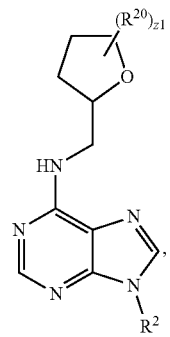

(IX) 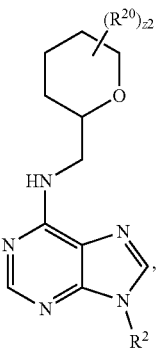

(X) 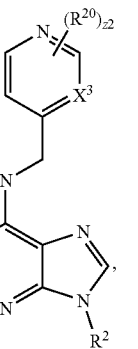

(XI) 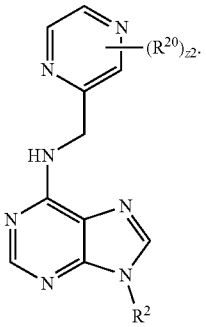

(XII)

$X^1$, $X^2$, and $X^3$ are independently —N— or —CH—. The symbol z1 is 0, 1, 2, or 3. The symbol z2 is 0, 1, 2, 3, 4 or 5. $R^2$ and $R^{20}$ are as described herein, including embodiments thereof. In embodiments, the symbol z1 is 0, 1, or 2. In embodiments, the symbol z2 is 0, 1, 2, or 3.

In embodiments, $R^2$ is substituted or unsubstituted cycloalkyl, substituted or unsubstituted heterocycloalkyl, substituted or unsubstituted aryl, or substituted or unsubstituted heteroaryl. In embodiments, $R^2$ hydrogen or substituted or unsubstituted heterocycloalkyl.

$R^2$ may be substituted or unsubstituted cycloalkyl. $R^2$ may be unsubstituted cycloalkyl. $R^2$ may be $R^{23}$-substituted or unsubstituted 3 to 20 membered cycloalkyl. $R^2$ may be substituted or unsubstituted 3 to 20 membered cycloalkyl. $R^2$ may be substituted or unsubstituted 3 to 10 membered cycloalkyl. $R^2$ may be $R^{23}$-substituted or unsubstituted 3 to 10 membered cycloalkyl. $R^2$ may be substituted or unsubstituted 3 to 6 membered cycloalkyl. $R^2$ may be $R^{23}$-substituted or unsubstituted 3 to 6 membered cycloalkyl.

$R^2$ may be substituted or unsubstituted heterocycloalkyl. $R^2$ may be unsubstituted heterocycloalkyl. $R^2$ may be substituted or unsubstituted 3 to 20 membered heterocycloalkyl. $R^2$ may be $R^{23}$-substituted or unsubstituted 3 to 20 membered heterocycloalkyl. $R^2$ may be substituted or unsubstituted 3 to 10 membered heterocycloalkyl. $R^2$ may be $R^{23}$-substituted or unsubstituted 3 to 10 membered heterocycloalkyl. $R^2$ may be substituted or unsubstituted 3 to 6 membered heterocycloalkyl. $R^2$ may be $R^{23}$-substituted or unsubstituted 3 to 6 membered heterocycloalkyl.

$R^2$ may be substituted or unsubstituted aryl. $R^2$ may be unsubstituted aryl. $R^2$ may be substituted or unsubstituted 5 to 10 membered aryl. $R^2$ may be $R^{23}$-substituted or unsubstituted 5 to 10 membered aryl. $R^2$ may be substituted or unsubstituted 5 to 8 membered aryl. $R^2$ may be $R^{23}$-substituted or unsubstituted 5 to 8 membered aryl. $R^2$ may be substituted or unsubstituted 5 or 6 membered aryl. $R^2$ may be $R^{23}$-substituted or unsubstituted 5 or 6 membered aryl.

$R^2$ may be substituted or unsubstituted heteroaryl. $R^2$ may be unsubstituted heteroaryl. $R^2$ may be substituted or unsubstituted 5 to 10 membered heteroaryl. $R^2$ may be $R^{23}$-substituted or unsubstituted 5 to 10 membered heteroaryl. $R^2$ may be substituted or unsubstituted 5 to 8 membered heteroaryl. $R^2$ may be $R^{23}$-substituted or unsubstituted 5 to 8 membered heteroaryl. $R^2$ may be substituted or unsubstituted 5 or 6 membered heteroaryl. $R^2$ may be $R^{23}$-substituted or unsubstituted 5 or 6 membered heteroaryl.

In embodiments, $R^2$ is substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl. $R^2$ may be substituted or unsubstituted tetrahydrofuranyl. $R^2$ may be substituted or unsubstituted 2,5-dihydrofuranyl. $R^2$ may be substituted or unsubstituted tetrahydrothienyl. $R^2$ may be substituted or unsubstituted 2,5-dihydrothienyl. $R^2$ may be substituted or unsubstituted pyrrolidinyl. $R^2$ may be substituted or unsubstituted 2,5-dihydro-1H-pyrrolyl. $R^2$ may be substituted or unsubstituted cyclopentyl. $R^2$ may be substituted or unsubstituted cyclopentenyl. $R^2$ may be substituted or unsubstituted 1,3-oxathiolanyl. $R^2$ may independently be $R^{23}$-substituted, where $R^{23}$ is as described herein, including embodiments thereof.

In embodiments, $R^2$ is $R^{23}$-substituted or unsubstituted monophosphate (or derivatives thereof), $R^{23}$-substituted or unsubstituted diphosphate (or derivatives thereof), $R^{23}$-substituted or unsubstituted triphosphate (or derivatives thereof), $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

$R^{23}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{24}$-substituted or unsubstituted monophosphate (or derivatives thereof), $R^{24}$-substituted or unsubstituted diphosphate (or derivatives thereof), $R^{24}$-substituted or unsubstituted triphosphate (or derivatives thereof), $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

$R^{24}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{25}$-substituted or unsubstituted monophosphate (or derivatives thereof), $R^{25}$-substituted or unsubstituted diphosphate (or derivatives thereof), $R^{25}$-substituted or unsubstituted triphosphate (or derivatives thereof), $R^{25}$-substituted or unsubstituted alkyl, $R^{25}$-substituted or unsubstituted heteroalkyl, $R^{25}$-substituted or unsubstituted cycloalkyl, $R^{25}$-substituted or unsubstituted heterocycloalkyl, $R^{25}$-substituted or unsubstituted aryl, or $R^{25}$-substituted or unsubstituted heteroaryl.

$R^{25}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted monophosphate, unsubstituted diphosphate, unsubstituted triphosphate, unsubstituted alkyl, unsubstituted heteroalkyl, unsubstituted cycloalkyl, unsubstituted heterocycloalkyl, unsubstituted aryl, or unsubstituted heteroaryl.

$R^2$ may be tetrahydrofuranyl, 2,5-dihydrofuranyl, tetrahydrothienyl, 2,5-dihydrothienyl, pyrrolidinyl, 2,5-dihydro-1H-pyrrolyl, cyclopentyl, cyclopentenyl, 1,3-oxathiolanyl,

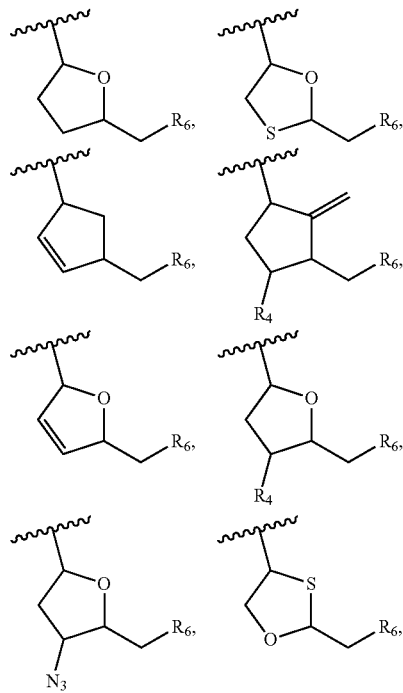

arabinose, D-arabinose, D-ribose, oxolanyl, or ribose, each of which may be substituted or unsubstituted. In embodiments of the method, $R^2$ is independently substituted with at least one substituted or unsubstituted phosphate (or derivative thereof), substituted or unsubstituted monophosphate (or derivative thereof), substituted or unsubstituted diphosphate (or derivative thereof), substituted or unsubstituted triphosphate (or derivative thereof), oxo, halogen, —OH, —CH$_2$OH, or —N$_3$.

$R^2$ may be independently substituted with at least one substituted or unsubstituted phosphate (or derivative thereof), substituted or unsubstituted monophosphate (or derivative thereof), substituted or unsubstituted diphosphate (or derivative thereof), substituted or unsubstituted triphosphate (or derivative thereof).

In embodiments, $R^2$ is hydrogen, substituted or unsubstituted cycloalkyl, or substituted or unsubstituted heterocycloalkyl. In embodiments, $R^2$ is hydrogen, or substituted or unsubstituted cycloalkyl. In embodiments, $R^2$ is hydrogen or substituted or unsubstituted heterocycloalkyl. In embodiments, $R^2$ is hydrogen, substituted or unsubstituted heterocycloalkyl, or substituted or unsubstituted heteroaryl. $R^2$ may be hydrogen. $R^2$ may be —OC(O)CH(CH$_3$)$_2$. $R^2$ may be hydrogen, substituted or unsubstituted $C_3$-$C_8$ cycloalkyl, or substituted or unsubstituted 3 to 8 membered heterocycloalkyl. $R^2$ may be substituted or unsubstituted tetrahydrofuranyl, 2,5-dihydrofuranyl, tetrahydrothienyl, 2,5-dihydrothienyl, pyrrolidinyl, 2,5-dihydro-1H-pyrrolyl, cyclopentyl, cyclopentenyl, or 1,3-oxathiolanyl. $R^2$ may be independently substituted with at least one oxo, halogen, —OH, —CH$_2$OH, or —N$_3$. $R^2$ may be an amino acid moiety (e.g. valine moiety).

In embodiments, $R^2$ has the formula:

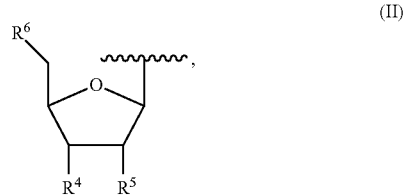

(II)

$R^4$ and $R^5$ are independently be hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl (e.g. $C_1$-$C_5$ alkyl), substituted or unsubstituted heteroalkyl (e.g. 2 to 6 membered heteroalkyl), substituted or unsubstituted cycloalkyl (e.g. 3 to 8 membered cycloalkyl), substituted or unsubstituted heterocycloalkyl (e.g. 3 to 8 membered heterocycloalkyl), substituted or unsubstituted aryl (e.g. 5 to 8 membered aryl), or substituted or unsubstituted heteroaryl (e.g. 5 to 8 membered aryl).

$R^6$ is hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted phosphate, substituted or unsubstituted monophosphate, substituted or unsubstituted diphosphate, or substituted or unsubstituted triphosphate. $R^4$ and $R^6$ may optionally form a substituted or unsubstituted cycle including —O—P(O)$_2$—O— in the ring, or derivatives of the phosphate group, including prodrug derivatives, including for example those prodrug moieties described in Reddy et al., BMCL, 2010, 20, 7376; Lam et al., J. Virol., 2011, 85, 12334; Sofia et al., J. Med. Chem., 2012, 55, 2481, all of which are incorporated herein by reference in their entirety for all purposes.

In embodiments and methods provided herein, $R^4$ and $R^5$ are independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{32}$-substituted or unsubstituted monophosphate (or derivatives thereof), $R^{32}$-substituted or unsubstituted diphosphate (or derivatives thereof), $R^{32}$-substituted or unsubstituted triphosphate (or derivatives thereof), $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

In embodiments, $R^4$ and $R^5$ are independently a prodrug moiety. In embodiments, at least one of $R^4$ and $R^5$ are a prodrug moiety. The prodrug moiety may be a prodrug moiety as described in Murakami et al. J. Med Chem., 2011, 54, 5902; Sofia et al., J. Med Chem. 2010, 53, 7202; Lam et al. ACC, 2010, 54, 3187; Chang et al., ACS Med Chem Lett., 2011, 2, 130; Furman et al., Antiviral Res., 2011, 91, 120; Vernachio et al., ACC, 2011, 55, 1843; Zhou et al, AAC, 2011, 44, 76; Reddy et al., BMCL, 2010, 20, 7376; Lam et al., J. Virol., 2011, 85, 12334; Sofia et al., J. Med. Chem., 2012, 55, 2481, Hecker et al., J. Med. Chem., 2008, 51, 2328; or Rautio et al., Nature Rev. Drug. Discov., 2008, 7, 255, Pierra et al., J. Med. Chem., 2006, 49, 6614, Sofia et al., J. Med. Chem., 2012, 55, 2481, Toniutto et al., IDRUGS, 2008, 11, 738, Jonckers et al., J. Med. Chem., 2010, 53, 8150, all of which are incorporated herein by reference in their entirety for all purposes.

In embodiments, $R^4$ is —OH. $R^4$ may be —OC(O)CH(CH$_3$)$_2$. $R^4$ may be an amino acid moiety (e.g. valine moiety) such as those as described in Pierra et al., J. Med. Chem., 2006, 49, 6614. In embodiments, $R^5$ is —OH. $R^5$ may be —OC(O)CH(CH$_3$)$_2$. $R^5$ may be an amino acid moiety (e.g. valine moiety) such as those as described in Pierra et al., J. Med. Chem., 2006, 49, 6614.

$R^{32}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{33}$-substituted or unsubstituted monophosphate (or derivatives thereof), $R^{33}$-substituted or unsubstituted diphosphate (or derivatives thereof), $R^{33}$-substituted or unsubstituted triphosphate (or derivatives thereof), $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl.

$R^{33}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{34}$-substituted or unsubstituted monophosphate (or derivatives thereof), $R^{34}$-substituted or unsubstituted diphosphate (or derivatives thereof), $R^{34}$-substituted or unsubstituted triphosphate (or derivatives thereof), $R^{34}$-substituted or unsubstituted alkyl, $R^{34}$-substituted or unsubstituted heteroalkyl, $R^{34}$-substituted or unsubstituted cycloalkyl, $R^{34}$-substituted or unsubstituted heterocycloalkyl, $R^{34}$-substituted or unsubstituted aryl, or $R^{34}$-substituted or unsubstituted heteroaryl.

$R^{34}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted monophosphate, unsubstituted diphosphate, unsubstituted triphosphate, unsubstituted alkyl, unsubstituted heteroalkyl, unsubstituted cycloalkyl, unsubstituted heterocycloalkyl, unsubstituted aryl, or unsubstituted heteroaryl.

In embodiments and methods provided herein, $R^6$ is independently a oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{35}$-substituted or unsubstituted monophosphate (or derivatives thereof), $R^{35}$-substituted or unsubstituted diphosphate (or derivatives thereof), $R^{35}$-substituted or unsubstituted triphosphate (or derivatives thereof), $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, $R^{35}$-substituted or unsubstituted heteroaryl, or $R^{35}$-substituted or unsubstituted phosphate.

$R^{35}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{36}$-substituted or unsubstituted monophosphate (or derivatives thereof), $R^{36}$-substituted or unsubstituted diphosphate (or derivatives thereof), $R^{36}$-substituted or unsubstituted triphosphate (or derivatives thereof), $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl.

$R^{36}$ is independently oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, $R^{37}$-substituted or unsubstituted monophosphate (or derivatives thereof), $R^{37}$-substituted or unsubstituted diphosphate (or derivatives thereof), $R^{37}$-substituted or unsubstituted triphosphate (or derivatives thereof), $R^{37}$-substituted or unsubstituted alkyl, $R^{37}$-substituted or unsubstituted heteroalkyl, $R^{37}$-substituted or unsubstituted cycloalkyl, $R^{37}$-substituted or unsubstituted heterocycloalkyl, $R^{37}$-substituted or unsubstituted aryl, or $R^{37}$-substituted or unsubstituted heteroaryl.

$R^{37}$ is independently hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted monophosphate, unsubstituted diphosphate, unsubstituted triphosphate, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^6$ is —OH. In embodiments, $R^6$ is monophosphate. $R^6$ may be diphosphate. $R^6$ may be triphosphate. $R^6$ may be a derivative of a monophosphate (e.g. including a prodrug moiety). $R^6$ may be a derivative of a diphosphate (e.g. including a prodrug moiety). $R^6$ may be a derivative of a triphosphate gamma-S moiety (e.g. including a prodrug moiety). $R^6$ may be a derivative of a triphosphate (e.g. including a prodrug moiety). In embodiments, the compound is a substrate for PINK1. In embodiments, the compound is a substrate for a mutant PINK1 (e.g. G309D PINK1).

$R^4$ and $R^5$ are as described herein, including embodiments thereof. $R^4$ and $R^5$ may independently be hydrogen or —OH. $R^6$ is as described herein, including embodiments thereof. $R^6$ may be a —OH, monophosphate, diphosphate, triphosphate, or a derivative thereof (e.g. a triphosphate gamma-S moiety). $R^6$ may be a triphosphate gamma-S moiety.

In embodiments, $R^2$ is a ribose moiety. $R^2$ may be hydrogen or a ribose moiety. $R^2$ may be a phosphorylated ribose moiety (e.g. $R^6$ is a monophosphate, diphosphate, triphosphate moiety). $R^2$ may be a substituted ribose moiety. $R^2$ may be ribose bonded to a 5' triphosphate gamma-S moiety (e.g. $R^6$ is a triphosphate gamma-S moiety).

Thus, in embodiments, $R^2$ has the formula:

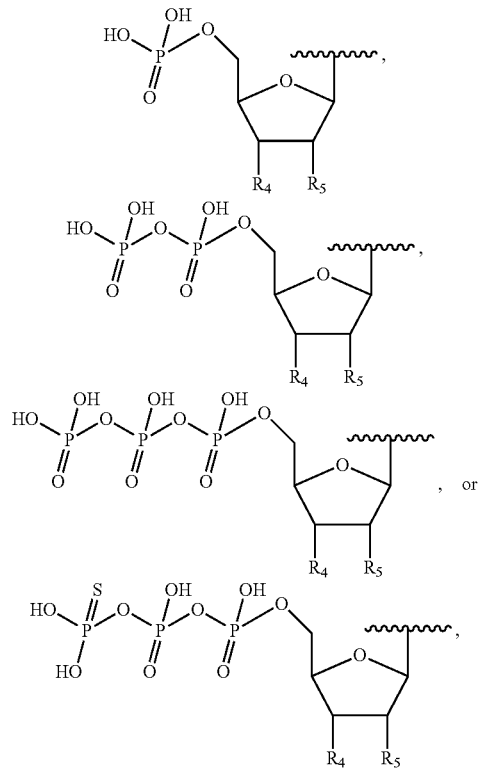

including derivatives thereof.

In embodiments, when $R^2$ is a moiety of formula (II), -L$^1$-R$^1$ is

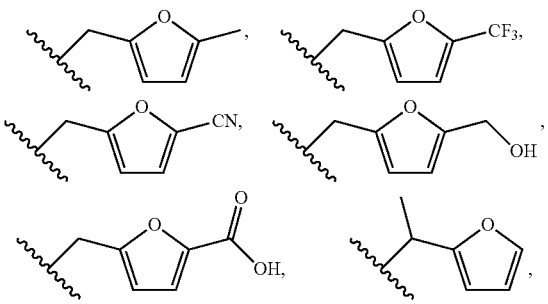

-continued

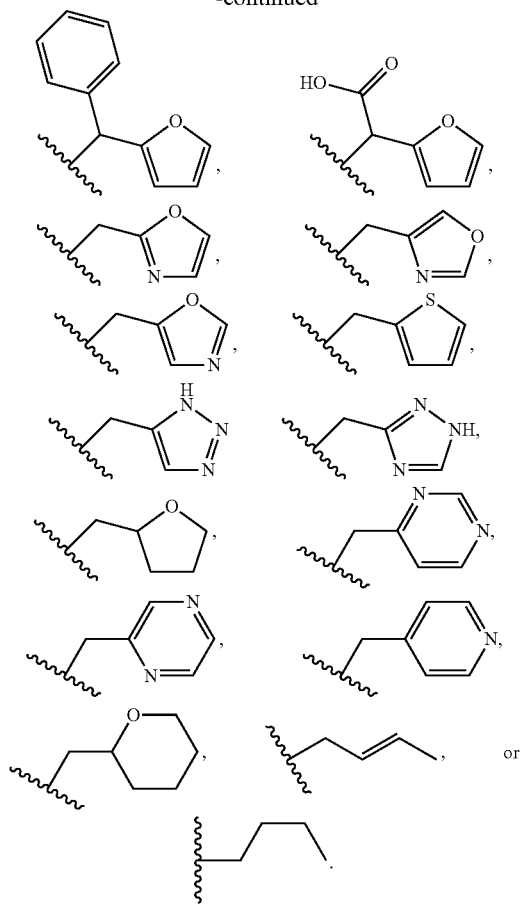

In embodiments, $R^7$, $R^8$, $R^9$, and $R^{10}$ are each independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, $R^{38}$-substituted or unsubstituted monophosphate (or derivatives thereof), $R^{38}$-substituted or unsubstituted diphosphate (or derivatives thereof), $R^{38}$-substituted or unsubstituted triphosphate (or derivatives thereof), $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl.

Each $R^{38}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{39}$-substituted or unsubstituted monophosphate (or derivatives thereof), $R^{39}$-substituted or unsubstituted diphosphate (or derivatives thereof), $R^{39}$-substituted or unsubstituted triphosphate (or derivatives thereof), $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl.

Each $R^{39}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, —$S(O)_2CHCH_2$, —$NHS(O)_2CHCH_2$, $R^{40}$-substituted or unsubstituted monophosphate (or derivatives thereof), $R^{40}$-substituted or unsubstituted diphosphate (or derivatives thereof), $R^{40}$-substituted or unsubstituted triphosphate (or derivatives thereof), $R^{40}$-substituted or unsubstituted alkyl, $R^{40}$-substituted or unsubstituted heteroalkyl, $R^{40}$-substituted or unsubstituted cycloalkyl, $R^{40}$-substituted or unsubstituted heterocycloalkyl, $R^{40}$-substituted or unsubstituted aryl, or $R^{40}$-substituted or unsubstituted heteroaryl.

$R^{40}$ is independently hydrogen, oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, unsubstituted monophosphate, unsubstituted diphosphate, unsubstituted triphosphate, unsubstituted alkyl, unsubstituted heteroalkyl, unsubstituted cycloalkyl, unsubstituted heterocycloalkyl, unsubstituted aryl, or unsubstituted heteroaryl.

In embodiments, the compound of formula (I) has the formula:

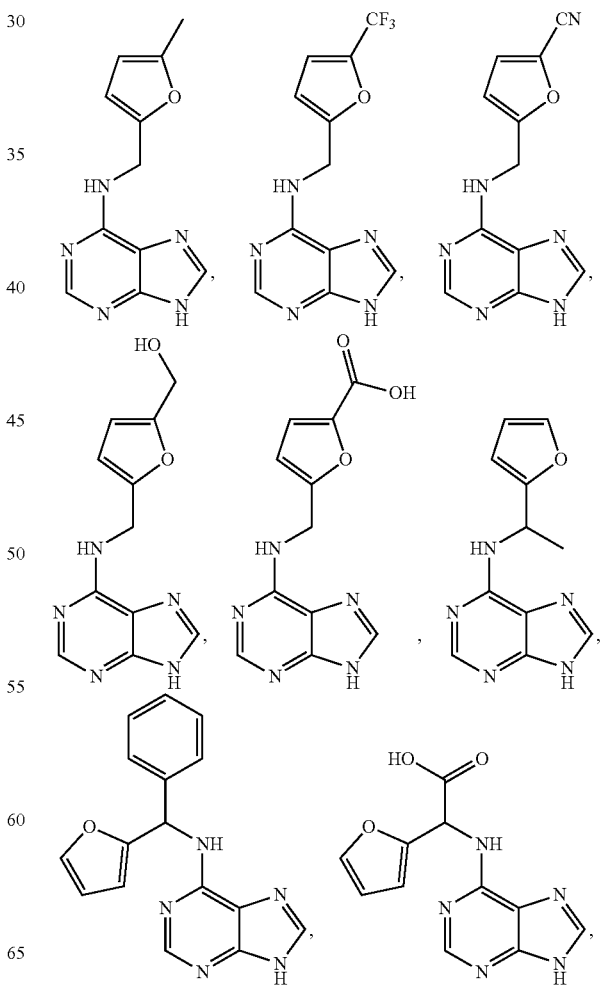

-continued

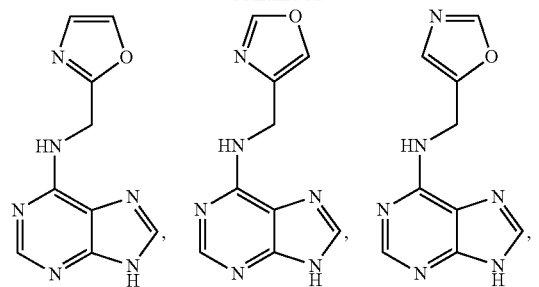

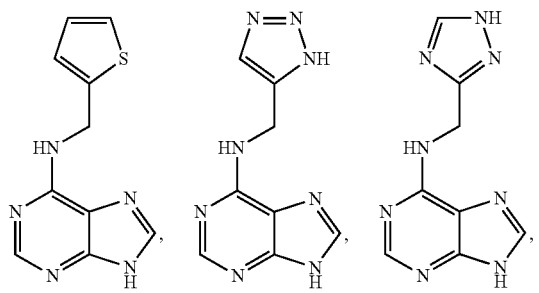

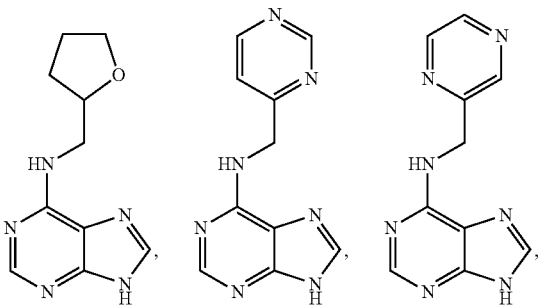

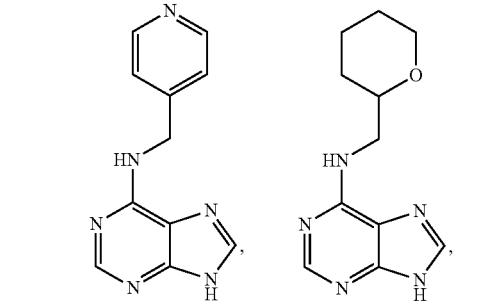

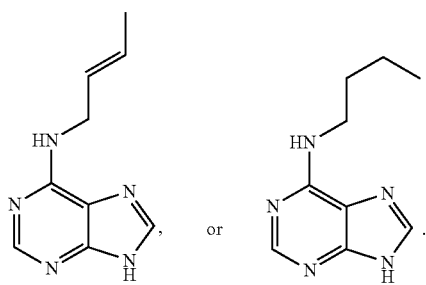

The compound described herein may have the formula:

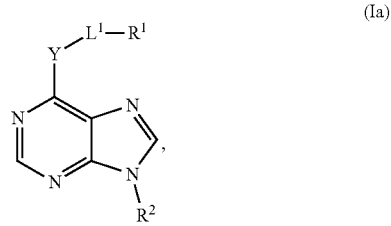

(Ia)

Y is $NR^3$ or $CR^{3a}R^{3b}$. $L^1$ is a bond, substituted or unsubstituted alkylene, or substituted or unsubstituted heteroalkylene. $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted cycloalkyl, substituted or unsubstituted heterocycloalkyl, substituted or unsubstituted aryl, or substituted or unsubstituted heteroaryl. $R^3$ is substituted or unsubstituted cycloalkyl, substituted or unsubstituted heterocycloalkyl, substituted or unsubstituted aryl, or substituted or unsubstituted heteroaryl. $R^{3a}$ and $R^{3b}$ are independently are independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)-$ $OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, if $R^2$ is hydrogen, then $-L^1-R^1$ is not hydrogen,

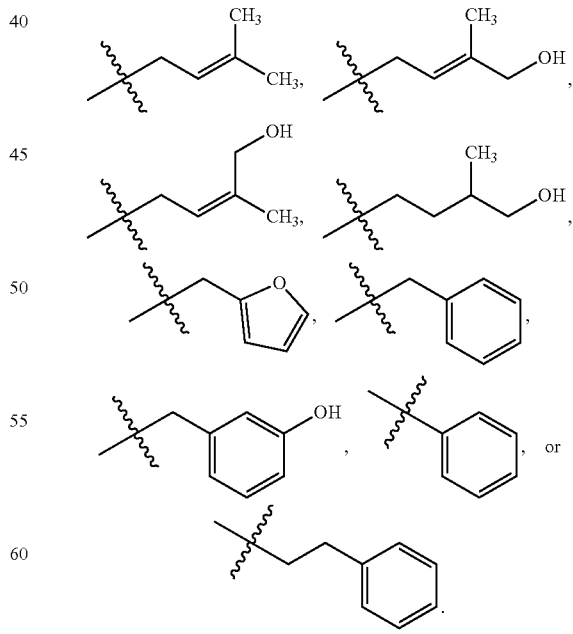

$L^1$, $R^1$, and $R^2$ are as described herein, including embodiments thereof. Y may be $-NR^3-$. Y may be $-CR^{3a}R^{3b}-$. Y may be $-N(CH_3)-$. Y may be $-CH_2-$.

$R^3$ may be $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl.

$R^3$ may be substituted or unsubstituted $C_1$-$C_{20}$ alkyl. $R^3$ may be $R^{41}$-substituted or unsubstituted $C_1$-$C_{20}$ alkyl. $R^3$ may be substituted or unsubstituted $C_1$-$C_{10}$ alkyl. $R^3$ may be $R^{41}$-substituted or unsubstituted $C_1$-$C_{10}$ alkyl. $R^3$ may be substituted or unsubstituted $C_1$-$C_5$ alkyl. $R^3$ may be $R^{41}$-substituted or unsubstituted $C_1$-$C_5$ alkyl. $R^3$ may be methyl, ethyl, or propyl. $R^3$ may be methyl.

$R^{3a}$ and $R^{3b}$ may independently be hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NHNH_2, —NHC(O) $NH_2$, —$NHSO_2H$, —NHC(O)H, —NHC(O)—OH, —NHOH, —$OCF_3$, —$OCHF_2$, $R^{3a}$ and $R^{3b}$ may independently be substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3a}$ and $R^{3b}$ may independently be hydrogen or substituted or unsubstituted alkyl.

In embodiments, the compound of formula (Ia) has the formula:

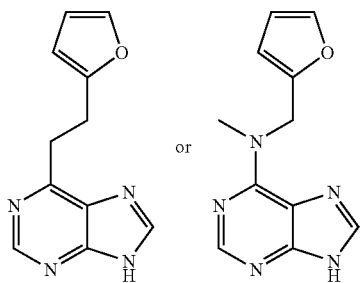

II. PHARMACEUTICAL COMPOSITIONS

Also provided herein are pharmaceutical compositions. The pharmaceutical compositions include a pharmaceutically acceptable excipient and a compound of formula (I) or formula (Ia), including pharmaceutically acceptable salts thereof and embodiments thereof. In embodiments, $R^1$ of the compound of formula (I) of the pharmaceutical composition is hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC(O)NHNH_2, —NHC(O)NR^7R^8, —N(O)_m, —$NR^7R^8$, —C(O)R^9, —C(O)OR^9, —C(O)NR^7R^8, —$OR^{10}$, —$NR^7SO_2R^{10}$, —N(R^7)C(O)R^9, —NR^7C(O)—OR^9, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbols m and v are independently 1 or 2. The symbol n is independently an integer from 0 to 4. The symbol X is independently —Cl, —Br, —I, or —F.

In embodiments, $R^1$ of the compound of formula (I) of the pharmaceutical composition is hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC(O)NHNH_2, —NHC(O)NR^7R^8, —N(O)_m, —$NR^7R^8$, —C(O)R^9, —C(O)OR^9, —C(O)NR^7R^8, —$OR^{10}$, —$NR^7SO_2R^{10}$, —N(R^7)C(O)R^9, —NR^7C(O)—OR^9, —$NR^7OR^9$, —$OCX_3$, or —$OCHX_2$. The symbols m, v, n, and X are as described herein, including embodiments thereof. $L^1$, $R^1$, and $R^2$ are as described herein, including embodiments thereof (e.g. formula (I) and embodiments thereof).

In embodiments of the pharmaceutical compositions, the pharmaceutical composition includes a second agent in a therapeutically effective amount. In embodiments of the pharmaceutical compositions, the second agent is an agent for treating a neurodegenerative disease. In embodiments of the pharmaceutical compositions, the second agent is a Parkinson's disease therapy. In embodiments of the pharmaceutical compositions, the Parkinson's disease therapy is selected from the group consisting of levodopa, dopamine agonists (e.g. bromocriptine, pergolide, pramipexole, ropinirole, piribedil, cabergoline, apomorphine, lisuride), MAO-B inhibitors (e.g. selegiline or rasagiline), amantadine, anticholinergics, antipsychotics (e.g. clozapine), cholinesterase inhibitors, modafinil, and non-steroidal anti-inflammatory drugs.

In embodiments of the pharmaceutical compositions, the pharmaceutical composition includes a second agent in a therapeutically effective amount. In embodiments of the pharmaceutical compositions, the second agent is an agent for treating a cardiomyopathy. In embodiments of the pharmaceutical compositions, the cardiomyopathy therapy is selected from the group consisting Angiotensin Converting Enzyme Inhibitors (e.g. Enalipril, Lisinopril), Angiotensin Receptor Blockers (e.g. Losartan, Valsartan), Beta Blockers (e.g. Lopressor, Toprol-XL), Digoxin, or Diuretics (e.g. Lasix).

III. METHODS OF TREATMENT

Also provided herein are methods of treating a neurodegenerative disease or a cardiomyopathy in a subject in need thereof. The method includes administering to the subject, a therapeutically effective amount of a compound having the formula:

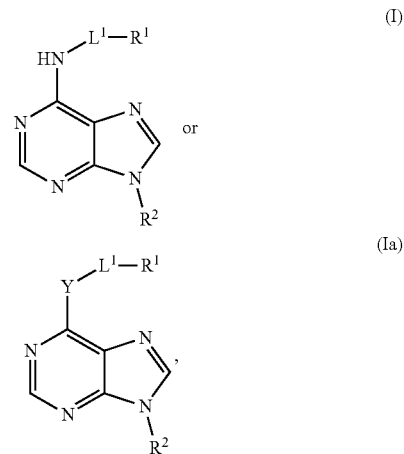

Y is $NR^3$ or $CR^{3a}R^{3b}$. $L^1$ is a bond, substituted or unsubstituted alkylene, or substituted or unsubstituted heteroalkylene. $R^1$ is hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC(O)NHNH_2, —NHC(O)NR^7R^8, —N(O)_m, —$NR^7R^8$, —C(O)R^9, —C(O)OR^9, —C(O)

$NR^7R^8$, $-OR^{10}$, $-NR^7SO_2R^{10}$, $-N(R^7)C(O)R^9$, $-NR^7C(O)-OR^9$, $-NR^7OR^9$, $-OCX_3$, $-OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, substituted or unsubstituted cycloalkyl, substituted or unsubstituted heterocycloalkyl, substituted or unsubstituted aryl, or substituted or unsubstituted heteroaryl. $R^3$ is substituted or unsubstituted cycloalkyl, substituted or unsubstituted heterocycloalkyl, substituted or unsubstituted aryl, or substituted or unsubstituted heteroaryl. $R^{3a}$ and $R^{3b}$ are independently hydrogen, halogen, $-CF_3$, $-CCl_3$, $-CBr_3$, $-CI_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $-NHC(O)$ $NH_2$, $-NHSO_2H$, $-NHC(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, and $R^{10}$ are independently hydrogen, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)$ $NHNH_2$, $-NHC=(O)$ $NH_2$, $-NHSO_2H$, $-NHC=(O)H$, $-NHC(O)-OH$, $-NHOH$, $-OCF_3$, $-OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl. The symbols m and v are independently 1 or 2. The symbol n is independently an integer from 0 to 4. The symbol X is independently $-Cl$, $-Br$, $-I$, or $-F$.

$L^1$ is as described herein, including embodiments thereof. $L^1$ may be substituted or unsubstituted alkylene. $L^1$ may be substituted or unsubstituted heteroalkylene. $L^1$ may be substituted or unsubstituted $C_1$-$C_8$ alkylene. $L^1$ may be substituted or unsubstituted $C_1$-$C_4$ alkylene. $L^1$ may be a bond. $L^1$ may be an unsubstituted methylene.

$R^1$ is as described herein, including embodiments thereof. In embodiments, $R^1$ is hydrogen, oxo, halogen, $-CX_3$, $-CN$, $-SO_2Cl$, $-SO_nR^{10}$, $-SO_vNR^7R^8$, $-NHNH_2$, $-ONR^7R^8$, $-NHC(O)NHNH_2$, $-NHC(O)NR^7R^8$, $-N(O)_m$, $-NR^7R^8$, $-C(O)R^9$, $-C(O)OR^9$, $-C(O)NR^7R^8$, $-OR^{10}$, $-NR^7SO_2R^{10}$, $-N(R^7)C(O)R^9$, $-NR^7C(O)-OR^9$, $-NR^7OR^9$, $-OCX_3$, $-OCHX_2$. $R^7$, $R^8$, $R^9$, $R^{10}$, X n, v, and m are as described herein, including embodiments thereof. In embodiments, $R^1$ is substituted or unsubstituted furanyl, pyrrolyl, thienyl, imidazolyl, pyrazolyl, oxazolyl, isoxazolyl, or thiazolyl.

$R^1$ may be hydrogen, oxo, halogen, $-CF_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC=(O)NHNH_2$, $-NHC=(O)$ $NH_2$, $-NHSO_2H$, $-NHC=(O)H$, $-NHC(O)-OH$, $-NHOH$, $-OCF_3$, $-OCHF_2$, $R^{20}$-substituted or unsubstituted monophosphate (or derivatives thereof), $R^{20}$-substituted or unsubstituted diphosphate (or derivatives thereof), $R^{20}$-substituted or unsubstituted triphosphate (or derivatives thereof), $R^{20}$-substituted or unsubstituted alkyl (e.g. $C_1$-$C_5$, $C_1$-$C_{10}$, or $C_1$-$C_{20}$ alkyl), $R^{20}$-substituted or unsubstituted heteroalkyl (e.g. 2 to 6 membered, 2 to 10 membered, or 2 to 20 membered heteroalkyl), $R^{20}$-substituted or unsubstituted cycloalkyl (e.g. 3 to 6 membered, 3 to 10 membered, or 3 to 20 membered cycloalkyl), $R^{20}$-substituted or unsubstituted heterocycloalkyl (e.g. 3 to 6 membered, 3 to 10 membered, or 3 to 20 membered heterocycloalkyl, $R^{20}$-substituted or unsubstituted aryl (e.g. 5 to 10 membered or 5 to 8 membered aryl), or $R^{20}$-substituted or unsubstituted heteroaryl (e.g. 5 to 10 membered or 5 to 8 membered heteroaryl).

$R^2$ is as described herein, including embodiments thereof. In embodiments, $R^2$ is hydrogen, substituted or unsubstituted cycloalkyl, or substituted or unsubstituted heterocycloalkyl. In embodiments, $R^2$ is hydrogen or substituted or unsubstituted heterocycloalkyl. In embodiments, $R^2$ is hydrogen, substituted or unsubstituted heterocycloalkyl, or substituted or unsubstituted heteroaryl. $R^2$ may be hydrogen. $R^2$ may be hydrogen or a ribose as described herein, including embodiments thereof. In embodiments of the method, $R^2$ is tetrahydrofuranyl, 2,5-dihydrofuranyl, tetrahydrothienyl, 2,5-dihydrothienyl, pyrrolidinyl, 2,5-dihydro-1H-pyrrolyl, cyclopentyl, cyclopentenyl, 1,3-oxathiolanyl,

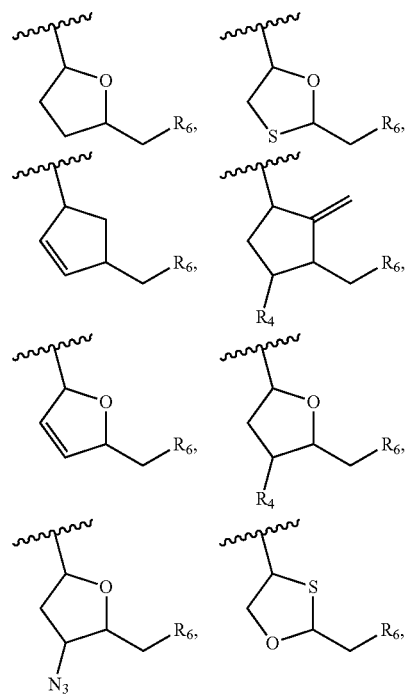

arabinose, D-arabinose, D-ribose, oxolanyl, or ribose, each of which may be substituted or unsubstituted.

$R^2$ may be independently substituted with at least one substituted or unsubstituted phosphate (or derivative thereof), substituted or unsubstituted monophosphate (or derivative thereof), substituted or unsubstituted diphosphate (or derivative thereof), substituted or unsubstituted triphosphate (or derivative thereof), oxo, halogen, $-OH$, $-CH_2OH$, or $-N_3$. In embodiments, $R^2$ is independently substituted with at least one substituted or unsubstituted phosphate (or derivative thereof), substituted or unsubstituted monophosphate (or derivative thereof), substituted or unsubstituted diphosphate (or derivative thereof), substituted or unsubstituted triphosphate (or derivative thereof).

In embodiments, $R^2$ has the formula:

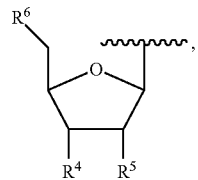
(II)

$R^4$, $R^5$ and $R^6$ are as described herein, including embodiments thereof. $R^4$ and $R^5$ may independently be hydrogen, —OH, or a prodrug moiety, as described herein including embodiments thereof. $R^6$ may be a —OH, monophosphate, diphosphate, triphosphate, or a derivative thereof, as described herein, including embodiments thereof. In embodiments, $R^2$ is a ribose moiety as described herein, including embodiments thereof.

In embodiments of the method, $-L^1-R^1$ is hydrogen,

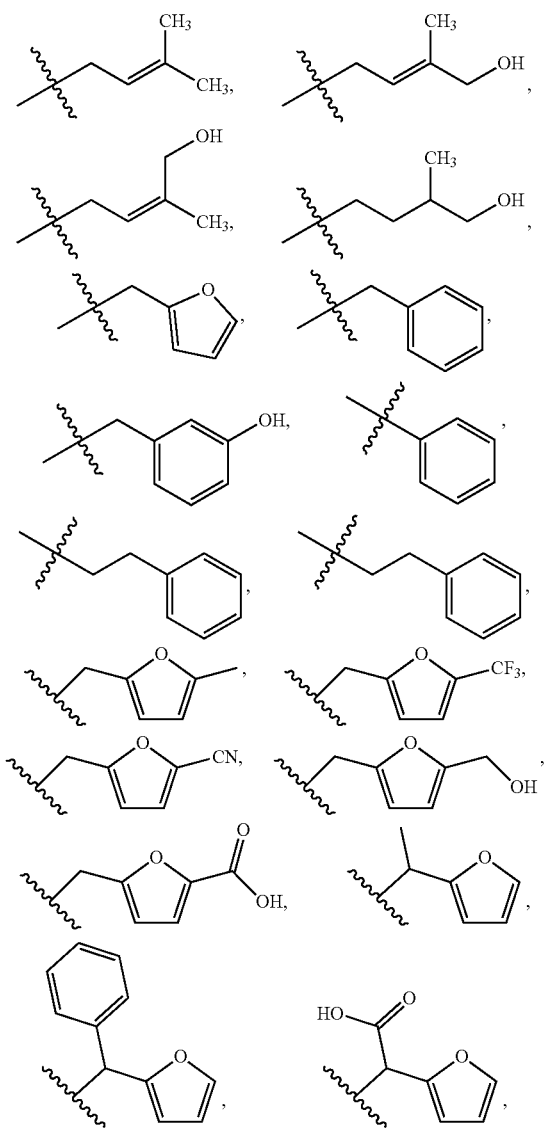

-continued

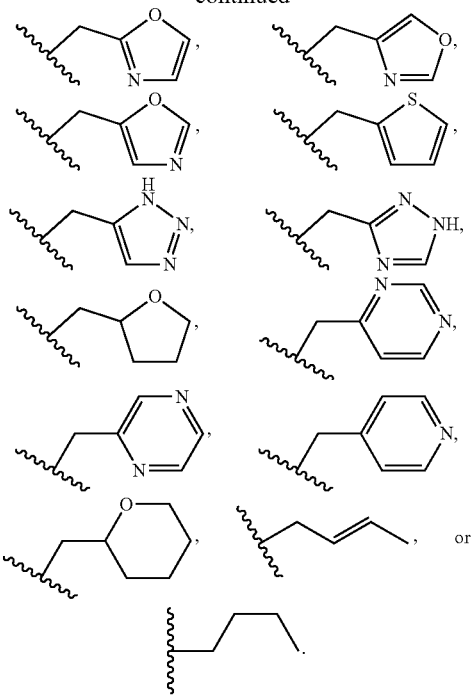

Figure 28:
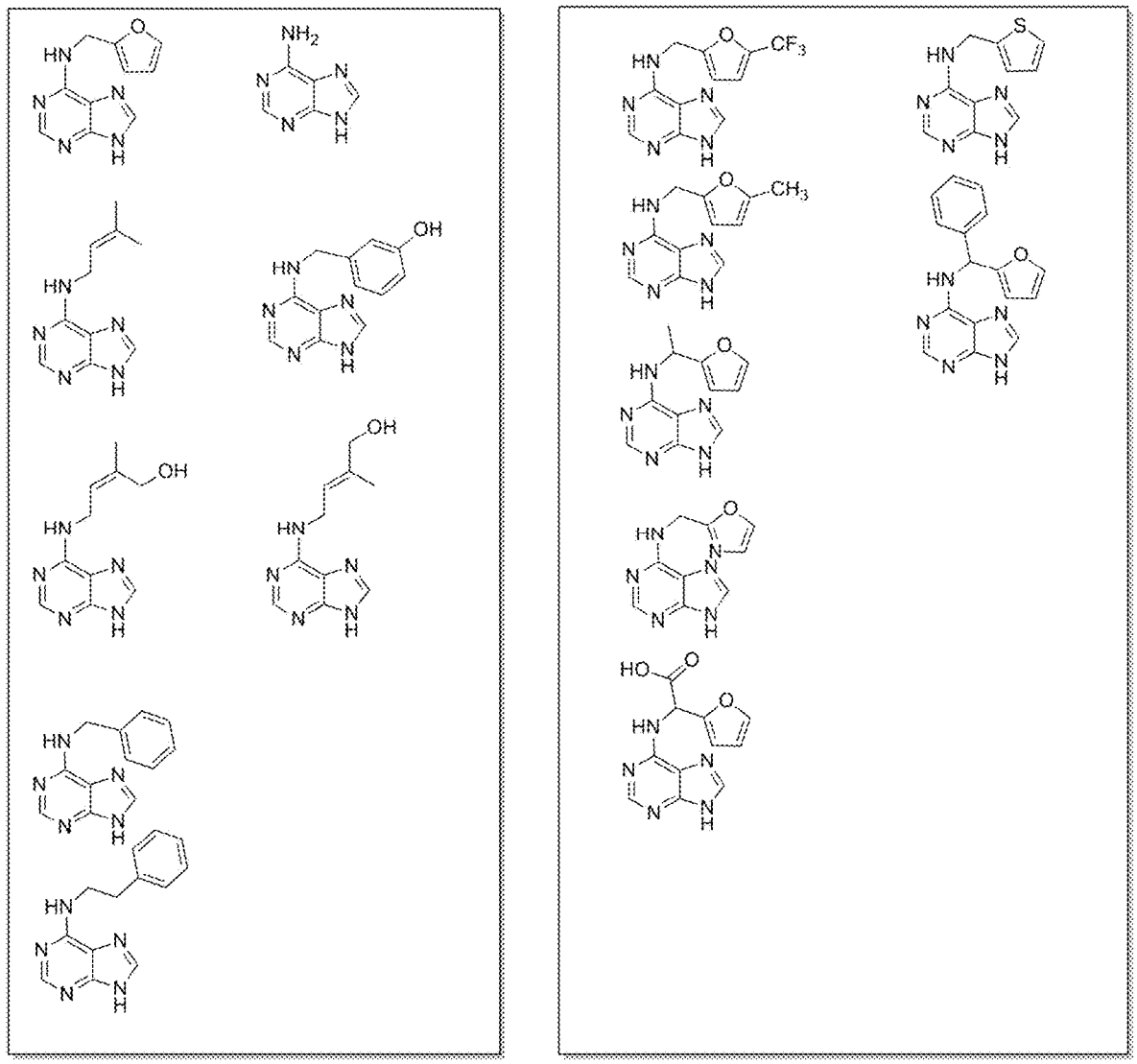
FIG. 28. Cytokinins and derivatives thereof.

In embodiments of the method, the compound is kinetin. In embodiments of the method, the compound is kinetin riboside. In embodiments of the method, the compound is kinetin riboside 5' monophosphate. In embodiments of the method, the compound is kinetin riboside 5' diphosphate. In embodiments of the method, the compound is kinetin riboside 5' triphosphate. In embodiments of the method, the compound is a derivative (e.g. prodrug) of kinetin, kinetin riboside, kinetin riboside 5' monophosphate, kinetin riboside 5' diphosphate, or kinetin riboside 5' triphosphate. In embodiments of the method, the compound is N6-(delta 2-Isopentenyl)-adenine. In embodiments of the method, the compound is N6-(delta 2-Isopentenyl)-adenosine, N6-(delta 2-Isopentenyl)-adenosine 5' monophosphate, N6-(delta 2-Isopentenyl)-adenosine 5' diphosphate, N6-(delta 2-Isopentenyl)-adenosine 5' triphosphate, or a derivative (e.g. prodrug) thereof. In embodiments of the method, the compound is a cytokinin. In embodiments of the method, the compound is a cytokinin riboside, cytokinin riboside 5' monophosphate, cytokinin riboside 5' diphosphate, cytokinin riboside 5' triphosphate, or a derivative (e.g. prodrug) thereof. In embodiments of the method, the compound is a cytokinin shown in FIG. 28. In embodiments of the method, the compound is a neo-substrate of PINK1. In embodiments of the method, the compound is a PINK1 agonist. In embodiments of the method, the compound is a PINK1 substrate. In embodiments of the method, the compound increases the activity of PINK1 compared to ATP, adenine, AMP, or ADP.

The neurodegenerative disease may be associated with mitochondrial dysfunction. The neurodegenerative disease may be associated with an increased level of oxidative stress. The neurodegenerative disease may be selected from the group consisting of Alzheimer's disease, Parkinson's disease, Huntington's disease, and Amyotrophic lateral sclerosis. The neurodegenerative disease may be Parkinson's Disease. The neurodegenerative disease may be selected from the group consisting of drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), and Mitochondrial Parkinson's disease.

The neurodegenerative disease may be characterized by a decrease in PINK1 activity relative to a person without the neurodegenerative disease. The neurodegenerative disease may be associated with a decrease in PINK1 activity relative to a person without the neurodegenerative disease. The neurodegenerative disease may be associated with a PINK1 mutation. The neurodegenerative disease may be characterized by a G309D mutation in PINK1. In embodiments, the neurodegenerative disease is not dysautonomia. In embodiments, the neurodegenerative disease is not familial dysautonomia. In embodiments, the neurodegenerative disease is not neurofibromatosis. In embodiments, the neurodegenerative disease is not characterized by misspliced IKBKAP mRNA. In embodiments, the neurodegenerative disease is not associated with a mutant IKBKAP gene. In embodiments, the neurodegenerative disease is not characterized by mRNA missplicing.

The neurodegenerative disease may be associated with mitochondrial dysfunction (e.g. Alzheimer's disease, Parkinson's disease, Huntington's disease, and/or Amyotrophic lateral sclerosis). The neurodegenerative disease may be associated with mitochondrial dysfunction (e.g. Alzheimer's disease, Parkinson's disease, Huntington's disease, and/or Amyotrophic lateral sclerosis) compared to mitochondrial function in the same type of cells in a person without the neurodegenerative disease. The neurodegenerative disease may be associated with oxidative stress (e.g. Alzheimer's disease, Parkinson's disease, Huntington's disease, and/or Amyotrophic lateral sclerosis). The neurodegenerative disease may be associated with increased oxidative stress (e.g. Alzheimer's disease, Parkinson's disease, Huntington's disease, and/or Amyotrophic lateral sclerosis) compared to the same types of cells in a patient without the neurodegenerative disease. The neurodegenerative disease may be associated with increased levels of reactive oxygen species in disease associated cells compared to the same type of cells not associated with the neurodegenerative disease (e.g. increased in a patient with a neurodegenerative disease compared to control sample or person without the neurodegenerative disease). The neurodegenerative disease may be selected from the group consisting of Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes *dorsalis*, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), and Mitochondrial Parkinson's disease. The neurodegenerative disease may be selected from the group consisting of Alzheimer's disease, Parkinson's disease, Huntington's disease, and Amyotrophic lateral sclerosis. The neurodegenerative disease may be Alzheimer's disease. The neurodegenerative disease may be Parkinson's disease. The neurodegenerative disease may be Huntington's disease. The neurodegenerative disease may be Amyotrophic lateral sclerosis. The neurodegenerative disease may be a prion disease.

In embodiments, the compound has the formula:

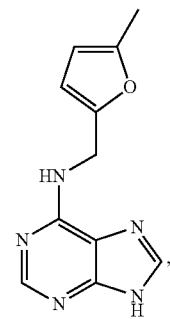

(1)

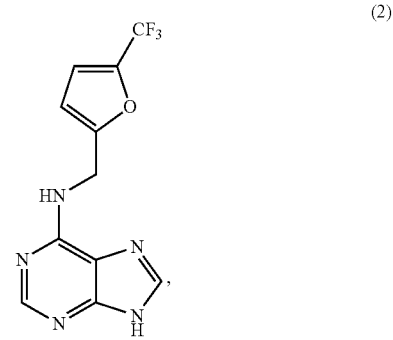

(2)

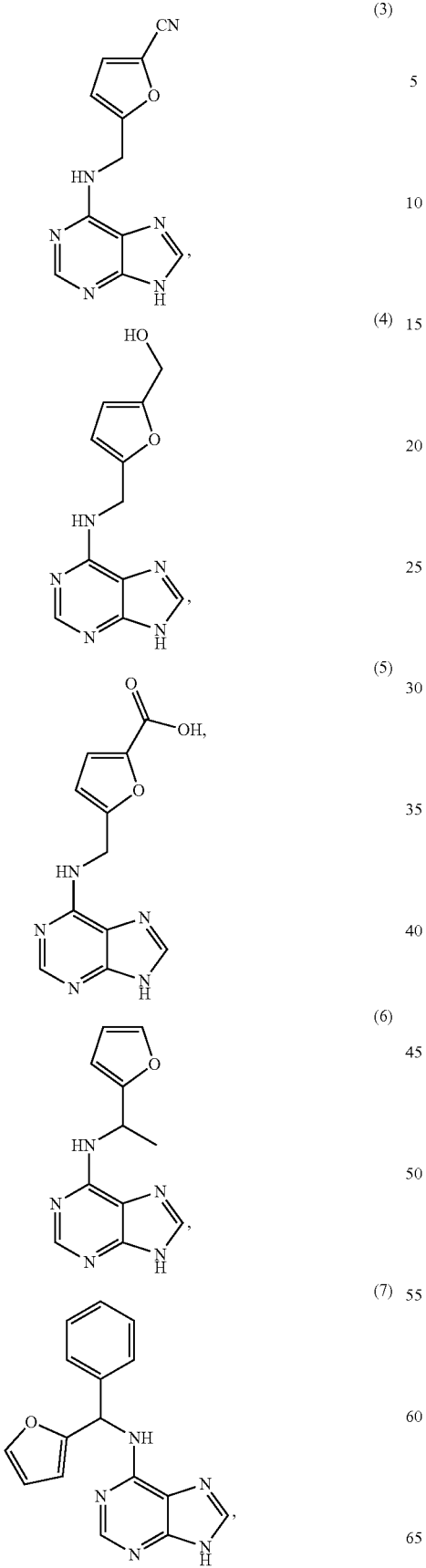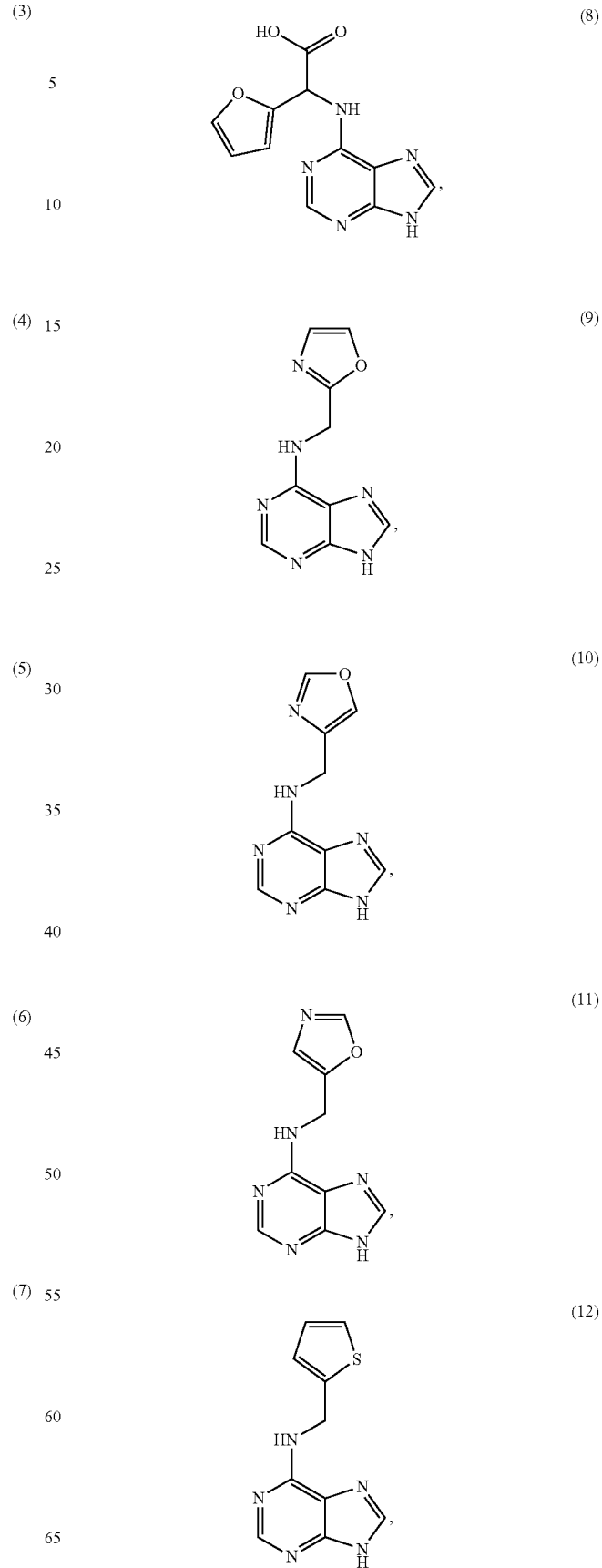

-continued
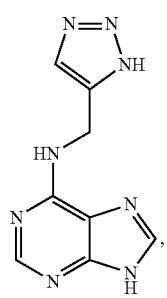 (13)
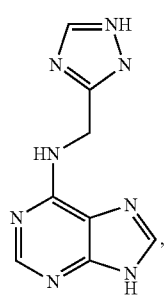 (14)
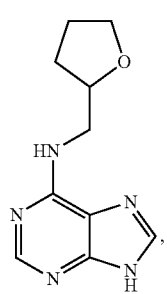 (15)
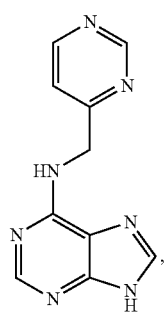 (16)
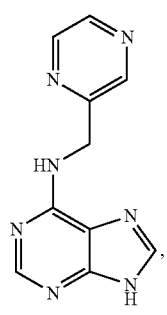 (17)
-continued
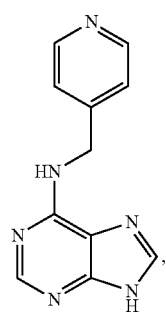 (18)
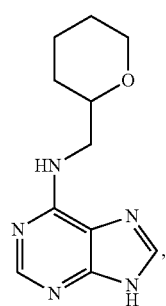 (19)
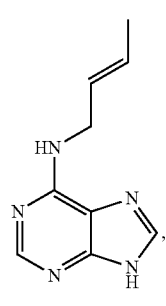 (20)
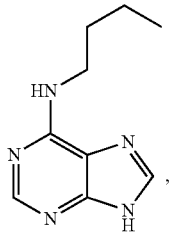 (21)
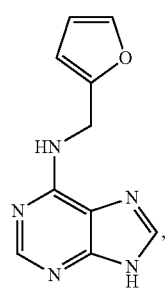 (22)

-continued

(23) 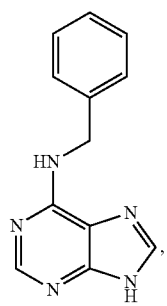

(24) 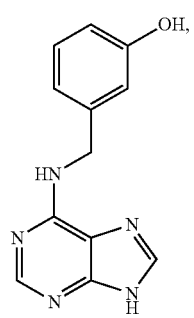

(25) 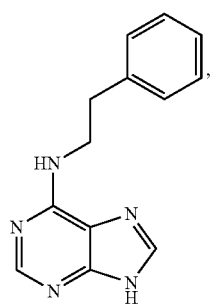

(26) 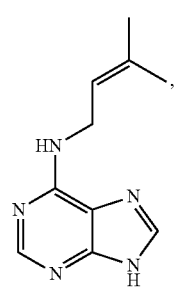

(27) 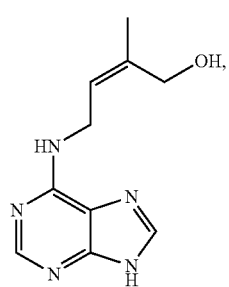

-continued

(28) 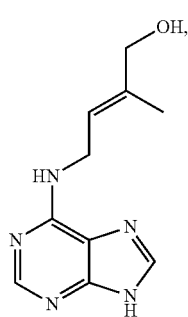

(29) 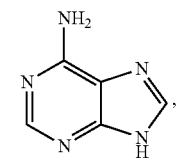

(30) 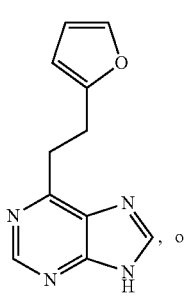, or

(31) 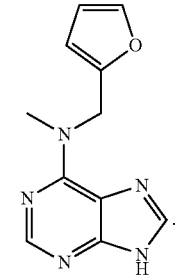

In embodiments, the compound is a compound of formula (1). In embodiments, the compound is a compound of formula (2). In embodiments, the compound is a compound of formula (3). In embodiments, the compound is a compound of formula (4). In embodiments, the compound is a compound of formula (5). In embodiments, the compound is a compound of formula (6). In embodiments, the compound is a compound of formula (7). In embodiments, the compound is a compound of formula (8). In embodiments, the compound is a compound of formula (9). In embodiments, the compound is a compound of formula (10). In embodiments, the compound is a compound of formula (11). In embodiments, the compound is a compound of formula (12). In embodiments, the compound is a compound of formula (13). In embodiments, the compound is a compound of formula (14). In embodiments, the compound is a compound of formula (15). In embodiments, the compound is a compound of formula (16). In embodiments, the compound is a compound of formula (17). In embodiments, the compound is a compound of formula (18). In embodiments, the compound is a compound of formula (19). In embodiments, the compound is a compound of formula (20). In embodiments, the compound is a compound of formula (21). In embodiments, the compound is a compound of formula (22). In embodiments, the compound is a compound of formula (23). In embodiments, the compound is a compound of formula (24). In embodiments, the compound is a compound of formula (25). In embodiments, the compound is a compound of formula (26). In embodiments, the compound is a compound of formula (27). In embodiments, the compound is a compound of formula (28). In embodiments, the compound is a compound of formula (29). In embodiments, the compound is a compound of formula (30). In embodiments, the compound is a compound of formula (31).

In embodiments, the compound is not kinetin. In embodiments, the compound is not kinetin riboside. In embodiments, the compound is not kinetin riboside 5' monophosphate. In embodiments, the compound is not kinetin riboside 5' diphosphate. In embodiments, the compound is not kinetin riboside 5' triphosphate. In embodiments, the compound is not a derivative (e.g. prodrug) of kinetin, kinetin riboside, kinetin riboside 5' monophosphate, kinetin riboside 5' diphosphate, or kinetin riboside 5' triphosphate. In embodiments, the compound is not N6-(delta 2-Isopentenyl)-adenine. In embodiments, the compound is not N6-(delta 2-Isopentenyl)-adenosine, N6-(delta 2-Isopentenyl)-adenosine 5' monophosphate, N6-(delta 2-Isopentenyl)-adenosine 5' diphosphate, N6-(delta 2-Isopentenyl)-adenosine 5' triphosphate, or a derivative (e.g. prodrug) thereof. In embodiments, the compound is not a cytokinin. In embodiments, the compound is not a cytokinin riboside, cytokinin riboside 5' monophosphate, cytokinin riboside 5' diphosphate, cytokinin riboside 5' triphosphate, or a derivative (e.g. prodrug) thereof. In embodiments, -L$^1$-R$^1$ is not hydrogen. In embodiments, -L$^1$-R$^1$ is not

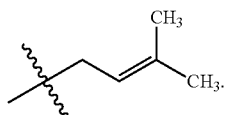 [SMILES: *CC=C(C)C]

In embodiments, -L$^1$-R$^1$ is not

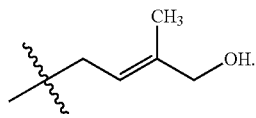 [SMILES: *C/C=C(\C)CO]

In embodiments, -L$^1$-R$^1$ is not

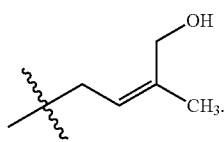

In embodiments, -L$^1$-R$^1$ is not

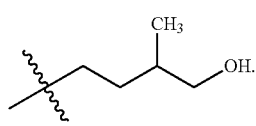 [SMILES: *CCC(C)CO]

In embodiments, -L$^1$-R$^1$ is not

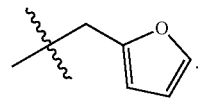

In embodiments, -L$^1$-R$^1$ is not

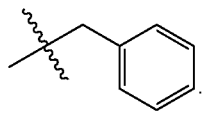 [SMILES: *Cc1ccccc1]

In embodiments, -L$^1$-R$^1$ is not

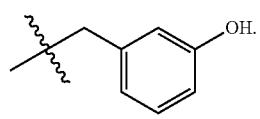 [SMILES: *Cc1cccc(O)c1]

In embodiments, -L$^1$-R$^1$ is not

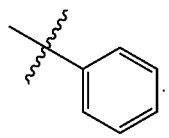 [SMILES: *c1ccccc1]

In embodiments, -L$^1$-R$^1$ is not

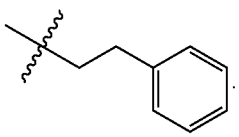

In embodiments, -L$^1$-R$^1$ is not

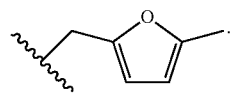 [SMILES: *Cc1ccc(C)o1]

In embodiments, -L$^1$-R$^1$ is not

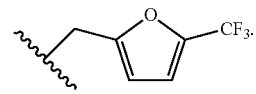 [SMILES: *Cc1ccc(C(F)(F)F)o1]

In embodiments, -L¹-R¹ is not

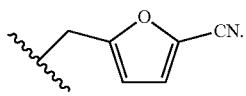 [SMILES: *Cc1ccc(C#N)o1]

In embodiments, -L¹-R¹ is not

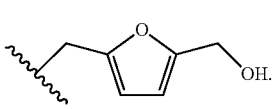 [SMILES: *Cc1ccc(CO)o1]

In embodiments, -L¹-R¹ is not

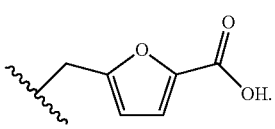 [SMILES: *Cc1ccc(C(=O)O)o1]

In embodiments, -L¹-R¹ is not

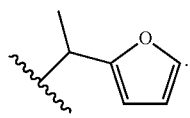 [SMILES: *C(C)c1ccco1]

In embodiments, -L¹-R¹ is not

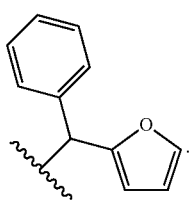 [SMILES: *C(c1ccccc1)c1ccco1]

In embodiments, -L¹-R¹ is not

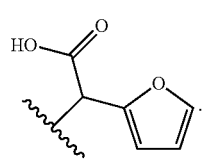 [SMILES: *C(C(=O)O)c1ccco1]

In embodiments, -L¹-R¹ is not

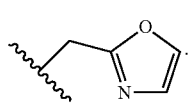

In embodiments, -L¹-R¹ is not

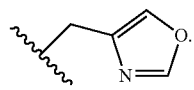 [SMILES: *Cc1cocn1]

In embodiments, -L¹-R¹ is not

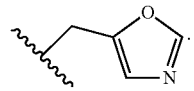 [SMILES: *Cc1cnco1]

In embodiments, -L¹-R¹ is not

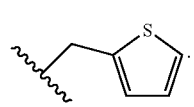 [SMILES: *Cc1cccs1]

In embodiments, -L¹-R¹ is not

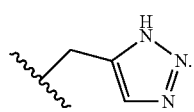 [SMILES: *Cc1cnn[nH]1]

In embodiments, -L¹-R¹ is not

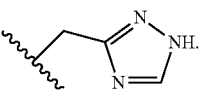 [SMILES: *Cc1nc[nH]n1]

In embodiments, -L¹-R¹ is not

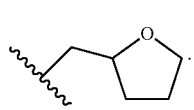

In embodiments, -L¹-R¹ is not

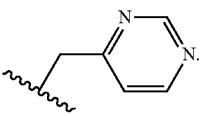

In embodiments, -L¹-R¹ is not

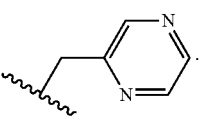

In embodiments, -L¹-R¹ is not

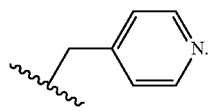 [SMILES: *Cc1ccncc1]

In embodiments, -L¹-R¹ is not

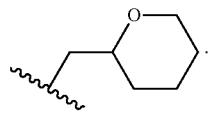

In embodiments, -L¹-R¹ is not

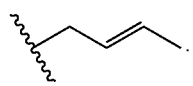 [SMILES: *C/C=C/C]

In embodiments, -L¹-R¹ is not

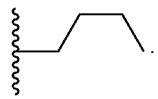 [SMILES: *CCCC]

Also provided herein are methods of treating a neurodegenerative disease in a patient in need thereof. The method includes administering to the subject, a therapeutically effective amount of a compound having formula (I) is as described herein, including embodiments thereof (e.g. embodiments of compositions, methods and references described herein). $L^1$, $R^1$, $R^2$, and all variables which define them are as described herein, including embodiments thereof.

Also provided herein are methods of treating a cardiomyopathy in a patient in need thereof. The method includes administering to the subject, a therapeutically effective amount of a compound having formula (I) is as described herein, including embodiments thereof (e.g. embodiments of compositions, methods and references described herein). $L^1$, $R^1$, $R^2$, and all variables which define them are as described herein, including embodiments thereof.

In embodiments, a cardiomyopathy is associated with mitochondrial dysfunction. The cardiomyopathy may be associated with an increased level of oxidative stress. The cardiomyopathy may be dilated cardiomyopathy, hypertrophic cardiomyopathy, restrictive cardiomyopathy, arrhytmogenic right ventriclular cardiomyopahty, or unclassified cardiomyopathy. In embodiments, a cardiomyopathy is characterized by a decrease in PINK1 activity relative to a person without the cardiomyopathy. The cardiomyopathy may be associated with a decrease in PINK1 activity relative to a person without the cardiomyopathy. The cardiomyopathy may be associated with a PINK1 mutation. The cardiomyopathy may be characterized by a G309D mutation in PINK1.

In embodiments, the cardiomyopathy is not characterized by misspliced IKBKAP mRNA. In embodiments, the cardiomyopathy is not associated with a mutant IKBKAP gene. In embodiments, the cardiomyopathy is not characterized by mRNA missplicing. The cardiomyopathy may be associated with mitochondrial dysfunction. The cardiomyopathy may be associated with mitochondrial dysfunction compared to mitochondrial function in the same type of cells in a person without the cardiomyopathy. The cardiomyopathy may be associated with oxidative stress. The cardiomyopathy may be associated with increased levels of reactive oxygen species in disease associated cells compared to the same type of cells not associated with cardiomyopathy (e.g. increased in a patient with a cardiomyopathy compared to control sample or person without the cardiomyopathy). The cardiomyopathy may be dilated cardiomyopathy, hypertrophic cardiomyopathy, restrictive cardiomyopathy, arrhytmogenic right ventriclular cardiomyopathy, or unclassified cardiomyopathy.

IV. METHODS OF INCREASING ENZYMATIC ACTIVITY

Therapeutic approaches for specifically enhancing the activity of PINK1 have not been previously considered because no allosteric regulatory sites for PINK1 are known. Discovered herein, inter alia, a neo-substrate involving $N^6$ furfuryl-ATP (kinetin triphosphate or KTP), can be used to increase the activity of both mutant $PINK1^{G309D}$ and $PINK1^{wt}$. Provided herein are applications of using this neo-substrate to oxidatively stressed neurons and, in embodiments, provide greater levels of Parkin recruitment, reduced mitochondrial motility, or lower levels of apoptosis in a PINK1 dependent manner. Thus, in embodiments, the methods and compositions provided herein may provide be useful in treating genetic $PINK1^{G309D}$, other forms of Parkinson's disease (e.g. idiopathic forms of Parkinson's disease) and other neurodegenerative diseases, and cardiomyopathy.

Further provided here are methods of increasing the level of activity of PINK1 in a cell by contacting the cell with a neo-substrate of PINK1.

In embodiments, the neo-substrate is a compound having the formula (I) or formula (Ia). The compound of formula (I) is as described herein, including embodiments thereof (e.g. embodiments of compositions, methods and references herein). The compound of formula (Ia) is as described herein, including embodiments thereof (e.g. embodiments of compositions, methods and references herein). $L^1$, $R^1$, $R^2$, Y, and all variables which define them are as described herein, including embodiments thereof.

In embodiments, the cell is in a patient. The cell may be isolated from a patient. The cell may be in cell culture. The cell may be a neuron. The cell may be a brain cell. In embodiments of the method, the cell has mitochondrial dysfunction. In embodiments, the cell has an increased level of oxidative stress compared to the same type of cell under normal conditions. The cell may have an aberrant level of oxidative stress. The cell may have an aberrant level of reactive oxygen species.

The cell may be associated with a neurodegenerative disease. The cell may be associated with Parkinson's Disease. The cell may be associated with a neurodegenerative disease selected from the group consisting of drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), and Mitochondrial Parkinson's disease.

In embodiments, the cell is associated with a neurodegenerative disease characterized by a decrease in PINK1 activity relative to a person without the neurodegenerative disease. The cell may be associated with a neurodegenerative disease associated with a decrease in PINK1 activity relative to a person without the neurodegenerative disease. The cell may be associated with a neurodegenerative disease associated with a PINK1 mutation. The cell may be associated with a neurodegenerative disease characterized by a G309D mutation in PINK1. The cell may be associated with a neurodegenerative disease that is not dysautonomia. The cell may be associated with a neurodegenerative disease that is not familial dysautonomia. The cell may be associated with a neurodegenerative disease that is not neurofibromatosis. The cell may be associated with a neurodegenerative disease that is not characterized by misspliced IKBKAP mRNA. The cell may be associated with a neurodegenerative disease that is not associated with a mutant IKBKAP gene. The cell may be associated with a neurodegenerative disease that is not characterized by mRNA missplicing. The cell may be associated with a neurodegenerative disease that is associated with mitochondrial dysfunction (e.g. Alzheimer's disease, Parkinson's disease, Huntington's disease, and/or Amyotrophic lateral sclerosis The cell may be associated with a neurodegenerative disease that is associated with oxidative stress (e.g. Alzheimer's disease, Parkinson's disease, Huntington's disease, and/or Amyotrophic lateral sclerosis). The cell may be associated with a neurodegenerative disease that is associated with increased levels of reactive oxygen species in disease associated cells compared to the same type of cells not associated with the neurodegenerative disease (e.g. increased in a patient with a neurodegenerative disease compared to control sample or person without the neurodegenerative disease). The cell may be associated with a neurodegenerative disease that is selected from the group consisting of Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Sträussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, Tabes dorsalis, drug-induced Parkinsonism, progressive supranuclear palsy, corticobasal degeneration, multiple system atrophy, Idiopathic Parkinson's disease, Autosomal dominant Parkinson disease, Parkinson disease, familial, type 1 (PARK1), Parkinson disease 3, autosomal dominant Lewy body (PARK3), Parkinson disease 4, autosomal dominant Lewy body (PARK4), Parkinson disease 5 (PARK5), Parkinson disease 6, autosomal recessive early-onset (PARK6), Parkinson disease 2, autosomal recessive juvenile (PARK2), Parkinson disease 7, autosomal recessive early-onset (PARK7), Parkinson disease 8 (PARK8), Parkinson disease 9 (PARK9), Parkinson disease 10 (PARK10), Parkinson disease 11 (PARK11), Parkinson disease 12 (PARK12), Parkinson disease 13 (PARK13), and Mitochondrial Parkinson's disease. The cell may be associated with a neurodegenerative disease that is selected from the group consisting of Alzheimer's disease, Parkinson's disease, Huntington's disease, and Amyotrophic lateral sclerosis. The cell may be associated with Alzheimer's disease. The cell may be associated with Parkinson's disease. The cell may be associated with Huntington's disease. The cell may be associated with Amyotrophic lateral sclerosis.

The cell may be associated with a cardiomyopathy. The cell may be a myocite. The cell may be a cardiac tissue cell. The cell may be associated with a cardiomyopathy associated with a decrease in PINK1 activity relative to a person without the cardiomyopathy. The cell may be associated with a cardiomyopathy associated with a PINK1 mutation. The cell may be associated with a cardiomyopathy characterized by a G309D mutation in PINK1.

The neo-substrate may contact PINK1. The neo-substrate may contact a mutant PINK1. The neo-substrate may contact a G309D PINK1. The neo-substrate may increase the activity of PINK1 relative to the activity of PINK1 without the neo-substrate. The neo-substrate may increase the activity of PINK1 relative to the activity of PINK1 with ATP. In embodiments of the method, the neo-substrate is a substrate for PINK1. In embodiments of the method, the neo-substrate is a substrate for a mutant PINK1 (e.g. G309D PINK1).

In embodiments, the neo-substrate is kinetin. In embodiments, the neo-substrate is kinetin riboside. In embodiments, the neo-substrate is kinetin riboside 5' monophosphate. In embodiments, the neo-substrate is kinetin riboside 5' diphosphate. In embodiments, the neo-substrate is kinetin riboside 5' triphosphate. In embodiments, the neo-substrate is a derivative (e.g. prodrug) of kinetin, kinetin riboside, kinetin riboside 5' monophosphate, kinetin riboside 5' diphosphate, or kinetin riboside 5' triphosphate. In embodiments, the neo-substrate is N6-(delta 2-Isopentenyl)-adenine. In embodiments, the neo-substrate is N6-(delta 2-Isopentenyl)-adenosine, N6-(delta 2-Isopentenyl)-adenosine 5' monophosphate, N6-(delta 2-Isopentenyl)-adenosine 5' diphosphate, N6-(delta 2-Isopentenyl)-adenosine 5' triphosphate, or a derivative (e.g. prodrug) thereof. In embodiments, the neo-substrate is a cytokinin.

In embodiments, the neo-substrate is a cytokinin riboside, cytokinin riboside 5' monophosphate, cytokinin riboside 5' diphosphate, cytokinin riboside 5' triphosphate, or a derivative (e.g. prodrug) thereof. In embodiments, -L$^1$-R$^1$ is hydrogen. In embodiments of the method, -L$^1$-R$^1$ is hydrogen,

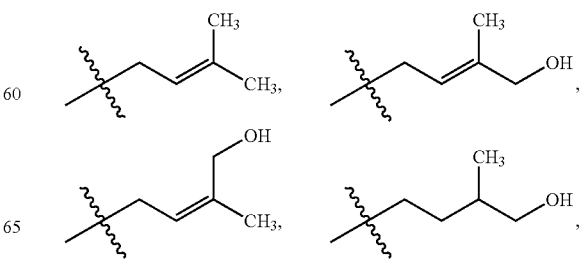

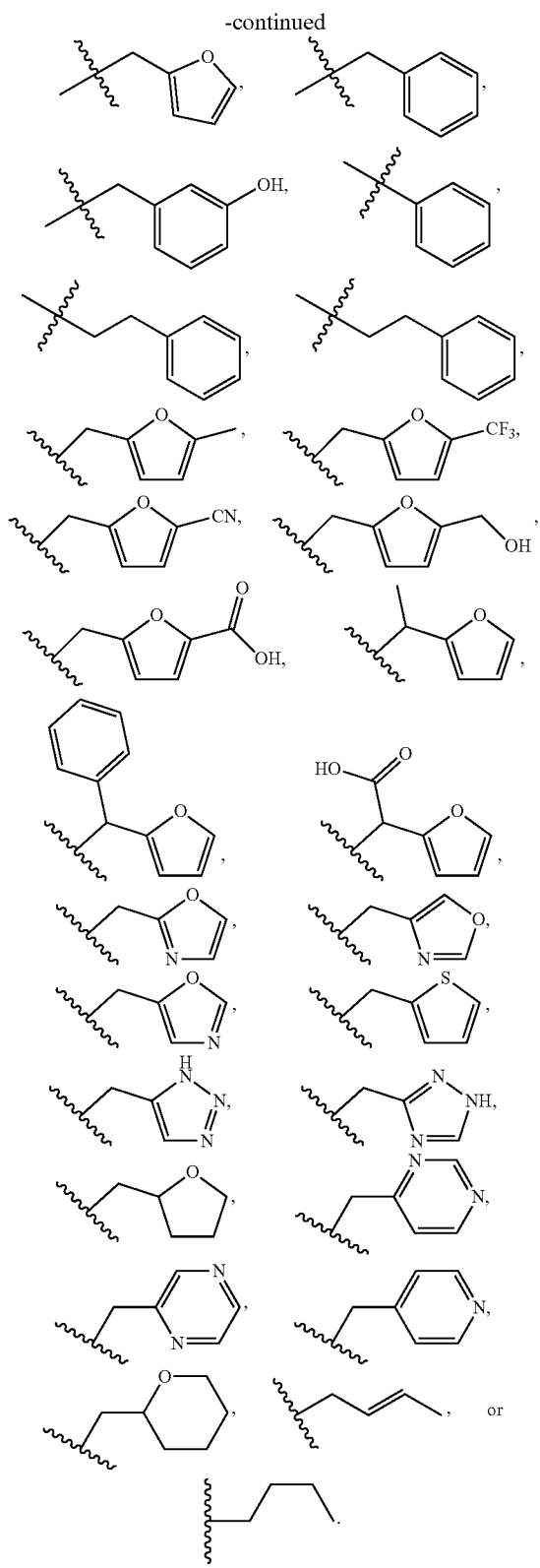

ments, the neo-substrate is not a derivative (e.g. prodrug) of kinetin, kinetin riboside, kinetin riboside 5' monophosphate, kinetin riboside 5' diphosphate, or kinetin riboside 5' triphosphate. In embodiments, the neo-substrate is not N6-(delta 2-Isopentenyl)-adenine. In embodiments, the neo-substrate is not N6-(delta 2-Isopentenyl)-adenosine, N6-(delta 2-Isopentenyl)-adenosine 5' monophosphate, N6-(delta 2-Isopentenyl)-adenosine 5' diphosphate, N6-(delta 2-Isopentenyl)-adenosine 5' triphosphate, or a derivative (e.g. prodrug) thereof. In embodiments, the neo-substrate is not a cytokinin. In embodiments, the neo-substrate is not a cytokinin riboside, cytokinin riboside 5' monophosphate, cytokinin riboside 5' diphosphate, cytokinin riboside 5' triphosphate, or a derivative (e.g. prodrug) thereof.

In embodiments, $-L^1-R^1$ is not hydrogen. In embodiments, $-L^1-R^1$ is not

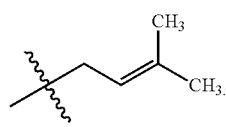 [SMILES: *CC=C(C)C]

In embodiments, $-L^1-R^1$ is not

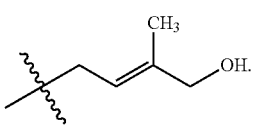 [SMILES: *C/C=C(\C)CO]

In embodiments, $-L^1-R^1$ is not

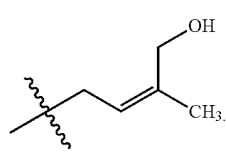 [SMILES: *C/C=C(/C)CO]

In embodiments, $-L^1-R^1$ is not

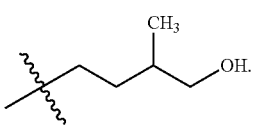 [SMILES: *CCC(C)CO]

In embodiments, $-L^1-R^1$ is not

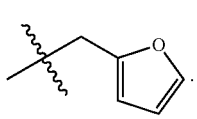

In embodiments, $-L^1-R^1$ is not

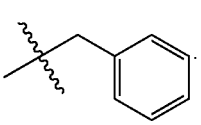 [SMILES: *Cc1ccccc1]

In embodiments, the neo-substrate is not kinetin. In embodiments, the neo-substrate is not kinetin riboside. In embodiments, the neo-substrate is not kinetin riboside 5' monophosphate. In embodiments, the neo-substrate is not kinetin riboside 5' diphosphate. In embodiments, the neo-substrate is not kinetin riboside 5' triphosphate. In embodi-

73

In embodiments, -L¹-R¹ is not

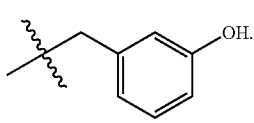 [SMILES: *Cc1cccc(O)c1]

In embodiments, -L¹-R¹ is not

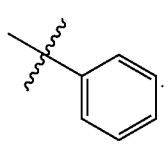

In embodiments, -L¹-R¹ is not

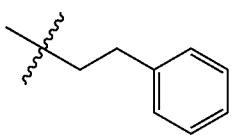 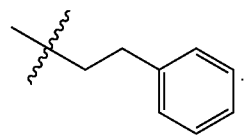

In embodiments, -L¹-R¹ is not

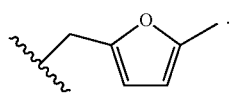 [SMILES: *Cc1ccc(C)o1]

In embodiments, -L¹-R¹ is not

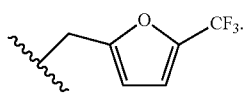 [SMILES: *Cc1ccc(C(F)(F)F)o1]

In embodiments, -L¹-R¹ is not

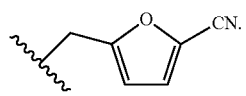 [SMILES: *Cc1ccc(C#N)o1]

In embodiments, -L¹-R¹ is not

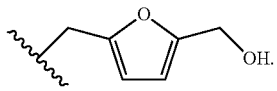 [SMILES: *Cc1ccc(CO)o1]

74

In embodiments, -L¹-R¹ is not

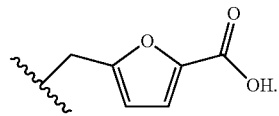 [SMILES: *Cc1ccc(C(=O)O)o1]

In embodiments, -L¹-R¹ is not

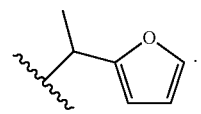

In embodiments, -L¹-R¹ is not

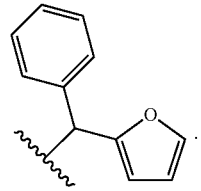 [SMILES: *C(c1ccccc1)c1ccco1]

In embodiments, -L¹-R¹ is not

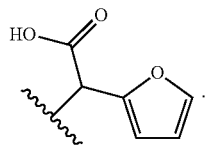

In embodiments, -L¹-R¹ is not

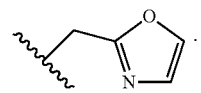

In embodiments, -L¹-R¹ is not

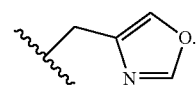

In embodiments, -L¹-R¹ is not

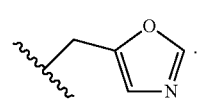

In embodiments, -L¹-R¹ is not

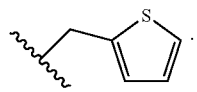 [SMILES: *Cc1cccs1]

In embodiments, -L¹-R¹ is not

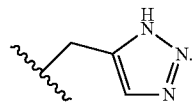 [SMILES: *Cc1cnn[nH]1]

In embodiments, -L¹-R¹ is not

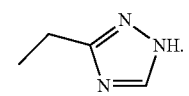

In embodiments, -L¹-R¹ is not

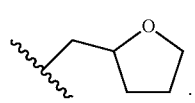

In embodiments, -L¹-R¹ is not

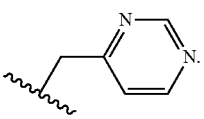

In embodiments, -L¹-R¹ is not

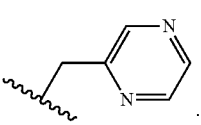

In embodiments, -L¹-R¹ is not

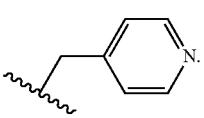 [SMILES: *Cc1ccncc1]

In embodiments, -L¹-R¹ is not

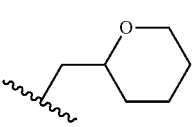

In embodiments, -L¹-R¹ is not

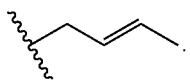 [SMILES: *C/C=C/C]

In embodiments, -L¹-R¹ is not

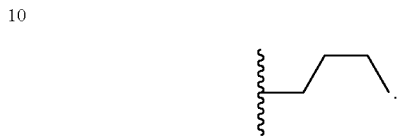

V. EMBODIMENTS

Embodiment 1

A compound having the formula:

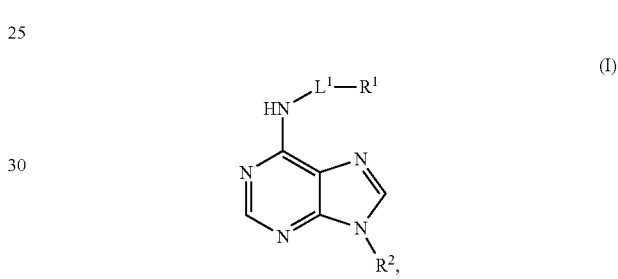

Wherein L¹ is a bond, substituted or unsubstituted alkylene, or substituted or unsubstituted heteroalkylene; R¹ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R² is hydrogen, substituted or unsubstituted cycloalkyl, substituted or unsubstituted heterocycloalkyl, substituted or unsubstituted aryl, or substituted or unsubstituted heteroaryl; and wherein if R² is hydrogen, then L¹-R¹ is not hydrogen,

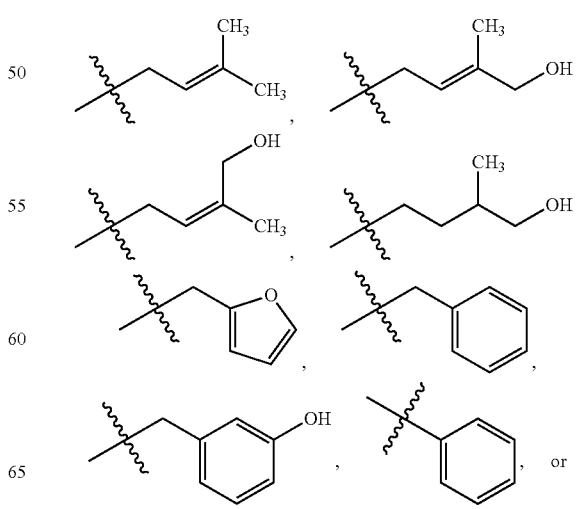

-continued

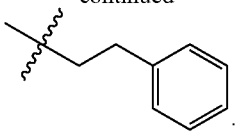

Embodiment 2

The compound of embodiment 1, wherein $L^1$ is a bond or substituted or unsubstituted alkylene.

Embodiment 3

The compound of embodiments 1-2, wherein $L^1$ is substituted or unsubstituted alkylene.

Embodiment 4

The compound of embodiments 1-3, wherein $L^1$ is substituted or unsubstituted $C_1$-$C_8$ alkylene.

Embodiment 5

The compound of embodiments 1-4, wherein $L^1$ is substituted or unsubstituted $C_1$-$C_4$ alkylene.

Embodiment 6

The compound of embodiments 1-5, wherein $L^1$ is substituted or unsubstituted methylene.

Embodiment 7

The compound of embodiments 1-6, wherein $L^1$ is substituted or unsubstituted heteroalkylene.

Embodiment 8

The compound of embodiments 1-7, wherein $L^1$ is a bond.

Embodiment 9

The compound of embodiments 1-8, wherein $R^1$ is substituted or unsubstituted alkyl.

Embodiment 10

The compound of embodiments 1-9, wherein $R^1$ is substituted or unsubstituted $C_1$-$C_{10}$ alkyl.

Embodiment 11

The compound of embodiments 1-10, wherein $R^1$ is substituted or unsubstituted $C_1$-$C_5$ alkyl.

Embodiment 12

The compound of embodiments 1-11, wherein $R^1$ is saturated substituted or unsubstituted $C_1$-$C_5$ alkyl.

Embodiment 13

The compound of embodiments 1-11, wherein $R^1$ is unsaturated substituted or unsubstituted $C_1$-$C_5$ alkyl.

Embodiment 14

The compound of embodiments 1-13, wherein $R^1$ is substituted or unsubstituted iso-pentenyl, substituted or unsubstituted hexenyl, substituted or unsubstituted propenyl, substituted or unsubstituted ethenyl, substituted or unsubstituted pentenyl, substituted or unsubstituted butenyl, substituted or unsubstituted 2-methylbut-1-enyl, substituted or unsubstituted 3-methylbut-1-enyl, substituted or unsubstituted 2-methylbut-2-enyl, substituted or unsubstituted 1-pentenyl, cis-2-pentenyl, or substituted or unsubstituted trans-2-pentenyl.

Embodiment 15

The compound of embodiments 1-14, wherein $R^1$ is substituted or unsubstituted cycloalkyl, substituted or unsubstituted heterocycloalkyl, substituted or unsubstituted aryl, or substituted or unsubstituted heteroaryl.

Embodiment 16

The compound of embodiments 1-15, wherein $R^1$ is substituted or unsubstituted aryl, or substituted or unsubstituted heteroaryl.

Embodiment 17

The compound of embodiments 1-16, wherein $R^1$ is substituted or unsubstituted $C_6$-$C_{10}$ aryl.

Embodiment 18

The compound of embodiments 1-17, wherein $R^1$ is substituted or unsubstituted 6 to 10 membered heteroaryl.

Embodiment 19

The compound of embodiments 1-18, wherein $R^1$ is $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl; and wherein $R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O) $NH_2$, —$NHSO_2H$, —NHC(O)H, —NHC(O)—OH, —NHOH, —$OCF_3$, —$OCHF_2$, substituted or unsubstituted monophosphate (or derivatives thereof), substituted or unsubstituted diphosphate (or derivatives thereof), substituted or unsubstituted triphosphate (or derivatives thereof), substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 20

The compound of embodiments 1-19, wherein $R^1$ is substituted or unsubstituted furanyl, substituted or unsubstituted tetrahydrofuranyl, substituted or unsubstituted thiofuranyl, substituted or unsubstituted pyrrolyl, substituted or unsubstituted thienyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted triazolyl, substituted or unsubstituted tetrahydropyranyl, substituted or unsubstituted pyrimidinyl, substituted or unsubstituted pyrazinyl, or substituted or unsubstituted pyridinyl.

Embodiment 21

The compound of embodiments 1-20 having the formula:

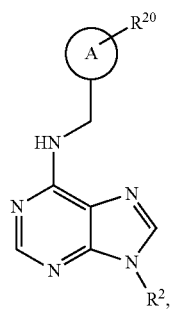
(III)

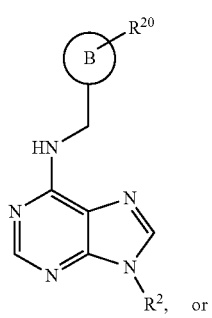
(IV)

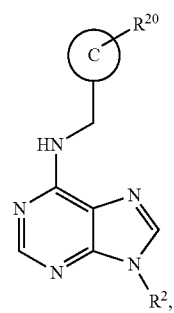
(V)

wherein, Ring A is substituted or unsubstituted furanyl, substituted or unsubstituted thiofuranyl, substituted or unsubstituted oxazolyl, substituted or unsubstituted isoxazolyl, or substituted or unsubstituted triazolyl; Ring B is substituted or unsubstituted pyrimidinyl, substituted or unsubstituted pyrazinyl, or substituted or unsubstituted pyridinyl; and Ring C is substituted or unsubstituted tetrahydrofuranyl, or substituted or unsubstituted tetrahydropyranyl; $R^{20}$ is independently halogen, —$CF_3$, —CN, —OH, —$NH_2$, —COOH, substituted or unsubstituted monophosphate, substituted or unsubstituted diphosphate, substituted or unsubstituted triphosphate, substituted or unsubstituted alkyl, or substituted or unsubstituted heteroalkyl.

Embodiment 22

The compound of embodiments 1-21 having the formula:

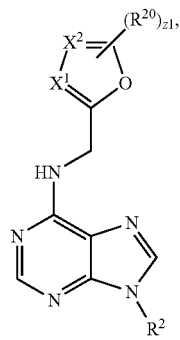
(VI)

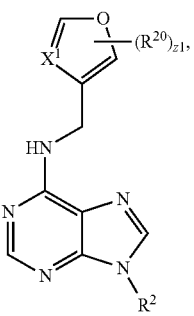
(VII)

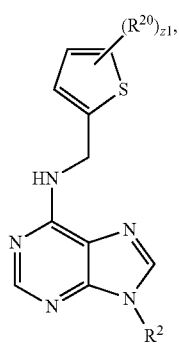
(VIII)

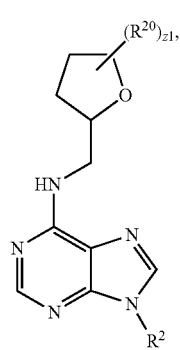
(IX)

81
-continued
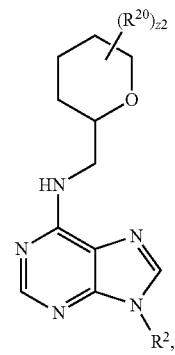
(X)
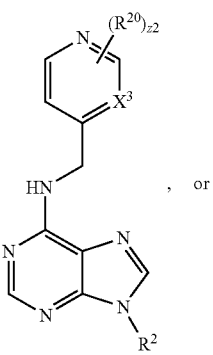
(XI)
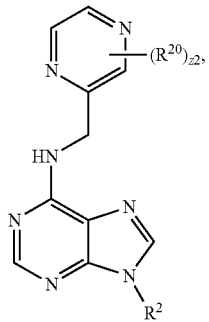
(XII)
wherein, X¹, X², and X³ are independently —N— or —CH—; z1 is 0, 1, 2, or 3; and z2 is 0, 1, 2, 3, 4 or 5.
Embodiment 23
The compound of embodiments 1-22, wherein the compound has the formula:
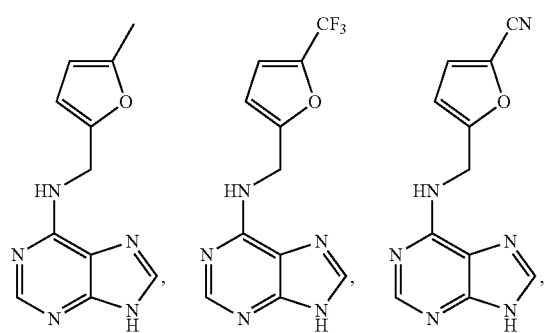
82
-continued
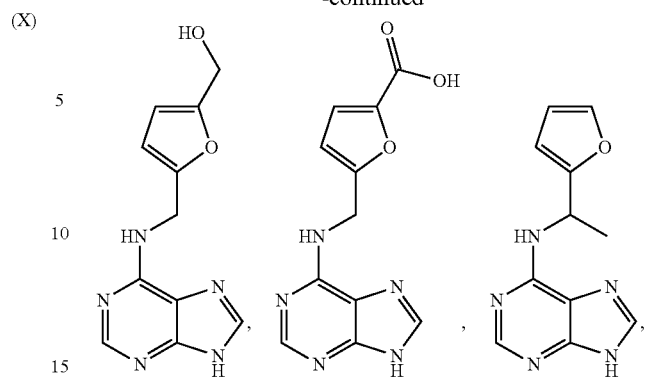
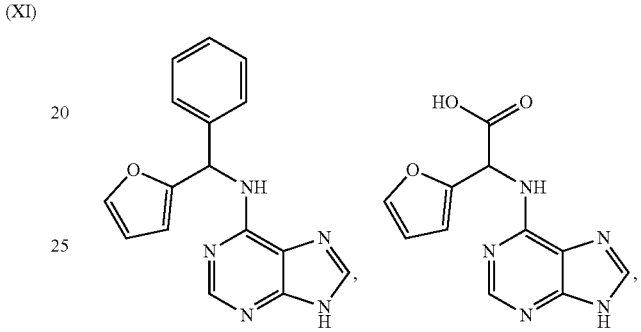
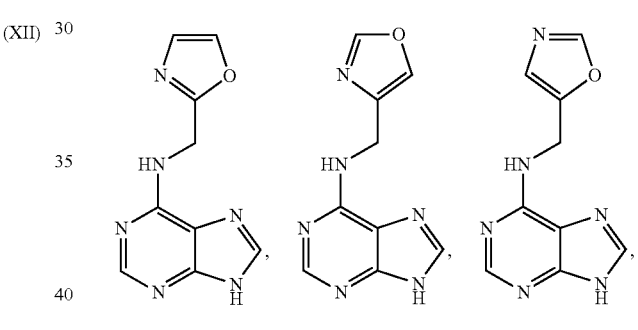
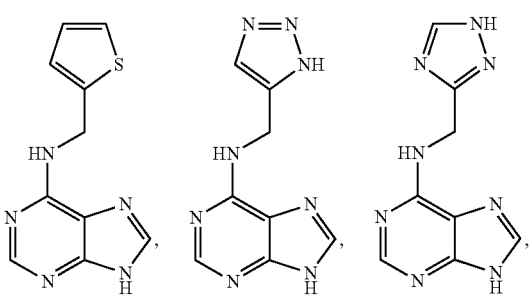
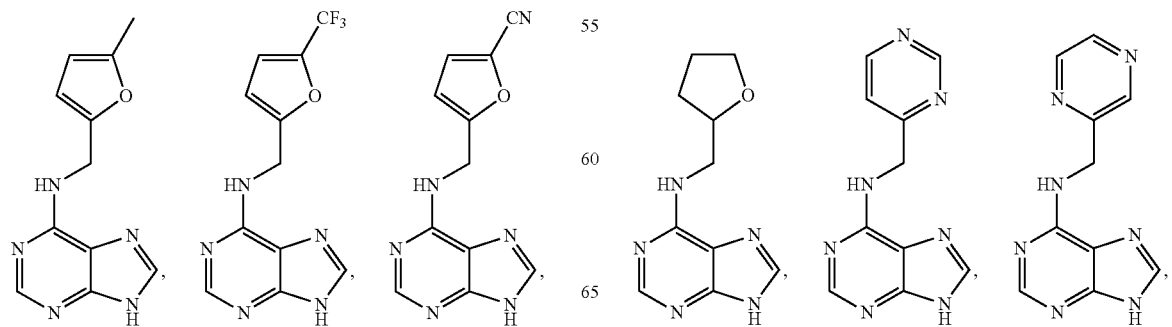

-continued

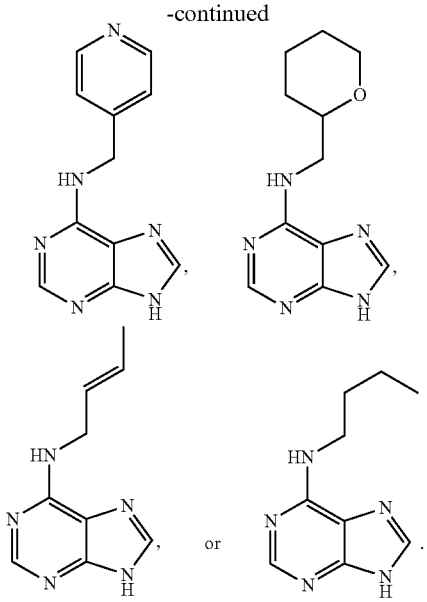

Embodiment 24

The compound of embodiments 1-23, wherein $R^2$ is hydrogen, substituted or unsubstituted heterocycloalkyl, or substituted or unsubstituted heteroaryl.

Embodiment 25

The compound of embodiments 1-24, wherein $R^2$ is substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl.

Embodiment 26

The compound of embodiments 1-25, wherein $R^2$ is independently substituted with at least one oxo; halogen; —OH; —CH$_2$OH; —N$_3$; or monophosphate, diphosphate, triphosphate, or a derivative thereof.

Embodiment 27

The compound embodiments 1-26, wherein $R^2$ has the formula:

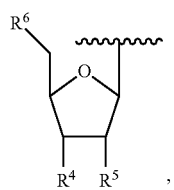

(II)

wherein, $R^4$ and $R^5$ are independently be hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^6$ is hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted phosphate, substituted or unsubstituted monophosphate, substituted or unsubstituted diphosphate, or substituted or unsubstituted triphosphate.

Embodiment 28

The compound of embodiments 1-27, wherein $R^4$ and $R^5$ are independently hydrogen or —OH; and $R^6$ is a —OH, monophosphate, diphosphate, triphosphate, or a derivative thereof.

Embodiment 29

A compound having the formula:

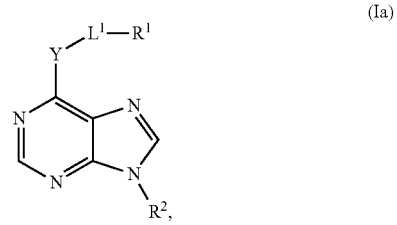

(Ia)

wherein, Y is NR$^3$ or CR$^{3a}$R$^{3b}$; L$^1$ is a bond, substituted or unsubstituted alkylene, or substituted or unsubstituted heteroalkylene; R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^2$ is hydrogen, substituted or unsubstituted cycloalkyl, substituted or unsubstituted heterocycloalkyl, substituted or unsubstituted aryl, or substituted or unsubstituted heteroaryl; R$^3$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3a}$ and $R^{3b}$ are independently hydrogen, halogen, —CF$_3$, —CCl$_3$, —CBr$_3$, —CI$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; wherein if $R^2$ is hydrogen, then -$L^1$-$R^1$ is not hydrogen,

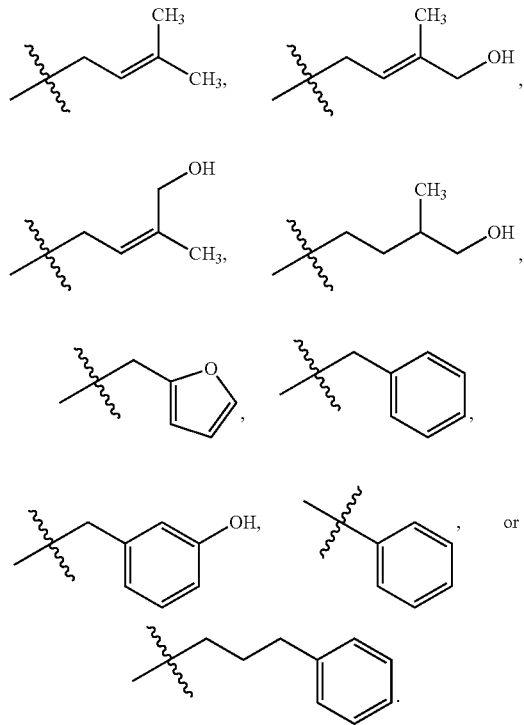

Embodiment 30

The compound of embodiment 29 having the formula:

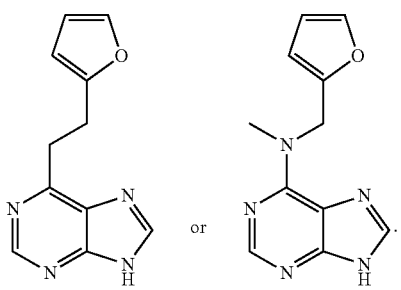 [SMILES: c1coc(CCc2ncnc3[nH]cnc23)c1 ; CN(Cc1ccco1)c1ncnc2[nH]cnc12]

Embodiment 31

A pharmaceutical composition comprising a pharmaceutically acceptable excipient and a compound of formula (I) or formula (Ia).

Embodiment 32

A method of treating a neurodegenerative disease or a cardiomyopathy in a patient in need thereof, said method comprising administering to said subject a therapeutically effective amount of a compound having the formula:

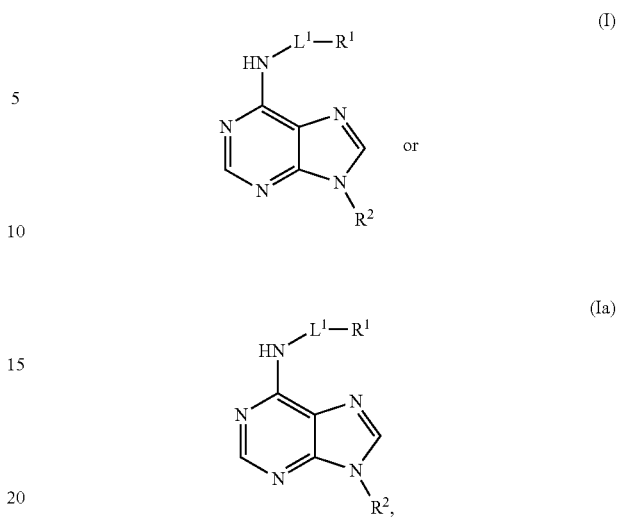

Wherein Y is $NR^3$ or $CR^{3a}R^{3b}$; $L^1$ is a bond, substituted or unsubstituted alkylene, or substituted or unsubstituted heteroalkylene; $R^1$ is hydrogen, oxo, halogen, —$CX_3$, —CN, —$SO_2Cl$, —$SO_nR^{10}$, —$SO_vNR^7R^8$, —$NHNH_2$, —$ONR^7R^8$, —$NHC(O)NHNH_2$, —$NHC(O)NR^7R^8$, —$N(O)_m$, —$NR^7R^8$, —$C(O)R^9$, —$C(O)OR^9$, —$C(O)NR^7R^8$, —$OR^{10}$, —$NR^7SO_2R^{10}$, —$N(R^7)C(O)R^9$, —$NR^7C(O)$—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, substituted or unsubstituted cycloalkyl, substituted or unsubstituted heterocycloalkyl, substituted or unsubstituted aryl, or substituted or unsubstituted heteroaryl; $R^3$ is substituted or unsubstituted cycloalkyl, substituted or unsubstituted heterocycloalkyl, substituted or unsubstituted aryl, or substituted or unsubstituted heteroaryl; $R^{3a}$ and $R^{3b}$ are independently hydrogen, halogen, —$CF_3$, —$CCl_3$, —$CBr_3$, —$CI_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)$—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)$—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

Embodiment 33

The method of embodiment 32, wherein said compound of formula (I) is administered in a therapeutically effective amount to said patient.

Embodiment 34

The method of embodiments 32-33, wherein $L^1$ is a bond or substituted or unsubstituted alkylene.

Embodiment 35

The method of embodiments 32-34, wherein $L^1$ is substituted or unsubstituted alkylene.

Embodiment 36

The method of embodiments 32-35, wherein $L^1$ is substituted or unsubstituted $C_1$-$C_8$ alkylene.

Embodiment 37

The method of embodiments 32-36, wherein $L^1$ is substituted or unsubstituted $C_1$-$C_4$ alkylene.

Embodiment 38

The method of embodiments 32-37, wherein $L^1$ is substituted or unsubstituted methylene.

Embodiment 39

The method of embodiments 32-38, wherein $L^1$ is substituted or unsubstituted heteroalkylene.

Embodiment 40

The method of embodiments 32-39, wherein $L^1$ is a bond.

Embodiment 41

The method of embodiments 32-40, $R^1$ is substituted or unsubstituted alkyl.

Embodiment 42

The method of embodiments 32-41, wherein $R^1$ is substituted or unsubstituted $C_1$-$C_{10}$ alkyl.

Embodiment 43

The method of embodiments 32-42, wherein $R^1$ is substituted or unsubstituted $C_1$-$C_5$ alkyl.

Embodiment 44

The method of embodiments 32-43, wherein $R^1$ is saturated substituted or unsubstituted $C_1$-$C_5$ alkyl.

Embodiment 45

The method of embodiments 32-43, wherein $R^1$ is unsaturated substituted or unsubstituted $C_1$-$C_5$ alkyl.

Embodiment 46

The method of embodiments 32-45, wherein $R^1$ is substituted or unsubstituted iso-pentenyl, substituted or unsubstituted hexenyl, substituted or unsubstituted propenyl, substituted or unsubstituted ethenyl, substituted or unsubstituted pentenyl, substituted or unsubstituted butenyl, substituted or unsubstituted 2-methylbut-1-enyl, substituted or unsubstituted 3-methylbut-1-enyl, substituted or unsubstituted 2-methylbut-2-enyl, substituted or unsubstituted 1-pentenyl, cis-2-pentenyl, or substituted or unsubstituted trans-2-pentenyl.

Embodiment 47

The method of embodiments 32-46, wherein $R^1$ is substituted or unsubstituted cycloalkyl, substituted or unsubstituted heterocycloalkyl, substituted or unsubstituted aryl, or substituted or unsubstituted heteroaryl.

Embodiment 48

The method of embodiments 32-47, wherein $R^1$ is substituted or unsubstituted aryl, or substituted or unsubstituted heteroaryl.

Embodiment 49

The method of embodiments 32-48, wherein $R^1$ is substituted or unsubstituted $C_6$-$C_{10}$ aryl.

Embodiment 50

The method of embodiments 32-49, wherein $R^1$ is substituted or unsubstituted 5 to 10 membered heteroaryl.

Embodiment 51

The method of embodiments 32-50, wherein $R^1$ is $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl; and wherein $R^{20}$ is independently oxo, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O) $NH_2$, —$NHSO_2H$, —NHC(O)H, —NHC(O)—OH, —NHOH, —$OCF_3$, —$OCHF_2$, substituted or unsubstituted monophosphate (or derivatives thereof), substituted or unsubstituted diphosphate (or derivatives thereof), substituted or unsubstituted triphosphate (or derivatives thereof), substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 52

The method of embodiments 32-51, wherein $R^1$ is substituted or unsubstituted furanyl, substituted or unsubstituted tetrahydrofuranyl, substituted or unsubstituted thiofuranyl, substituted or unsubstituted pyrrolyl, substituted or unsubstituted thienyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted triazolyl, substituted or unsubstituted tetrahydropyranyl, substituted or unsubstituted pyrimidinyl, substituted or unsubstituted pyrazinyl, or substituted or unsubstituted pyridinyl.

Embodiment 53

The method of embodiments 32-52, having the formula:

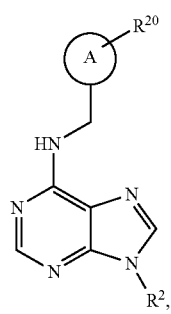
(III)

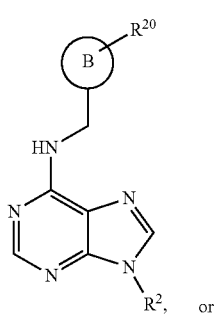
(IV)

or

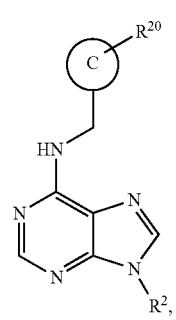
(V)

wherein, Ring A is substituted or unsubstituted furanyl, substituted or unsubstituted thiofuranyl, substituted or unsubstituted oxazolyl, substituted or unsubstituted isoxazolyl, or substituted or unsubstituted triazolyl; Ring B is substituted or unsubstituted pyrimidinyl, substituted or unsubstituted pyrazinyl, or substituted or unsubstituted pyridinyl; and Ring C is substituted or unsubstituted tetrahydrofuranyl, or substituted or unsubstituted tetrahydropyranyl; $R^{20}$ is independently halogen, $-CF_3$, $-CN$, $-OH$, $-NH_2$, $-COOH$, substituted or unsubstituted monophosphate, substituted or unsubstituted diphosphate, substituted or unsubstituted triphosphate, substituted or unsubstituted alkyl, or substituted or unsubstituted heteroalkyl.

Embodiment 54

The method of embodiments 32-53, wherein said compound has the formula:

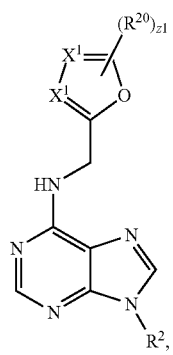
(VI)

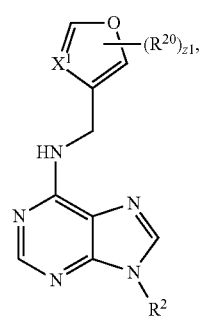
(VII)

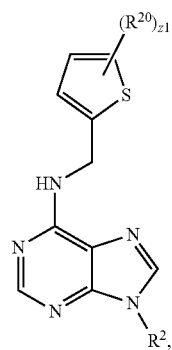
(VIII)

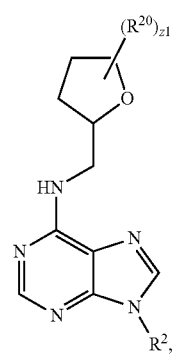
(IX)

-continued
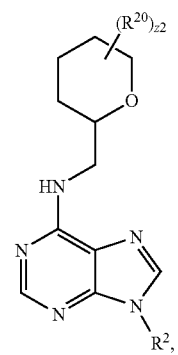
(X)
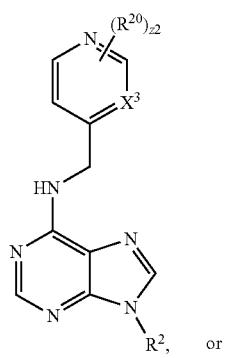
(XI)
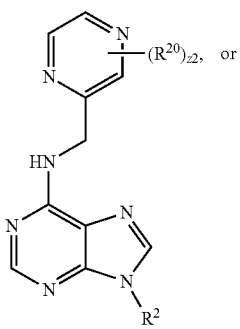
(XII)
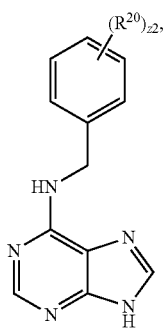
(XIII)
wherein X¹, X², X³ are independently —N— or —CH—, z1 is 0, 1, 2, or 3; and z2 is 0, 1, 2, 3, 4 or 5.
Embodiment 55 The method of embodiments 32-54, wherein said compound has the formula
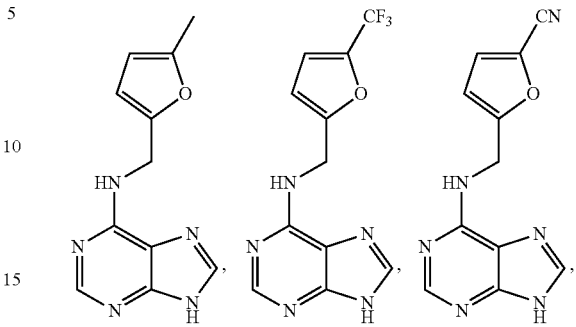
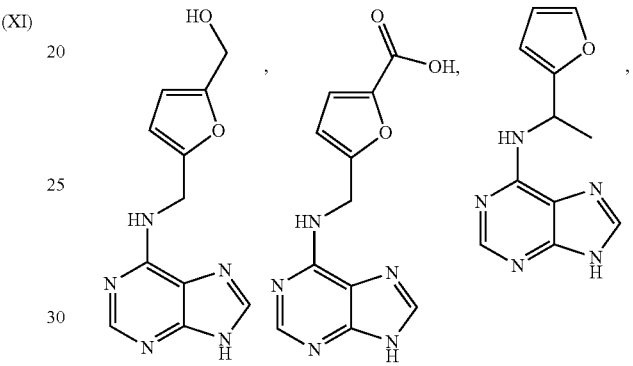
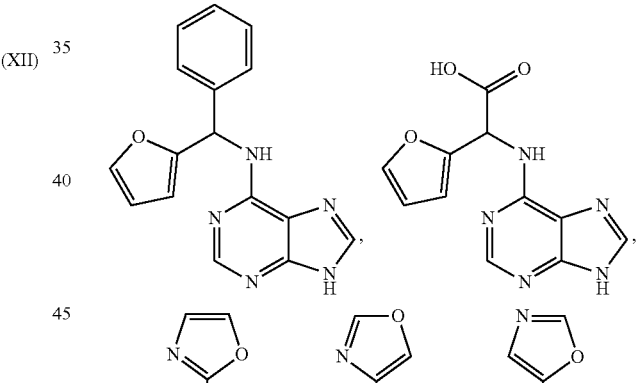
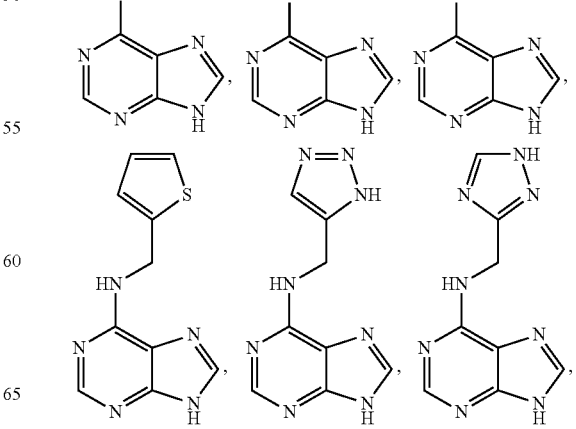

-continued

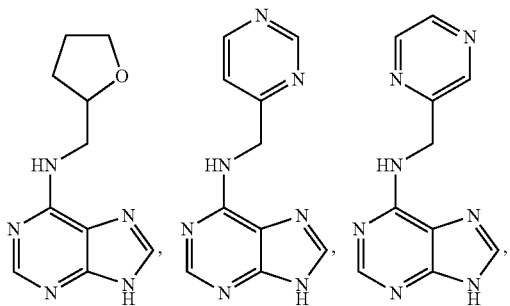

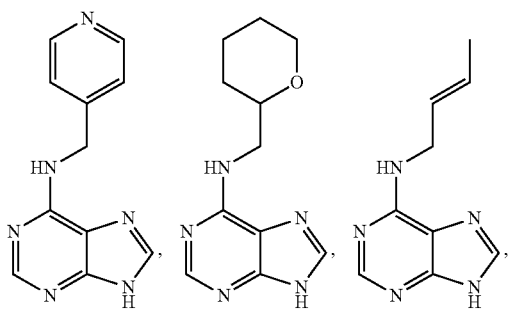

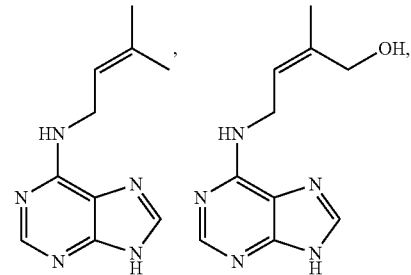

-continued

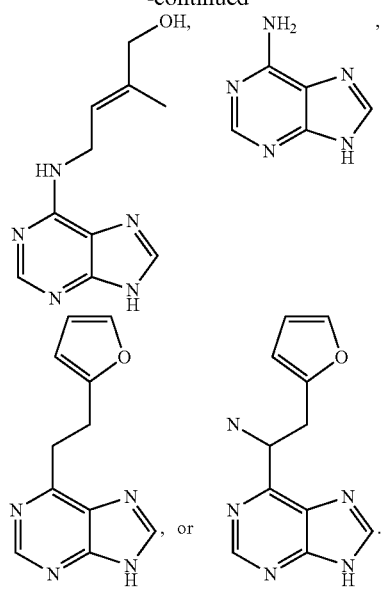

Embodiment 56

The method of embodiments 32-54, wherein R² is hydrogen, substituted or unsubstituted heterocycloalkyl, or substituted or unsubstituted heteroaryl.

Embodiment 57

The method of embodiments 32-54, wherein R² is substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl.

Embodiment 58

The method of embodiments 32-54, wherein R² is independently substituted with at least one oxo; halogen; —OH; —CH₂OH; —N₃; or monophosphate, diphosphate, triphosphate, or a derivative thereof.

Embodiment 59

The method of embodiments 32-58, wherein R² has the formula:

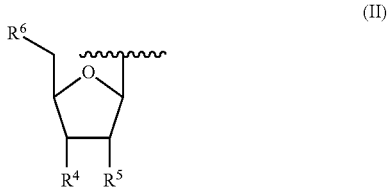

(II)

wherein, R⁴ and R⁵ are independently be hydrogen, oxo, halogen, —CF₃, —CN, —OH, —NH₂, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O) NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and R$^6$ is hydrogen, oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted phosphate, substituted or unsubstituted monophosphate, substituted or unsubstituted diphosphate, or substituted or unsubstituted triphosphate Embodiment 60

The method of embodiments 32-59, wherein, R$^4$ and R$^5$ are independently hydrogen or —OH; and R$^6$ is a —OH, monophosphate, diphosphate, triphosphate, or a derivative thereof.

Embodiment 61

The method of embodiments 32-60, wherein said compound is administered to treat a neurodegenerative disease a patient in thereof.

Embodiment 62

The method of embodiments 32-61, wherein the neurodegenerative disease is associated with mitochondrial dysfunction.

Embodiment 63

The method of embodiments 32-62, wherein the neurodegenerative disease is associated with an increased level of oxidative stress.

Embodiment 64

The method of embodiments 32-63, wherein the neurodegenerative disease is selected from the group consisting of Alzheimer's disease, Parkinson's disease, Huntington's disease, and Amyotrophic lateral sclerosis.

Embodiment 65

The method of embodiments 32-64, wherein the neurodegenerative disease is Parkinson's Disease.

Embodiment 66

The method of embodiments 32-60, wherein said compound is administered to treat a cardiomyopathy a patient in thereof.

Embodiment 67

The method of embodiments 32-60 and 66, wherein the cardiomyopathy is associated with mitochondrial dysfunction.

Embodiment 68

The method of embodiments 32-60 and 66-67, wherein the cardiomyopathy is associated with an increased level of oxidative stress.

Embodiment 69

The method of embodiments 32-60 and 66-68, wherein the cardiomyopathy is dilated cardiomyopathy, hypertrophic cardiomyopathy, restrictive cardiomyopathy, arrhythmogenic right ventriclular cardiomyopathy, or unclassified cardiomyopathy Embodiment 70

A method of increasing the level of activity of PINK1 in a cell by contacting the cell with a neo-substrate of PINK1.

Embodiment 71

The method of embodiment 70 wherein the neo-substrate is a compound of formula (I) or formula (Ia).

Embodiment 72

A method of treating a neurodegenerative disease in a patient in need of such treatment, said method comprising administering a therapeutically effective amount of a compound to said patient, wherein said compound has the formula:

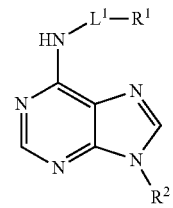

Wherein L$^1$ is a bond, substituted or unsubstituted alkylene, or substituted or unsubstituted heteroalkylene; R$^1$ is hydrogen, oxo, halogen, —CX$_3$, —CN, —SO$_2$Cl, —SO$_n$R$^{10}$, —SO$_v$NR$^7$R$^8$, —NHNH$_2$, —ONR$^7$R$^8$, —NHC=(O)NHNH$_2$, —NHC=(O)NR$^7$R$^8$, —N(O)$_m$, —NR$^7$R$^8$, —C(O)R$^9$, —C(O)OR$^9$, —C(O)NR$^7$R$^8$, —OR$^{10}$, —NR$^7$SO$_2$R$^{10}$, —N(R$^7$)C=(O)R$^9$, —NR$^7$C(O)—OR$^9$, —NR$^7$OR$^9$, —OCX$_3$, —OCHX$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^2$ is hydrogen, substituted or unsubstituted cycloalkyl, substituted or unsubstituted heterocycloalkyl, substituted or unsubstituted aryl, or substituted or unsubstituted heteroaryl; R$^7$, R$^8$, R$^9$, and R$^{10}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R$^7$ and R$^8$ are bonded to the same nitrogen atom, they may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

Embodiment 73

The method of embodiment 72, wherein R$^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 74

The method of embodiments 72-73, wherein R$^1$ is hydrogen, substituted or unsubstituted alkenyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl Embodiment 75

The method of embodiments 72-74, wherein R$^1$ is substituted or unsubstituted cycloalkyl, substituted or unsubstituted heterocycloalkyl, substituted or unsubstituted aryl, or substituted or unsubstituted heteroaryl.

Embodiment 76

The method of embodiments 72-75 wherein R$^1$ is substituted or unsubstituted aryl or substituted or unsubstituted heteroaryl.

Embodiment 77

The method of embodiments 72-76, wherein R$^1$ is substituted or unsubstituted C$_6$-C$_{10}$ aryl.

Embodiment 78

The method of embodiments 72-77, wherein R$^1$ is substituted or unsubstituted 5 to 10 membered heteroaryl.

Embodiment 79

The method of embodiments 72-78, wherein R$^1$ is substituted or unsubstituted furanyl, pyrrolyl, thienyl, imidazolyl, pyrazolyl, oxazolyl, isoxazolyl, or thiazolyl.

Embodiment 80

The method of embodiments 72-79 wherein L$^1$ is substituted or unsubstituted alkylene.

Embodiment 81

The method of embodiments 72-80, wherein L$^1$ is substituted or unsubstituted C$_1$-C$_8$ alkylene.

Embodiment 82

The method of embodiments 72-81, wherein L$^1$ is substituted or unsubstituted C$_1$-C$_4$ alkylene.

Embodiment 83

The method of embodiments 72-82, wherein L$^1$ is substituted or unsubstituted methylene.

Embodiment 84

The method of embodiments 72-83, wherein L$^1$ is substituted or unsubstituted heteroalkylene.

Embodiment 85

The method of embodiments 72-84, wherein L$^1$ is a bond.

Embodiment 86

The method of embodiments 72-85, wherein R$^2$ is hydrogen, substituted or unsubstituted cycloalkyl, or substituted or unsubstituted heterocycloalkyl.

Embodiment 87

The method of embodiments 72-86, wherein R$^2$ is hydrogen, substituted or unsubstituted C$_3$-C$_8$ cycloalkyl, or substituted or unsubstituted 3 to 8 membered heterocycloalkyl.

Embodiment 88

The method of embodiments 72-87, wherein R$^2$ is substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl.

Embodiment 89

The method of embodiments 72-88, wherein R$^2$ is independently substituted with at least one oxo; halogen; —OH; —CH$_2$OH; —N$_3$; or monophosphate, diphosphate, triphosphate, or a derivative thereof.

Embodiment 90

The method of embodiments 72-89, wherein R$^2$ has the formula:

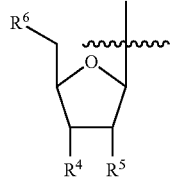

wherein, R$^4$ and R$^5$ are independently hydrogen or —OH; and R$^6$ is a —OH, monophosphate, diphosphate, triphosphate, or a derivative thereof.

Embodiment 91

The method of embodiments 72-90, wherein -L¹-R¹ is selected from the group consisting of: hydrogen,

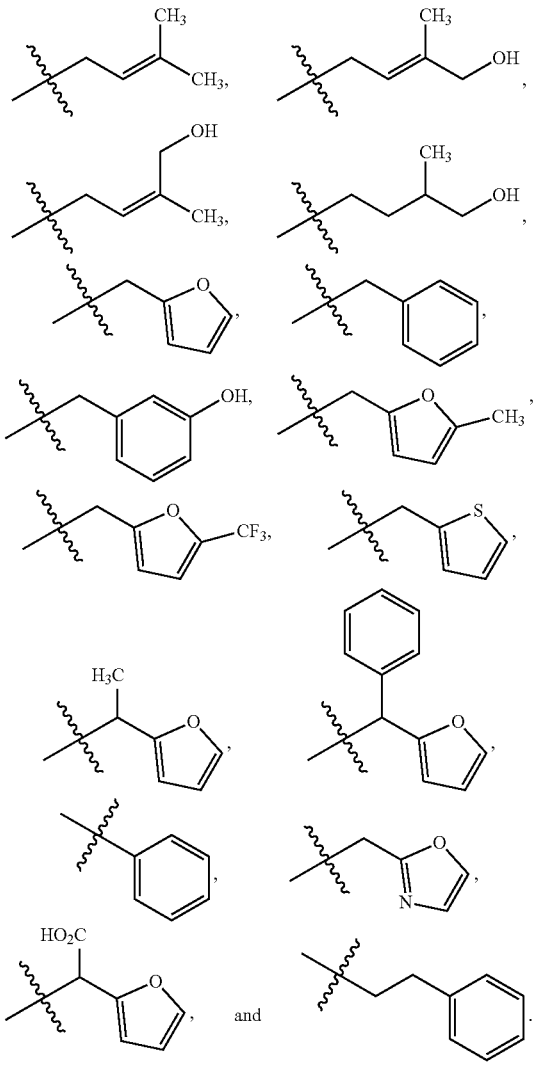

Embodiment 92

The method of embodiments 72-91 wherein the neurodegenerative disease is associated with mitochondrial dysfunction.

Embodiment 93

The method of embodiments 72-92, wherein the neurodegenerative disease is associated with an increased level of oxidative stress.

Embodiment 94

The method of embodiments 72-93, wherein the neurodegenerative disease is selected from the group consisting of Alzheimer's disease, Parkinson's disease, Huntington's disease, and Amyotrophic lateral sclerosis.

Embodiment 95

The method of embodiments 72-94, wherein the neurodegenerative disease is Parkinson's Disease.

Embodiment 96

A method of increasing the level of activity of PINK1 in a cell by contacting the cell with a neo-substrate of PINK1.

Embodiment 97

The method of embodiment 96, wherein the neo-substrate is a compound having the formula:

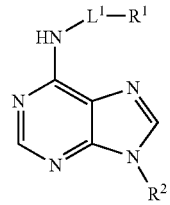

Wherein $L^1$ is a bond, substituted or unsubstituted alkylene, or substituted or unsubstituted heteroalkylene; $R^1$ is hydrogen, oxo, halogen, —$CX_3$, —CN, —$SO_2Cl$, —$SO_nR^{10}$, —$SO_vNR^7R^8$, —$NHNH_2$, —$ONR^7R^8$, —NHC=(O) $NHNH_2$, —NHC=(O)$NR^7R^8$, —N(O)$_m$, —$NR^7R^8$, —C(O) $R^9$, —C(O)$OR^9$, —C(O)$NR^7R^8$, —$OR^{10}$, —$NR^7SO_2R^1$, —N($R^7$)C=(O)$R^9$, —$NR^7C(O)$—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, substituted or unsubstituted cycloalkyl, substituted or unsubstituted heterocycloalkyl, substituted or unsubstituted aryl, or substituted or unsubstituted heteroaryl; $R^7$, $R^8$, $R^9$, and $R^{10}$ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where $R^7$ and $R^8$ are bonded to the same nitrogen atom, they may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

Embodiment 98

A compound having the formula:

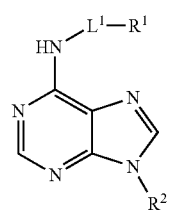

Wherein $L^1$ is a bond, substituted or unsubstituted alkylene, or substituted or unsubstituted heteroalkylene; $R^1$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^2$ is hydrogen, substituted or unsubstituted cycloalkyl, substituted or unsubstituted heterocycloalkyl, substituted or unsubstituted aryl, or substituted or unsubstituted heteroaryl; with the proviso that if $R^2$ is hydrogen, then -$L^1$-$R^1$ is not hydrogen

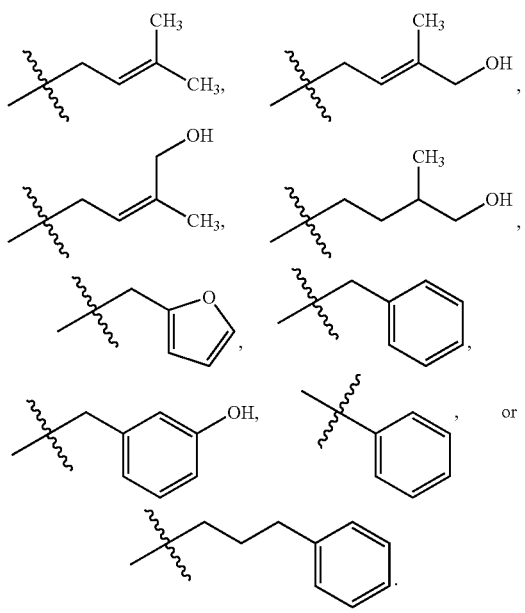

Embodiment 99

The compound of embodiment 98, wherein $R^1$ is substituted aryl or substituted heteroaryl.

Embodiment 100

The compound of embodiments 98-99, wherein $L^1$ is a bond

Embodiment 101

The compound of embodiments 98-100, wherein $R^2$ is substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl.

Embodiment 102

The compound of embodiments 98-101, wherein $R^2$ is independently substituted with at least one oxo; halogen; —OH; —CH$_2$OH; —N$_3$; or monophosphate, diphosphate, triphosphate, or a derivative thereof.

Embodiment 103

The compound of embodiments 98-102, wherein $R^2$ has the formula:

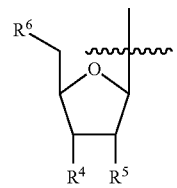

wherein, $R^4$ and $R^5$ are independently hydrogen or —OH; and $R^6$ is a —OH, monophosphate, diphosphate, triphosphate, or a derivative thereof.

Embodiment 104

The compound of embodiments 98-103, wherein -$L^1$-$R^1$ is selected from the group consisting of

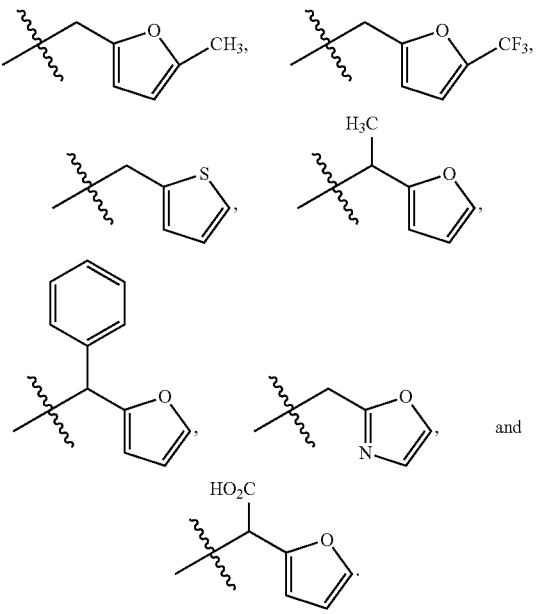

and

Embodiment 105

A pharmaceutical composition comprising a pharmaceutically acceptable excipient and a compound of embodiments 98-104.

Embodiment 106

A method of treating a cardiomyopathy in a patient in need of such treatment, said method comprising administering a therapeutically effective amount of a compound to said patient, wherein said compound has the formula:

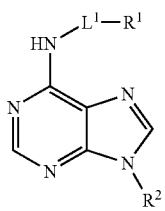

wherein
L¹ is a bond, substituted or unsubstituted alkylene, or substituted or unsubstituted heteroalkylene;
R¹ is hydrogen, oxo, halogen, —$CX_3$, —CN, —$SO_2Cl$, —$SO_nR^{10}$, —$SO_vNR^7R^8$, —$ONR^7R^8$, —$NHNH_2$, —$ONR^7R^8$, —NHC=(O)$NHNH_2$, —NHC=(O)$NR^7R^8$, —$N(O)_m$, —$NR^7R^8$, —$C(O)R^9$, —$C(O)OR^9$, —$C(O)NR^7R^8$, —$OR^{10}$, —$NR^7SO_2R^{10}$, —$N(R^7)C$=(O)$R^9$, —$NR^7C(O)$—$OR^9$, —$NR^7OR^9$, —$OCX_3$, —$OCHX_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R² is hydrogen, substituted or unsubstituted cycloalkyl, substituted or unsubstituted heterocycloalkyl, substituted or unsubstituted aryl, or substituted or unsubstituted heteroaryl; R⁷, R⁸, R⁹, and R¹⁰ are independently hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, —NHC=(O) $NH_2$, —$NHSO_2H$, —NHC=(O)H, —NHC(O)—OH, —NHOH, —$OCF_3$, —$OCHF_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; where R⁷ and R⁸ are bonded to the same nitrogen atom, they may optionally be joined to form a substituted or unsubstituted heterocycloalkyl or substituted or unsubstituted heteroaryl; m and v are independently 1 or 2; n is independently an integer from 0 to 4; X is independently —Cl, —Br, —I, or —F.

Embodiment 107

The method of embodiment 106, wherein R¹ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 108

The method of embodiments 106-107, wherein R¹ is hydrogen, substituted or unsubstituted alkenyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl Embodiment 109

The method of embodiments 106-108, wherein R¹ is substituted or unsubstituted cycloalkyl, substituted or unsubstituted heterocycloalkyl, substituted or unsubstituted aryl, or substituted or unsubstituted heteroaryl.

Embodiment 110

The method of embodiments 106-109, wherein R¹ is substituted or unsubstituted aryl or substituted or unsubstituted heteroaryl.

Embodiment 111

The method of embodiments 106-110, wherein R¹ is substituted or unsubstituted $C_6$-$C_{10}$ aryl.

Embodiment 112

The method of embodiments 106-111, wherein R¹ is substituted or unsubstituted 5 to 10 membered heteroaryl.

Embodiment 113

The method of embodiments 106-112, wherein R¹ is substituted or unsubstituted furanyl, pyrrolyl, thienyl, imidazolyl, pyrazolyl, oxazolyl, isoxazolyl, or thiazolyl.

Embodiment 114

The method of embodiments 106-113, wherein L¹ is substituted or unsubstituted alkylene.

Embodiment 115

The method of embodiments 106-114, wherein L¹ is substituted or unsubstituted $C_1$-$C_8$ alkylene.

Embodiment 116

The method of embodiments 106-115 wherein L¹ is substituted or unsubstituted $C_1$-$C_4$ alkylene.

Embodiment 117

The method of embodiments 1 to 116, wherein L¹ is substituted or unsubstituted methylene.

Embodiment 118

The method of embodiments 106-117, wherein L¹ is substituted or unsubstituted heteroalkylene.

Embodiment 119

The method of embodiments 106-118, wherein L¹ is a bond.

Embodiment 120

The method of embodiments 106-119, wherein R² is hydrogen, substituted or unsubstituted cycloalkyl, or substituted or unsubstituted heterocycloalkyl.

Embodiment 121

The method of embodiments 106-120, wherein R² is hydrogen, substituted or unsubstituted $C_3$-$C_8$ cycloalkyl, or substituted or unsubstituted 3 to 8 membered heterocycloalkyl Embodiment 122

The method of embodiments 106-121, wherein R² is substituted or unsubstituted tetrahydrofuranyl, substituted or unsubstituted 2,5-dihydrofuranyl, substituted or unsubstituted tetrahydrothienyl, substituted or unsubstituted 2,5-dihydrothienyl, substituted or unsubstituted pyrrolidinyl, substituted or unsubstituted 2,5-dihydro-1H-pyrrolyl, substituted or unsubstituted cyclopentyl, substituted or unsubstituted cyclopentenyl, or substituted or unsubstituted 1,3-oxathiolanyl.

Embodiment 123

The method of embodiments 106-122, wherein $R^2$ is independently substituted with at least one oxo; halogen; —OH; —CH$_2$OH; —N$_3$; or monophosphate, diphosphate, triphosphate, or a derivative thereof.

Embodiment 124

The method of embodiments 106-123, wherein $R^2$ has the formula:

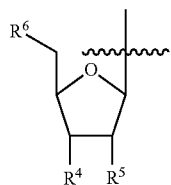

wherein, $R^4$ and $R^5$ are independently hydrogen or —OH; and $R^6$ is a —OH, monophosphate, diphosphate, triphosphate, or a derivative thereof.

Embodiment 125

The method of embodiments 106-124, wherein -L$^1$-R$^1$ is selected from the group consisting of: hydrogen,

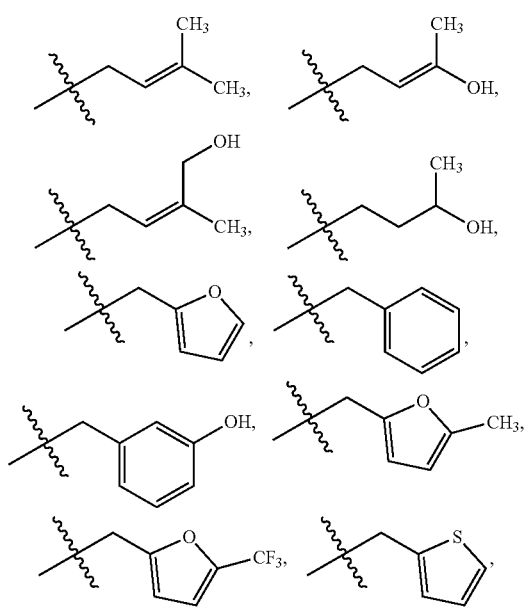

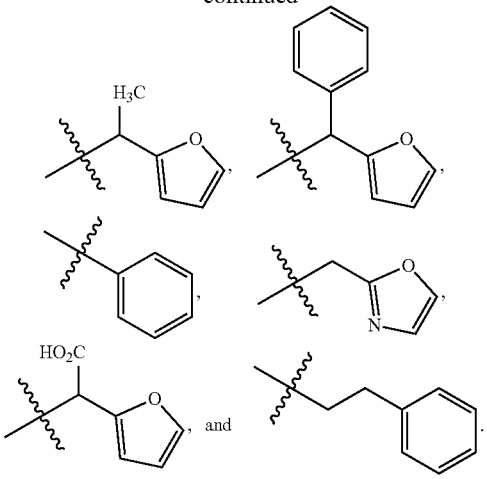

Embodiment 126

The method of embodiments 106-125, wherein the cardiomyopathy is associated with mitochondrial dysfunction.

Embodiment 127

The method of embodiments 106-126, wherein the cardiomyopathy is associated with an increased level of oxidative stress.

Embodiment 128

The method of embodiments 106-127, wherein the cardiomyopathy is dilated cardiomyopathy, hypertrophic cardiomyopathy, restrictive cardiomyopathy, arrhythmogenic right ventriclular cardiomyopathy, or unclassified cardiomyopathy.

VI. EXAMPLES

The following examples illustrated various embodiments of the invention are not intended to limit the invention in any way.

In healthy mitochondria, PINK1 is rapidly degraded; but in the presence of inner membrane depolarization, PINK1 is stabilized on the outer membrane, where it recruits and activates the E3 ubiquitin ligase Parkin, blocks mitochondrial fusion and trafficking, and, ultimately, triggers mitochondrial autophagy.[3,4,8,10]

Parkinson's Disease (PD) is one of the most common neurodegenerative disorders, however no disease modifying therapies are currently approved to treat PD. Both environmental and genetic factors are believed to lead to progressive apoptosis of dopaminergic neurons, lowered dopamine levels and ultimately PD. One autosomal recessive genetic form is caused by mutations in the mitochondrial kinase PTEN Induced Kinase 1 (PINK1). In healthy dopaminergic neurons PINK1 opposes apoptosis in response to oxidative stress and dopaminergic neurotoxins by halting mitochondrial motility and inducing mitophagy and clearance of depolarized mitochondria. This neuroprotective effect may be abrogated by PINK1 PD associated loss of function mutations and by accumulated oxidative stress in sporadic cases. PINK1 kinase activity appears to mediate its neuroprotective activity; therefore recovery of the kinase activity of mutant PINK1 or activation of the wild-type kinase activity of PINK1 could prevent the neurodegeneration associated with PD. Likewise, recovery of the kinase activity of mutant PINK1 or activation of the wild-type kinase activity of PINK1 could prevent the cardiac cell degeneration associated with cardiomyopathy.

Regulation of mitochondrial movement, distribution and clearance is a key part of neuronal oxidative stress response. Disruptions to these regulatory pathways have been shown to contribute to chronic neurodegenerative disease[1,2]. The mitochondrial kinase PINK1 plays a critical role in these processes by regulating the fate of depolarized mitochondria[3-5]. Decreased kinase activity in PINK1$^{G309D}$-mutant neurons is associated with a defect in Parkin recruitment to damaged mitochondria and increased levels of neuronal apoptosis, leading to early-onset (~40 years old) Parkinson's Disease (PD)[6-8]. The importance of mitochondrial quality control for neuron health and survival is well established[1,2,9]. The mitochondrial kinase PTEN Induced Kinase 1 (PINK1) plays an important role in these quality control processes by responding to damage at the level of individual mitochondria. In healthy mitochondria, PINK1 is rapidly degraded; but in the presence of inner membrane depolarization, PINK1 is stabilized on the outer membrane, where it recruits and activates the E3 ubiquitin ligase Parkin, blocks mitochondrial fusion and trafficking, and, ultimately, triggers mitochondrial autophagy[3-5,8,10]. The PINK1 pathway has also been linked to the induction of mitochondrial biogenesis, and, critically, the reduction of mitochondrially induced apoptosis[3,4,11]. The PINK1/Parkin pathway has been implicated in several autosomal recessive forms of Parkinson's Disease (PD)[6,10]. PINK1 loss-of-function mutations block the neuroprotective effect of PINK1 expression and in homozygous individuals cause early onset PD that shares the Lewy-body physiology of sporadic PD[7,12-16]. One of the most common of these mutants, PINK1$^{G309D}$, which shows a ~70% decrease in kinase activity was analyzed. Interestingly, overexpression of PINK1$^{wt}$ reverses the phenotype of mutant PINK1, and can block apoptosis when overexpressed in unaffected cells[7,13].

PINK1 kinase activity is necessary to mediate its cardioprotective activity; Regulation of mitochondrial movement, distribution and clearance is a key part of cardiac cell oxidative stress response. Disruptions to these regulatory pathways have been shown to contribute to cardiomyopathy.[1,2] The mitochondrial kinase PINK1 plays a critical role in these processes by regulating the fate of depolarized mitochondria.[3-5] The mitochondrial kinase PTEN Induced Kinase 1 (PINK1) plays an important role in these quality control processes by responding to damage at the level of individual mitochondria. In healthy mitochondria, PINK1 is rapidly degraded; but in the presence of inner membrane depolarization, PINK1 is stabilized on the outer membrane, where it recruits and activates the E3 ubiquitin ligase Parkin, blocks mitochondrial fusion and trafficking, and, ultimately, triggers mitochondrial autophagy.[3,4,8,10] The PINK1 pathway has also been linked to the induction of mitochondrial biogenesis, and, critically, the reduction of mitochondrially induced apoptosis[3,4,11]. The PINK1/Parkin pathway has been implicated in several autosomal recessive forms of Parkinson's Disease (PD).[10] PINK1 loss-of-function mutations block the neuroprotective effect of PINK1 expression and in homozygous individuals cause early onset PD that shares the Lewy-body physiology of sporadic PD.[7,12-16] One of the most common of these mutants, PINK1$^{G309D}$, showed a ~70% decrease in kinase activity was analyzed. Interestingly, overexpression of PINK1$^{wt}$ reverses the phenotype of mutant PINK1, and can block apoptosis when overexpressed in unaffected cells[7,13].

1. Alternate Substrates of PINK1

Mammalian cells regulate oxidative stress by modulating mitochondrial movement, distribution and clearance. The mitochondrial kinase, PINK1 plays a critical role in these processes by regulating clearance of depolarized mitochondria[1,2]. Decreased kinase activity in PINK1$^{G309D}$ mutant neurons is associated with an autosomal recessive form of Parkinson's Disease (PD). Therapeutic approaches for specifically enhancing the activity of PINK1 have not been considered since no allosteric regulatory sites for PINK1 are known. Here we show that an alternative strategy, a neo-substrate approach involving $N^6$ furfuryl-ATP (kinetin triphosphate or KTP), can be used to increase the activity of both mutant PINK1$^{G309D}$ and PINK1$^{wt}$. Application of the neo-substrate to oxidatively stressed cells results in higher levels of Parkin recruitment, reduced mitochondrial motility, and lower levels of apoptosis in a PINK1 dependent manner in cellular models. These results suggest a potential therapeutic opportunity for treating genetic G309D and idiopathic forms of Parkinson's disease. These results also suggest a potential therapeutic opportunity for treating genetic G309D and idiopathic forms of cardiomyopathy. Discovery of neo-substrates for kinases whose loss of function mediate disease provides a heretofore unappreciated therapeutic modality for targeting such diseases.

Recognizing the therapeutic potential of PINK1/Parkin pathway activation and/or amplification, we began investigating chemical-genetic mechanisms for manipulating PINK1. Since no PINK1 allosteric regulatory sites have yet been discovered, we chose to pursue a strategy of looking for alternative substrates for both PINK1$^{wt}$ and the disease associated PINK1$^{G309D}$ mutant. Recent work showed in cells expressing hypomorphic mutant CDK2 alleles that the activity of CDK2 could be increased by providing nucleotide analogs which fit into the hypomorphic CDK2[17]. Comparison of the sequence of PINK1 to kinases for which structural data is available revealed large insertions in several regions of the n-lobe of the PINK1 kinase domain surrounding the ATP binding site (FIG. 5A).[18] These insertions suggested that the active site of PINK1 might accommodate alternative nucleotide substrates besides ATP. Though it is uncommon for eukaryotic protein kinases to accept alternative substrates in the ATP binding site, kinases engineered with gatekeeper mutations tolerate substitutions to ATP at the N6 position. Additionally, prominent examples exist for naturally occurring kinases. CK2, for example, accepts ATP as well as GTP.

Figure 1B:
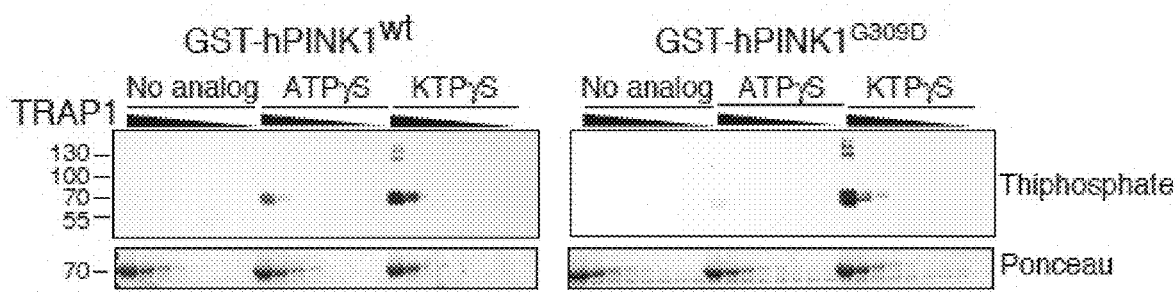

We expressed both PINK1$^{wt}$ and PINK1$^{G309D}$ GST tagged kinase domain ($_{156-496}$PINK1) in $E.\ coli$ and performed kinase assays with a series of ATP analogs. As expected, PINK1$^{G309D}$ displayed reduced activity with ATP; interestingly, however, incubation with $N^6$ furfuryl ATP (kinetin triphosphate or KTP) led to increased levels of autophosphorylation (FIGS. 1D, 1F, and FIGS. 6B, 6C). Using a capture and release strategy pioneered by our lab[19,20], we were able to identify the T257 autophosphorylation site[21] using KTP as the phospho-donor for PINK1 (FIG. 1E), which showed that this neo-substrate is utilized similarly to ATP. To assess transphosphorylation, we incubated the kinase domain of PINK1$^{G309D}$ and PINK1$^{wt}$ (FIG. 1B) with KTP and a substrate protein (TRAP1), and found that the activity of both PINK1 constructs was amplified by using the neo-substrate KTP versus ATP.

Experiments to determine whether the $N^6$ furfuryl adenine analogs cross the SH-SY5Y plasma membrane and are incorporated into ATP analogs using TLC were conducted. We confirmed presence of a membrane impermeable metabolite after incubation with N6 furfuryl adenine. We included negative control analogs of Kinetin which prevent metabolism.

Experiments were conducted to test whether the rescue of PINK1 ATP dependent kinase activity also increases the survival of cells in the face of stress agents. Pre-treatment with kinetin but not adenine blocks apoptosis induced by oxidative stress in SH-SY5Y cells.

2. Expression of PINK1

Expression, purification and enzymatic characterization of PINK1: *H. sapiens* PINK1 kinase domain (PINK1, residues 156-496) with an N-terminal GST tag was expressed using a pGEX vector using standard techniques. *H. sapiens* PINK1 kinase domain with c-terminal extension (PINK1, residues 148-581) with a C-terminal $FLAG_3$ tag was co-expressed with full length TRAP1 baculovirus/Sf21 insect cell system. Following lysis, $PINK1_{1148-581}$ kinase was purified using magnetic M2 FLAG affinity resin (Sigma) with the kinase reaction performed on beads after no more than 2 hours following lysis. The reaction was performed using 50 mM Tris-HCl, 150 mM NaCl, 10 mM $MgCl_2$, 3 mM $MnCl_2$, 0.5 mM DTT and 1 mg/ml substrate if indicated.

Figure 1C:
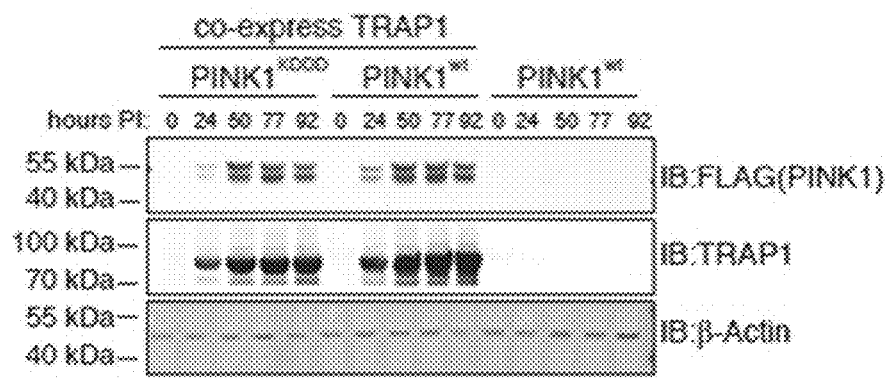
Figure 1D:
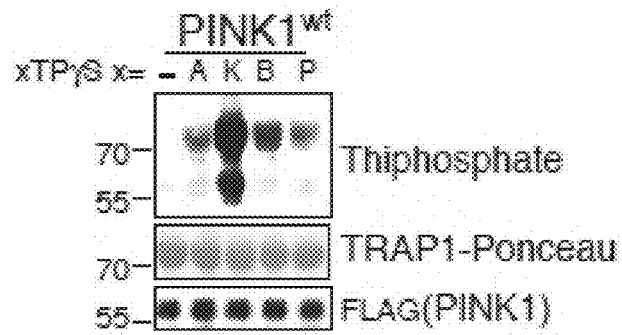
Figure 1E:
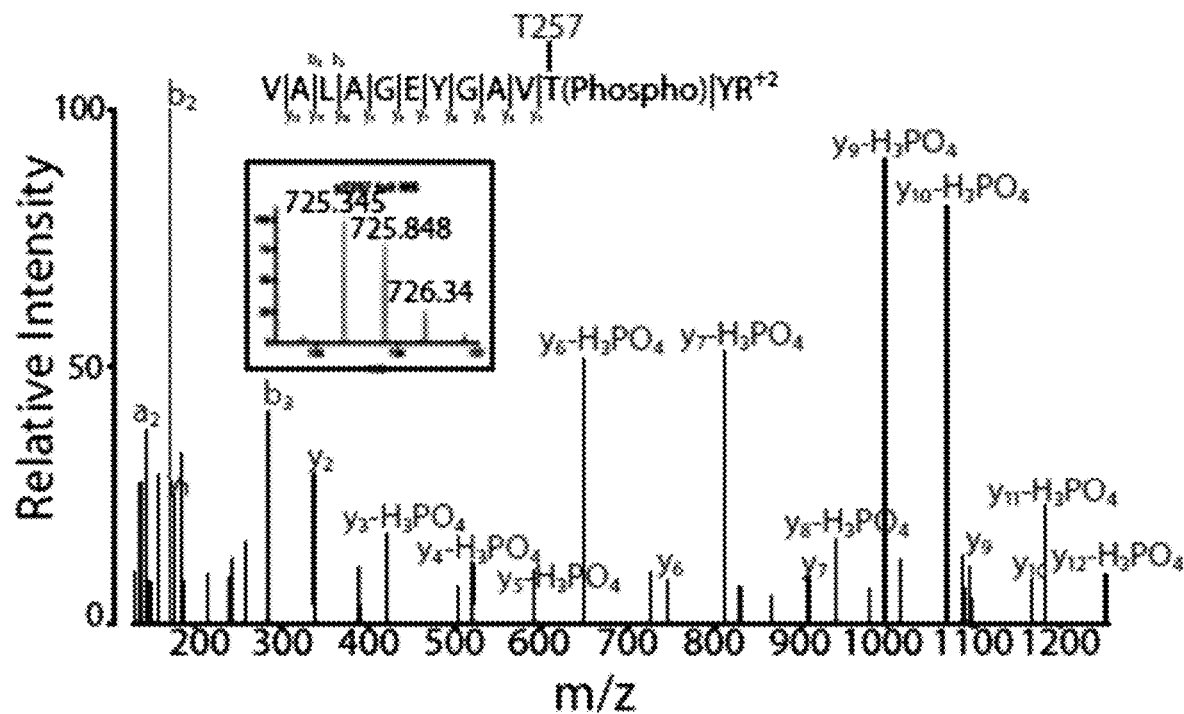
Figure 1F:
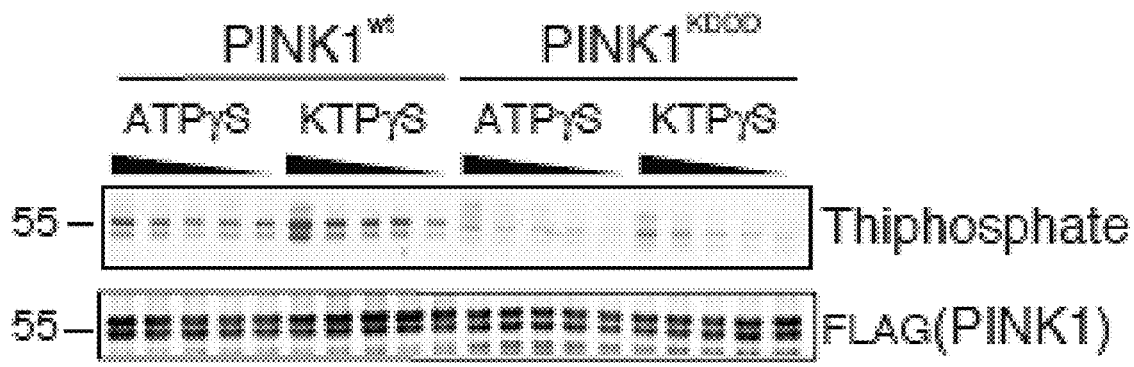
Figure 6A:
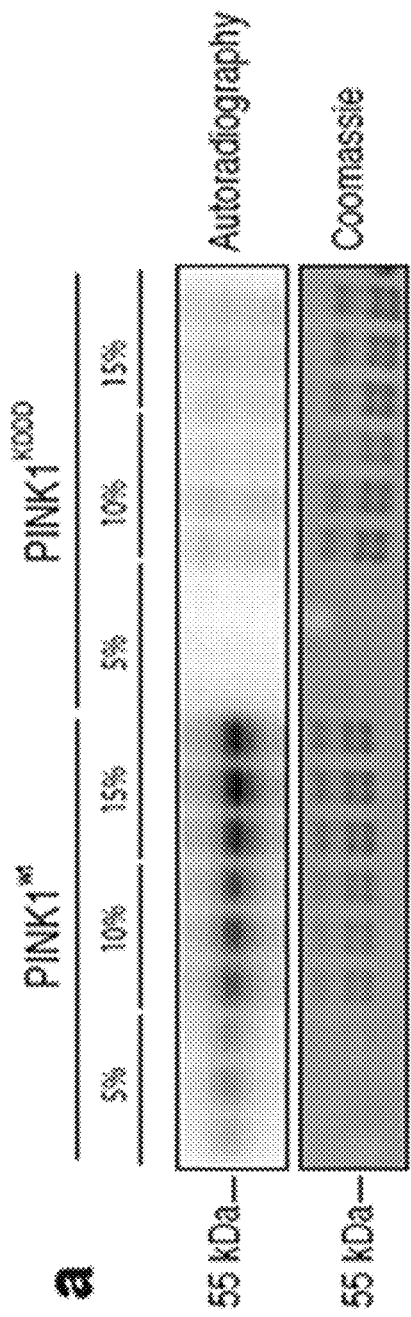
FIGS. 6A-6C.
Figure 6C:
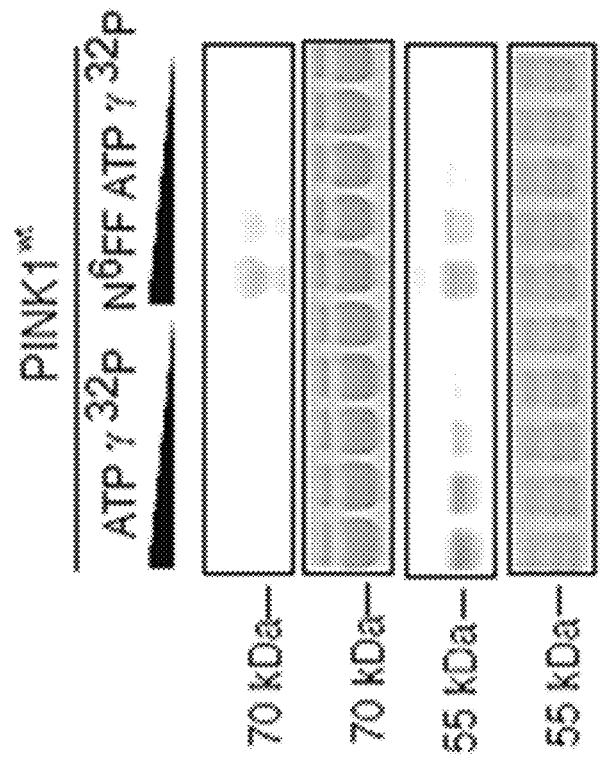
Figure 6B:
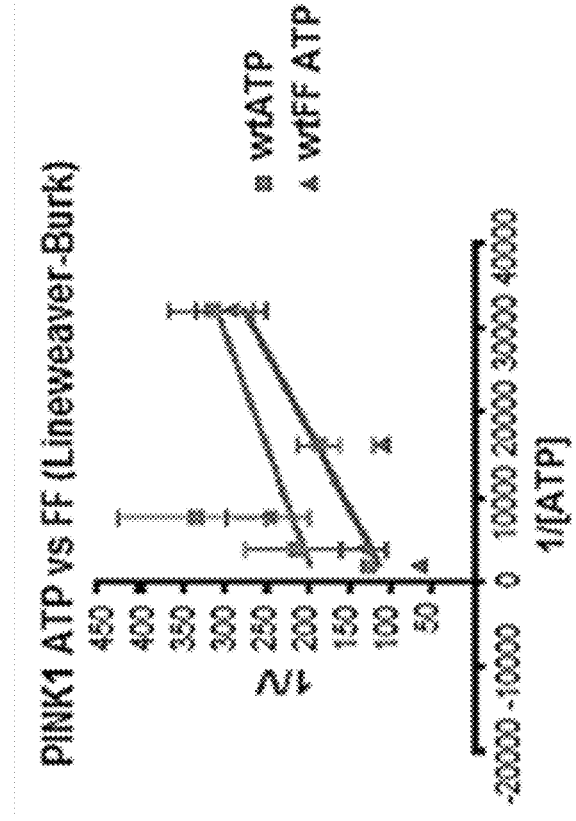

To confirm the PINK1-dependency of the observed kinase activity we took several steps to optimize PINK1 expression. We constructed several $FLAG_3$ tagged truncation variants of PINK1 and induced expression using baculovirus infected SF21 insect cells. C-terminally tagged 148-581 $PINK1FLAG_3$ expressed the most soluble protein (FIG. 1C). However, PINK1 is intrinsically very unstable and there was a very low amount of purified PINK1[22,23]. Hypothesizing that co-expression of interacting proteins might help PINK1 to fold properly, we co-expressed proteins known to associate with PINK1 such as DJ-1, PARKIN, and TRAP1. TRAP1, a mitochondrial chaperone, proved to have a major effect on the stability of PINK1 (FIG. 1C). This finding enabled us to express larger amounts of properly folded $PINK1^{wt}$, $PINK1^{G309D}$ and a triple kinase dead $PINK1^{kddd}$ (residues 148-581 with K219A, D362A, and D384A). In line with our initial observations, SF21 expressed PINK1 activity is also amplified using KTP. In order to confirm that the observed phosphorylation activity derived from PINK1 and not a contaminating kinase we confirmed that $PINK1^{kddd}$ had no activity (FIG. 1F, and FIG. 6A), and were able to show that PINK1 could also autophosphorylate at a 1.84 fold higher $V_{max}$ with the neosubstrate KTP versus ATP (Table 1). Additionally we generated KTP with a $\gamma^{32}P$ labeled phosphate, and were able to see increased transphosphorylation of TRAP1 (FIG. 6C). SF21 expressed PINK1 also utilizes the $N^6$ FF ATP but not $N^6$ Benzyl or $N^6$ Phenethyl ATP as well to phosphorylate TRAP1. We confirmed that kdddPINK1 had no activity and were able to show that PINK1 could also autophosphorylate with a higher catalytic rate using the xeno-substrate $N^6$ FF ATP. PINK1 utilizes $N^6$ FF ATP with a 1.84 fold higher $V_{max}$ than ATP (Table 1). This is probably due to the higher $K_m$ observed for $N^6$ FF ATP (51.7 μM) over ATP (18.4 μM) as the release of ADP is the rate-limiting step in phosphate hydrolysis. Using a capture and release strategy pioneered by our lab, we were able to identify the T257 autophosphorylation site that was recently reported using $N^6$ FF ATPγS as a substrate.

We expressed GST tagged kinase domain ($PINK1_{156-496}$) in *E. coli* and performed a kinase assay. We saw that wtPINK1 was able to utilize ATP to phosphorylate a substrate protein TRAP1, and surprisingly also to utilize the $N^6$ Furfuryl ATP analog. To test the catalytic efficiency with these analogs, we incubated $wtPINK1_{156-496}$ and $G309DPINK1_{156-496}$ with $N^6$ FF ATP and a substrate protein TRAP1, and found that PINK1 appeared to use the N6 FF ATP analog more efficiently than ATP. In fact PD associated G309D mutant PINK1 that retains some kinase activity was also able to use this modified ATP analog with an increased catalytic rate than ATP. Taken together, these data suggest the ability to activate PINK1 by using this xeno-substrate as an alternative to ATP.

3. Co-Localization and Phosphorylation Assays

Parkin phosphorylation and mitochondrial translocation assay: HeLa cells were grown in DMEM supplemented with 10% FBS. Log phase cells were plated in 24 well plates with glass coverslips (Mattek) pretreated with fibronectin. Cells were pretreated with 50 μM of the indicated compound, followed by transfection with MitoGFP, mCherry Parkin, and full length $PINK1FLAG_3$ in a 1:4:2 ratio using Fugene 6 (Promega). Fields of cells were selected by expression of MitoGFP (6 fields/well-3 wells/condition) and imaged at five-minute intervals following depolarization with 5 μM CCCP. Quantification was performed according to published protocols[3] and by creation of a Matlab based script.

Our ability to enhance PINK1 activity in-vitro using KTP led us to investigate means by which to achieve enhanced activity in cells expressing PINK1. ATP analogs are not membrane permeable; however, previous work has shown that cytokinins like kinetin (nucleobase precursor to KTP) can be taken up by human cells and converted to the triphosphorylated form[24]. We treated cells with either kinetin or adenine (FIG. 2A) and measured Parkin localization following mitochondrial depolarization with CCCP (FIG. 2B). HeLa cells, which have low levels of endogenous PINK1 and PARKIN, were transfected with wildtype or $PINK1^{G309D}$, mCherryParkin, and mitoGFP. After 48 hours of incubation with 25 μM adenine, kinetin or equivalent DMSO, we imaged CCCP-mediated depolarization of mitochondria (FIGS. 2C, 2D) and calculated the percentage of GFP labelled mitochondria with mCherryParkin associated (FIG. 2E). In line with previous reports[3], transfection of $PINK1^{G309D}$ slowed the 50% recruitment ($R_{50}$) time of mCherryParkin to depolarized mitochondria (23±2 min vs 15±1 min $R_{50}$) (FIGS. 2C-2E Table.2). The addition of kinetin, but not adenine, increased the $R_{50}$ for mCherryParkin $PINK1^{G309D}$ cells from 23±2 to 15±2 min and surprisingly also increased the $R_{50}$ for $PINK1^{wt}$ cells from 15±1 to 10±2 min (FIG. 2E). Using an algorithm to accurately quantify the time dependent change in co-localization, we calculated that $PINK1^{wt}$ expressing cells achieved a mean change in co-localization of 0.112 with DMSO or adenine and 0.13 with kinetin treatment (FIGS. 7A-7F); $PINK1^{G309D}$ expressing cells treated with DMSO or adenine achieved delta co-localization of 0.076, but upon addition of kinetin returned to near-PINK1-wildtype levels (0.124). These results suggested near-complete rescue of $PINK1^{G309D}$ activity using kinetin. Two-way ANOVA analysis revealed that kinetin has an effect in both cases (wt; F=24.10 p<0.0001, G309D; F=54.14, p<0.0001). Importantly, N6 benzyl adenine, which was not as active in-vitro, is also less active than kinetin in cells (FIGS. 8A-8D)

Figure 2F:
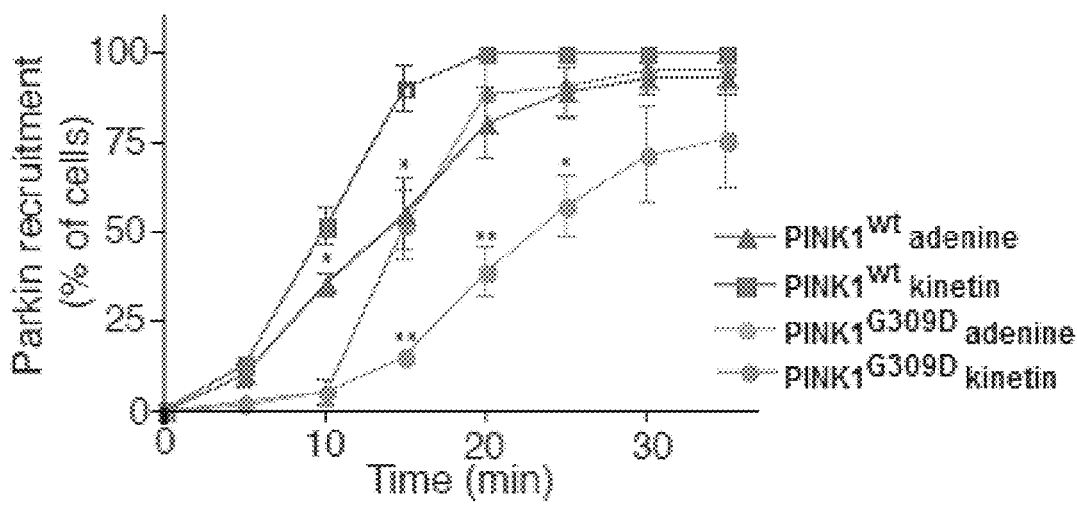
Figure 2G:
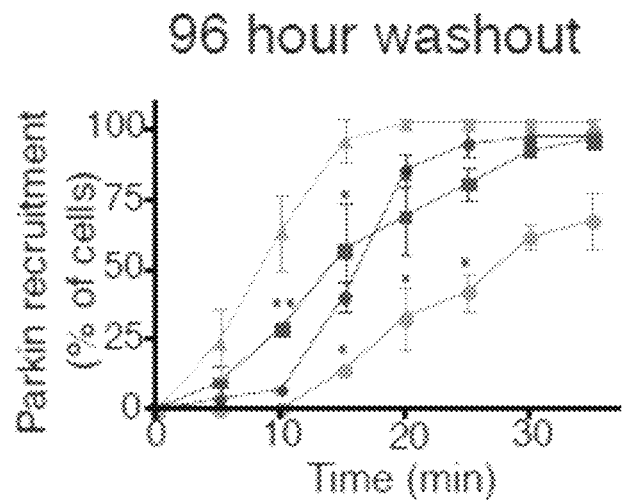
Figure 2H:
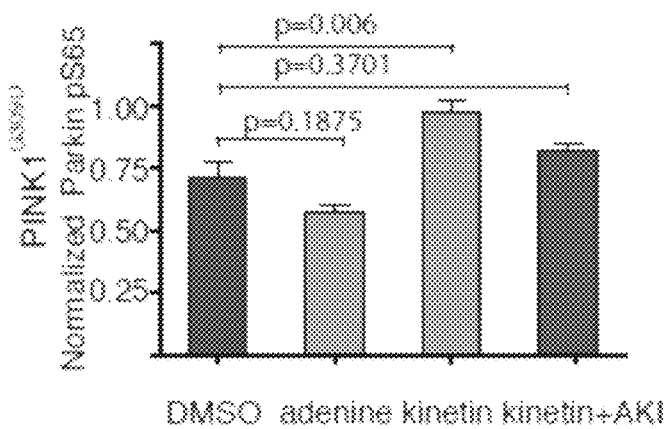
Figure 2I:
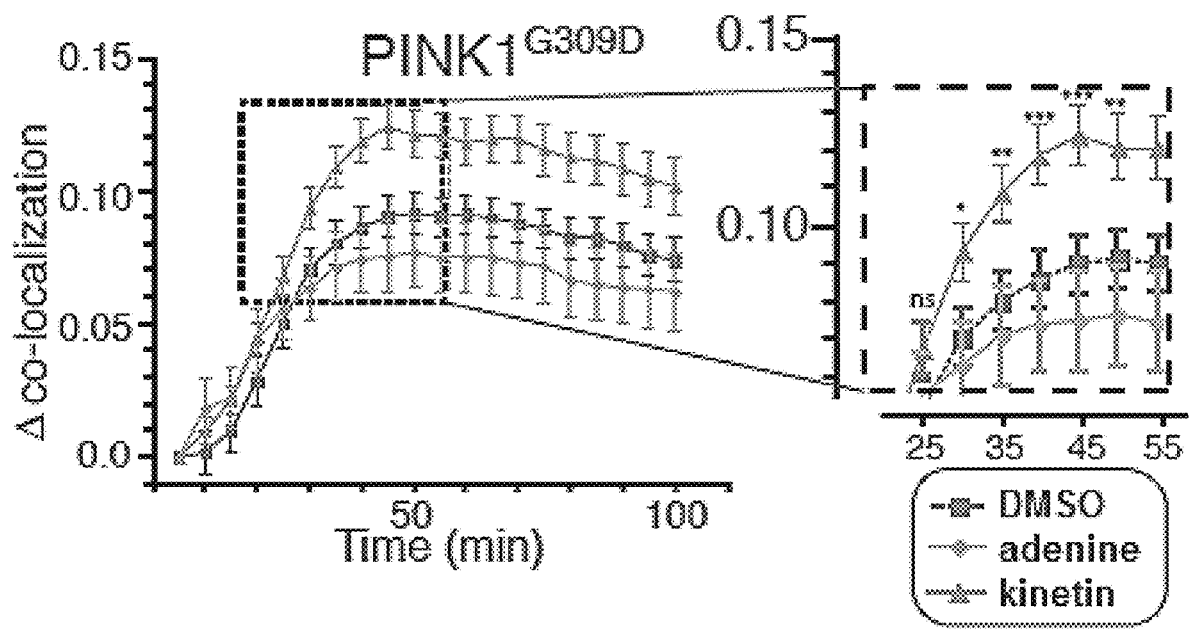
Figure 7A:
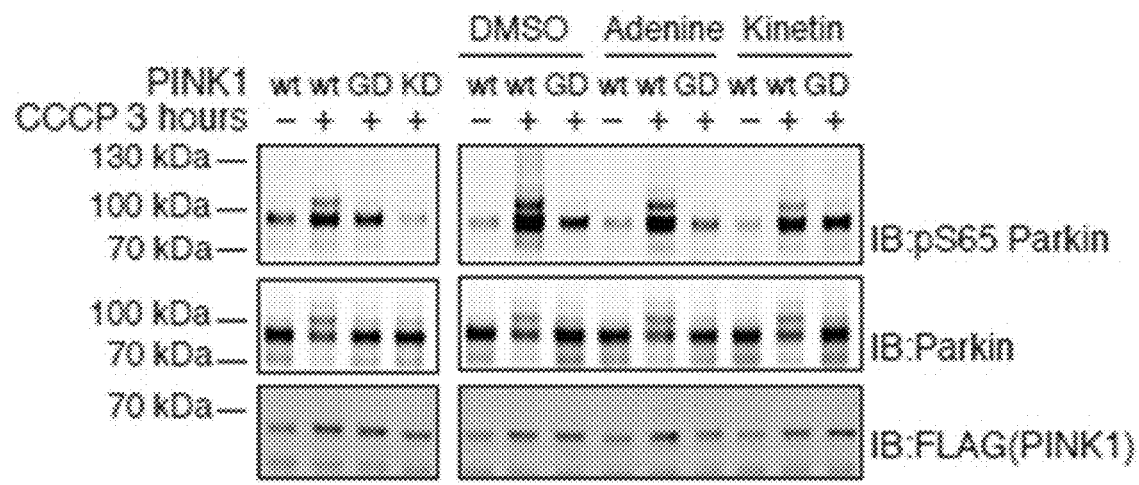
FIGS. 7A-7F. Using an algorithm to accurately quantify the time dependent change in co-localization.
Figure 7B:
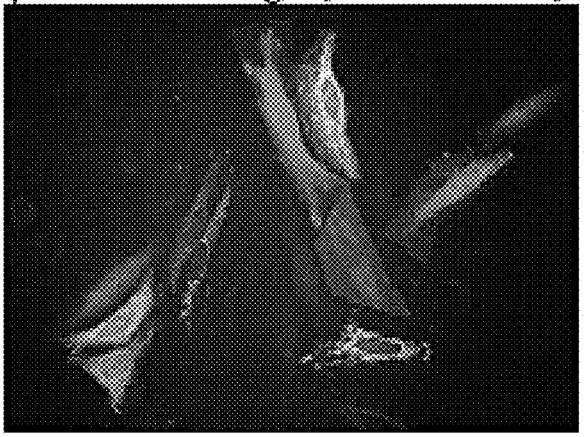
Figure 7C:
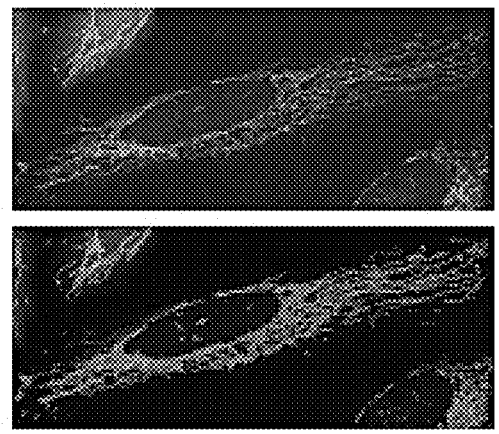
Figure 7D:
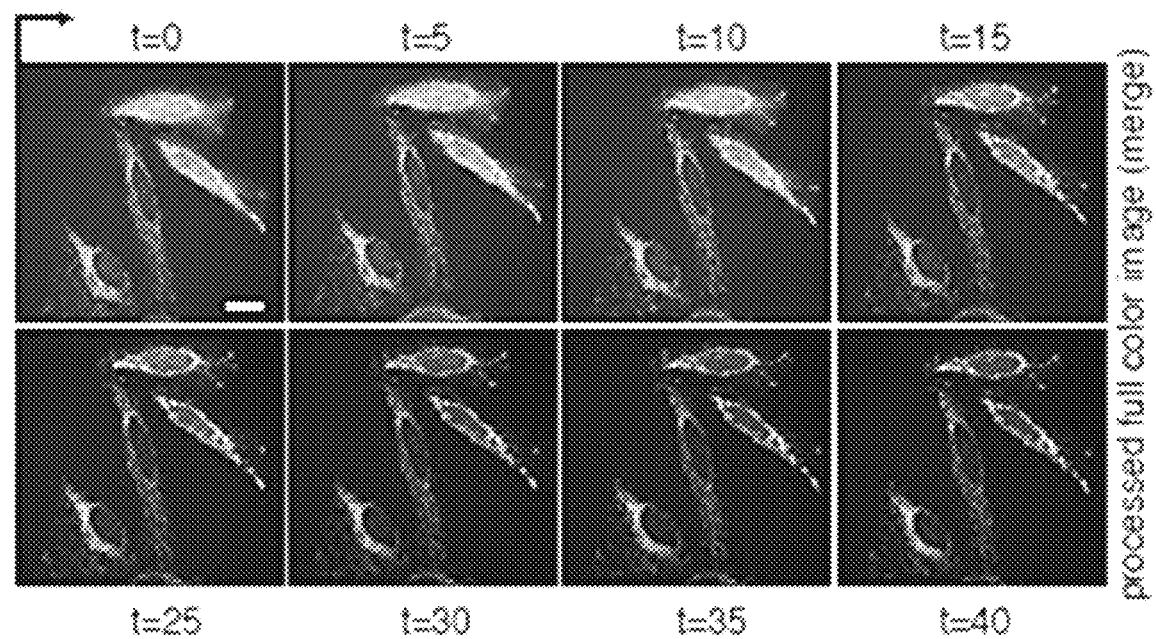
Figure 7E:
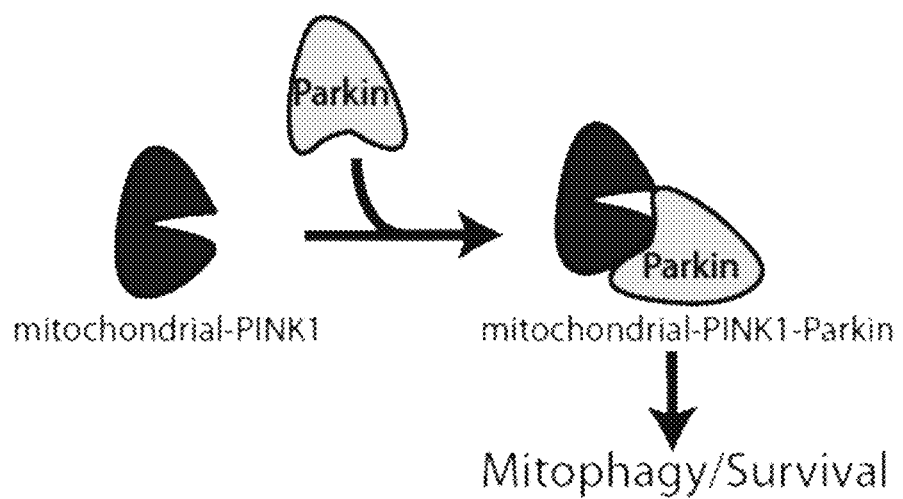
Figure 7F:
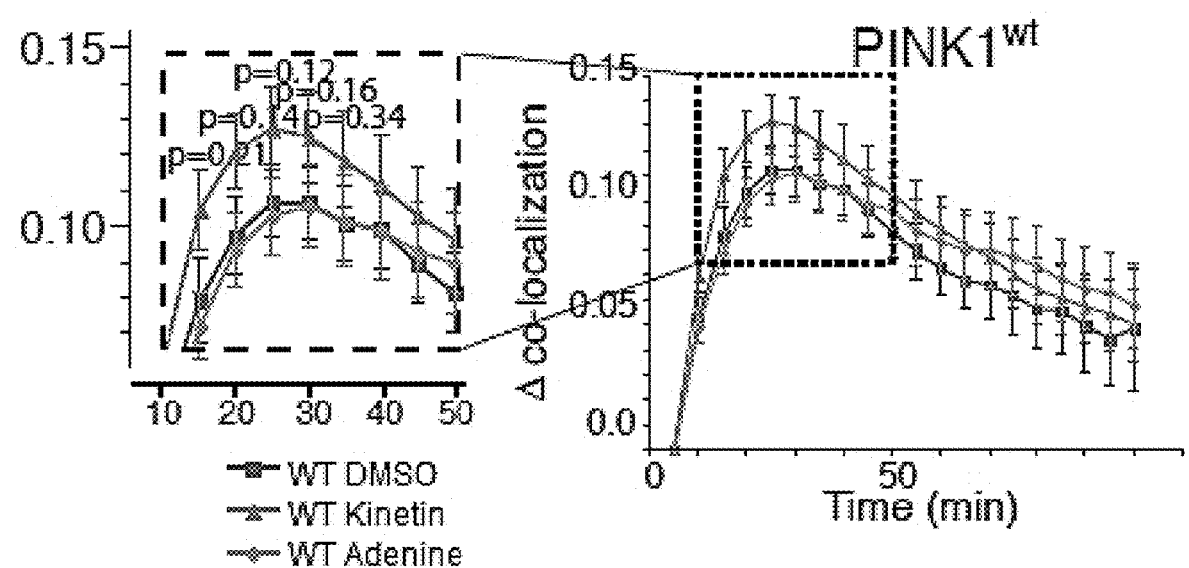
Figure 8A:
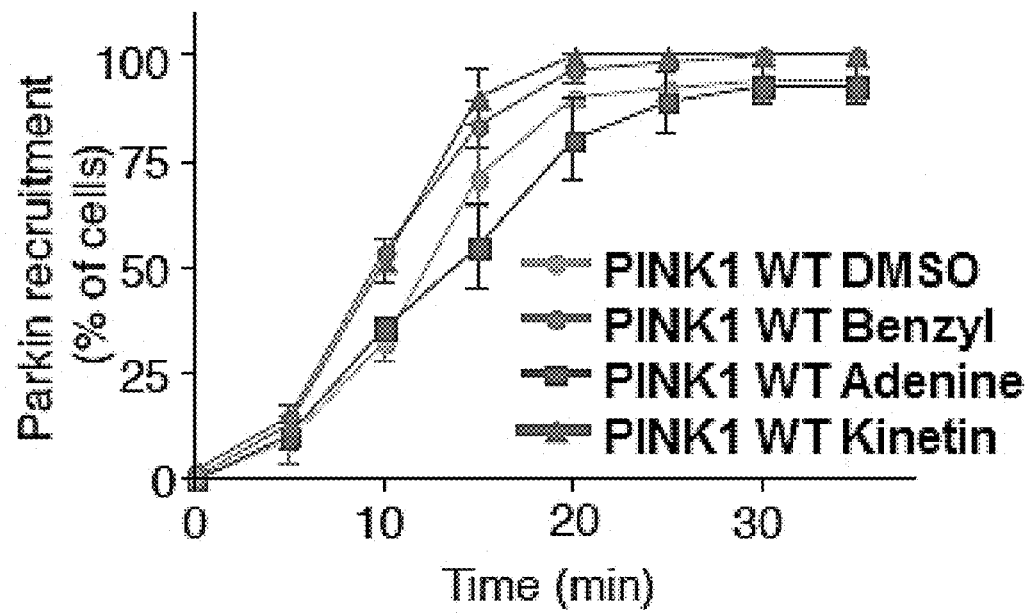
FIGS. 8A-8D. N6 benzyl adenine, which was not as active in-vitro, is also less active than kinetin in cells.
Figure 8B:
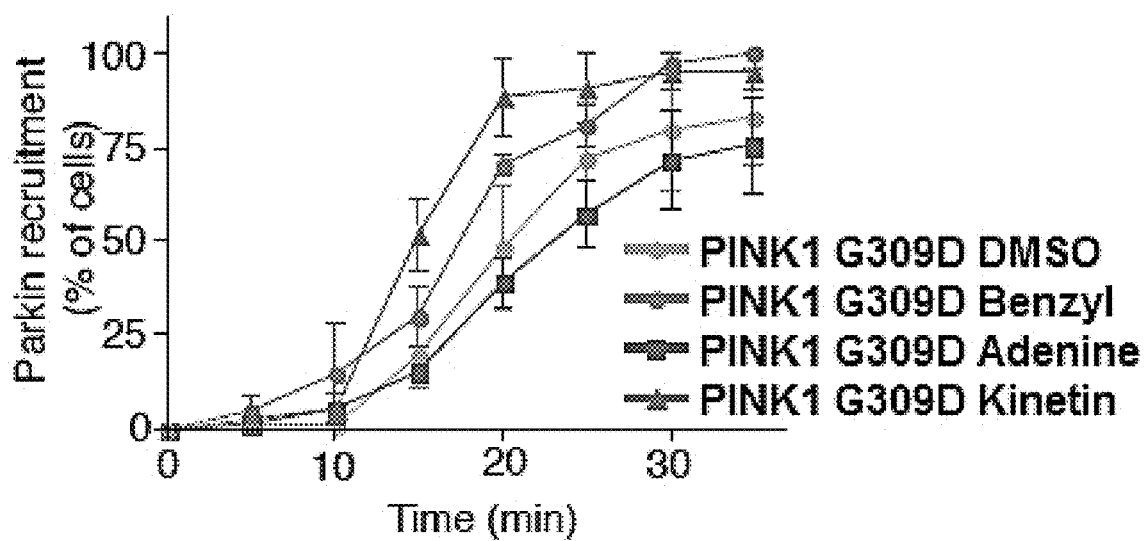
Figure 8C:
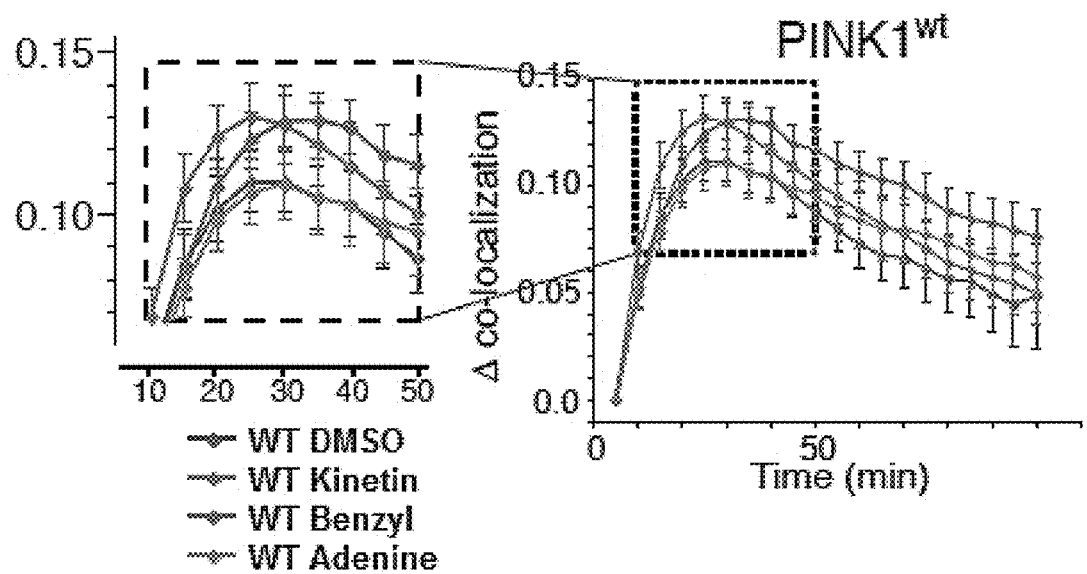
Figure 8D:
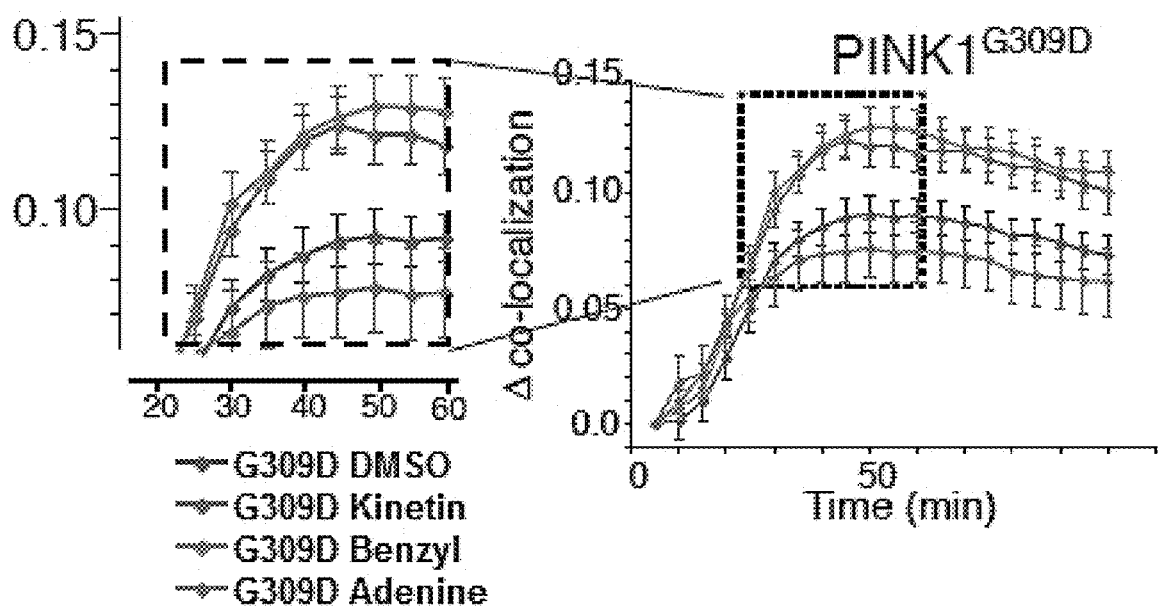
Figure 9A:
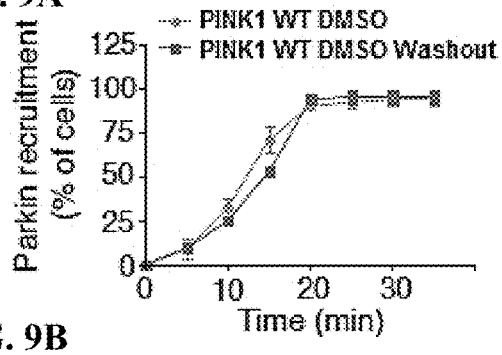
FIGS. 9A-9F.
Figure 9B:
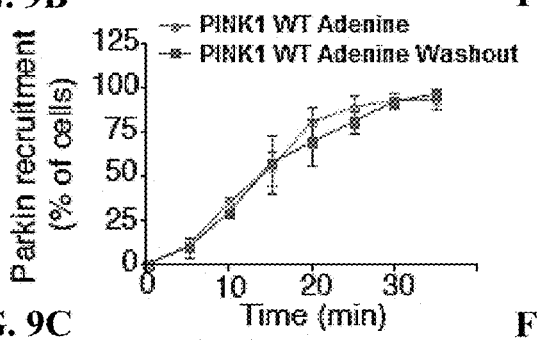
Figure 9C:
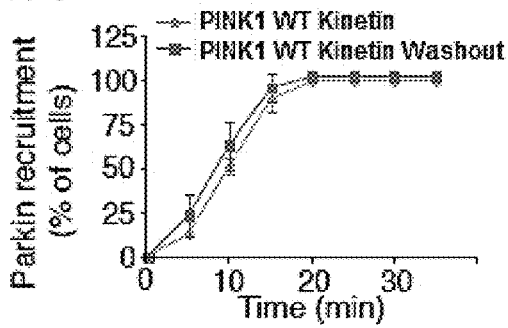
Figure 9D:
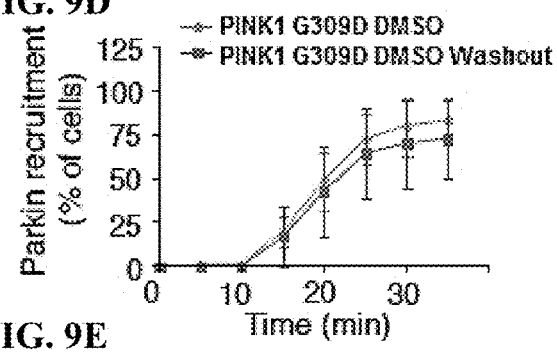
Figure 9E:
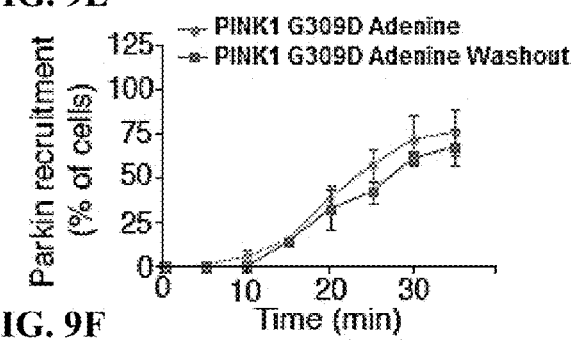
Figure 9F:
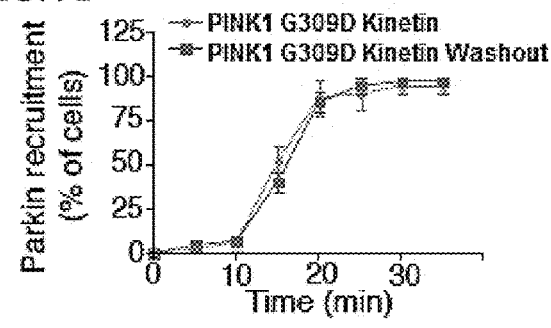
Figure 12:
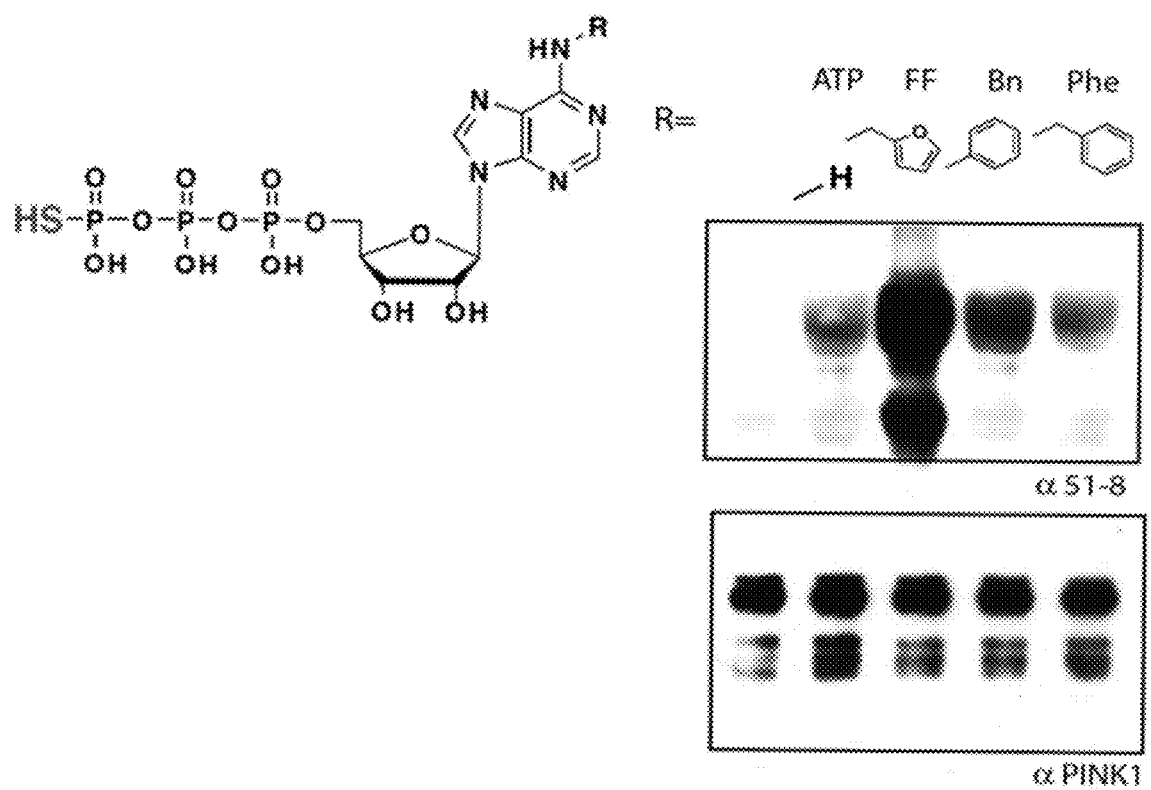
FIG. 12. PINK1 activity is stimulated by Furfuryl ATP better than some other N6 substituted ATP analogs.
Figure 13:
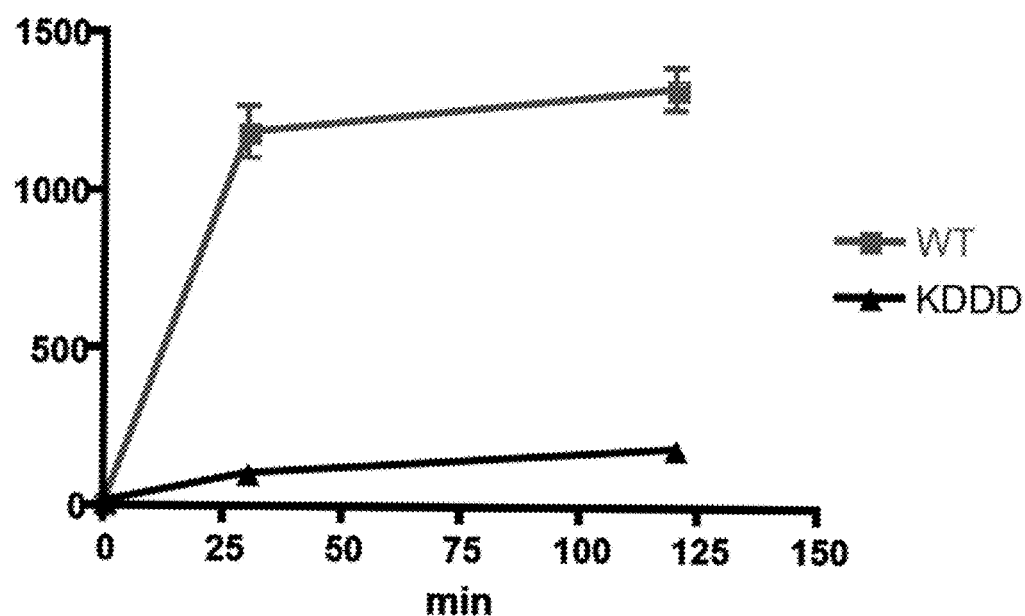
FIG. 13. PINK1 could also autophosphorylate with a higher catalytic rate using the xeno-substrate $N^6$ FF ATP.
Figure 14A:
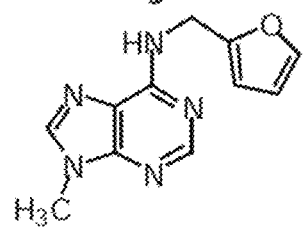
FIGS. 14A-14C.
Figure 14B:
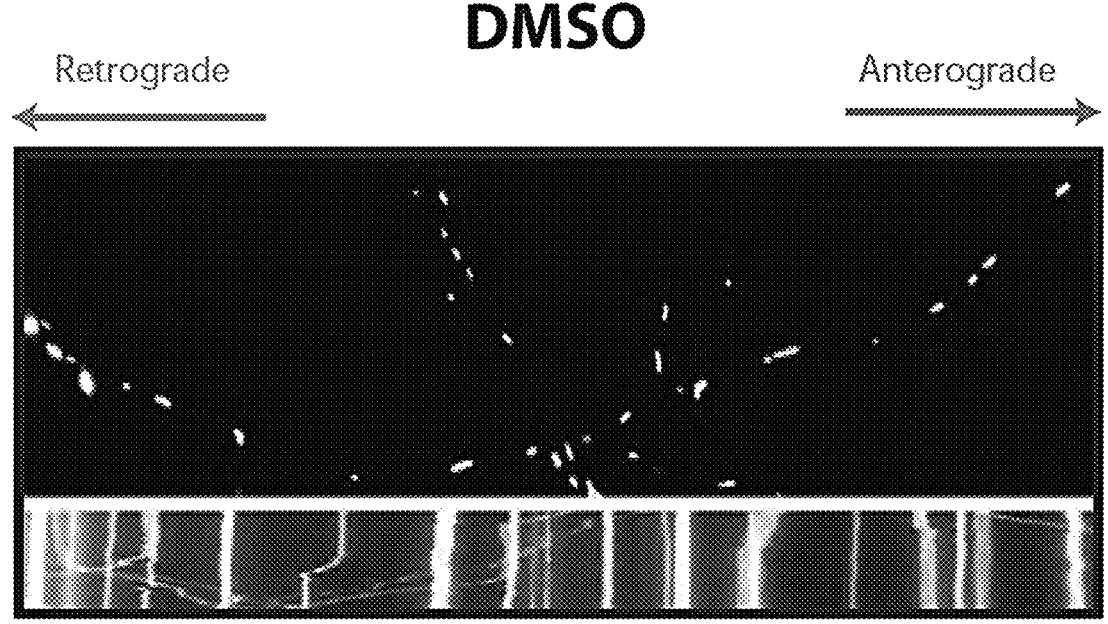
Figure 14C:
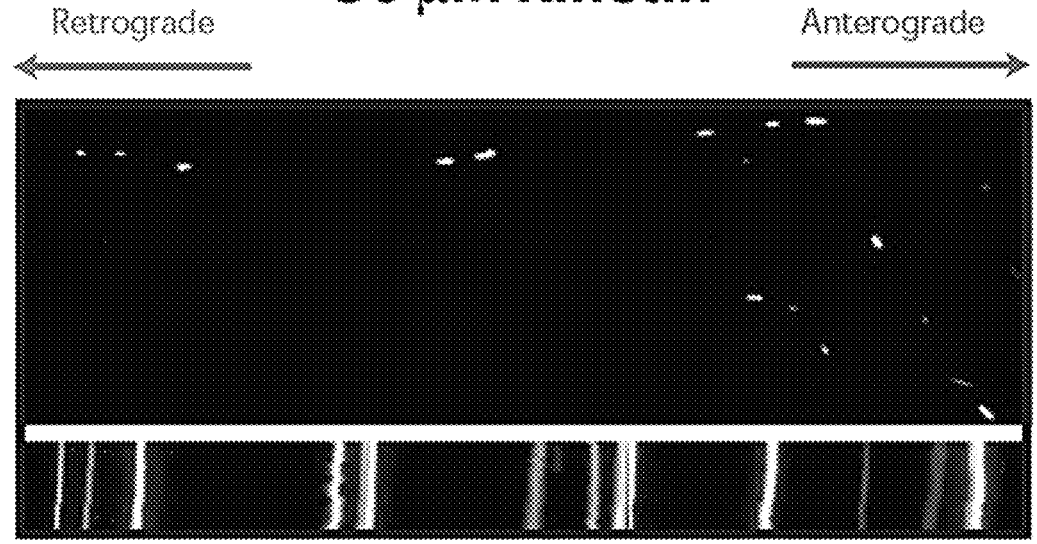
Figure 15A:
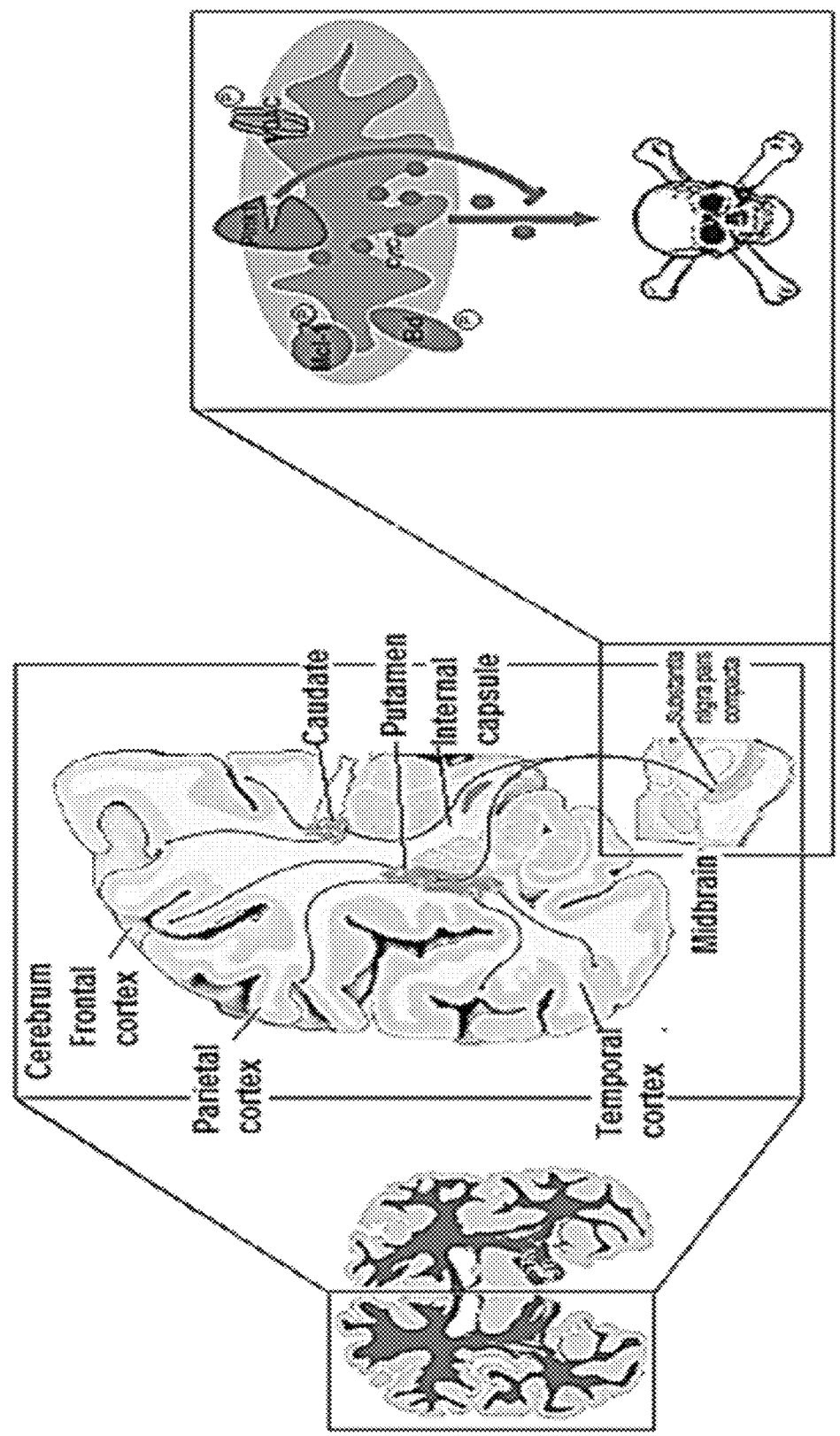
FIGS. 15A-15D. Oxidative stress leads to apoptosis of dopaminergic (Da) neurons.
Figure 15B:
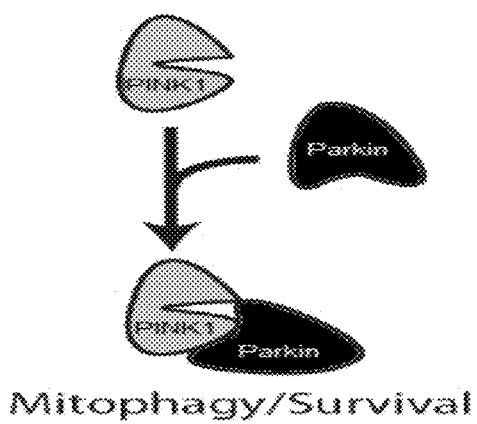
Figure 15D:
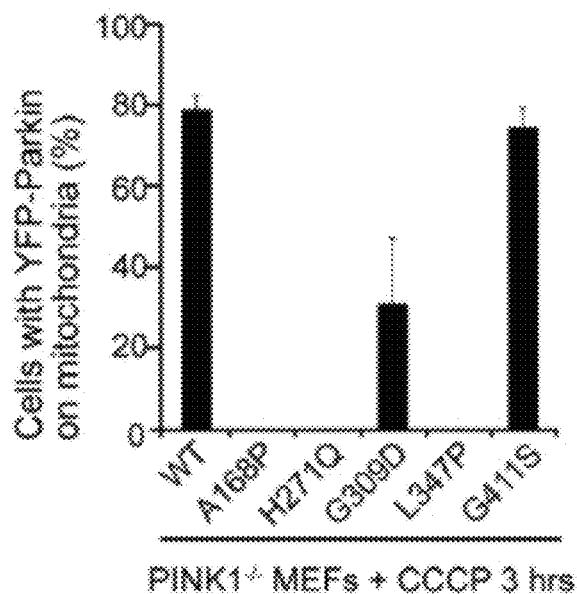
Figure 15C:
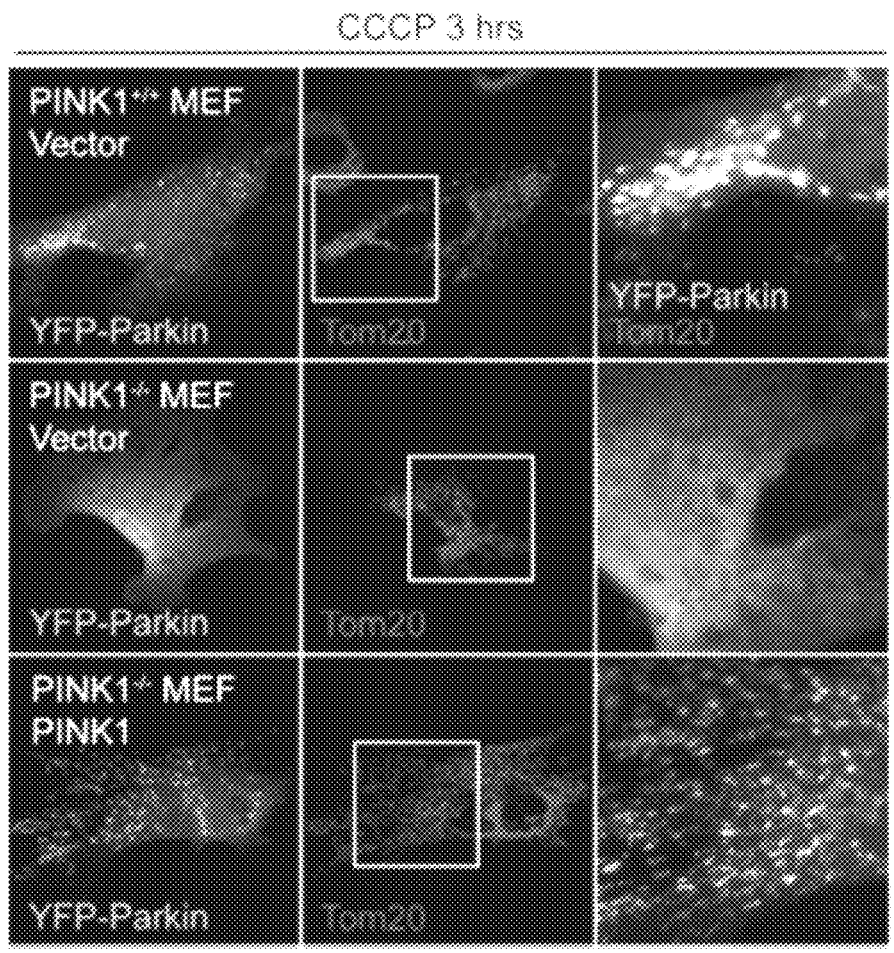
Figure 18:
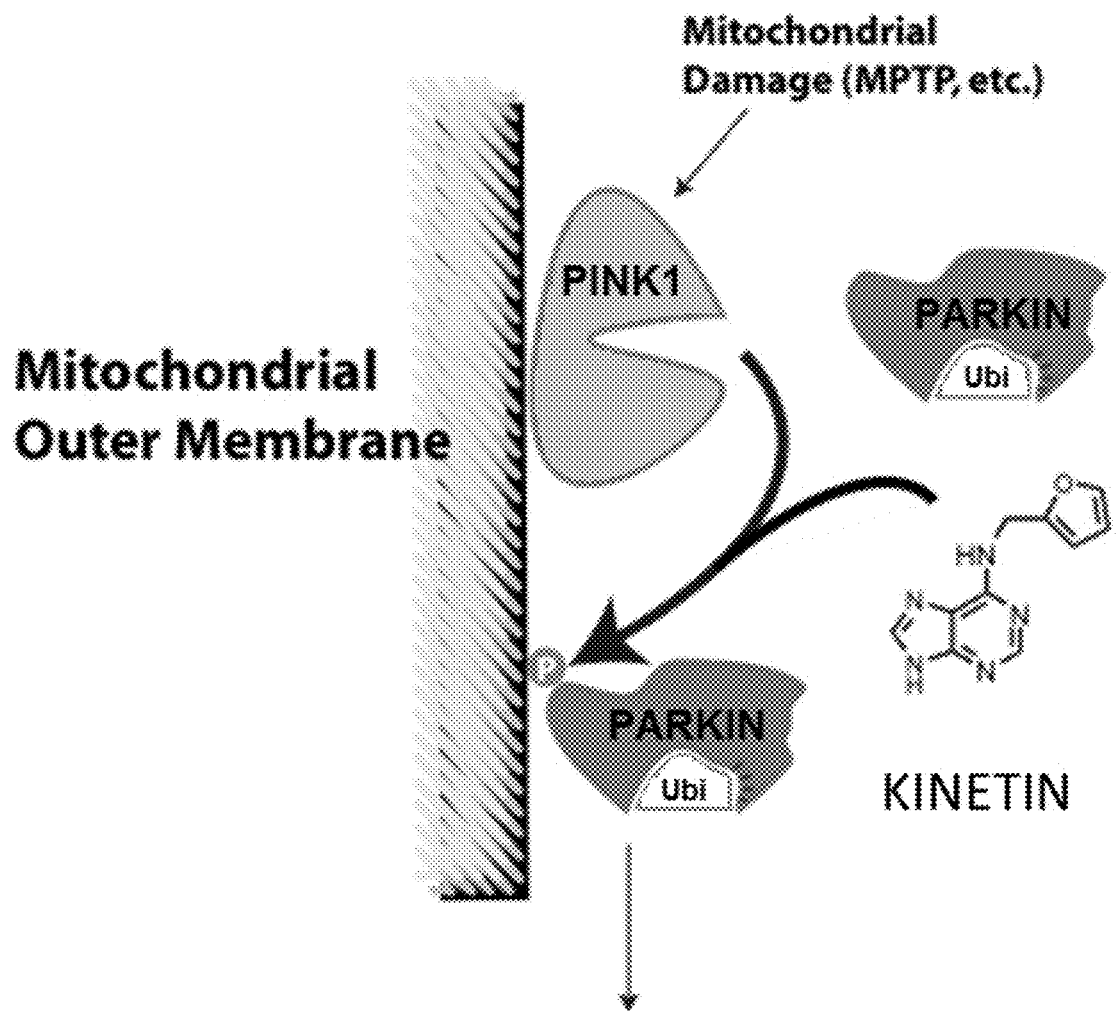
FIG. 18. Schematic depticting PINK1 associated functions and possible mechanisms of modulation.
Figure 19:
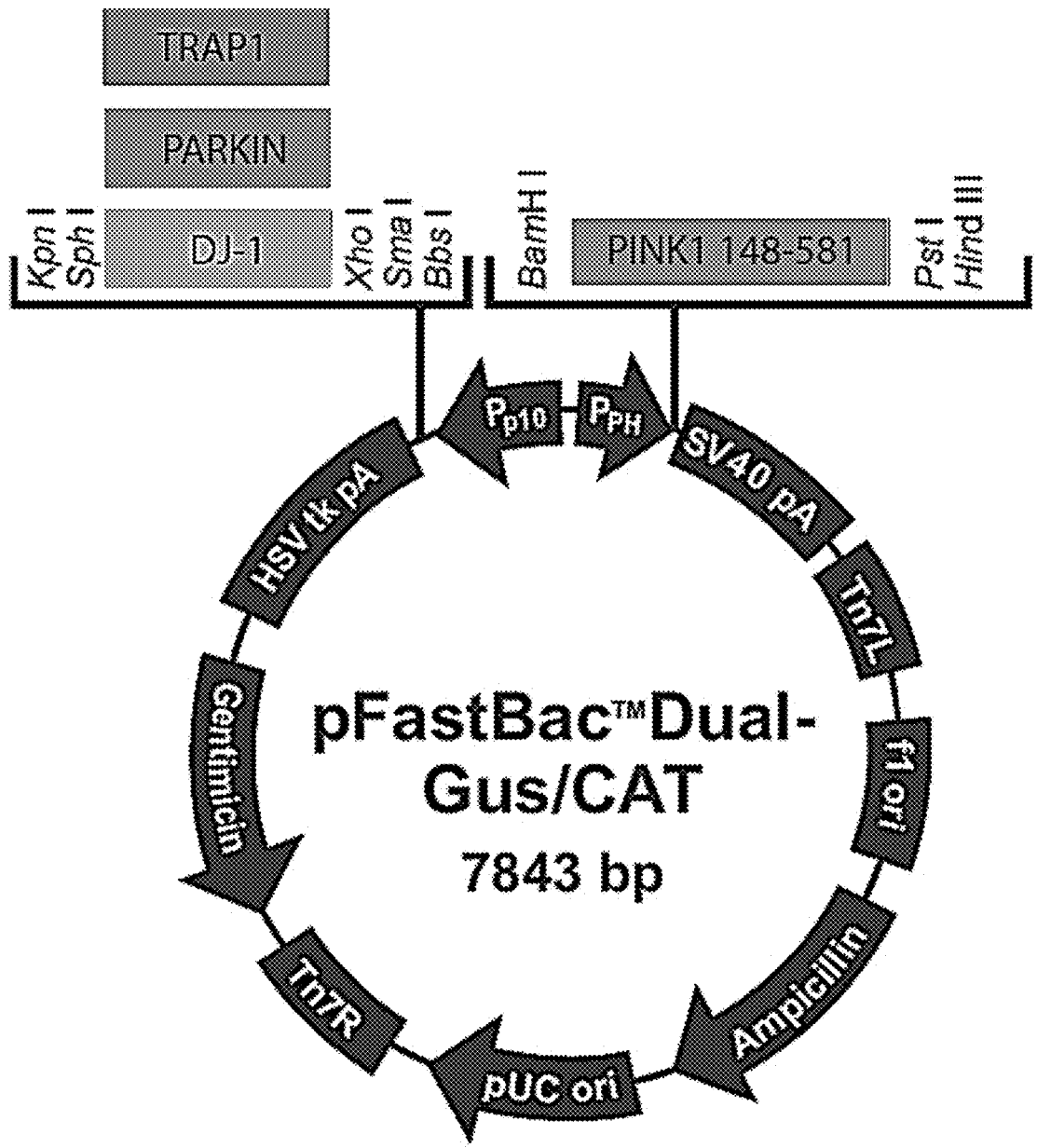
FIG. 19. Robust expression system for PINK1 tested with a c-Terminal 3× FLAG tag, residues 148-581, co-expressed with TRAP1 or Parkin.
Figure 20:
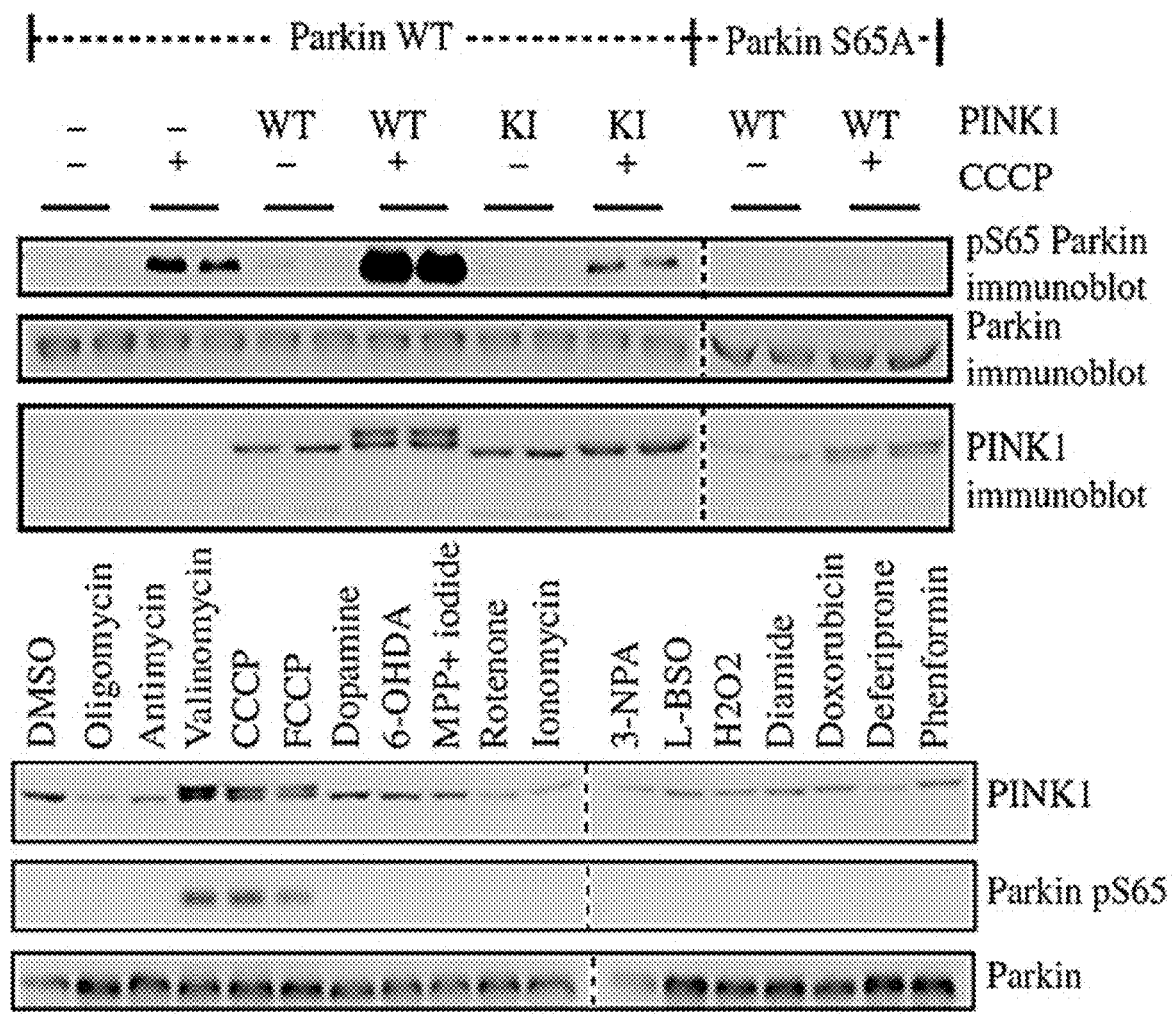
FIG. 20. In-cell readout for PINK1 activity-PINK1 phosphorylates Parkin at Serine 65 where Parkin is phosphorylated in response to mitochondrial depolarizing agents.
Figure 21:
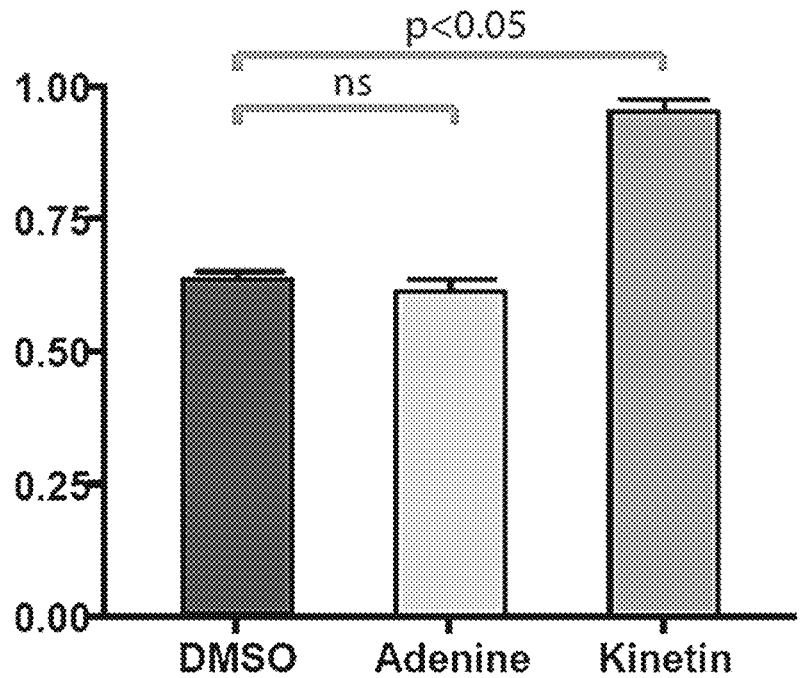
FIG. 21. Robust increase in the level of phosphorylation of Parkin in PINK1 G309D mutant expressing cells upon treatment with kinetin followed by depolarization with CCCP.
Figure 22:
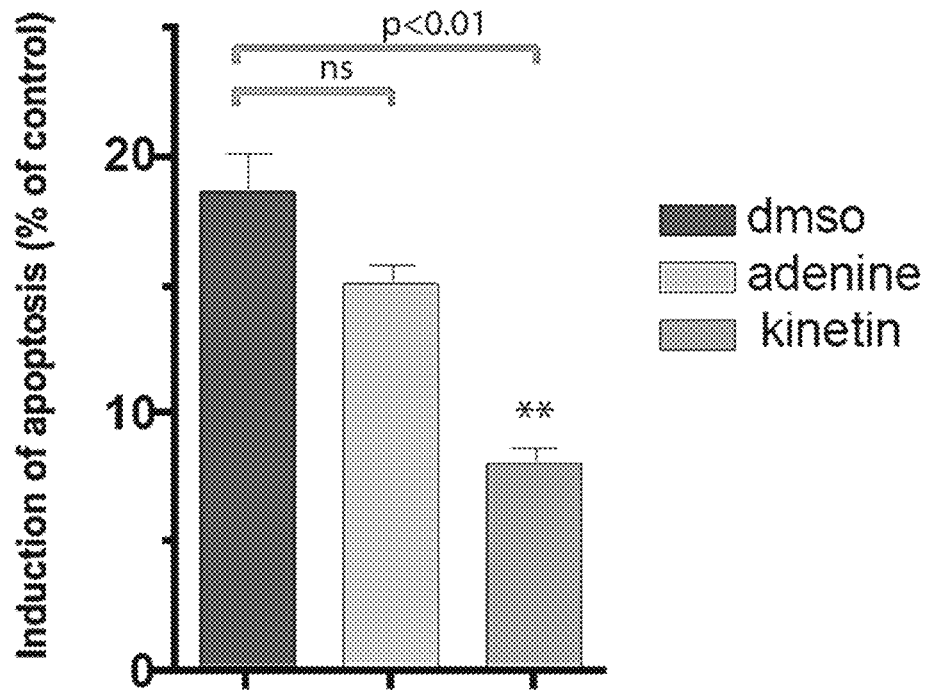
FIG. 22. Decrease in the total number of apoptotic cells after 48 hours of treatment with kinetin followed by 24 hours of 400 uM hydrogen peroxide treatment.
Figure 23:
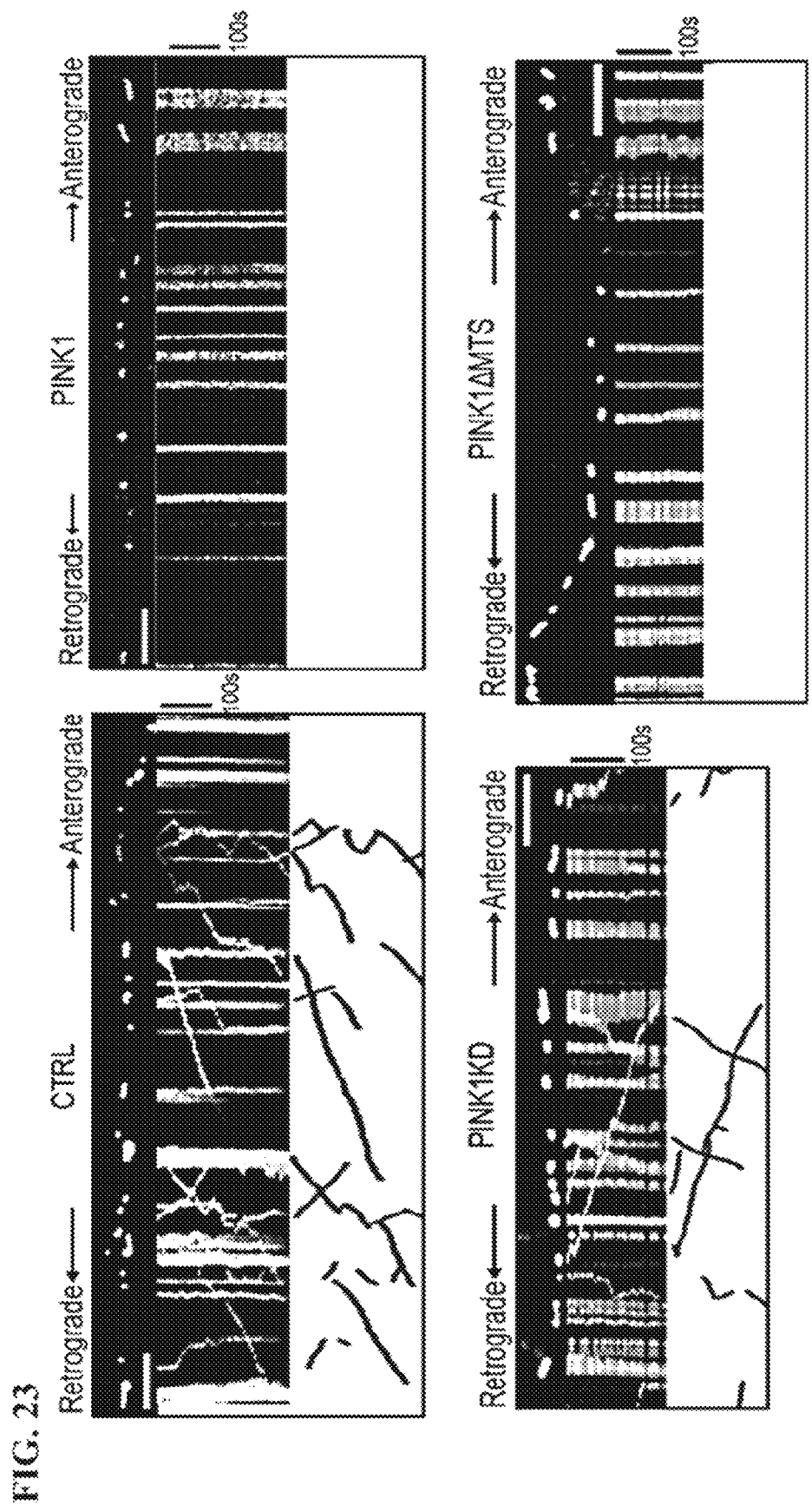
FIG. 23. PINK1/Parkin control mitochondrial motility along axons of hippocampal neurons where increased wt-PINK1 expression blocks mitochondrial transport.
Figure 24:
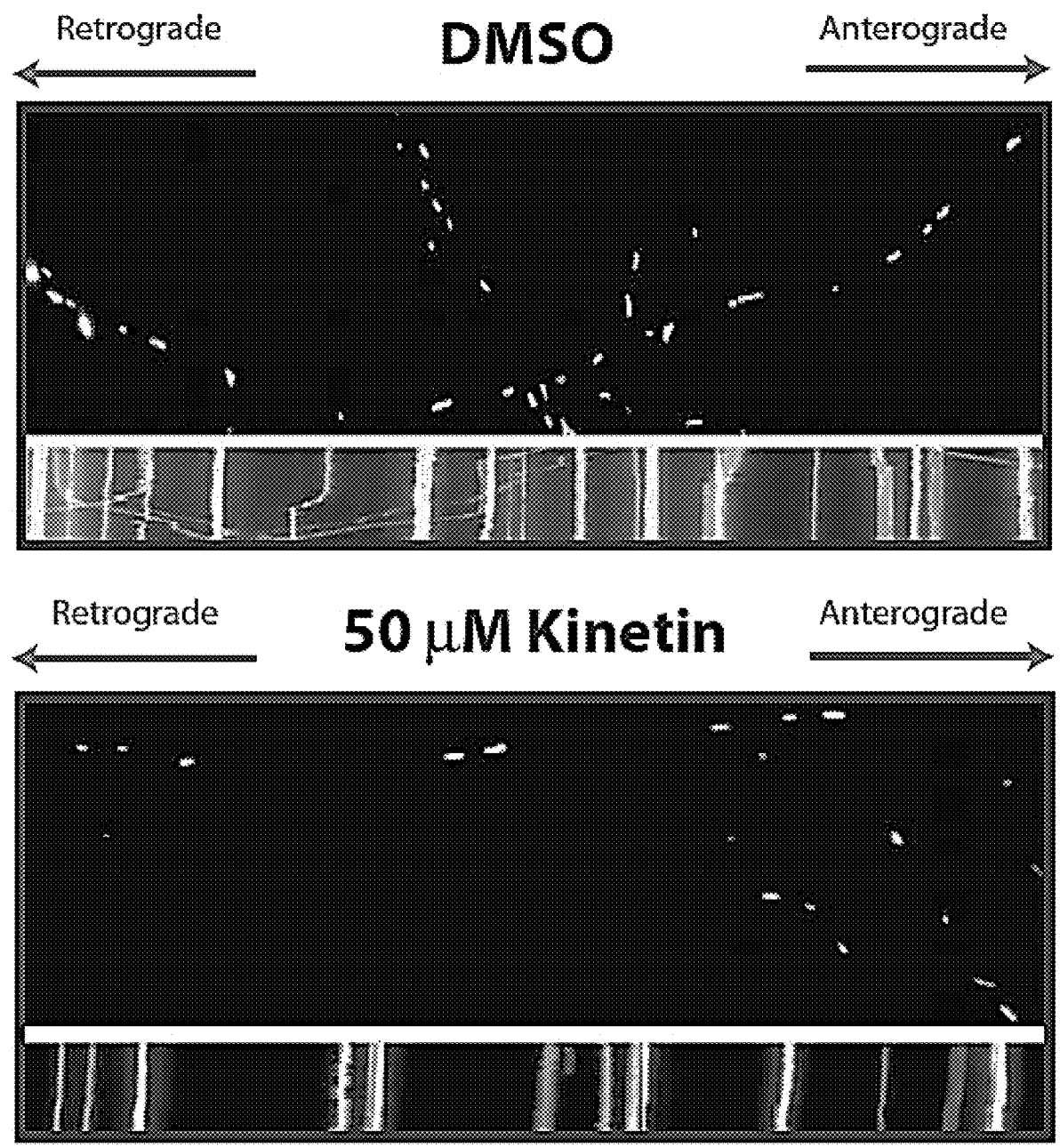
FIG. 24. Kinetin activates PINK1 to halt mitochondrial motility: Kinetin has no effect on mitochondrial motility in PINK1 KO neurons.
Figure 25:
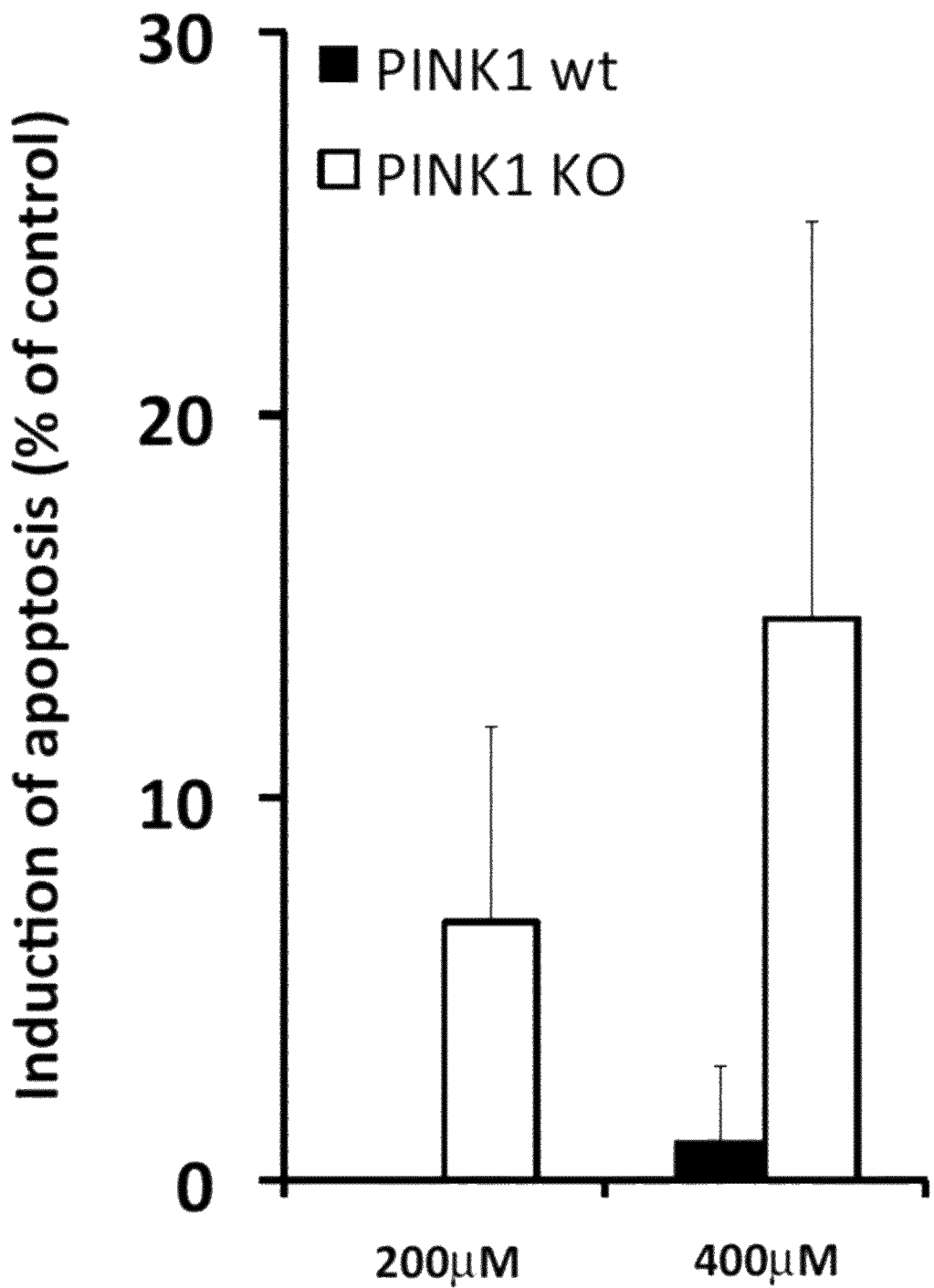
FIG. 25. PINK1 KO MEFs undergo increased apoptosis in response to $H_2O_2$ treatment: Annexin V FACS assay reveals increased apoptosis in PINK1 KO MEFS. This assay was done with P3 MEFS, higher passage MEFS did not respond to hydrogen peroxide or drug treatment.
Figure 26:
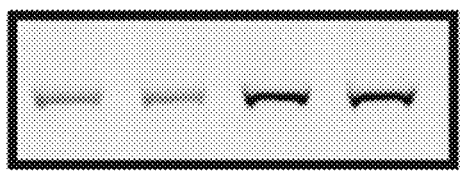
FIG. 26. Generating PINK1 shRNA lentivirus to test kinetin specificity in SH-SY5Y cells: PINK1 knockdown in SH-SY5Y leads to an increase in PARP cleavage in response to CCCP—Kinetin blocks apoptosis in SH-SY5Y cells and cells are well behaved for FACS assays.

To test the PINK1-dependency of our findings, we assayed PINK1 activity by using phospho specific antibodies raised against Parkin's PINK1-specific S65 phospho-site[21] after immuno-precipitating Parkin. We observed a robust increase in the phosphorylation levels of Parkin following CCCP treatment in a PINK1-dependent manner (FIG. 7A). In a finding that supported our earlier co-localization results, we also found that the addition of a neo-substrate kinetin (p=0.04; t-test), but not adenine (p=0.1875; t-test), to PINK1$^{G309D}$ mutant expressing cells significantly increased the phosphorylation levels of Parkin (FIG. 2G). The addition of an adenosine kinase inhibitor (AKI) blocking the conversion of kinetin to KTP prevented this effect (p=0.3701; t-test) (FIG. 2G, and FIG. 7A). To test whether kinetin stimulated Parkin localization was due to reversible binding of kinetin to PINK1, we treated the cells with fresh medium for 96 hours before performing a new recruitment assay. Similar recruitment rates were observed following the washout (FIG. 2F). These data suggest the buildup of a membrane impermeable metabolite like KTP that activates PINK1 in cells. We followed previously published methods to calculate the percentage of GFP labeled mitochondria with mCherryParkin associated. Transfection of G309DPINK1$_{1-581}$ slowed the rate of mCherryParkin recruitment (23+2 min vs 15+1 min R$_{50}$) as per reported results. The addition of kinetin, but not adenine, increased the rate of mCherryParkin recruitment in wt cells from 15+1 to 10+2 min and G309D cells from 23+2 to 15+2 min. We then incubated the cells with kinetin for 2 days, washed the cells with fresh medium then performed the recruitment assay and saw the same increase in the rate of recruitment. This suggests the buildup of a membrane impermeable metabolite that can activate PINK1 in cells. We developed an algorithm to calculate the change in co-localization. The wtPINK1 cells achieved a mean change in co-localization of 0.11 with DMSO, adenine or kinetin treatment. G309DPINK1 expressing cells treated with DMSO or Adenine, achieved delta co-localization of 0.075 but upon addition of kinetin indicating rescue to the wt level (0.11) (P>0.05). These data suggest the activation of PINK1 by utilization of an introduced xeno-substrate in mammalian cells.

4. Mitochondrial Motility, Cell Survival, and Apoptosis

Figures 3A, 3B, 3C, 3D, 3E:
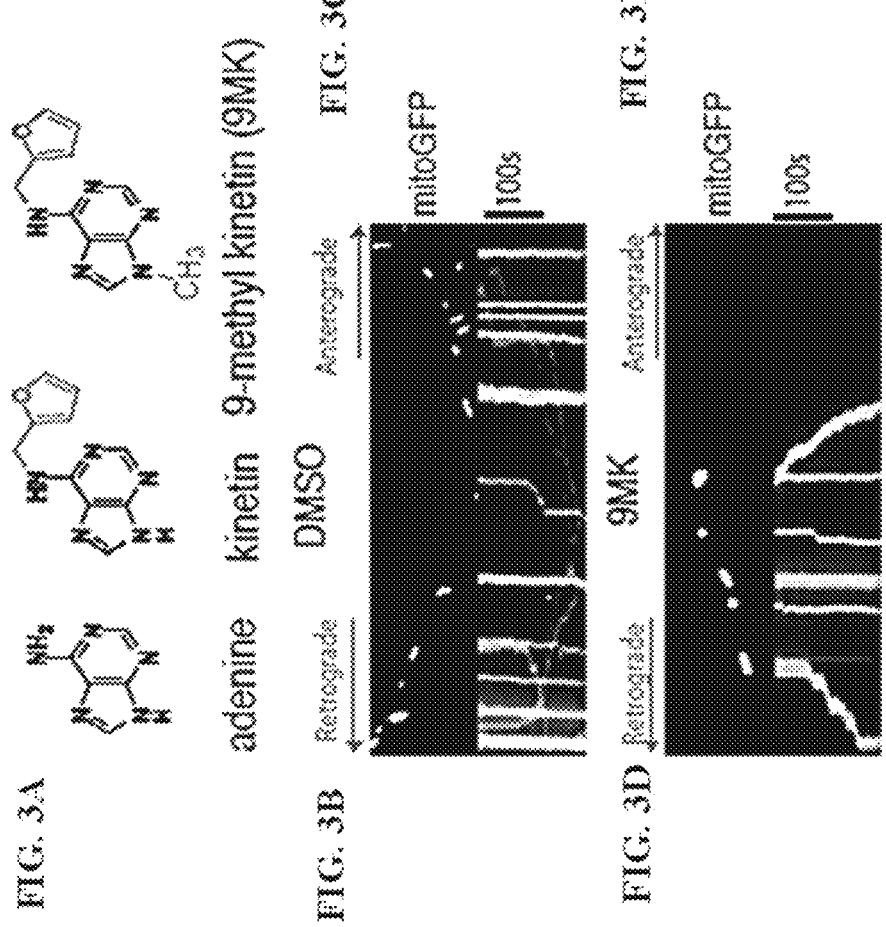
FIGS. 3A-3I. Kinetin halts axonal mitochondrial motility in a PINK1 dependent manner.

Mitochondrial motility assay: Primary hippocampal neuronal cultures were co-transfected with mitochondrial targeted GFP (mitoGFP) and mCherry-tagged synaptophysin (mCherrySynaptophysin) to allow for the live identification of mitochondria in axons. Cells were pre-treated for 48 hours with 50 µM Kinetin, adenine or equivalent DMSO and mitochondrial motility was imaged live and kymographs were generated (FIG. 3A) using approaches similar to those described previously[4].

Apoptosis assays and PINK1 shRNA: SH-SY5Y cells (ATCC) were cultured in 1:1 mix of F12K and DMEM supplemented with 20% FBS. PINK1 shRNA lentivirus were produced using a pLKO.1 based shRNA (Sigma) by contransfection with Δ8.9 and pMGD2 vectors in HEK293T cells. SH-SY5Y cells were infected with lentivirus followed by selection with puromycin (0.5 mg/ml). The indicated cells were plated in 6-well plates at about 500,000 cells/well, pretreated with 50 µM of the indicated drug or DMSO for 96 hours followed by 400 µM H$_2$O$_2$ treatment. Subsequently, cells were stained with Annexin V-FITC and PI and analyzed (FACS Diva) on a FACS LSRII Cytometer (Beckman Coulter) Apoptosis was calculated as the difference between H$_2$O$_2$ treated samples and the respective control.

Figure 3F:
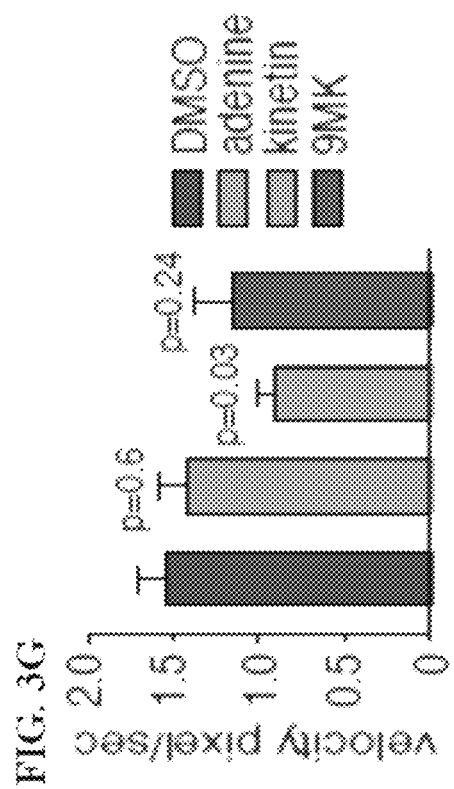
Figure 3G:
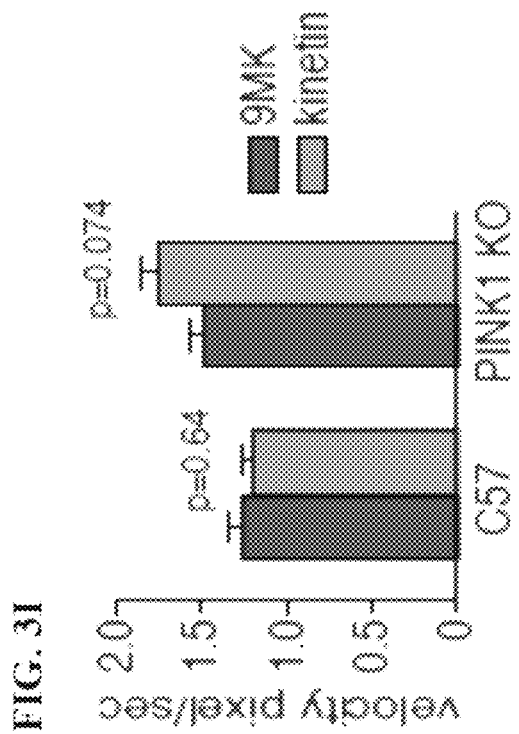
Figure 3H:
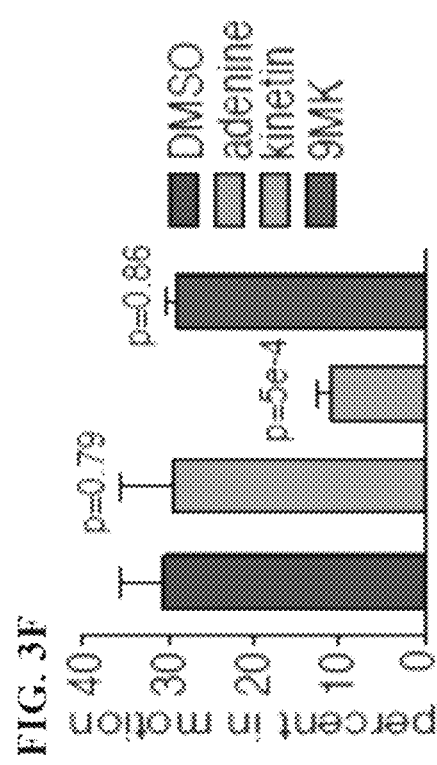
Figure 3I:
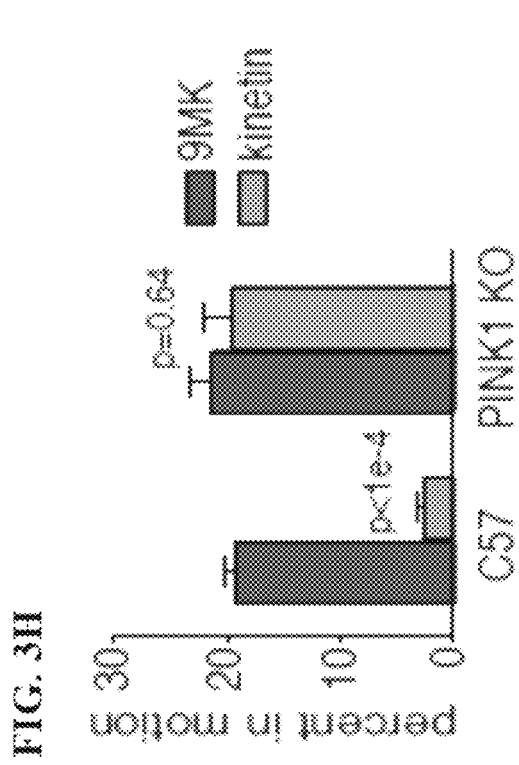

Overexpression of PINK1 in primary neurons leads to loss of mitochondrial trafficking in axons. These effects appear to precede any PINK1 effect on mitophagy, and depend on PINK1 phosphorylation of Miro[4]. To test if kinetin decreases motility we examined the mobility of axonal mitochondria in hippocampal neurons. Primary hippocampal neuronal cultures were co-transfected with mito-GFP and mCherry-tagged Synaptophysin (mCherrySynaptophysin) to allow for the live identification of mitochondria in axons. Cells were pre-treated for 48 hours with 50 µM Kinetin, adenine, or equivalent DMSO, and mitochondrial motility was imaged live and kymographs were generated (FIGS. 3A-3D) using approaches similar to those described previously[4]. We found that kinetin potently and specifically inhibited mitochondrial movement (p=0.0005; t-test)(FIGS. 3E-3F) in rat hippocampal neurons. In contrast, kinetin analog 9-methyl-Kinetin (9MK)(FIGS. 3A, 3D, 3F), which cannot be converted to a tri-phospho form, did not affect mitochondrial motility (p=0.86; t-test). Kinetin also has an effect on velocity of mitochondria that remain in motion (p=0.03; t-test), and this reflects a decrease in the velocity of mitochondria in the retrograde direction (p=0.0026; t-test) not in the anterograde direction (p=0.3644; t-test)(FIG. 10A), suggesting that the velocity of damaged mitochondria in the direction of the nucleus is modified. To test the PINK1 dependency of this process, we treated control mouse C57 (PINK1 wildtype) and PINK1 knockout derived hippocampal neurons with kinetin or 9MK and imaged their mitochondria. Similar to rat derived neurons, we observed a significant (p<0.0001; t-test) decrease in motility in C57 derived neurons, but no change in motility when PINK1−/− derived neurons were treated with kinetin (FIG. 3H) (p=0.64; t-test) or 9MK. These data suggest that kinetin can block mitochondrial motility in a PINK1 dependent manner and that the metabolism of kinetin to KTP is necessary and sufficient for this effect.

Figure 4A:
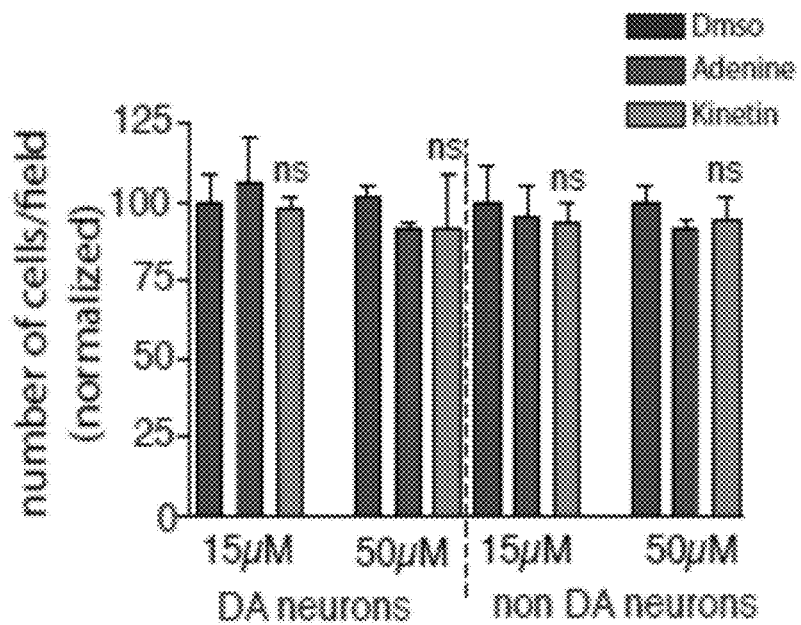
FIGS. 4A-4F. Kinetin blocks oxidative stress induced apoptosis in human SH-SY5Y cells.
Figure 4B:
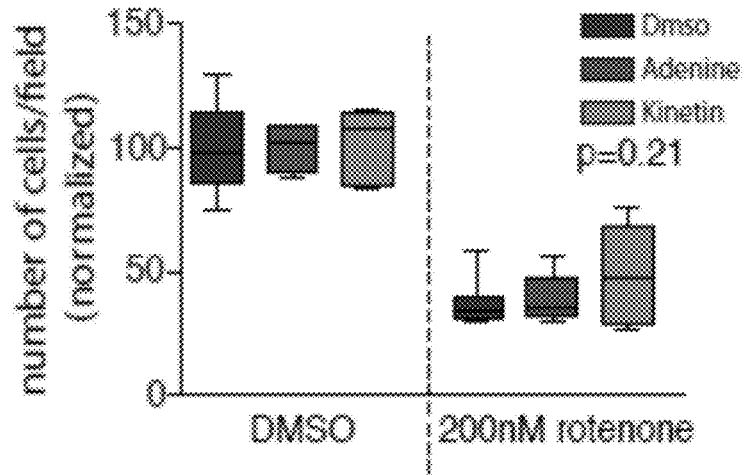
Figure 4C:
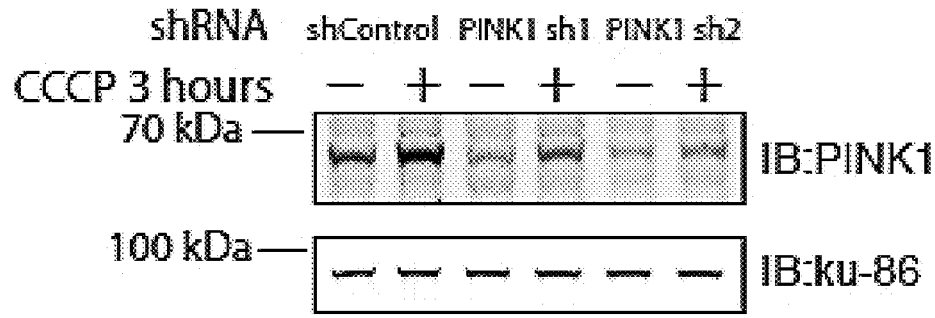
Figure 4D:
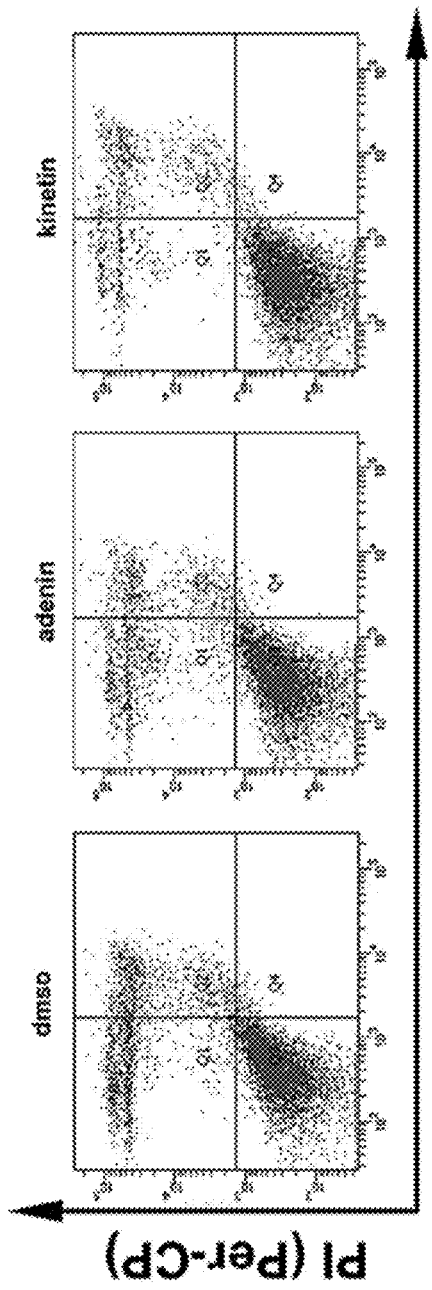
Figure 4F:
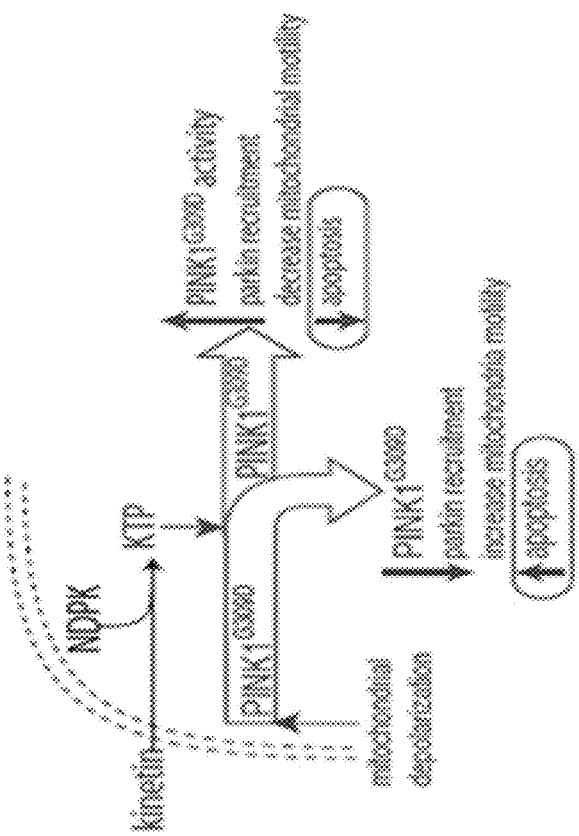
Figure 4E:
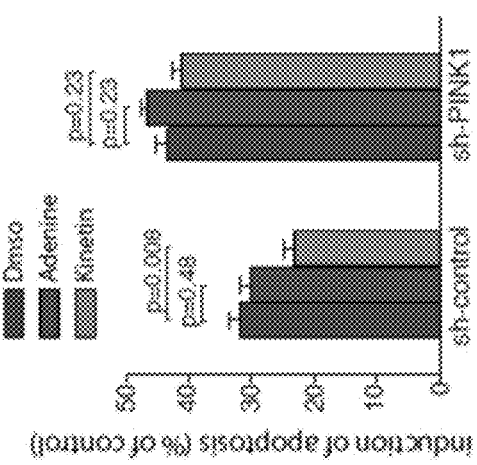

Overexpression of PINK1 in neuronal cells (e.g. dopaminergic (DA)) promotes survival in response to oxidative stress and other mitochondrial toxins[7]. Before testing the effects of kinetin on apoptosis, we treated DA neurons with 50 µM of either kinetin or adenine and measured cell density after 10 days. Kinetin and adenine have no effect on cell density, indicating both are non-toxic to DA neurons (FIG. 4A). To determine whether amplification of PINK1 kinase activity by KTP in cells promotes survival, we utilized human-derived neuroblastoma SH-SY5Y cells which exhibit decreased apoptosis upon overexpression of PINK1[7]. SH-SY5Y cells were treated with 50 µM kinetin, adenine or DMSO for 96 hours, followed by 400 µM H$_2$O$_2$ treatment for additional 24 hours. Using a cytometry-based FACS assay involving cellular annexin V and propidium iodide staining, we determined the percentage of apoptotic cells after treatment with DMSO, adenine or kinetin. We saw a significant decrease in the total amount of apoptotic cells following kinetin treatment (FIG. 4E) DMSO vs kinetin p=0.008; Wilcoxon T test), but no significant change with adenine (DMSO vs adenine, p=0.48; Wilcoxon T test) and no kinetin effect with infection of a lentivirus expressing PINK1-silencing shRNA (FIGS. 4C, 4E) (DMSO vs kinetin, p=0.23; Wilcoxon T test). These data suggest that PINK1 is activated by kinetin, and that its presence is required to mediate the anti-apoptotic effects of kinetin.

5. Experimental Analysis

Our investigation of a neo-substrate approach to modulate PINK1 activity have yielded three significant findings: 1) the ATP analog kinetin triphosphate (KTP) can be used by both PINK1$^{G309D}$ and PINK1$^{wt}$; 2) KTP amplifies both PINK1$^{G309D}$ and PINK1$^{wt}$ activity, and in the case of the former, returns it to near-wt catalytic efficiency; 3) kinetin can be applied to neuronal cell cultures to reduce apoptosis in a PINK1-dependent manner.

Current kinase targeted drugs are striking for the single modality of regulating kinase function—inhibition. However, a wide range of kinase dysregulation in disease is characterized by a lack of kinase activity: desensitization of insulin receptor kinase in diabetes[25]; inactivation of the death associated protein kinase (DAPK) in cancer[26]; inactivation of the LKB1 tumor suppressor kinase in cancer[27]; and decreased PINK1 activity in early-onset Parkinson's Disease. Although many examples of inactive kinases causing disease have been uncovered, there have been no therapeutic approaches for enhancing kinase activity. We show here that kinetin can be used to rescue PINK1$^{G309D}$ catalytic activity to near-wt levels in-vitro and in cells, and that wt PINK1 can be amplified to halt mitochondrial motility and to oppose apoptosis in the presence of oxidative stress. These data suggest that kinetin mediated activation of PINK1 may be a potential therapeutic for PINK1-related and possibly even idiopathic Parkinson's Disease. As Parkinson's Disease has heretofore lacked any disease modifying therapies, kinetin-induced amplification of the PINK1 pathway could prove the first disease modifying therapy for PD. Additionally, our insights into the kinase-dependent alternative use of neo-substrates may presage the ability to treat other diseases resulting from kinase misregulation with a novel class of neo-substrate kinase activators.

TABLE 1

Catalytic constants for PINK1

| | $k_m$ | $V_{max}$ |
|---|---|---|
| ATP | 18.4 ± 10 µM | 0.0053 ± 0.001 min−1 |
| KTP | 51.7 ± 14 µM | 0.0098 ± 0.002 min−1 |

TABLE 2

50% Recruitment Times ($R_{50}$)
mCherry Parkin to depolarized mitochondria

| | DMSO | adenine | kinetin |
|---|---|---|---|
| PINK1$^{wt}$ | 14 ± 1 | 15 ± 1 | 10 ± 2 |
| PINK1$^{G309D}$ | 20 ± 2 | 23 ± 2 | 15 ± 2 |

6. Amplifying PINK1 Activity by Application of a Neo-Substrate to Protect Cardiomyocytes in Models for Heart Disease Mitochondria constitute 30% of myocardial mass, therefore normal mechanisms of mitochondrial repair are essential for cardiac homeostasis (Chen et al., 2011; Lee et al., 2012). PTEN induced putative kinase 1 (PINK1) plays an important role in repairing mitochondrial dysfunction by responding to damage at the level of individual mitochondria. In healthy mitochondria, PINK1 is rapidly degraded by the protease ParL (Meissner et al., 2011); but in the presence of inner membrane depolarization, PINK1 is stabilized on the outer membrane, where it recruits and activates Parkin (Narendra et al., 2010), blocks mitochondrial fusion and trafficking (Clark et al., 2006; Deng et al., 2008; Wang et al., 2011), and ultimately triggers mitochondrial autophagy (Geisler et al., 2010; Narendra et al., 2008; Youle and Narendra, 2011). The PINK1 pathway has also been linked to the induction of mitochondrial biogenesis and the reduction of apoptosis in neurons (Deng et al., 2005; Petit et al., 2005; Pridgeon et al., 2007; Shin et al., 2011; Wang et al., 2011). This important pathway for neuronal mitochondrial health and cell survival has only recently been connected with cardiac mitochondrial maintenance and survival.

PINK1 is expressed downstream of the pro-growth PI3K/Akt pathway, which is associated with reduced myocardial infarction, therefore early research sought to connect PINK1 to cardiac survival (Siddall et al., 2008). This connection was strengthened by the discovery that PINK1 expression is severely reduced in end stage human heart failure and that PINK1 knockout mice show impaired cardiac mitochondrial function and pathological cardiac hypertrophy at an early age (2 months of age)(Billia et al., 2011). Thus, PINK1 related protein Parkin appears essential for normal mitochondrial survival in cardiac myocytes and that PINK1 expression opposes hypertrophic cardiomyopathy (Lee et al., 2012; Lee et al., 2011; Liu et al., 2012).

PINK1, Parkin and mitochondrial health are connected to maintenance in cardiac tissue. The mitochondrial outer membrane guanosine triphosphatase mitofusin (Mfn) 2 is likely directly phosphorylated by PINK1 following mitochondrial depolarization. The phosphorylated form of Mfn2 likely serves as the receptor for Parkin on depolarized mitochondria, leading to Parkin activation and mitophagy (Chen and Dorn, 2013). The knockout of Mfn2 in mice causes defective mitophagy in heart tissue, impaired $O_2$ consumption and significantly impaired contractile performance in the left ventricle (LV), all of which phenocopy characteristics of aging hearts. In agreement with these data, Drosophila lacking Parkin exhibited impaired respiration in heart tubes, contractile impairment in the LV and cardiomyocyte mitochondria were enlarged all characteristics of dilated cardiomyopathy (Chen and Dorn, 2013). Indeed, PINK1 appears to play an important role in kinase activity in normal heart function in mice and zebrafish (Priyadarshini et al., 2013; Siddall et al., 2013). Amplification of PINK1 kinase activity could prove to have a potential therapeutic role in preventing cardiac dysfunction.

Recognizing the therapeutic potential of PINK1/Parkin pathway activation, mechanisms were investigated for the pharmacological activation of PINK1. Discovered herein, the sequence of PINK1 has three insertions in PINK1's adenine binding N-terminal subdomain. These insertions led us to believe that PINK1 might also exhibit altered substrate specificity. Though it is uncommon for eukaryotic protein kinases to accept alternative substrates in the ATP binding site, kinases engineered with a single mutation to the gatekeeper residue often tolerate ATP analogs with substitutions at the N6 position (Liu et al., 1998; Shah et al., 1997). Importantly, no wildtype kinase we had previously studied had shown the ability to accept N6 modified ATP analogs.

We discovered that, unlike any kinase we have studied, PINK1 accepts the neo-substrate N6 furfuryl ATP (kinetin triphosphate or KTP) with higher catalytic efficiency than its endogenous substrate, ATP. We also discovered herein that the metabolic precursor of this neo-substrate (kinetin) can be taken up by cells and converted to the nucleotide triphosphate form, which leads to accelerated Parkin recruitment to depolarized mitochondria, diminished mitochondrial motility in axons, and suppression of apoptosis in human derived neural cells, all in a PINK1 dependent manner. We believe that the fact that PINK1 can be activated in neural cells could portend a role for our small molecule in modulating PINK1 kinase activity in a cardiac model.

Example 6.1: Characterize Amplification of PINK1 Kinase Activity in Cardiomyocyte Cell Lines Kinetin mediated PINK1 activity amplification was characterized using a variety of cell lines and primary cells. The HL-1 cell line, an established cardiomyocyte cell line that retains characteristic properties of differentiated cardiac tissue (Claycomb et al., 1998) as well as freshly isolated cardiomyocytes from PINK1wt or PINK1−/− mice. Infected HL-1 cells with a lentivirus expressing shRNA targeting PINK1, were developed to generate a PINK1 knockdown control. To analyze the amplification of PINK1 kinase activity we analyzed the phosphorylation level of Bcl-xL, Mfn2, and Parkin following treatment of PINK1wt and PINK1 knockdown or −/− cell lines with DMSO or 25 µM adenine, kinetin or 9-methyl kinetin (9MK negative control) and fCCCP for three to twenty-four hours following published protocols (Arena et al., 2013; Chen and Dorn, 2013; Kondapalli et al., 2012). Neuronal cell lines treated with kinetin result in a significant increase in phosphorylation level of Parkin and Bcl-xL. Accordingly, PINK1wt expressing cells see an increase in PINK1 dependent phosphorylation, but not in those cells where PINK1 has been depleted.

PINK1wt and PINK1 knockdown or −/− cell lines were treated with DMSO or 25 µM adenine, kinetin or 9MK and assess characteristics of mitochondrial health following treatment with the mitochondrial toxins antimycin, fCCCP, and H2O2. The health of the mitochondria was assessed using established techniques, including mitochondria fluorophore JC-1 staining (Lin and Lai, 2013; Lin et al., 2013), mtDNA abundance and mitochondrial oxidative phosphorylation potential (Billia et al., 2011). Decreased mitochondrial health in the PINK1 knockdown or −/− derived cell lines compared to PINK1wt cells in all conditions was measured.

Additionally, results were obtained with regard to kinetin treatment in which PINK1 expression blocks apoptosis of cardiomyocyte cell lines. The amount of early apoptosis was measured using caspase 3/7 cleavage activity and later stage apoptosis by measuring the number of Terminal deoxynucleotidyl transferase dUTP nick end labeling (TUNEL) positive cells and Annexin V binding by FACS analysis following treatment with mitochondrial toxins. The amount of decrease in apoptosis for PINK1wt expressing cells was compared to the PINK1 knockdown cells. Upon kinetin treatment, PINK1wt HL-1 cells or cardiomyocytes derived from PINK1wt mice exhibit significantly lower levels than either PINK1wt treated with control compounds, or PINK1 knockdown or −/− cells treated with any compound. These results replicate the results herein with respect to neurons in which kinetin treatment reduces apoptosis in a PINK1 dependent manner.

Example 6.2: Characterize Amplification of PINK1 Kinase Activity in Animal Models of Heart Failure PINK1 expression is protective in several mouse models of heart failure. PINK1wt expression will block pathological hypertrophy, increase heart fractional shortening, and prevent ischemia induced death of heart tissue. To assay the effect of kinetin PINK1wt or PINK1−/− mice were treated with vehicle, adenine or kinetin from birth following published protocols for administration of kinetin (Hims et al., 2007; Shetty et al., 2011). The mice were sacrificed and whole hearts analyzed, and isolated cardiomyocytes from mice at appropriate time periods (e.g. 2 and 6 months). $O_2$ consumption, mitochondrial integrity (mtDNA abundance, mitochondrial capacity and JC-1 fluorescence) caspase 3/7 cleavage activity and TUNEL staining were measured to assess the health of these tissues. According to published results (Billia et al., 2011; Chen and Dorn, 2013), PINK1 activity is essential for normal O2 consumption and maintenance of mitochondrial integrity. Decreased O2 consumption and mitochondrial integrity in PINK1−/− mice was compared to PINK1wt mice. Improved values for the PINK1wt mice treated with kinetin demonstrated improved health. Additionally, caspase 3/7 cleavage activity and TUNEL staining of the left ventricle were increased in PINK1−/− mice derived cardiomyocytes compared to PINK1wt. Kinetin treated mice demonstrated further reduced TUNEL staining and thus apoptosis replicating our results from neurons in which kinetin blocked induction of apoptosis.

In addition to these analyses we analyzed the performance of the heart in whole animals. We utilized the same procedure as above and treated either PINK1wt or PINK1−/− mice with vehicle, adenine or kinetin from birth following published protocols for administration of kinetin (Hims et al., 2007; Shetty et al., 2011). PINK1−/− mice have been shown to display pathological hypertrophy, including increased cross sectional area and total extracellular matrix area, fractional shortening and increased oxidative stress. We measured the heart weight:body weight (HBW) ratio and total cross sectional area and total extracellular matrix which increased significantly in PINK1−/− mice in an age dependent manner. These characteristics of pathological hypertrophy indicate heart failure in the PINK1−/− mice will not increase as dramatically in PINK1wt mice (Billia et al., 2011). Treatment with kinetin reduces this age induced pathological hypertrophy in PINK1wt mice but treatment with adenine or kinetin in PINK1−/− mice have no effect. Fractional shortening, as measured by non-invasive echocardiography, becomes significantly lower in PINK1−/− mice indicating reduced capacity, but not in PINK1wt mice. Six month old PINK1wt mice treated with kinetin exhibit still higher fractional shortening than the PINK1wt treated with adenine or PINK1−/− mice treated with adenine or kinetin. These experiments indicate that amplification of PINK1 activity by treatment with kinetin can block age-induced loss in heart function.

Stress on the heart also induces pathological hypertrophy and increased apoptosis, and serves as a good model for heart disease. We utilized trans-aortic banding (TAB) and treatment with angiotensin II to increase pressure in the heart and a model for heart attack by induced myocardial infarction. We treated mice as above with kinetin as well as adenine and vehicle controls for two weeks. We then increased pressure in the heart by performing surgery to partially occlude the aorta (TAB) or sham operation. Additionally we directly injected of a bolus of Angiotensin II or saline into the heart (Billia et al., 2011) to increase blood pressure. Following treatment for 14 days we measured HBW ratio, total cross sectional area and total extracellular matrix which increased significantly in PINK1−/− mice following stress (Billia et al., 2011). The PINK1wt expressing mice have reduced defects and the addition of kinetin but not adenine reduces the pathological hypertrophy as measured. Additionally we analyzed the left ventricle for TUNEL staining where the addition of kinetin reduced the total number of TUNEL positive cells, but only in the PINK1wt background, not in PINK1−/− mice. As the depletion of PINK1 leads to more pathological hypertrophy and increased apoptosis, by amplifying PINK1 activity these characteristics of heart failure will be further reduced.

Utilizing mice dosed with kinetin, adenine or vehicle for two weeks, we induced myocardial infarction by ligating the left anterior descending artery at the level of the left atrial appendage (Wang et al., 2006) or sham surgery. Following infarct for 24 or 72 hours, we sacrificed the mice and analyzed the heart by TUNEL staining as cardiomyocytes are susceptible to cell death following infarct. Significant increase in the percentage of TUNEL positive nuclei in the peri-infarct area in PINK1−/− mice over PINK1wt mice is shown, and a significant decrease in TUNEL positive cells in PINK1wt mice treated with kinetin is demonstrated. A significant decrease in the scar size and the level of collagen deposition, which indicates post-infarct remodelling, in the heart of the kinetin treated PINK1wt mice, but not in the adenine or kinetin treated PINK1−/− mice is deomsntrated. These experiments replicate our results in neurons in which kinetin treatment will block apoptosis in response to a number of cellular stressors.

REFERENCES (EXAMPLE 6)

Arena, G., Gelmetti, V., Torosantucci, L., Vignone, D., Lamorte, G., De Rosa, P., Cilia, E., Jonas, E. A., and Valente, E. M. (2013). PINK1 protects against cell death induced by mitochondrial depolarization, by phosphorylating Bcl-xL and impairing its pro-apoptotic cleavage. Cell Death Differ., in press.

Billia, F., Hauck, L., Konecny, F., Rao, V., Shen, J., and Mak, T. W. (2011). PTEN-inducible kinase 1 (PINK1)/Park6 is indispensable for normal heart function. Proc Natl Acad Sci USA 108, 9572-9577.

Chen, Y., and Dorn, G. W., 2nd (2013). PINK1-phosphorylated mitofusin 2 is a Parkin receptor for culling damaged mitochondria. Science 340, 471-475.

Chen, Y., Liu, Y., and Dorn, G. W., 2nd (2011). Mitochondrial fusion is essential for organelle function and cardiac homeostasis. Circ Res 109, 1327-1331.

Clark, I. E., Dodson, M. W., Jiang, C., Cao, J. H., Huh, J. R., Seol, J. H., Yoo, S. J., Hay, B. A., and Guo, M. (2006). Drosophila pink1 is required for mitochondrial function and interacts genetically with parkin. Nature 441, 1162-1166.

Claycomb, W. C., Lanson, N. A., Jr., Stallworth, B. S., Egeland, D. B., Delcarpio, J. B., Bahinski, A., and Izzo, N. J., Jr. (1998). HL-1 cells: a cardiac muscle cell line that contracts and retains phenotypic characteristics of the adult cardiomyocyte. Proc Natl Acad Sci USA 95, 2979-2984.

Deng, H., Dodson, M. W., Huang, H., and Guo, M. (2008). The Parkinson's disease genes pink1 and parkin promote mitochondrial fission and/or inhibit fusion in Drosophila. Proc Natl Acad Sci USA 105, 14503-14508.

Deng, H., Jankovic, J., Guo, Y., Xie, W., and Le, W. (2005). Small interfering RNA targeting the PINK1 induces apoptosis in dopaminergic cells SH-SY5Y. Biochem Biophys Res Commun 337, 1133-1138.

Geisler, S., Holmstrom, K. M., Treis, A., Skujat, D., Weber, S. S., Fiesel, F. C., Kahle, P. J., and Springer, W. (2010). The PINK1/Parkin-mediated mitophagy is compromised by PD-associated mutations. Autophagy 6, 871-878.

Hims, M. M., Ibrahim, E. C., Leyne, M., Mull, J., Liu, L., Lazaro, C., Shetty, R. S., Gill, S., Gusella, J. F., Reed, R., et al. (2007). Therapeutic potential and mechanism of kinetin as a treatment for the human splicing disease familial dysautonomia. J Mol Med (Berl) 85, 149-161.

Kondapalli, C., Kazlauskaite, A., Zhang, N., Woodroof, H. I., Campbell, D. G., Gourlay, R., Burchell, L., Walden, H., Macartney, T. J., Deak, M., et al. (2012). PINK1 is activated by mitochondrial membrane potential depolarization and stimulates Parkin E3 ligase activity by phosphorylating Serine 65. Open Biol 2, 120080.

Lee, Y., Lee, H. Y., and Gustafsson, A. B. (2012). Regulation of autophagy by metabolic and stress signaling pathways in the heart. J Cardiovasc Pharmacol 60, 118-124.

Lee, Y., Lee, H. Y., Hanna, R. A., and Gustafsson, A. B. (2011). Mitochondrial autophagy by Bnip3 involves Drp1-mediated mitochondrial fission and recruitment of Parkin in cardiac myocytes. Am J Physiol Heart Circ Physiol 301, H1924-1931.

Lin, H. C., and Lai, I. R. (2013). Mitotracker probes and mitochondrial membrane potential. Shock 39, 543.

Lin, H. C., Liu, S. Y., Lai, H. S., and Lai, I. R. (2013). Isolated mitochondria infusion mitigates ischemia-reperfusion injury of the liver in rats. Shock 39, 304-310.

Liu, X., Ye, B., Miller, S., Yuan, H., Zhang, H., Tian, L., Nie, J., Imae, R., Arai, H., Li, Y., et al. (2012). Ablation of ALCAT1 mitigates hypertrophic cardiomyopathy through effects on oxidative stress and mitophagy. Mol Cell Biol 32, 4493-4504.

Liu, Y., Shah, K., Yang, F., Witucki, L., and Shokat, K. M. (1998). A molecular gate which controls unnatural ATP analogue recognition by the tyrosine kinase v-Src. Bioorg Med Chem 6, 1219-1226.

Meissner, C., Lorenz, H., Weihofen, A., Selkoe, D. J., and Lemberg, M. K. (2011). The mitochondrial intramembrane protease PARL cleaves human Pink1 to regulate Pink1 trafficking. J Neurochem 117, 856-867.

Narendra, D., Tanaka, A., Suen, D. F., and Youle, R. J. (2008). Parkin is recruited selectively to impaired mitochondria and promotes their autophagy. J Cell Biol 183, 795-803.

Narendra, D. P., Jin, S. M., Tanaka, A., Suen, D. F., Gautier, C. A., Shen, J., Cookson, M. R., and Youle, R. J. (2010). PINK1 is selectively stabilized on impaired mitochondria to activate Parkin. PLoS Biol 8, e1000298.

Petit, A., Kawarai, T., Paitel, E., Sanjo, N., Maj, M., Scheid, M., Chen, F., Gu, Y., Hasegawa, H., Salehi-Rad, S., et al. (2005). Wild-type PINK1 prevents basal and induced neuronal apoptosis, a protective effect abrogated by Parkinson disease-related mutations. J Biol Chem 280, 34025-34032.

Pridgeon, J. W., Olzmann, J. A., Chin, L. S., and Li, L. (2007). PINK1 Protects against Oxidative Stress by Phosphorylating Mitochondrial Chaperone TRAP1. PLoS Biol 5, e172.

Priyadarshini, M., Tuimala, J., Chen, Y. C., and Panula, P. (2013). A zebrafish model of PINK1 deficiency reveals key pathway dysfunction including HIF signaling. Neurobiol Dis 54, 127-138.

Shah, K., Liu, Y., Deirmengian, C., and Shokat, K. M. (1997). Engineering unnatural nucleotide specificity for Rous sarcoma virus tyrosine kinase to uniquely label its direct substrates. Proc Natl Acad Sci USA 94, 3565-3570.

Shetty, R. S., Gallagher, C. S., Chen, Y. T., Hims, M. M., Mull, J., Leyne, M., Pickel, J., Kwok, D., and Slaugenhaupt, S. A. (2011). Specific correction of a splice defect in brain by nutritional supplementation. Hum Mol Genet 20, 4093-4101.

Shin, J. H., Ko, H. S., Kang, H., Lee, Y., Lee, Y. I., Pletinkova, O., Troconso, J. C., Dawson, V. L., and Dawson, T. M. (2011). PARIS (ZNF746) repression of PGC-1alpha contributes to neurodegeneration in Parkinson's disease. Cell 144, 689-702.

Siddall, H. K., Warrell, C. E., Davidson, S. M., Mocanu, M. M., and Yellon, D. M. (2008). Mitochondrial PINK1—a novel cardioprotective kinase? Cardiovasc Drugs Ther 22, 507-508.

Siddall, H. K., Yellon, D. M., Ong, S. B., Mukherjee, U. A., Burke, N., Hall, A. R., Angelova, P. R., Ludtmann, M. H., Deas, E., Davidson, S. M., et al. (2013). Loss of PINK1 Increases the Heart's Vulnerability to Ischemia-Reperfusion Injury. *PLoS ONE* 8, e62400.

Wang, J., Bo, H., Meng, X., Wu, Y., Bao, Y., and Li, Y. (2006). A simple and fast experimental model of myocardial infarction in the mouse. *Tex Heart Inst J* 33, 290-293.

Wang, X., Winter, D., Ashrafi, G., Schlehe, J., Wong, Y. L., Selkoe, D., Rice, S., Steen, J., LaVoie, M. J., and Schwarz, T. L. (2011). PINK1 and Parkin target Miro for phosphorylation and degradation to arrest mitochondrial motility. *Cell* 147, 893-906.

Youle, R. J., and Narendra, D. P. (2011). Mechanisms of mitophagy. *Nat Rev Mol Cell Biol* 12, 9-14.

B. REFERENCES (EXCEPT EXAMPLE 6)

1 Schapira, A. H. Mitochondrial disease. Lancet 379, 1825-1834, (2012).
2 Chen, Y. and Dorn, G. PINK1-Phosphorylated Mitofusin-2 Is a Parkin Receptor for Culling Damaged Mitochondria. Science 340, 471-475, (2013).
3 Narendra, D. P. et al. PINK1 is selectively stabilized on impaired mitochondria to activate Parkin. PLoS Biol 8, e1000298 (2010).
4 Wang, X., (2011). et al. PINK1 and Parkin target Miro for phosphorylation and degradation to arrest mitochondrial motility. Cell 147, 893-906, (2011).
5 Richardson P, et al. Report of the 1995 World Health Organization/International Society and Federation of Cardiology Task Force on the Definition and Classification of cardiomyopathies. Circulation 1996; 93:841.
6 Longo, D, et al. Harrison's Internal Medicine. 18$^{th}$ ed. (online), Ch. 238 (2011).
7 Petit, A. et al. Wild-type PINK1 prevents basal and induced neuronal apoptosis, a protective effect abrogated by Parkinson disease-related mutations. J Biol Chem 280, 34025-34032 (2005).
8 Koh, H. & Chung, J. PINK1 as a molecular checkpoint in the maintenance of mitochondrial function and integrity. Mol Cells 34, 7-13, (2012).
9 Martins-Branco, D. et al. Ubiquitin proteasome system in Parkinson's disease: a keeper or a witness? Exp Neurol 238, 89-99, (2012).
10 Geisler, S. et al. The PINK1/Parkin-mediated mitophagy is compromised by PD-associated mutations. Autophagy 6, 871-878, (2010).
11 Shin, J. H. et al. PARIS (ZNF746) repression of PGC-1alpha contributes to neurodegeneration in Parkinson's disease. Cell 144, 689-702, (2011).
12 Henchcliffe, C. & Beal, M. F. Mitochondrial biology and oxidative stress in Parkinson disease pathogenesis. Nat Clin Pract Neurol 4, 600-609 (2008).
13 Pridgeon, J. W., Olzmann, J. A., Chin, L. S. & Li, L. PINK1 Protects against Oxidative Stress by Phosphorylating Mitochondrial Chaperone TRAP1. PLoS Biol 5, e172 (2007).
14 Haque, M. E. et al. Cytoplasmic Pink1 activity protects neurons from dopaminergic neurotoxin MPTP. Proc Natl Acad Sci USA 105, 1716-1721 (2008).
15 Gautier, C. A., Kitada, T. & Shen, J. Loss of PINK1 causes mitochondrial functional defects and increased sensitivity to oxidative stress. Proc Natl Acad Sci USA 105, 11364-11369 (2008).
16 Samaranch, L. et al. PINK1-linked parkinsonism is associated with Lewy body pathology. Brain 133, 1128-1142, (2010).
17 Merrick, K. A. et al. Switching Cdk2 on or off with small molecules to reveal requirements in human cell proliferation. Mol Cell 42, 624-636, (2011).
18 Mills, R. D. et al. Biochemical aspects of the neuroprotective mechanism of PTEN-induced kinase-1 (PINK1). J Neurochem 105, 18-33 (2008).
19 Hertz, N. T. et al. Chemical Genetic Approach for Kinase-Substrate Mapping by Covalent Capture of Thiophosphopeptides and Analysis by Mass Spectrometry. Current Protocols in Chemical Biology 2, 15-36, (2010).
20 Blethrow, J. D., Glavy, J. S., Morgan, D. O. & Shokat, K. M. Covalent capture of kinase-specific phosphopeptides reveals Cdk1-cyclin B substrates. Proc Natl Acad Sci USA 105, 1442-1447 (2008).
21 Kondapalli, C. et al. PINK1 is activated by mitochondrial membrane potential depolarization and stimulates Parkin E3 ligase activity by phosphorylating Serine 65. Open Biol 2, 120080, (2012).
22 Beilina, A. et al. Mutations in PTEN-induced putative kinase 1 associated with recessive parkinsonism have differential effects on protein stability. Proc Natl Acad Sci USA 102, 5703-5708 (2005).
23 Hertz, N. T. & Shokat, K. M.
24 Ishii, Y., Sakai, S. & Honma, Y. Cytokinin-induced differentiation of human myeloid leukemia HL-60 cells is associated with the formation of nucleotides, but not with incorporation into DNA or RNA. Biochim Biophys Acta 1643, 11-24 (2003).
25 Kulkarni, R. N. et al. Tissue-specific knockout of the insulin receptor in pancreatic beta cells creates an insulin secretory defect similar to that in type 2 diabetes. Cell 96, 329-339, (1999).
26 Kissil, J. L. et al. DAP-kinase loss of expression in various carcinoma and B-cell lymphoma cell lines: possible implications for role as tumor suppressor gene. Oncogene 15, 403-407, (1997).
27 Gao, Y., Ge, G. & Ji, H. LKB1 in lung cancerigenesis: a serine/threonine kinase as tumor suppressor. Protein Cell 2, 99-107, (2011).
28. I. Martin, V. L. Dawson, T. M. Dawson, Recent advances in the genetics of Parkinson's disease. Annu Rev Genomics Hum Genet 12, 301 (Sep. 22, 2011).
29. A. M. Edwards et al., Too many roads not taken. Nature 470, 163 (Feb. 10, 2011).
30. J. D. Sadowsky et al., Turning a protein kinase on or off from a single allosteric site via disulfide trapping. Proc Natl Acad Sci USA 108, 6056 (Apr. 12, 2011).
31. O. Goransson et al., Mechanism of action of A-769662, a valuable tool for activation of AMP-activated protein kinase. J Biol Chem 282, 32549 (Nov. 9, 2007).
32. S. Lourido et al., Calcium-dependent protein kinase 1 is an essential regulator of exocytosis in Toxoplasma. Nature 465, 359 (May 20, 2010).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a cardiomyopathy in a patient in need thereof, comprising administering to said patient an effective amount of a neo-substrate of PINK1, or a pharmaceutically acceptable salt thereof, wherein said neo-substrate of PINK1 is:

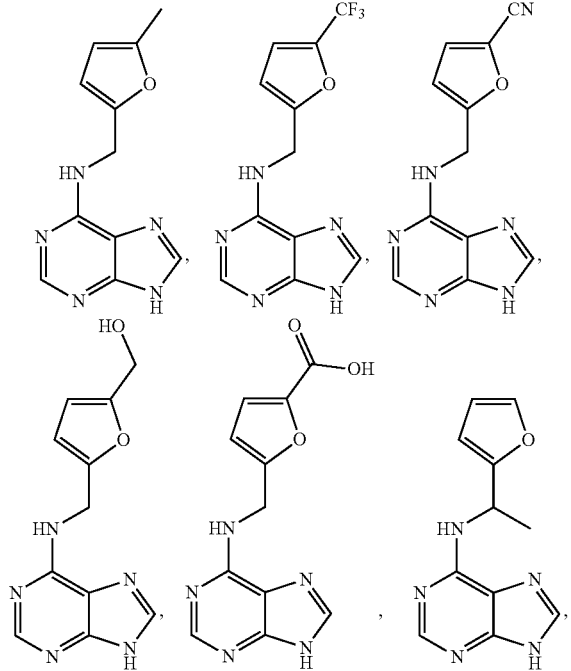

-continued

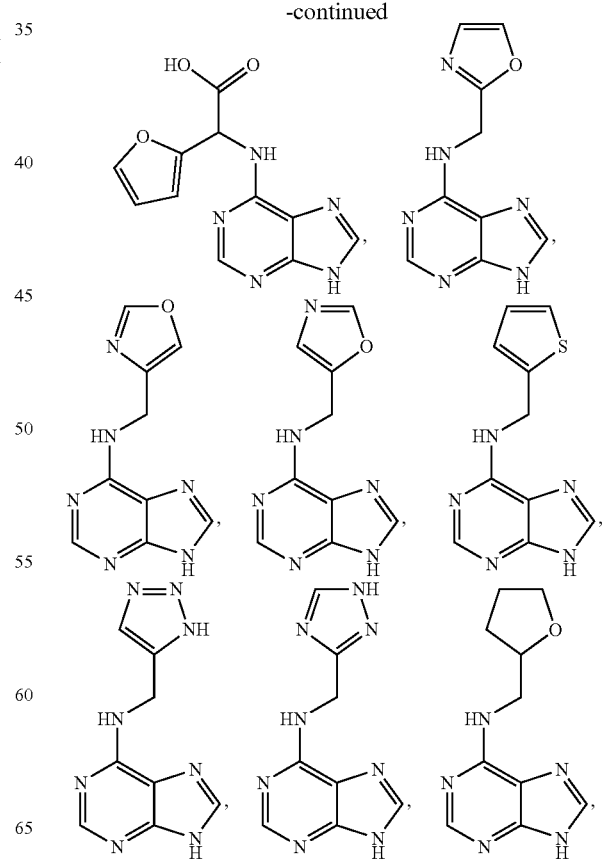

131
-continued
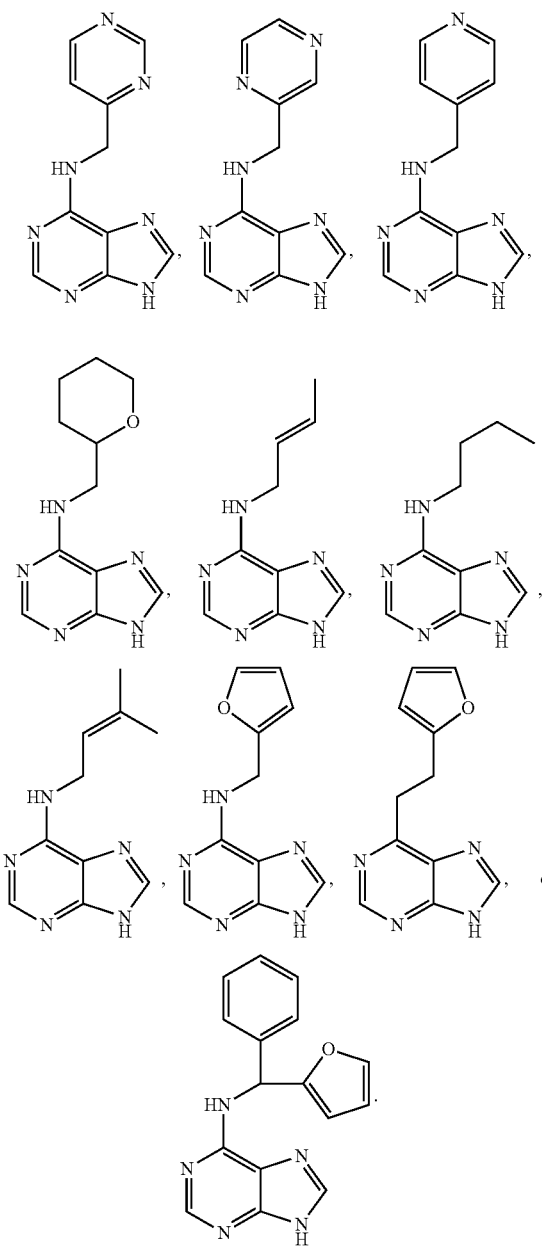
2. The method according to claim 1, wherein said neo-substrate of PINK1 is:
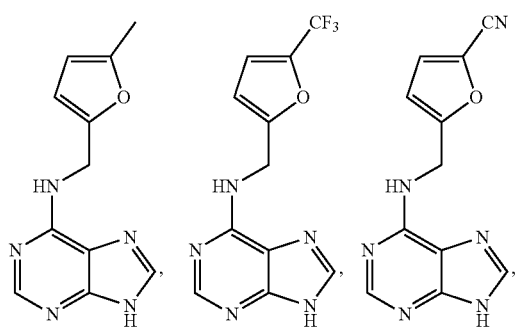
132
-continued
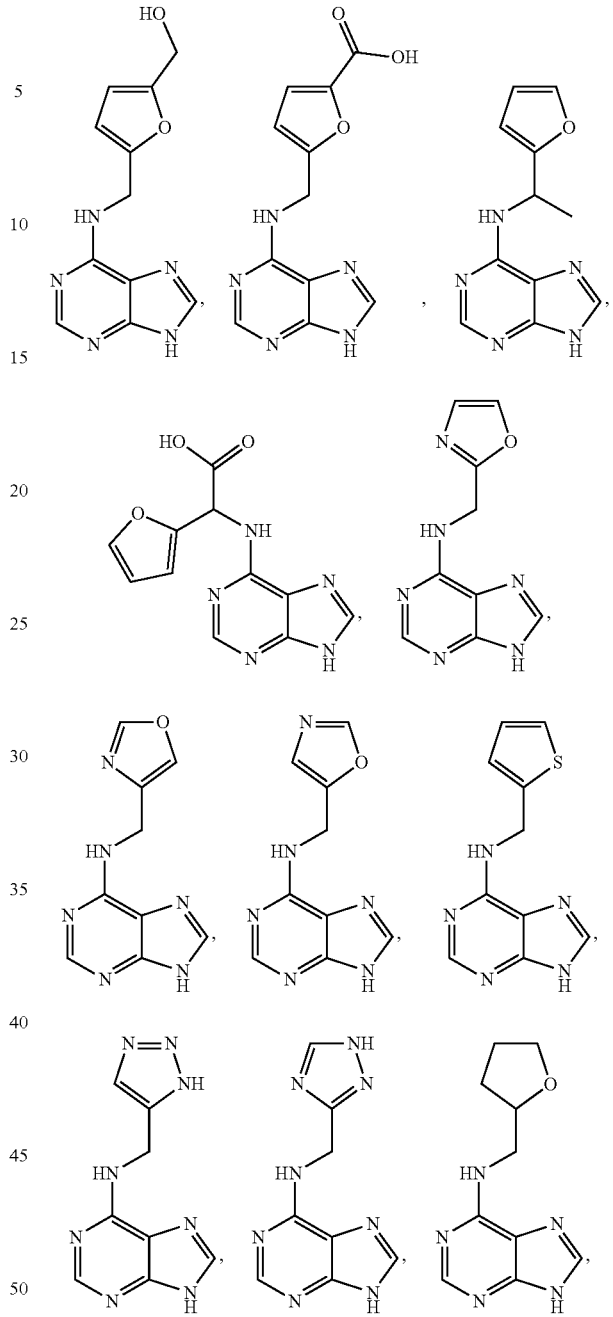
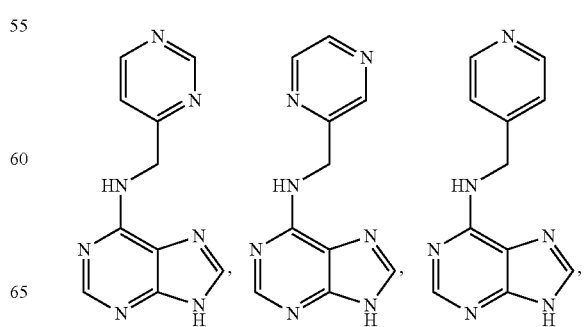

133
-continued

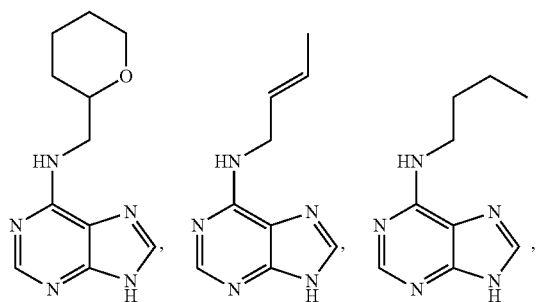

3. The method according to claim 1, wherein said neo-substrate of PINK1 is:

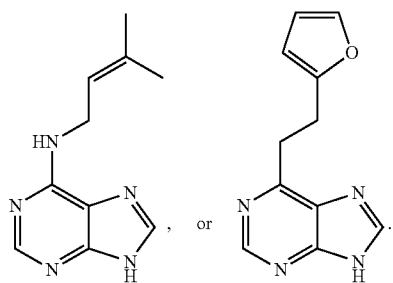

4. The method according to claim 1, wherein said neo-substrate of PINK1 is administered as a pharmaceutical composition comprising said neo-substrate of PINK1 and a pharmaceutically acceptable excipient.

5. The method according to claim 1, wherein said neo-substrate of PINK1 is:

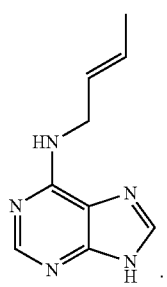

6. The method according to claim 1, wherein said neo-substrate of PINK1 is:

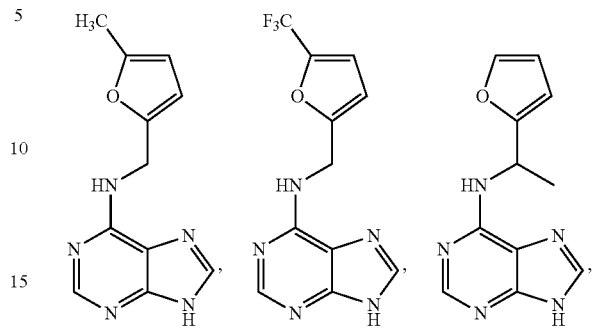

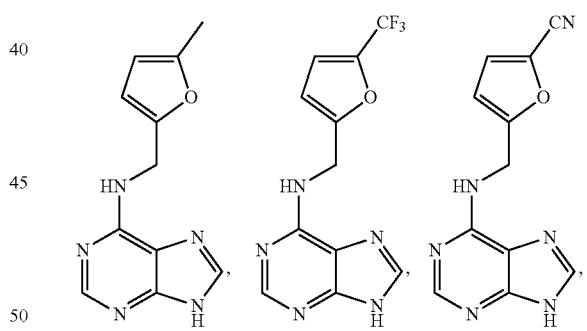

7. A method of treating a neurodegenerative disease in a patient in need thereof, comprising administering to said patient an effective amount of a neo-substrate of PINK1, or a pharmaceutically acceptable salt thereof, wherein said neo-substrate of PINK1 is:

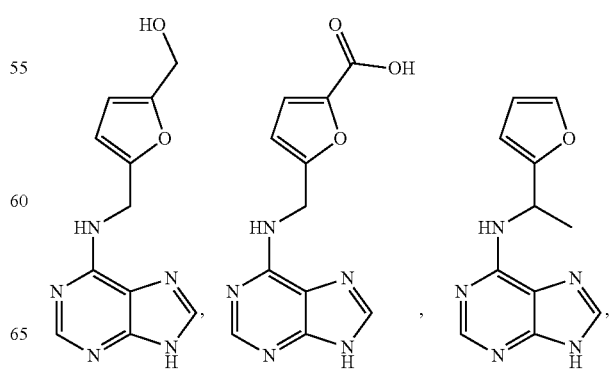

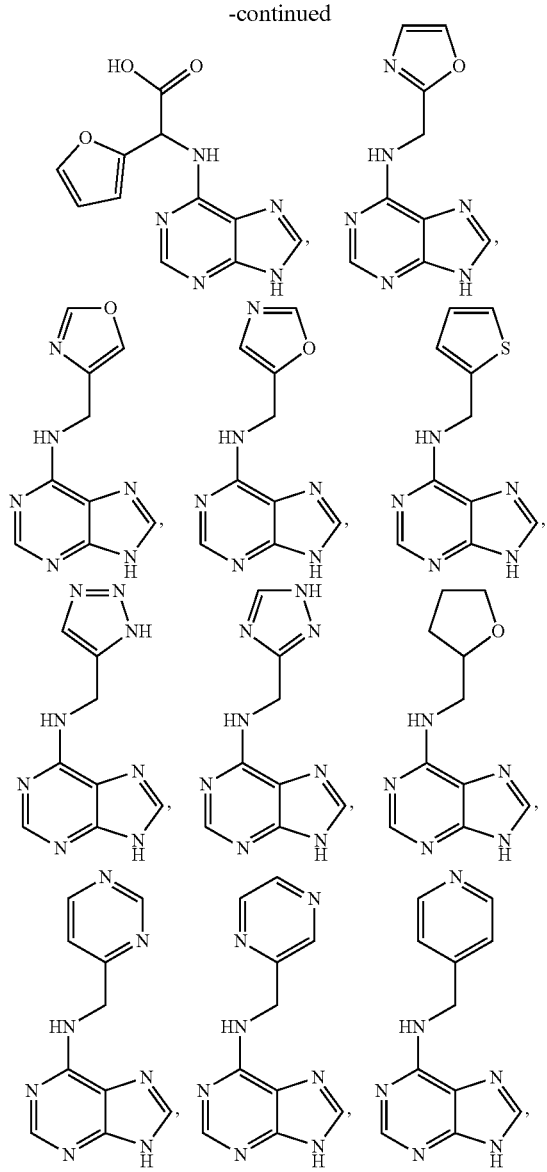
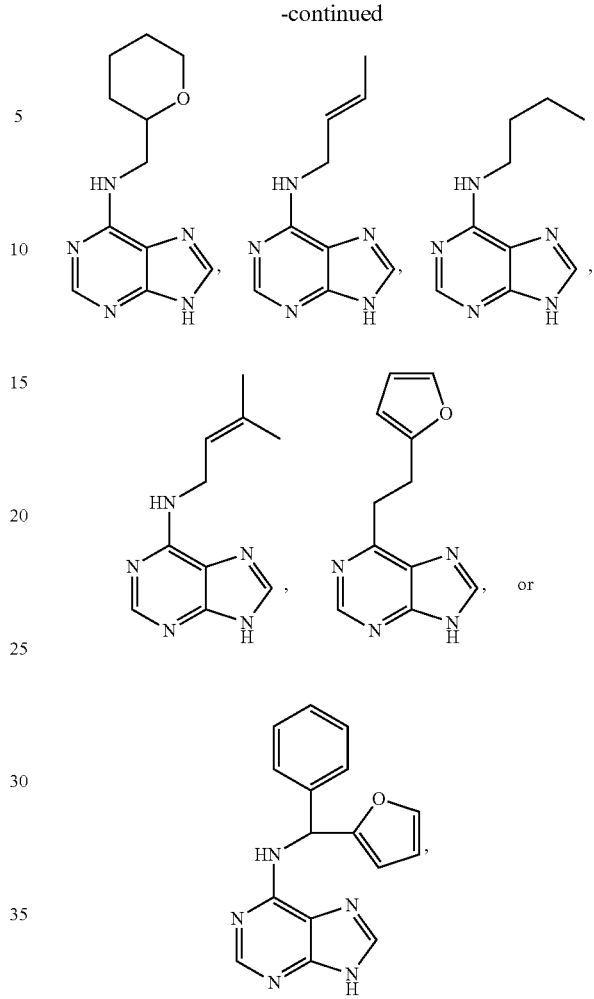
wherein the neurodegenerative disease is selected from the group consisting of Alzheimer's disease, Parkinson's disease, Huntington's disease, and Amyotrophic lateral sclerosis.
* * * * *

UNITED STATES PATENT AND TRADEMARK OFFICE
CERTIFICATE OF CORRECTION

PATENT NO. : 10,723,737 B2
APPLICATION NO. : 15/438496
DATED : July 28, 2020
INVENTOR(S) : Nicholas T. Hertz et al.

Page 1 of 1

It is certified that error appears in the above-identified patent and that said Letters Patent is hereby corrected as shown below:

In the Specification

In Column 1, Line 14, delete "2103" and insert -- 2013 --, therefor.

In Column 1, Line 22, delete "R01 EB1987" and insert -- R01 EB001987 --, therefor.

Signed and Sealed this
Fifteenth Day of September, 2020

Andrei Iancu
*Director of the United States Patent and Trademark Office*

SEQUENCE LISTING

<160> NUMBER OF SEQ ID NOS: 9

<210> SEQ ID NO 1
<211> LENGTH: 101
<212> TYPE: PRT
<213> ORGANISM: Homo sapiens

<400> SEQUENCE: 1

Ser Leu Arg Leu Glu Val Lys Leu Gly Gln Gly Cys Phe Gly Glu Val
1               5                   10                  15

Trp Met Gly Thr Trp Asn Gly Thr Thr Arg Val Ala Ile Lys Thr Leu
            20                  25                  30

Lys Pro Gly Thr Met Ser Pro Glu Ala Phe Leu Gln Glu Ala Gln Val
        35                  40                  45

Met Lys Lys Leu Arg His Glu Lys Leu Val Gln Leu Tyr Ala Val Val
    50                  55                  60

Ser Glu Glu Pro Ile Tyr Ile Val Thr Glu Tyr Met Ser Lys Gly Ser
65                  70                  75                  80

Leu Leu Asp Phe Leu Lys Gly Glu Thr Gly Lys Tyr Leu Arg Leu Pro
                85                  90                  95

Gln Leu Val Asp Met
            100

<210> SEQ ID NO 2
<211> LENGTH: 104
<212> TYPE: PRT
<213> ORGANISM: Homo sapiens

<400> SEQUENCE: 2

Phe Gln Lys Val Glu Lys Ile Gly Glu Gly Thr Tyr Gly Val Val Tyr
1               5                   10                  15

Lys Ala Arg Asn Lys Leu Thr Gly Glu Val Val Ala Leu Lys Lys Ile
            20                  25                  30

Arg Leu Asp Thr Glu Thr Glu Gly Val Pro Ser Thr Ala Ile Arg Glu
        35                  40                  45

Ile Ser Leu Leu Lys Glu Leu Asn His Pro Asn Ile Val Lys Leu Leu
    50                  55                  60

Asp Val Ile His Thr Glu Asn Lys Leu Tyr Leu Val Phe Glu Phe Leu
65                  70                  75                  80

His Gln Asp Leu Lys Lys Phe Met Asp Ala Ser Ala Leu Thr Gly Ile
                85                  90                  95

Pro Leu Pro Leu Ile Lys Ser Tyr
            100

<210> SEQ ID NO 3
<211> LENGTH: 104
<212> TYPE: PRT
<213> ORGANISM: Toxoplasma gondii

<400> SEQUENCE: 3

Tyr Lys Gly Gln Arg Val Leu Gly Lys Gly Ser Phe Gly Glu Val Ile
1               5                   10                  15

Leu Cys Lys Asp Lys Ile Thr Gly Gln Glu Cys Ala Val Lys Val Ile
            20                  25                  30

Ser Lys Arg Gln Val Lys Gln Lys Thr Asp Lys Glu Ser Leu Leu Arg
        35                  40                  45

Glu Val Gln Leu Leu Lys Gln Leu Asp His Pro Asn Ile Met Lys Leu
    50                  55                  60

Tyr Glu Phe Phe Glu Asp Lys Gly Tyr Phe Tyr Leu Val Gly Glu Val
65                  70                  75                  80

Tyr Thr Gly Gly Glu Leu Phe Asp Glu Ile Ile Ser Arg Lys Arg Phe
                85                  90                  95

Ser Glu Val Asp Ala Ala Arg Ile
            100

<210> SEQ ID NO 4
<211> LENGTH: 187
<212> TYPE: PRT
<213> ORGANISM: Homo sapiens

<400> SEQUENCE: 4

Tyr Leu Ile Gly Gln Ser Ile Gly Lys Gly Cys Ser Ala Ala Val Tyr
1               5                   10                  15

Glu Ala Thr Met Pro Thr Leu Pro Gln Asn Leu Glu Val Thr Lys Ser
                20                  25                  30

Thr Gly Leu Leu Pro Gly Arg Gly Pro Gly Thr Ser Ala Pro Gly Glu
            35                  40                  45

Gly Gln Glu Arg Ala Pro Gly Ala Pro Ala Phe Pro Leu Ala Ile Lys
        50                  55                  60

Met Met Trp Asn Ile Ser Ala Gly Ser Ser Glu Ala Ile Leu Asn
65                  70                  75                  80

Thr Met Ser Gln Glu Leu Val Pro Ala Ser Arg Val Ala Leu Gln Gly
                85                  90                  95

Glu Tyr Gly Ala Val Thr Tyr Arg Lys Ser Lys Arg Gly Pro Lys Gln
                100                 105                 110

Leu Ala Pro His Pro Asn Ile Ile Arg Val Leu Arg Ala Phe Thr Ser
            115                 120                 125

Ser Val Pro Leu Leu Pro Gly Ala Leu Val Asp Tyr Pro Asp Val Leu
130                 135                 140

Pro Ser Arg Leu His Pro Glu Gly Leu Gly His Gly Arg Thr Leu Arg
145                 150                 155                 160

Leu Val Met Lys Asn Tyr Pro Cys Thr Leu Arg Gln Tyr Leu Cys Val
                165                 170                 175

Asn Thr Pro Ser Pro Arg Leu Ala Ala Met Met
            180                 185

<210> SEQ ID NO 5
<211> LENGTH: 186
<212> TYPE: PRT
<213> ORGANISM: Mus musculus

<400> SEQUENCE: 5

Tyr Leu Ile Gly Gln Ala Ile Gly Lys Gly Cys Asn Ala Ala Val Tyr
1               5                   10                  15

Glu Ala Thr Met Pro Thr Leu Pro Gln His Leu Glu Lys Ala Lys His
                20                  25                  30

Leu Gly Leu Ile Gly Lys Gly Pro Asp Val Val Leu Lys Gly Ala Asp
            35                  40                  45

Gly Glu Gln Ala Pro Gly Thr Pro Thr Phe Pro Phe Ala Ile Lys Met
        50                  55                  60

Met Trp Asn Ile Ser Ala Gly Ser Ser Ser Glu Ala Ile Leu Ser Lys
65                  70                  75                  80

Met Ser Gln Glu Leu Val Pro Ala Ser Arg Val Ala Leu Ala Gly Glu
                85                  90                  95

```
Tyr Gly Ala Val Thr Tyr Arg Arg Ser Arg Asp Gly Pro Lys Gln Leu
            100                 105                 110

Ala Pro His Pro Asn Ile Ile Arg Val Phe Arg Ala Phe Thr Ser Ser
            115                 120                 125

Val Pro Leu Leu Pro Gly Ala Leu Ala Asp Tyr Pro Asp Met Leu Pro
        130                 135                 140

Pro His Tyr Tyr Pro Glu Gly Leu Gly His Gly Arg Thr Leu Phe Leu
145                 150                 155                 160

Val Met Lys Asn Tyr Pro Cys Thr Leu Arg Gln Tyr Leu Glu Glu Gln
                165                 170                 175

Thr Pro Ser Ser Arg Leu Ala Thr Met Met
            180                 185

<210> SEQ ID NO 6
<211> LENGTH: 187
<212> TYPE: PRT
<213> ORGANISM: Macaca mulatta

<400> SEQUENCE: 6

Tyr Leu Ile Gly Gln Ser Ile Gly Lys Gly Cys Ser Ala Ala Val Tyr
1               5                   10                  15

Glu Ala Thr Met Pro Ala Leu Pro Gln Asn Leu Glu Val Thr Lys Ser
            20                  25                  30

Thr Gly Ser Leu Pro Gly Arg Gly Pro Gly Thr Ser Ala Pro Gly Glu
        35                  40                  45

Glu Gln Glu Gln Ala Leu Gly Ala Pro Ala Phe Pro Leu Ala Ile Lys
    50                  55                  60

Met Met Trp Asn Ile Ser Ala Gly Ser Ser Glu Ala Ile Leu Asn
65                  70                  75                  80

Thr Met Ser Gln Glu Leu Val Pro Ala Ser Arg Val Ala Leu Gln Gly
                85                  90                  95

Glu Tyr Gly Ala Val Thr Tyr Arg Lys Ser Lys Arg Gly Pro Lys Gln
            100                 105                 110

Leu Ala Pro His Pro Asn Ile Ile Arg Val Leu Arg Ala Phe Thr Ser
        115                 120                 125

Ser Val Pro Leu Leu Pro Gly Ala Leu Val Asp Tyr Pro Asp Val Leu
    130                 135                 140

Pro Pro Arg Leu His Pro Glu Gly Leu Gly His Gly Arg Thr Leu Phe
145                 150                 155                 160

Leu Val Met Lys Asn Tyr Pro Cys Thr Leu Arg Gln Tyr Leu Arg Ala
                165                 170                 175

Asn Thr Pro Ser Pro Arg Leu Ala Thr Met Met
            180                 185

<210> SEQ ID NO 7
<211> LENGTH: 189
<212> TYPE: PRT
<213> ORGANISM: Salmo salar

<400> SEQUENCE: 7

Tyr Val Ile Gly Lys Gln Ile Gly Lys Gly Ser Asn Ala Ala Val Tyr
1               5                   10                  15

Glu Ala Ala Ala Pro Phe Ala Val Pro Arg Asp Arg Glu Ser Asp Arg
            20                  25                  30

Cys Ser Leu Asn Asp Gln Pro Ser Asp Asp Gly Glu Val Ala Asn Gly
        35                  40                  45
```

-continued

Ser Leu Arg Ser Pro Ser Ser Leu Cys Ile Tyr Pro Leu Ala Val
            50                  55                  60

Lys Met Met Trp Asn Phe Gly Ala Gly Ser Ser Glu Ala Ile Leu
 65                  70                  75                  80

Arg Ser Met Ser Gln Glu Leu Val Pro Ala Gly Pro Leu Ala Met Lys
                85                  90                  95

Gln Glu Lys Glu Gln Ile Ala Leu Asn Gly Tyr Phe Gly Glu Val
            100                 105                 110

Pro Lys Arg Val Ser Ala His Pro Asn Val Ile Arg Val Phe Arg Ala
            115                 120                 125

Phe Thr Ala Asp Val Pro Leu Leu Pro Gly Ala Gln Glu Glu Tyr Pro
            130                 135                 140

Asp Val Leu Pro Ala Arg Leu Asn Glu Gly Leu Gly Asn Asn Arg Thr
145                 150                 155                 160

Leu Phe Leu Val Met Lys Asn Tyr Pro Cys Thr Leu Arg Gln Tyr Leu
                165                 170                 175

Glu Val Asn Val Pro Ser Arg Arg Glu Gly Ser Leu Met
                180                 185

<210> SEQ ID NO 8
<211> LENGTH: 188
<212> TYPE: PRT
<213> ORGANISM: Danio rerio

<400> SEQUENCE: 8

Tyr Val Ile Gly Lys Gln Ile Gly Lys Gly Cys Asn Ala Ala Val Tyr
 1                   5                  10                  15

Glu Ala Ala Ala Pro Phe Ala Pro Pro Val Glu Ser Lys Lys Cys Ser
                20                  25                  30

Leu Val Glu Leu Asn Pro Lys Glu Ala Glu Asp Asp Asn Lys Lys Glu
            35                  40                  45

Glu Pro Leu Arg Leu Ser Ala Ser Pro Ser Phe Pro Leu Ala Met Lys
            50                  55                  60

Met Met Trp Asn Ile Gly Ala Gly Ser Ser Ser Asp Ala Ile Leu Arg
 65                  70                  75                  80

Ser Met Ser Met Glu Leu Val Pro Ser Cys Pro Gln Ala Leu Arg Lys
                85                  90                  95

Glu Gln Gly Glu Leu Thr Leu Asn Gly His Phe Gly Ala Val Pro Lys
            100                 105                 110

Arg Leu Ser Ala His Pro Asn Val Ile Thr Val Tyr Arg Ala Phe Thr
            115                 120                 125

Ala Glu Val Pro Leu Leu Pro Gly Ala Arg Glu Glu Tyr Pro Asp Val
            130                 135                 140

Leu Pro Ala Arg Leu Asn Pro His Gly Leu Gly Ser Asn Arg Thr Leu
145                 150                 155                 160

Phe Leu Val Met Lys Asn Tyr Pro Cys Thr Leu Arg Gln Tyr Leu Glu
                165                 170                 175

Val Cys Val Pro Lys Arg Thr Gln Ala Ser Leu Met
            180                 185

<210> SEQ ID NO 9
<211> LENGTH: 182
<212> TYPE: PRT
<213> ORGANISM: Caenorhabditis elegans

<400> SEQUENCE: 9

| | | | | | | | | | | | | |
|---|---|---|---|---|---|---|---|---|---|---|---|---|
| Tyr 1 | Glu | Phe | Gly 5 | Glu | Phe | Leu | Gly | Gln 10 | Gly | Cys | Asn | Ala | Ala | Val 15 | Tyr |
| Ser | Ala | Arg | Leu 20 | Ala | Asn | Ser | Asp | Ala 25 | Glu | Ser | Ser | Gly | Asn 30 | Thr | His |
| Tyr | Gly | Ala 35 | Gly | Phe | Asn | Glu | Val 40 | Thr | Asn | Ile | Leu | Ala 45 | Glu | Ile | Pro |
| Pro | Val | Ser 50 | Lys | Val | Ala | Gln | Lys 55 | Lys | Phe | Pro | Leu 60 | Ala | Ile | Lys | Leu |
| Met 65 | Phe | Asn | Phe | Glu | His 70 | Asp | Arg | Asp | Gly | Asp 75 | Ala | His | Leu | Leu | Lys 80 |
| Ser | Met | Gly | Asn | Glu 85 | Leu | Ala | Pro | Tyr | Pro 90 | Asn | Ala | Ala | Lys | Leu 95 | Leu |
| Asn | Gly | Gln | Met 100 | Gly | Thr | Phe | Arg | Pro 105 | Leu | Pro | Ala | Lys | His 110 | Pro | Asn |
| Val | Val | Arg 115 | Ile | Gln | Thr | Ala | Phe 120 | Ile | Asp | Ser | Leu | Lys 125 | Val | Leu | Pro |
| Asp | Ala | Ile 130 | Glu | Arg | Tyr | Pro 135 | Asp | Ala | Leu | His | Thr 140 | Ala | Arg | Trp | Tyr |
| Glu 145 | Ser | Ile | Ala | Ser | Glu 150 | Pro | Lys | Thr | Met | Tyr 155 | Val | Val | Met | Arg | Arg 160 |
| Tyr | Arg | Gln | Thr | Leu 165 | His | Glu | Tyr | Val | Trp 170 | Thr | Arg | His | Arg | Asn 175 | Tyr |
| Trp | Thr | Gly | Arg 180 | Val | Ile | | | | | | | | | | |